(12) United States Patent
Rosenquist et al.

(10) Patent No.: US 7,608,590 B2
(45) Date of Patent: Oct. 27, 2009

(54) HCV NS-3 SERINE PROTEASE INHIBITORS

(75) Inventors: Asa Rosenquist, Huddinge (SE); Fredrik Thorstensson, Linkoping (SE); Per-Ola Johansson, Linkoping (SE); Ingemar Kvarnstrom, Linkoping (SE); Susana Ayesa, Huddinge (SE); Bjorn Classon, Huddinge (SE); Laszlo Rakos, Huddinge (SE); Bertil Samuelsson, Huddinge (SE)

(73) Assignee: Medivir AB, Huddinge (SE)

( * ) Notice: Subject to any disclaimer, the term of this patent is extended or adjusted under 35 U.S.C. 154(b) by 0 days.

(21) Appl. No.: 10/572,418

(22) PCT Filed: Jan. 28, 2005

(86) PCT No.: PCT/SE2005/000096

§ 371 (c)(1), (2), (4) Date: Jan. 22, 2007

(87) PCT Pub. No.: WO2005/073216

PCT Pub. Date: Aug. 11, 2005

(65) Prior Publication Data

US 2007/0161574 A1 Jul. 12, 2007

(30) Foreign Application Priority Data

| Jan. 30, 2004 | (SE) | 0400199 |
|---|---|---|
| May 19, 2004 | (SE) | 0401288 |
| Oct. 22, 2004 | (SE) | 0402562 |

(51) Int. Cl.
A61K 38/00 (2006.01)
A61K 38/04 (2006.01)
A61K 38/05 (2006.01)
C07K 5/08 (2006.01)
C07K 5/10 (2006.01)

(52) U.S. Cl. .............. 514/18; 514/2; 514/10; 514/19; 530/331; 544/141; 544/372; 546/208

(58) Field of Classification Search .............. None
See application file for complete search history.

(56) References Cited

U.S. PATENT DOCUMENTS

| 6,265,380 B1 | 7/2001 | Tung et al. | |
|---|---|---|---|
| 7,125,845 B2 * | 10/2006 | Wu et al. | 514/10 |
| 2003/0186895 A1 | 10/2003 | Llinas-Brunet et al. | |
| 2004/0048802 A1 | 3/2004 | Ripka et al. | |

FOREIGN PATENT DOCUMENTS

| EP | 0 126 587 | 11/1984 |
|---|---|---|
| EP | 0 443 132 | 8/1991 |
| EP | 1 090 997 | 4/2001 |
| EP | 1 408 031 | 4/2004 |
| WO | WO 99/07733 | 2/1999 |
| WO | WO 99/07734 | 2/1999 |
| WO | WO 00/09543 | 2/2000 |
| WO | WO 00/09558 | 2/2000 |
| WO | WO00/47561 | 8/2000 |
| WO | WO 00/59929 | 10/2000 |
| WO | WO01/74768 | 10/2001 |
| WO | WO02/08198 | 1/2002 |
| WO | WO 02/060926 | 8/2002 |
| WO | WO03/035060 | 5/2003 |
| WO | WO 03/053349 | 7/2003 |
| WO | WO03/062228 | 7/2003 |
| WO | WO03/062265 | 7/2003 |
| WO | WO 03/064416 | 8/2003 |
| WO | WO 03/064455 | 8/2003 |
| WO | WO 03/064456 | 8/2003 |
| WO | WO 03/066103 | 8/2003 |
| WO | WO03/087092 | 10/2003 |
| WO | WO 03/099274 | 12/2003 |
| WO | WO 03/099316 | 12/2003 |
| WO | WO 2004/009121 | 1/2004 |
| WO | WO2004/026896 | 4/2004 |
| WO | WO 2004/032827 | 4/2004 |
| WO | WO 2004/037855 | 5/2004 |
| WO | WO2004/039833 | 5/2004 |
| WO | WO 2004/039970 | 5/2004 |
| WO | WO 2004/043339 | 5/2004 |
| WO | WO 2004/072243 | 8/2004 |

(Continued)

OTHER PUBLICATIONS

NPL-Flavivirus from www.medterms.com/script/main/art.asp?articlekey=6502, Accessed on Feb. 26, 2008.*

(Continued)

Primary Examiner—Cecilia Tsang
Assistant Examiner—Julie Ha
(74) Attorney, Agent, or Firm—Butzel Long

(57) ABSTRACT

Compounds of the formula

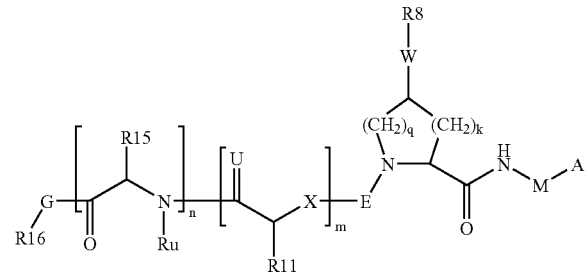

where the variables are as defined in the specification inhibit the NS3 protease of flavivirus such as hepatitis C virus (HCV). The compounds comprise a novel linkage between a heterocyclic P2 unit and those portions of the inhibitor more distal to the nominal cleavage site of the native substrate, which linkage reverses the orientation of peptidic bonds on the distal side relative to those proximal to the cleavage site.

47 Claims, No Drawings

FOREIGN PATENT DOCUMENTS

| WO | WO2004/092161 | 10/2004 |
|---|---|---|
| WO | WO2004/093798 | 11/2004 |
| WO | WO 2004/093915 | 11/2004 |
| WO | WO 2004/094452 | 11/2004 |
| WO | WO 2004/101602 | 11/2004 |
| WO | WO 2004/103996 | 12/2004 |
| WO | WO2004/113365 | 12/2004 |
| WO | WO 2005/010029 | 2/2005 |
| WO | WO2005/073195 | 8/2005 |
| WO | WO 2005/073216 | 8/2005 |
| WO | WO2007/014918 | 2/2007 |
| WO | WO2007/014919 | 2/2007 |
| WO | WO2007/014920 | 2/2007 |
| WO | WO2007/014921 | 2/2007 |
| WO | WO2007/014922 | 2/2007 |
| WO | WO2007/014923 | 2/2007 |
| WO | WO2007/014924 | 2/2007 |
| WO | WO2007/014925 | 2/2007 |
| WO | WO2007/014927 | 2/2007 |
| WO | WO2007/017144 | 2/2007 |

OTHER PUBLICATIONS

NPL-Dengue from www.medterms.com/script/main/art.asp?articlekey=6625, Accessed on Feb. 26, 2008.*

NPL-Encephalitis from www.medterms.com/script/main/art.asp?articlekey=3231, Accessed on Feb. 26, 2008.*

Zanotti, Giancarlo, et al, "Synthesis of analogues of amaninamide, an amatoxin from the white *Amanita virosa* mushroom", *Int. J. Peptide Protein Res*: 450-459 (1987).

U.S. Appl. No. 10/572,349, filed Mar. 17, 2006.

U.S. Appl. No. 11/632,102, filed Jan. 10, 2007.

Zanotti, et al, "Synthesis of Ile3-Amaninamide and its Diastereoisomeric (S)-Sulfoxide from the Analogs of Amanin", (Feb. 25, 1981), Int J. Peptide Protein Res, 18; 1981, pp. 162-168; Munksgaard, Copenhagen, Denmark.

* cited by examiner

HCV NS-3 SERINE PROTEASE INHIBITORS

RELATED APPLICATION

This is a '371 of PCT Application No. having Serial Number PCT/SE2005/000096, filed on Jan. 28. 2005.

TECHNICAL FIELD

This invention relates to novel inhibitors of the NS3 serine protease of the flavivirus HCV and to methods for their use in the treatment or prophylaxis of HCV.

BACKGROUND ART

The NS3 serine protease of HCV is a multifunctional protein which contains a serine protease domain and a RNA helicase domain. The protease cofactor NS4A, which is a relatively small protein, is absolutely required for enhanced serine protease activity. The NS3 serine protease is essential in the viral lifecycle. From analysis of the substrate binding site as revealed by X-ray crystal structure, it has been shown that the binding site of the NS3 protease is remarkably shallow and solvent exposed making small molecule inhibitor design a challenge.

It is believed that two HCV protease inhibitors have entered clinical trials, namely Boehringer Ingelheim's BILN-2061 disclosed in WO 0059929 and Vertex' VX-950 disclosed in WO 0387092. A number of similarly peptidomimetic HCV protease inhibitors have also been proposed in the academic and patent literature. Common for the vast majority of such prior art peptidomimetics is the presence of an L-proline derivative at the P2 position of the inhibitor and interacting with the S2 subsite of the HCV protease enzyme. In the case of BILN-2061, the L-proline is 4-substituted with a quinoline ether, whereas VX-950 has a carboyclic ring fused to the L-proline ring. Most peptidomimetics additionally comprise additional L-amino acid derivatives peptide bonded at the P3 position, with many proposed inhibitors also including additional L-amino acid derivatives extending Into P4, P5 and P6.

It has already become apparent that the sustained administration of BILN-2061 or VX-950 selects HCV mutants which are resistant to the respective drug, so called drug escape mutants. These drug escape mutants have characteristic mutations In the HCV protease genome, notably D168V, D168Y and/or A165S. Treatment paradigms for HCV will thus have to resemble HIV treatment, where drug escape mutations also arise readily. Accordingly, additional drugs with different resistance patterns will consistently be required to provide failing patients with treatment options, and combination therapy with multiple drugs is likely to be the norm in the future, even for first line treatment.

Experience with HIV drugs, and HIV protease inhibitors in particular, has further emphasized that sub-optimal pharmacokinetics and complex dosage regimes quickly result in inadvertent compliance failures. This in turn means that the 24 hour trough concentration (minimum plasma concentration) for the respective drugs in an HIV regime frequently falls below the $IC_{90}$ or $ED_{90}$ threshold for large parts of the day. It is considered that a 24 hour trough level of at least the $IC_{50}$, and more realistically, the $IC_{90}$ or $ED_{90}$ is essential to slow down the development of drug escape mutants and achieving the necessary pharmacokinetics and drug metabolism to allow such trough levels provides a stringent challenge to drug design. The strongly peptidomimetic nature of prior art HCV protease inhibitors, with multiple peptide bonds in native configurations poses pharmacokinetic hurdles to effective dosage regimes.

BRIEF DESCRIPTION OF THE INVENTION

In accordance with a first aspect of the invention, there are provided compounds of the formula I:

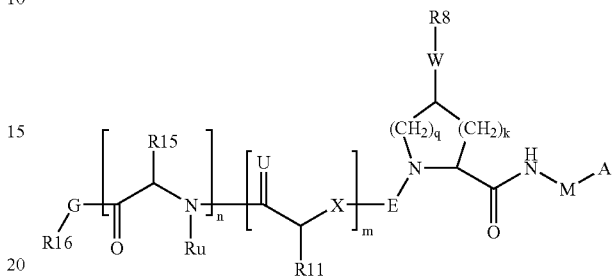

wherein
A is $C(=O)OR^1$, $C(=O)NHSO_2R^2$, $C(=O)NHR^3$, or $CR^4R^{4'}$ wherein;
$R^1$ is hydrogen, $C_1$-$C_6$alkyl, $C_0$-$C_3$alkylcarbocyclyl, $C_0$-$C_3$alkylheterocyclyl;
$R^2$ is $C_1$-$C_6$alkyl, $C_0$-$C_3$alkylcarbocyclyl, $C_0$-$C_3$alkylheterocyclyl;
$R^3$ is $C_1$-$C_6$alkyl, $C_0$-$C_3$alkylcarbocyclyl, $C_0$-$C_3$alkylheterocyclyl, —$OC_1$-$C_6$alkyl, —$OC_0$-$C_3$alkylcarbocyclyl, —$OC_0$-$C_3$alkylheterocyclyl;
$R^4$ is halo, amino, or OH; or $R^4$ and $R^{4'}$ together are =O;
$R^{4'}$ is $C_1$-$C_6$alkyl, $C_0$-$C_3$alkylcarbocyclyl, $C_0$-$C_3$alkylheterocyclyl;
 wherein $R^2$, $R^3$, and $R^{4'}$ are each optionally substituted with 1 to 3 substituents independently selected from the group consisting of halo, oxo, nitrile, azido, nitro, $C_1$-$C_6$alkyl, $C_0$-$C_3$alkylcarbocyclyl, $C_0$-$C_3$alkylheterocyclyl, $NH_2CO$—, Y—NRaRb, Y—O—Rb, Y—C(=O)Rb, Y—(C=O)NRaRb, Y—NRaC(=O)Rb, Y—NHSO$_p$Rb, Y—S(=O)$_p$Rb, Y—S(=O)$_p$NRaRb, Y—C(=O)Orb and Y—NRaC(=O)ORb;
Y is independently a bond or $C_1$-$C_3$alkylene;
Ra is independently H or $C_1$-$C_3$alkyl;
Rb is independently H, $C_1$-$C_6$alkyl, $C_0$-$C_3$alkylcarbocyclyl or $C_0$-$C_3$alkylheterocyclyl;
p is independently 1 or 2;
M is $CR^7R^{7'}$ or NRu;
$R^7$ is $C_1$-$C_6$alkyl, $C_0$-$C_3$alkylC$_3$-$C_7$cycloalkyl, or $C_2$-$C_6$alkenyl, any of which is optionally substituted with 1-3 halo atoms, or an amino, —SH or $C_0$-$C_3$alkylcycloalkyl group; or
$R^7$ is J;
$R^{7'}$ is H or taken together with $R^7$ forms a $C_3$-$C_6$cycloalkyl ring optionally substituted with $R^{7'a}$ wherein;
 $R^{7'a}$ is $C_1$-$C_6$alkyl, $C_3$-$C_5$cycloalkyl, $C_2$-$C_6$alkenyl any of which may be optionally substituted with halo; or $R^{7'a}$ can be J;
q is 0 to 3 and k is 0 to 3; where q+k≧1;
W is —$CH_2$—, —O—, —OC(=O)H—, —OC(=O)—, —S—, —NH—, —NRa, —NHSO$_2$—, —NHC(=O)NH— or —NHC(=O)—, —NHC(=S)NH— or a bond;
$R^8$ is a ring system containing 1 or 2 saturated, partially unsaturated or unsaturated rings each of which has 4-7 ring atoms and each of which has 0 to 4 hetero atoms independently selected from S, O and N, the ring system being optionally spaced from W by a $C_1$-$C_3$ alkyl group; or $R^8$ is $C_1$-$C_6$ alkyl; any of which $R^8$ groups can be optionally mono, di, or tri substituted with $R^9$, wherein $R^9$ is independently selected from the group consisting of halo, oxo, nitrile, azido, nitro, $C_1$-$C_6$alkyl, $C_0$-$C_3$alkylcarbocyclyl, $C_0$-$C_3$alkylheterocyclyl, $NH_2C(=O)$—, Y—NRaRb, Y—O—Rb, Y—C(=O)Rb, Y—(C=O)NRaRb, Y—NRaC(=O)Rb, Y—NHSO$_p$Rb, Y—S(=O)$_p$Rb, Y—S(—O)$_p$NRaRb, Y—C(=O)ORb and Y—NRaC(=O)ORb; wherein said carbocyclyl or heterocyclyl moiety is optionally substituted with $R^{10}$; wherein $R^{10}$ is $C_1$-$C_6$alkyl, $C_3$-$C_7$cycloalkyl, $C_1$-$C_6$alkoxy, amino, sulfonyl, ($C_1$-$C_3$ alkyl)sulfonyl, $NO_2$, OH, SH, halo, haloalkyl, carboxyl, amido;

E is —C(=O)—, —C(=S)—, —S(=O)$_2$—, —S(=O)—, —C(=N—Rf)—;

Rf is H, —CN, —C(=O)NRaRb; —C(=O)$C_1$-$C_3$alkyl;

X is —NRx- where Rx is H, $C_1$-$C_5$alkyl or J; or in the case where E is —C(=O), X can also be —O— or —NR-jNRj—;

wherein one of Rj is H and the other is H, $C_1$-$C_5$ alkyl or J;

$R^{11}$ is H, $C_1$-$C_6$alkyl, $C_0$-$C_3$alkylcarbocyclyl, $C_0$-$C_3$alkylheterocyclyl, any of which can be substituted with halo, oxo, nitrile, azido, nitro, $C_1$-$C_6$alkyl, $C_0$-$C_3$alkylcarbocyclyl, $C_0$-$C_3$alkylheterocyclyl, $NH_2CO$—, Y—NRaRb, Y—O—Rb, Y—C(=O)Rb, Y—(C=O)NRaRb, Y—NRaC(=O)Rb, Y—NHSO$_p$Rb, Y—S(=O)$_p$Rb, Y—S(=O)$_p$NRaRb, Y—C(=O)ORb, Y—NRaC(=O)ORb; or $R^{11}$ is J;

J, if present, is a single 3 to 10-membered saturated or partially unsaturated alkylene chain extending from the $R^7$/$R^{7'}$ cycloalkyl or from the carbon atom to which $R^7$ is attached to one of Rj, Rx, Ry or $R^{11}$ to form a macrocycle, which chain is optionally interrupted by one to three heteroatoms independently selected from: —O—, —S— or —NR$^{12}$—, and wherein 0 to 3 carbon atoms in the chain are optionally substituted with $R^{14}$;

wherein;

$R^{12}$ is H, $C_1$-$C_6$alkyl, $C_3$-$C_6$cycloalkyl, or C(=O)$R^{13}$;

$R^{13}$ is $C_1$-$C_6$alkyl, $C_0$-$C_3$alkylcarbocyclyl, $C_0$-$C_3$alkylheterocyclyl;

$R^{14}$ is independently selected from the group consisting of H, $C_1$-$C_6$alkyl, $C_1$-$C_6$haloalkyl, $C_1$-$C_6$alkoxy, hydroxy, halo, amino, oxo, thio and $C_1$-$C_6$thioalkyl;

Ru is independently H or $C_1$-$C_3$alkyl;

m is 0 or 1; n is 0 or 1;

U is =O or is absent;

$R^{15}$ is H, $C_1$-$C_6$alkyl, $C_0$-$C_3$alkylcarbocyclyl, $C_0$-$C_3$alkylheterocyclyl, any of which can be substituted with halo, oxo, nitrile, azido, nitro, $C_1$-$C_6$ alkyl, $C_0$-$C_3$alkylheterocyclyl, $C_0$-$C_3$alkylcarbocyclyl, $NH_2CO$—, Y—NRaRb, Y—O—Rb, Y—C(=O)Rb, Y—(C=O)NRaRb, Y—NRaC(=O)Rb, Y—NHS(=O)$_p$Rb, Y—S(=O)$_p$Rb, Y—S(=O)$_p$NRaRb, Y—C(=O)ORb, Y—NRaC(=O)ORb;

G is —O—, —NRy-, —NRjNRj—: where one Rj is H and the other is H, $C_1$-$C_5$ alkyl or J;

Ry is H, $C_1$-$C_3$ alkyl; or Ry is J;

$R^{16}$ is H; or $C_1$-$C_6$alkyl, $C_0$-$C_3$alkylcarbocyclyl, $C_0$-$C_3$alkylheterocyclyl, any of which can be substituted with halo, oxo, nitrile, azido, nitro, $C_1$-$C_6$alkyl, $C_0$-$C_3$alkylcarbocyclyl, $C_0$-$C_3$alkylheterocyclyl, $NH_2CO$—, Y—NRaRb, Y—O—Rb, Y—C(=O)Rb, Y—(C=O)NRaRb, Y—NRaC(=O)Rb, Y—NHSO$_p$Rb, Y—S(=O)$_p$Rb, Y—S(=O)$_p$NRaRb, Y—C(=O)ORb, Y—NRaC(=O)ORb;

with the proviso that when m=n=0 and G is O then $R^{16}$ is not tert.butyl or phenyl;

or a pharmaceutically acceptable salt or prodrug thereof.

Without in any way wishing to be bound by theory, or the ascription of tentative binding modes for specific variables, the notional concepts P1, P2, P3 and P4 as used herein are provided for convenience only and have substantially their conventional meanings, as illustrated by Schechter & Berger, (1976) Biochem Biophys Res Comm 27 157-162, and denote those portions of the inhibitor believed to fill the S1, S2, S3 and S4 subsites respectively of the enzyme, where S1 is adjacent the cleavage site and S4 remote from the cleavage site. Regardless of binding mode, the components defined by Formula I are intended to be within the scope of the invention. For example it is expected that capping group $R^{16}$-G may interact with the S3 and S4 subsites especially when m and/or n is 0.

Various embodiments of the present invention can be notionally represented as $R^{16}$-G-P4-P3-link-P2-P1, wherein P3 and/or P4 may be absent, and P1, P3 and P4 each represents a building block constituted of a derivative of a natural or unnatural amino acid, P2 is a heterocyclic residue and G-$R^{16}$ is a capping group. The link is a carbonyl or other function as defined for E. The P1 and P2 building blocks and the P3 and P4 building blocks are thus typically linked together by amide bonds whereas the P2 and P3 building blocks are linked through the above described link. The amide bonds are thereby typically reversed relative to each other on each side of the link in the compounds of the invention.

Additional aspects of the invention include a pharmaceutical composition comprising a compound of the invention as defined above and a pharmaceutically acceptable carrier or diluent therefor.

The compounds and compositions of the invention have utility in methods of medical treatment or prophylaxis of HCV infections in humans. Accordingly, a further aspect of the invention is the use of a compound as defined above in therapy, such as in the manufacture of a medicament for the prophylaxis or treatment of flavivirus infections in humans or animals. Exemplary flavivirus include BVDV, dengue and especially HCV.

The compounds of the invention have a non-peptidic linkage at the bond between P2 and P3 building blocks, resulting In the orientation of the P3 and P4 residues being reversed relative to a native substrate. This non-peptidic link is also typically longer than the corresponding peptide bond would have been and means that the P3 and/or P4 groups (including the R16 cap to the extent this interacts with S3 or S4) are displaced outwardly relative to a native peptide substrate. Reversal and displacement in this fashion would be expected to favour the non-natural D stereochemistries for the pocket filling groups (eg side chains) of P3 and/or P4 and/or R16. Indeed, such compounds are typically highly active and within the scope of the invention. However, it has been surprisingly found that even compounds of the invention bearing L-amino acid side chains at P3 and/or P4 exhibit good activity, notwithstanding that the respective side chain entity must approach the S3 or S4 pocket from a different angle relative to a native peptide substrate. Accordingly L-stereochemistry at $R^{11}$ and/or $R^{15}$ and/or the corresponding configuration at $R^{16}$ to mimic L stereochemistry represents a favoured aspect of the invention.

The different angle of approach to the S3 and/or S4 pockets also has implications for the ability of the compounds of the invention to avoid resistance patterns exhibited by prior art HCV protease inhibitors which hitherto have all had a conventional peptide backbone of natural or non-natural L-amino acid residues. As with the reverse transcriptase of HIV which is notorious for quickly generating drug escape mutants under the selective pressure of antiviral therapy, the RNA dependent RNA polymerase NS5A of HCV has a very poor proof reading capacity. This in turn means that the HCV polymerase is highly error prone and it is likely that characteristic resistance patterns will arise when HCV antivirals are administered over long periods. Even before launch, it is apparent that BILN 2061 with a substantially peptidic backbone (albeit macrocyclised) and Vertex' NS3 protease inhibitor VX-950 with a linear peptide backbone at P3 and P4 quickly give rise to characteristic resistance mutations at positions 155, 156 or 168 of the NS3 protease (Lin et al J Biol Chem 2004 279(17):17808-17).

A preferred group of compounds of the invention comprises those wherein P1 represents a hydrazine derivative, that is M is NRu where Ru is typically H or $C_1$-$C_3$alkyl. Compounds wherein M is $CR^7R^{7'}$ constitute a further preferred aspect of the invention.

Preferred embodiments wherein M is $CR^7R^{7'}$ in formulae I include formulae IA:

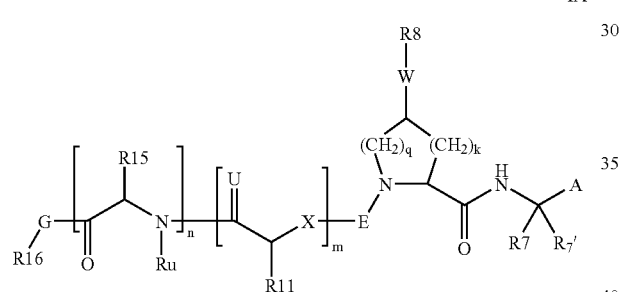

IA

Preferred values for q and k in Formula I include 2:1, 2:2, 2:3, 3:2, 3:3, more preferably 1:2 and 1:0; and most preferably 1:1, in which case preferred compounds have the partial structure:

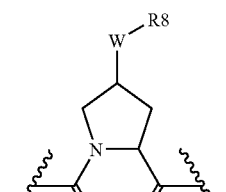

Ia

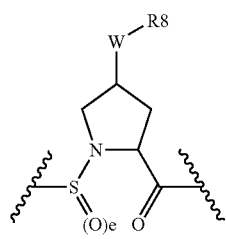

Ib

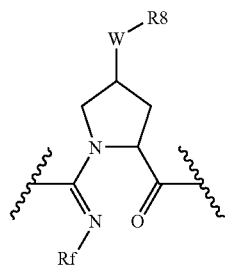

Ic where e is 1 or 2.

It is currently preferred that E is —C(=O)— or —C=N— Rf, for example where Rf is —CN or —C(=O)NH$_2$.

Compounds of the invention may comprise both a P3 and a P4 function, viz m and n are each 1. Favoured embodiments within formula I include formula Ida-Idd below:

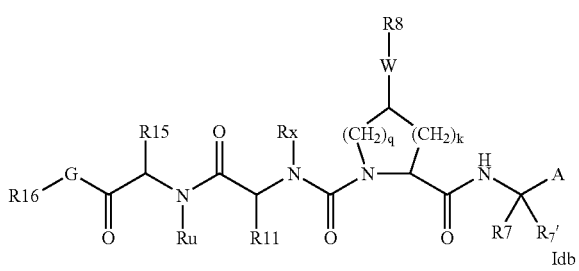

Ida

Idb

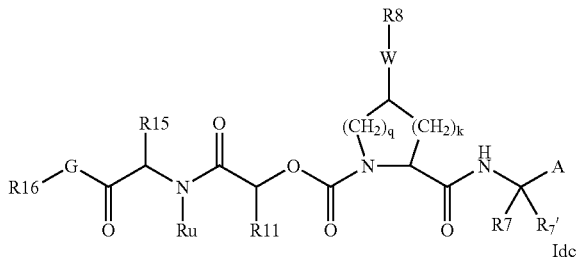

Idc

Idd

Alternative embodiments include the structures corresponding to Ida, Idb, Idc and Idd wherein M is NRu.

Alternative configurations of the compounds of the invention comprise a P3, but no P4 function, viz m is 1 and n is zero. Preferred embodiments within Formula I include formulae Iea-Iee below:

Favoured embodiments within Formula I include formulae Ifa-Ife below:

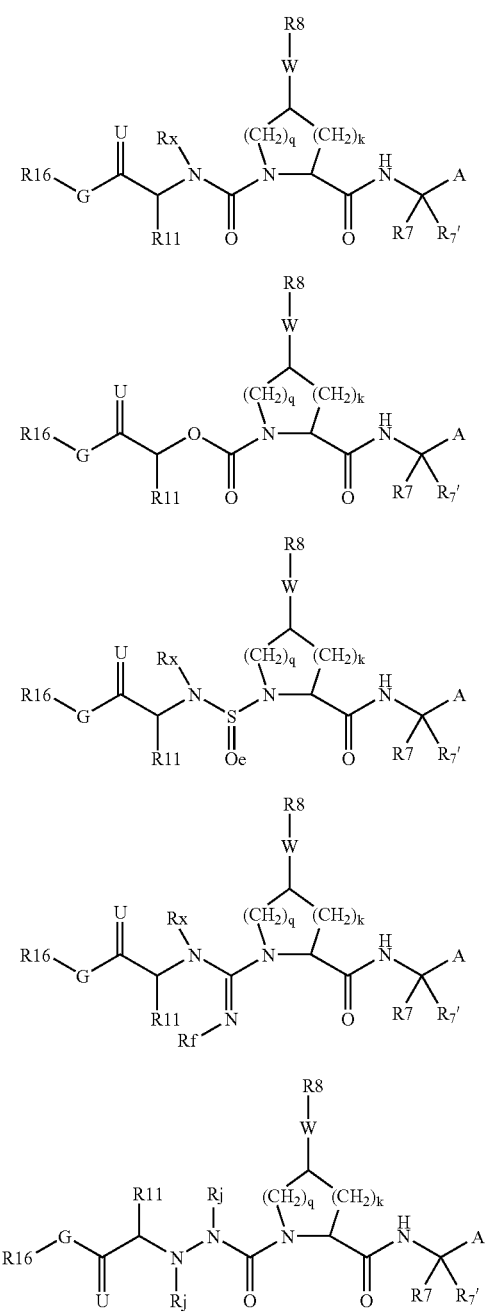

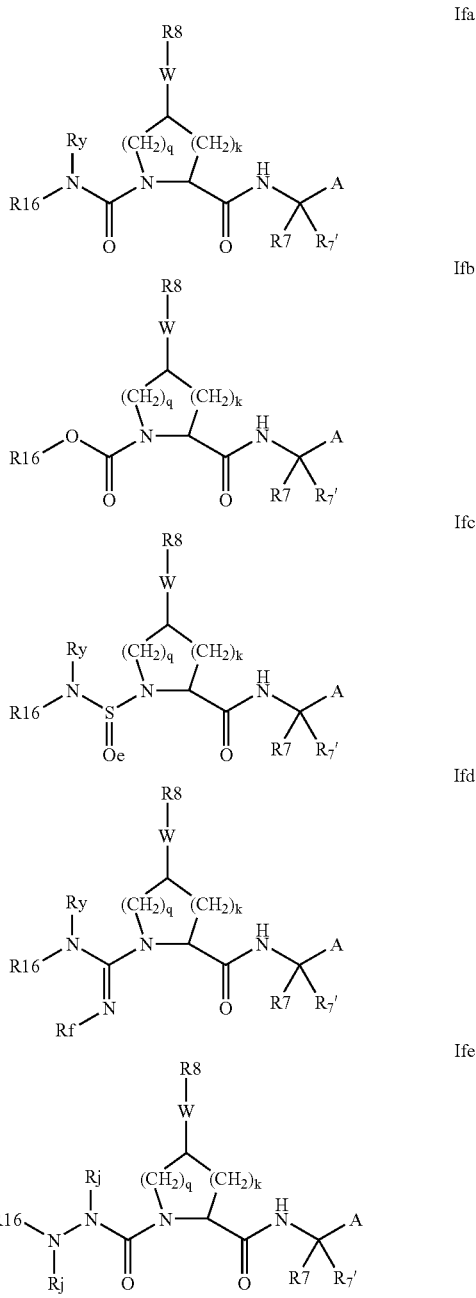

Alternative embodiments include the structures corresponding to Iea, Ieb, Iec, Ied and Iee wherein M is NRu.

Still further alternative configurations of the compounds of the invention include those where m and n are zero and thus groups $R^{16}$-G abut P2, but as mentioned above, the capping group $R^{16}$-G may interact favourably with S3 and/or S4.

$R^{16}$ in figure Ifb and elsewhere is typically H, $C_1$-$C_3$alkyl, $C_5$-$C_6$alkyl, $C_0$-$C_3$alkylheterocyclyl, $C_1$-$C_3$alkylcarbocyclyl or $C_3$-$C_7$cycloalkyl, any of which being optionally substituted, as described above. For example, $R^{16}$ ca be phenyl substituted as described above.

Alternative embodiments include the structures corresponding to Ifa, Ifb, Ifc, Ife, and Ife wherein M is NRu.

The compounds of the invention may comprise linear molecules, as depicted above. Alternatively, in embodiments wherein $R^7$ and $R^{7'}$ together define a spiro cycloalkyl group, such as spiro-cyclopropyl, the compounds of the invention may be configured as macrocycles, wherein a linking group J extends between one of Rj, Rx, Ry or $R^{11}$ of formula I.

Alternatively the macrocycle J may extend from the carbon adjacent to $R^7$ to one of Rj, Rx, Ry or $R^{11}$.

Favoured embodiments of such macrocyclic structures within formula I wherein m is 0 and n is 1 include those of Formulae Iga-Igd below:

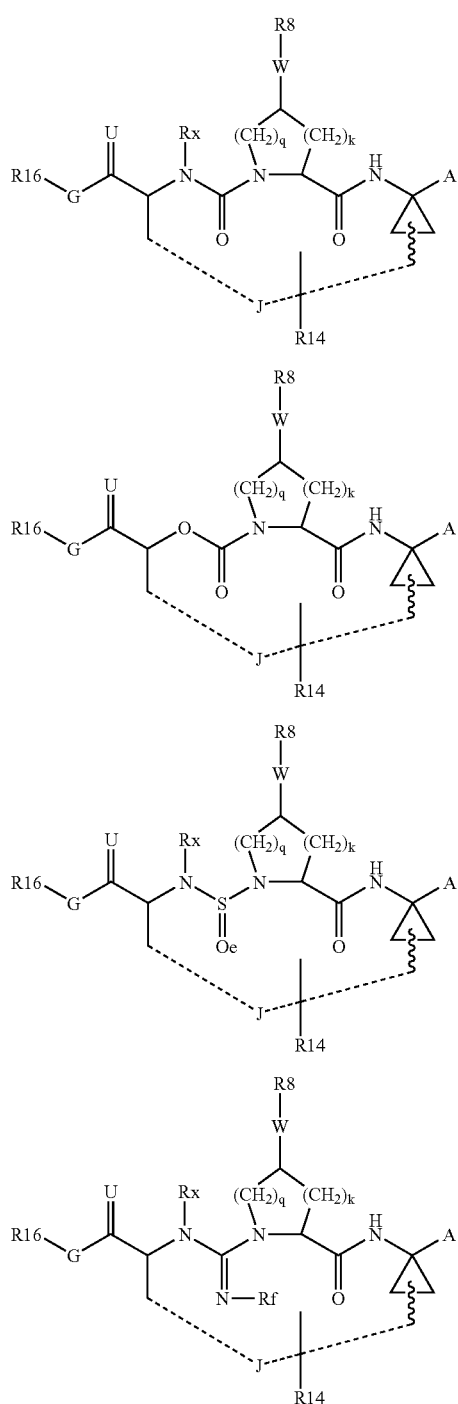

The corresponding structures wherein the J chain bonds to the carbon adjacent $R^7$ are also favoured.

Additional favoured embodiments of such macrocyclic structures within formula I wherein m is 0 and n is 1 include those of Formulae Ige-Igf below:

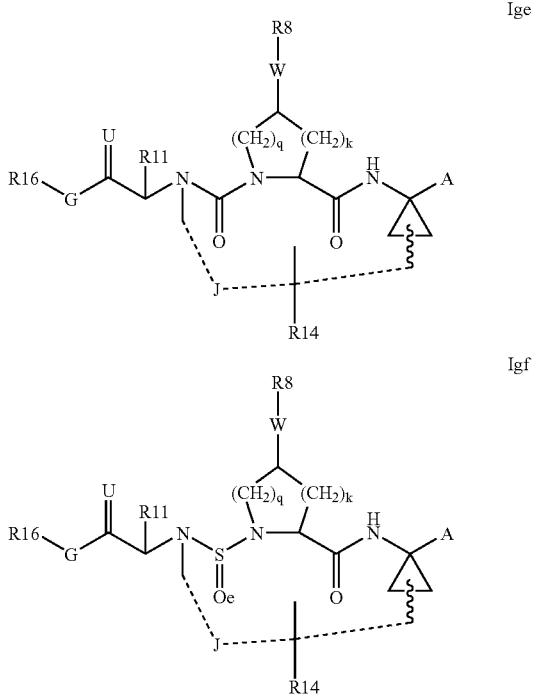

The corresponding structures wherein the J chain bonds to the carbon adjacent $R^7$ are also favoured Favoured macrocyclic structures within Formula I, comprising both a P3 and P4 function, ie wherein m and n are each 1, include those of the formulae Iha-Ihd below.

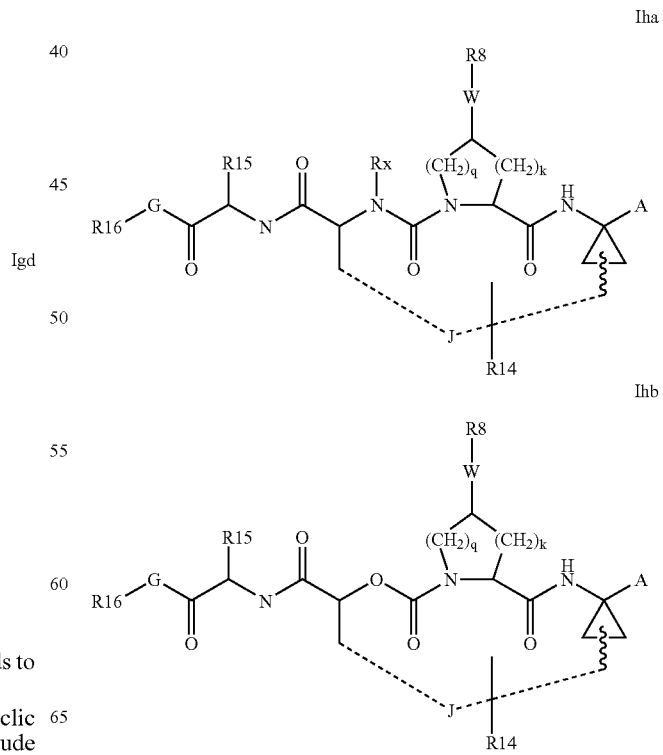

-continued

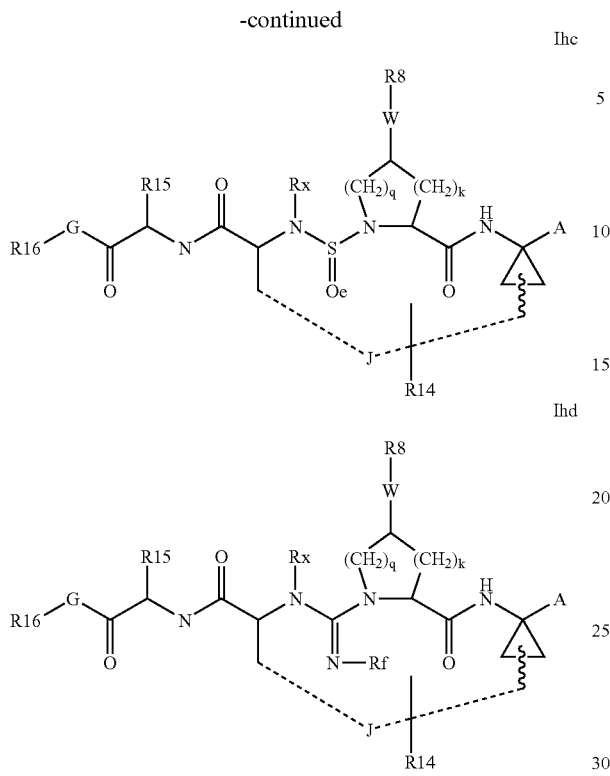

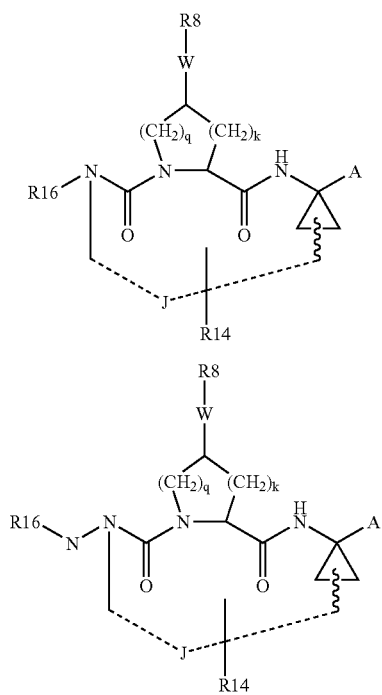

The corresponding structures wherein the J chain bonds to the carbon adjacent $R^7$ are also favoured.

Favoured macrocyclic structures within Formula I, wherein both of the P3 and P4 functions are absent, i.e. wherein m and n are each 0, include those of the formulae Ihe-Ihh below, especially 1 he and 1 hf.

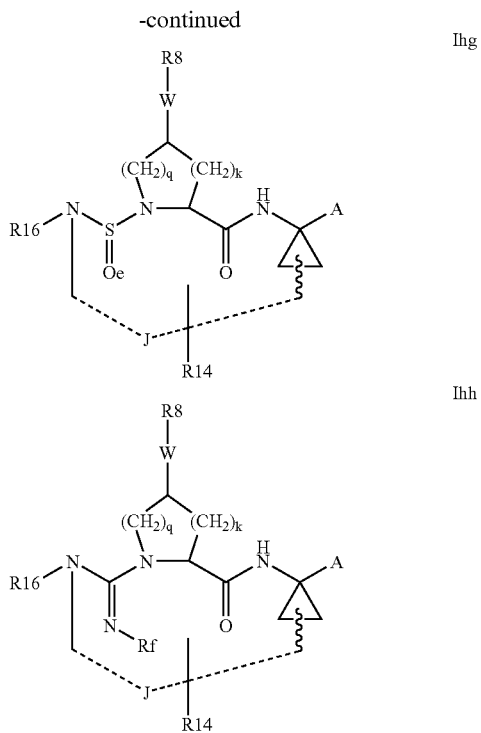

The corresponding structures wherein the J chain bonds to the carbon adjacent $R^7$ are also favoured, especially formula Ihe and 1 hf:

In general, in the optionally macrocyclic structures such as those illustrated above, linker J is a 3 to 10 chain atom, preferably 5 to 8 chain atom, such as 6 or 7 chain atom, saturated alkylene chain or a partially unsaturated alkylene chain, that is an alkylene chain bearing 1 to 3 unsaturated bonds between adjacent carbons, typically one unsaturation. The length of the chain will, of course, depend on whether J extends from Rd, Rj, Rx, Ry, $R^{11}$ or the carbon adjacent to $R^7$. Suitable chains are described in detail in WO 00/59929. Typically J will be dimensioned to provide a macrocycle of 13 to 16 ring atoms (including those atoms in the P1, P2 and if present P3 groups contributing to the ring). Conveniently J is dimensioned to provide a macrocycle of 14 or 15 ring atoms.

Conveniently, the J chain contains one or two heteroatoms selected from: O, S, NH, $NC_1$-$C_8$ alkyl or N—C(=O)$C_1$-$C_6$alkyl. More preferably, the J chain optionally contains one heteroatom selected from: NH, or N—C(=O)$C_1$-$C_6$alkyl, most preferably N(Ac). Most preferably, the chain containing a nitrogen atom is saturated. In an alternative embodiment, J contains one heteroatom selected from O or S. The chain may be substituted with $R^{14}$, such as H or methyl.

Typically, the J linker structure is saturated. Alternatively, J contains 1 to 3, preferably 1 double bond, typically spaced one carbon from the cycloalkyl $R^7$ function, if present. The double bond may be cis or trans.

Representative examples of J thus include pentylene, hexylene, heptylene, any of which are substituted with $C_1$-$C_6$alkyl, $C_1$-$C_6$haloalkyl, $C_1$-$C_6$alkoxy, hydroxyl, halo, amino, oxo, thio or $C_1$-$C_6$ thioalkyl; penten-3-yl, hexen-4-yl, hepten-5-yl, where 3, 4 or 5 refers to a double bond between carbon atoms 3 and 4, 4 and 5 etc.

Convenient $R^7$ and $R^{7'}$ groups include those wherein $R^{7'}$ is H and $R^7$ is n-ethyl, n-propyl, cyclopropylmethyl, cyclopropyl, cyclobutylmethyl, cyclobutyl, 2,2-difluoroethyl, or mercaptomethyl. Preferred embodiments include those wherein $R^7$ is n-propyl or 2,2-difluoroethyl.

Alternative favoured configurations for $R^7$ and $R^{7'}$ include those wherein $R^{7'}$ is H and $R^7$ is $C_3$-$C_7$ cycloalkyl or $C_1$-$C_3$alkyl$C_3$-$C_7$cycloalkyl.

Still further favoured configurations for $R^7$ and $R^{7'}$ include these wherein $R^{7'}$ is H and $R^7$ is J.

Alternatively, $R^7$ and $R^{7'}$ together define a spiro-cycloalkyl function, such as a spiro-cyclobutyl ring, and more preferably a spiro-cyclopropyl ring. "Spiro" in this context simply means that the cycloalkyl ring shares a single carbon atom with the peptidic backbone of the compound. The ring is substituted or unsubstituted. Preferred substituents include mono or di-substitutions with $R^{7'a}$ wherein $R^{7'a}$ is $C_1$-$C_6$ alkyl, $C_3$-$C_5$cycloalkyl, or $C_2$-$C_6$ alkenyl, any of which is optionally substituted with halo. Alternatively the substituent may be a J linker as described above. Currently preferred stereochemistries for a spiro-cyclopropyl ring are defined below.

Particularly preferred substituents include $R^{7'a}$ as ethyl, vinyl, cyclopropyl (ie a spiro-cyclopropyl substituent to the "spiro" cycloalkyl ring of $R^7/R^{7'}$), 1- or 2-bromoethyl, 1- or 2-fluoroethyl, 2-bromovinyl or 2-fluoroethyl.

In one embodiment of the invention, A is —$CR^4R^{4'}$ as illustrated in detail in PCT/EP03/10595, the contents of which are incorporated by reference.

Convenient $R^{4'}$ groups thus include $C_1$-$C_6$alkyl, such as methyl, ethyl, propyl, ethenyl and —$CHCHCH_3$. Alternative preferred $R^{4'}$ groups include aryl or heteroaryl such as optionally substituted phenyl, pyridyl, thiazolyl or benzimidazolyl or $C_1$-$C_3$alkylaryl or $C_1$-$C_3$alkylheteroaryl, where the alkyl moiety is methyl, ethyl, propyl, ethenyl and —$CH=CHCH_3$. Preferred aryl moieties include optionally substituted: phenyl, benzothiazole and benzimidazole.

Favoured $R^4$ groups include —$NH_2$, fluoro or chloro. Alternative preferred $R^4$ groups include —OH and especially =O.

An alternative embodiment for A is $C(=O)NHR^3$, where $R^3$ is optionally substituted $C_0$-$C_3$alkylaryl, $C_0$-$C_3$alkylheteroaryl, $OC_0$-$C_3$alkylaryl or $OC_0$-$C_3$alkylheterocyclyl. Appropriate substituents appear in the definitions section below.

A currently favoured configuration for A is $C(=O)OR^1$, especially where $R^1$ is $C_1$-$C_6$alkyl, such as methyl, ethyl, or tert-butyl and most preferably hydrogen.

A particularly preferred configuration for A is $C(=O)NHSO_2R^2$, especially where $R^2$ is optionally substituted $C_1$-$C_6$alkyl, preferably methyl, or optionally substituted $C_3$-$C_7$cycloalkyl, preferably cyclopropyl, or optionally substituted $C_0$-$C_6$alkylaryl, preferably optionally substituted phenyl. Appropriate substituents appear in the definitions section below.

Substituent —W—R8 on the cyclic P2 group can employ any of the proline substituents which are extensively described in WO 00/59929, WO 00/09543, WO 00/09558, WO 99/07734, WO 99/07733, WO 02/60926, WO03/35060, WO 03/53349, WO03/064416, W=03/66103, WO03/064455, WO03/064456, WO03/62265, WO03/062228, WO03/87092, WO 03/99274, WO03/99316, WO03/99274, WO04/03670, WO04/032827, WO04/037855, WO04/43339, WO04/92161, WO04/72243, 5WO04/93798. WO04/93915, WO04/94452, WO04/101505, WO04/101602, WO04/103996, WO04/13365 and the like.

Favoured W functions include W as —$OC(=O)NH$—, —$OC(=O)$—, —$NH$—, —$NR^{8'}$—, —$NHS(O)_2$— or —$NHC(=O)$—, especially —$OC(=O)NH$— or —$NH$—. Favoured $R^8$ groups for such W functions include optionally substituted $C_0$-$C_3$alkylcarbocyclyl or $C_0$-$C_3$alkyl-heterocyclyl, including those described in WO0009543, WO0009558 and WO 00/174768. For example ester substituents, —W—$R^8$, on the cyclic P2 group, include those disclosed in WO 01/74768 such as $C_1$-$C_6$alkanoyloxy, $C_0$-$C_3$alkylaryloyloxy, particularly (optionally substituted) benzoyloxy or $C_0$-$C_3$alkylheterocyclyloxy, especially

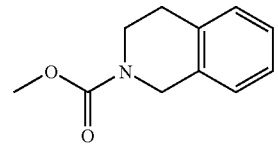

This publication also describes alternative —W—$R^8$ possibilities for example $C_1$-$C_6$alkyl, such as ethyl, isopropyl, $C_0$-$C_3$alkylcarbocyclyl such as cyclohexyl, 2,2-difluoroethyl, —$C(=O)NRc$, where Rc is $C_1$-$C_6$ alkyl, $C_0$-$C_3$alkylcyclopropyl, $C_0$-$C_3$alkylaryl or $C_0$-$C_3$alkylheterocyclyl.

Currently preferred W functions include —S— and especially —O—. Convenient values for $R^8$ in such embodiments include $C_0$-$C_3$alkylaryl, or $C_0$-$C_3$alkylheteroaryl either of which is optionally mono, di, or tri substituted with $R^9$, wherein;

$R^9$ is $C_1$-$C_6$ alkyl, $C_1$-$C_6$alkoxy, $NO_2$, OH, halo, trifluoromethyl, amino or amido (for example amido or amino optionally mono- or di-substituted with $C_1$-$C_6$alkyl), $C_0$-$C_3$alkylaryl, $C_0$-$C_3$alkylheteroaryl, or carboxyl, wherein the aryl or heteroaryl moiety is optionally substituted with $R^{10}$; wherein $R^{10}$ is $C_1$-$C_6$alkyl, $C_3$-$C_7$cycloalkyl, $C_1$-$C_6$alkoxy, amino, amido, sulfonyl$C_1$-$C_3$alkyl, $NO_2$, OH, halo, trifluoromethyl, carboxyl, or heteroaryl.

Typically, the $C_0$-$C_3$ alkyl component of $R^8$ as $C_0$-$C_3$alkylaryl, or $C_0$-$C_3$alkylheteroaryl is methyl and especially absent, ie $C_0$. The aryl or heteroaryl component is as extensively illustrated in the definition section below.

Preferred $R^9$ include $C_1$-$C_6$ alkyl, $C_1$-$C_6$alkoxy, amino, (such as di-$C_1$-$C_3$alkylamino), amido (such as —$NHC(O)C_1$-$C_6$alkyl or $C(=O)NHC_1$-$C_6$alkyl), aryl or heteroaryl, the aryl or heteroaryl being optionally substituted with $R^{10}$; wherein $R^{10}$ is $C_1$-$C_6$alkyl, $C_3$-$C_7$cycloalkyl, $C_1$-$C_6$alkoxy, amino, (such as mono- or di-$C_1$-$C_3$ alkylamino), amido (such as —$NHC(O)C_1$-$C_3$alkyl or $C(=O)NHC_1$-$C_3$alkyl), halo, trifluoromethyl, or heteroaryl.

Preferred $R^{10}$ include $C_1$-$C_6$alkyl, $C_1$-$C_6$alkoxy, amino, amido (such as —$NHC(O)C_1$-$C_6$alkyl or $C(=O)NHC_1$-$C_6$alkyl), halo, or heteroaryl.

Particularly preferred $R^{10}$ include methyl, ethyl, isopropyl, tert-butyl, methoxy, chloro, amino, amido (such as —$NHC(O)C_1$-$C_6$alkyl, for example —$NC(=O)CHC(CH_3)_3$, or $C(=O)NHC_1$-$C_3$alkyl) or $C_1$-$C_3$alkyl thiazole.

Favoured embodiments of $R^8$ include 1-naphthylmethyl, 2-naphthylmethyl, benzyl, 1-naphthyl, 2-naphthyl, or quinolinyl, any of which is unsubstituted, mono, or disubstituted with $R^9$ as defined, in particular 1-naphthylmethyl, or quinolinyl unsubstituted, mono-, or disubstituted with $R^9$ as defined.

A currently preferred $R^8$ is:

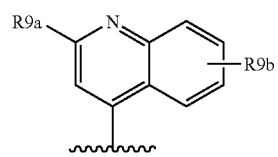

wherein $R^{9a}$ is $C_1$-$C_6$alkyl; $C_1$-$C_6$alkoxy; thio$C_1$-$C_3$alkyl; amino optionally substituted with $C_1$-$C_6$alkyl; $C_0$-$C_3$alkylaryl; or $C_0$-$C_3$alkylheteroaryl; $C_0$-$C_3$alkylheterocyclyl, said aryl, heteroaryl or heterocycle being optionally substituted with $R^{10}$ wherein
$R^{10}$ is $C_1$-$C_6$alkyl, $C_3$-$C_7$cycloalkyl, $C_1$-$C_6$alkoxy, amino, amido, heteroaryl or heterocyclyl; and $R^{9b}$ is $C_1$-$C_6$alkyl, $C_1$-$C_6$alkoxy, amino, amido, $NO_2$, OH, halo, trifluoromethyl, carboxyl.

Convenient $R^{9a}$ include aryl or heteroaryl, all optionally substituted with $R^{10}$ as defined, especially where $R^{9a}$ is selected from the group consisted of:

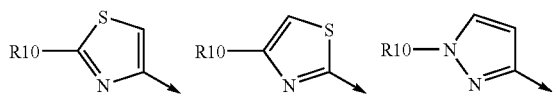

wherein $R^{10}$ is H, $C_1$-$C_6$alkyl, or $C_0$-$C_3$alkyl-$C_3$-$C_6$cycloalkyl, amino optionally mono- or di-substituted with $C_1$-$C_6$alkyl, amido (such as —NHC(O)$C_1$-$C_6$alkyl or C(=O)NH$C_1$-$C_6$alkyl), heteroaryl or heterocyclyl.

$R^{9a}$ is conveniently phenyl and thus $R^8$ is:

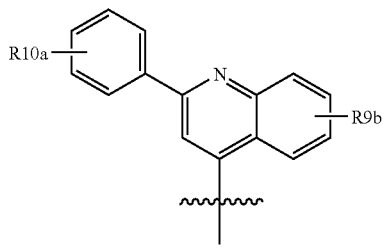

wherein $R^{10a}$ is H, $C_1$-$C_6$alkyl; $C_1$-$C_6$alkoxy; or halo; and $R^{9b}$ is $C_1$-$C_6$ alkyl, $C_1$-$C_6$-alkoxy, amino such as di($C_1$-$C_3$alkyl)amine, amido (such as —NHC(O)$C_1$-$C_3$alkyl or C(=O)NH$C_1$-$C_3$alkyl), $NO_2$, OH, halo, trifluoromethyl, carboxyl.

An alternative preferred $R^8$ is:

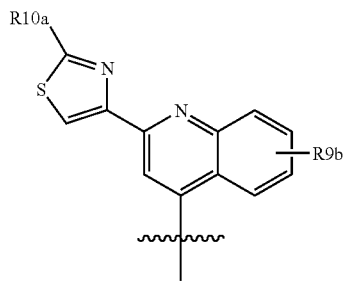

wherein $R^{10a}$ is H, $C_1$-$C_6$alkyl, or $C_0$-$C_3$alkyl-$C_3$-$C_6$cycloalkyl, amine (such as amine mono- or di-substituted with $C_1$-$C_6$alkyl), amido (such as —NHC(O)$C_1$-$C_6$alkyl or C(=O)NH$C_1$-$C_6$alkyl), heteroaryl or heterocyclyl; and $R^{9b}$ is $C_1$-$C_8$ alkyl, $C_0$-$C_6$-alkoxy, amino (such as di($C_1$-$C_3$ alkyl) amino), amido (such as —NHC(O)$C_1$-$C_3$alkyl or C(=O)NH$C_1$-$C_3$alkyl), $NO_2$, OH, halo, trifluoromethyl, or carboxyl.

In the immediately above described embodiments $R^{9b}$ is conveniently $C_1$-$C_6$-alkoxy, preferably methoxy.

A further convenient $R^8$, for example when W is an ether, has the formula

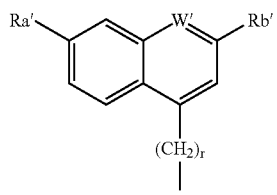

where W' is N or CH, r is 0 or 1, Ra' is H, $C_1$-$C_6$ alkyl, $C_0$-$C_3$alkylcycloalkyl, $C_1$-$C_6$alkyloxy, hydroxy or amine and Rb' is H, halo, $C_1$-$C_6$alkyl, $C_0$-$C_3$alkylcycloalkyl, $C_1$-$C_6$alkyloxy, $C_1$-$C_6$thioalkyl, cycloalkyl$C_0$-$C_3$alkyloxy, $C_1$-$C_3$alkyloxy$C_0$-$C_3$alkyl, $C_0$-$C_3$alkylaryl or $C_0$-$C_3$alkylheterocyclyl. A particularly preferred ether substituent is 7-methoxy-2-phenyl-quinolin-4-yl oxy.

When W is a bond then $R^8$ is preferably a substituted or unsubstituted heterocyclic ring system as described in WO2004/072243 or WO2004/113665.

Representative examples of $R^8$ when W is a bond include the following aromatics which may optionally be substituted: 1H-pyrrole, 1H-imidazole, 1H-pyrazole, furan, thiophene, oxazole, thiazole, isoxazole, isothiazole, pyridine, pyridazine, pyrimidine, pyrazine, phthalazine, quinoxaline, quinazoline, quinoline, cinnoline, 1H-pyrrolo[2,3]-b]pyridine, 1H-indole, 1H-benzoimidazole, 1H-indazole, 7H-purine, benzothiazole, benzooxazole, 1H-imidazo[4,5c]pyridine, 1H-imidazo[4,5b]pyridine, 1,3-dihydro-benzoimidazol-2-one, 1,3-dihydro-benzoimidazol-2-thione, 2,3-dihydro-1H-indole, 1,3-dihydro-indol-2-one, 1H-indole-2,3-dione, 1,3-dihydro-benzoimidazole-2-one, 1H, 1H-pyrrolo [2,3-c]pyridine, benzofuran, benzo[b]thiophene, benzo[d]isoxazole, benzo[d]isothiazole, 1H-quinotin-2-one, 1H-quinolin-4-one, 1H-quinazolin-4-one, 9H-carbazole, 1H-quinazolin-2-one.

Additional representative examples of $R^8$ when W is a bond, include the following non-aromatics, which may be optionally substituted: aziridine, azetidine, pyrrolidine, 4,5-dihydro-1H-pyrazole, pyrazolidine, imidazolidin-2-one, imidazolidine-2-thione, pyrrolidin-2-one, pyrrolidine-2,5-dione, piperidine-2,6-dione, piperidin-2-one, piperazine-2,6-dione, piperazin-2-one, piperazine, morpholine, thiomorpholine-1,1-dioxide, pyrazolidin-3-one, imidazolidine-2,4-dione, piperidine, tetrahydrofuran, tetrahydropyran, [1,4]dioxane, 1,2,3,6-tetrahydropyridine.

Preferred values for $R^8$ when W is a bond, include tetrazole and derivatives thereof. The tetrazole moiety is linked to the cyclic P2 scaffold and optionally substituted as shown below:

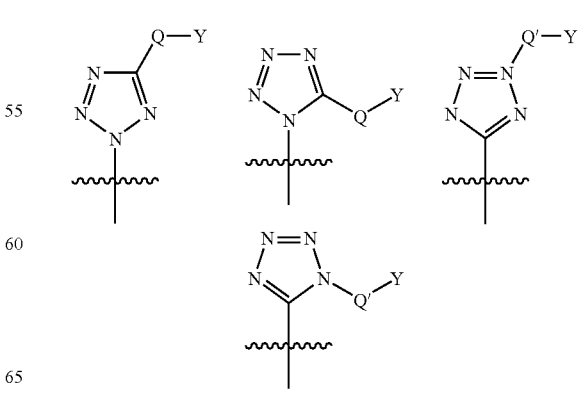

wherein Q* is selected from the group consisting of absent, —CH$_2$—, —O—, —NH—, —N(R$^{1*}$), —S—, —S(=O)$_2$— and —(C=O)—; Q* is selected from the group consisting of: absent, —CH$_2$— and —NH; Y* is selected from the group consisting of: H, C$_1$-C$_6$alkyl, C$_0$-C$_3$aryl, C$_0$-C$_3$heterocyclyl; R$^{1*}$ is selected from the group consisting of: H, C$_1$-C$_6$alkyl, carbocyclyl, C$_0$-C$_3$aryl, C$_0$-C$_3$heterocyclyl, Representative examples of substituted tetrazoles are as described in table 1 of WO2004/072243 and the structures following immediately after, or WO2004/113665.

Further preferred values for R$^8$ when W is a bond, include triazole and derivatives thereof. The triazole moiety is linked to the cyclic P2 scaffold and optionally substituted as shown below:

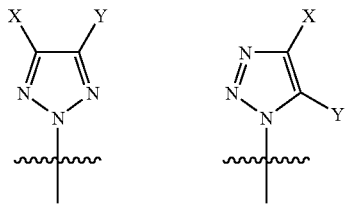

wherein X* and Y* are independently selected from the group consisting of: H, halogen, C$_1$-C$_6$alkyl, C$_0$-C$_3$carbocyclyl, —CH$_2$-amino, —CH$_2$-arylamino, —CH$_2$-diarylamino, —(C=O)-amino, —(C=O)-arylamino, —(C=O)-diarylamino, C$_0$-C$_3$aryl, C$_0$-C$_3$heterocyclyl or alternatively, X* and Y* taken together with the carbon atoms to which they are attached, form a cyclic moiety selected from the group consisting of aryl and heteroaryl.

Representative examples of substituted triazoles are as described in table 2 of WO2004/072243 and the structures following immediately after, and in the tables of WO2004/113365.

Further preferred values for R$^8$ when W is a bond, include pyridazinone and derivatives thereof. The pyridazinone moiety is linked to the cyclic P2 scaffold and optionally substituted as shown below:

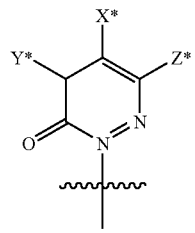

wherein X*, Y* and Z* are independently selected from the group consisting of: H, N$_3$, halogen, C$_1$-C$_6$alkyl, carbocyclyl, amino, C$_0$-C$_3$aryl, —S-aryl, —O-aryl, —NH-aryl, diarylamino, diheteroarylamino, C$_0$-C$_3$heterocyclyl, —S-heteroaryl, —O-heteroaryl, NH-heteroaryl, or alternatively, X and Y or Y and Z taken together with the carbon atoms to which they are attached, form an aryl or heteroaryl cyclic moiety.

Representative examples of substituted pyridazinones are as described in table 3 of WO2004/072243 and the structures following immediately after, and in the tables of WO2004/113365.

Preferred P3 groups, i.e. when m is 1, resemble natural or unnatural amino acids, especially aliphatic amino acids, such as L-valyl, L-leucyl, L-isoleucyl or L-t-leucyl. Further preferred P3 groups, as shown in WO 02/01898 include C$_0$-C$_3$alkylcycloalkylalanine, especially cyclohexylalanine, optionally substituted with CO$_2$Rg, where Rg is H, is C$_1$-C$_6$alkyl, C$_0$-C$_3$alkylaryl, C$_0$-C$_3$alkylheterocyclyl, C$_0$-C$_3$alkylcycloalkyl or amine; or N-acetylpiperidin or tetrahydropyran. Preferred R$^{11}$ groups thus include C$_1$-C$_6$alkyl, C$_0$-C$_3$alkylcarbocyclyl for example C$_0$-C$_3$alkylC$_3$-C$_7$cycloalkynyl, C$_0$-C$_3$alkylaryl or C$_0$-C$_3$alkylheteroaryl, any of which is optionally substituted with hydroxy, halo, amino, C$_1$-C$_5$alkoxy, C$_1$-C$_6$thioalkyl, C(=O)OR$^{14}$, carboxyl, (C$_1$-C$_6$alkoxy)carbonyl, aryl, heteroaryl or heterocyclyl, especially where the substituent is hydroxy or C(=O)OR$^{14}$.

Particularly preferred R$^{11}$ include tert-butyl, iso-butyl, cyclohexyl, phenylethyl, 2,2-dimethyl-propyl, cyclohexylmethyl, phenylmethyl, 2-pyridylmethyl, 4-hydroxy-phenylmethyl, or carboxylpropyl. The most preferred R$^{11}$ values are currently tert-butyl, isobutyl, or cyclohexyl.

An embodiment of the invention include compounds wherein P4 is absent (ie n is 0) and wherein the P3 function lacks a carbonyl, ie U is absent. Representative substructures include those of formula Ii below:

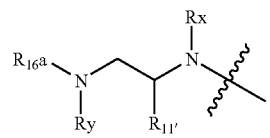

Ii wherein

Rx and Ry are as defined above, preferably H,

R$^{11'}$ is C$_1$-C$_6$ alkyl, preferably C$_3$-C$_5$ branched alkyl such as the side chains of L-valyl, L-leucyl, L-isoleucyl, L-t-leucyl; or C$_0$-C$_2$alkylC$_3$-C$_7$ cycloalkyl such as cyclohexyl or cyclohexylmethyl;

R$^{16a}$ is —Rba, —S(=O)pRba, —C(=O)Rba;

Rba is C$_1$-C$_6$ alkyl, C$_0$-C$_3$alkylheterocyclyl, C$_0$-C$_3$alkylcarbocyclyl.

Alternatively, compounds of partial structure Ii may be macrocyclised between an appropriate value of R$^7$ and one of Rx, Ry or R$^{11'}$.

Representative embodiments of P3 groups which lack a carboxy function (ie variable U is absent) include those of formula Iia-Iid below:

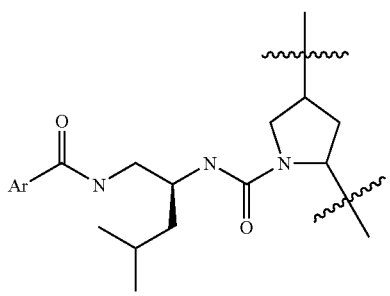

Iia

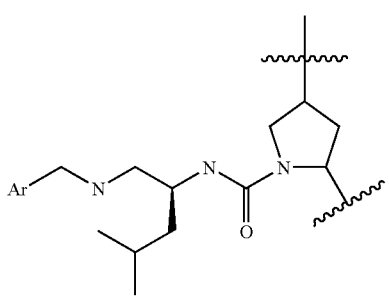

Iib

-continued

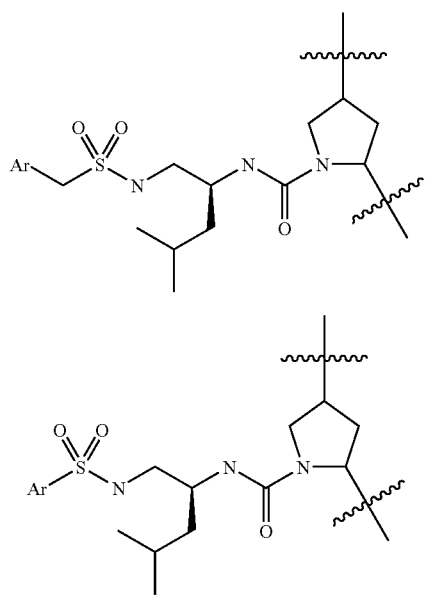

Iic

Iid where Ar is carbocyclyl or heterocyclyl, especially aryl or heteroaryl, any of which is optionally substituted with $R^9$. Although the partial structures of Formulae Iia-Iid have been illustrated in the context of a compound within Formula I, it will be apparent that such configurations of Formula Ii apply also to other values of q and k. Similarly, although the partial structures of formulae Iic and Iid show an $R^{11}$ group corresponding to leucine, it will be apparent that these configurations will be applicable to other $R^{11}$ groups, especially those resembling the side chains of natural or unnatural L-amino acids, for example t-butyl alanine/t-leucine.

$R^{15}$ in those compounds of the invention wherein n is 1, is preferably optionally substituted $C_1$-$C_6$alkyl or $C_0$-$C_3$alkylcarbocyclyl for example $C_0$-$C_3$alkyl$C_3$-$C_7$cycloalkyl, any of which may be optionally substituted. Preferred P4 groups are typically analogues of natural or unnatural amino acids, especially aliphatic amino acids such as L-valyl, L-leucyl, L-isoleucyl, L-t-leucyl or L-cyclohexylalanine and thus favoured $R^{15}$ groups include cyclohexyl, cyclohexylmethyl, tert-butyl, iso-propyl, or iso-butyl.

Preferred G values include —NRy-, especially wherein Ry is methyl or preferably H, or hydrazine.

A further preferred G value is O thereby defining an ester with the carbonyl of P4 (if present) or the carbonyl of P3 (if present) or an ether in the case of variants wherein group U is absent. Conventional pharmaceutically acceptable ethers or esters capping groups for $R^{16}$ include $C_1$-$C_6$alkyl (especially methyl or t-butyl), $C_0$-$C_3$alkylheterocyclyl (especially pyridyl, benzimidazolyl, piperidyl, morpholinyl, piperazinyl) or $C_0$-$C_3$alkylcarbocyclyl (especially phenyl, benzyl, indanyl) any of which is optionally substituted with hydroxy, halo, amino, or $C_1$-$C_6$alkoxy.

It will be apparent that for compounds of formula I, when m=n=0, then $R^{16}$G- is not a BOC or CBz protecting group, but this restriction does not apply to other permutations of m and n. The Boc or CBz protected-4-substituted proline synthetic intermediates described for example in WO 0059929 are thus outside the scope of the invention.

Favoured compounds of the invention can comprise a hydrazine functionality, for example where X is —NHNH— and m is 1; with n being zero or 1. Alternatively, especially where m is zero, G can be —NRjNRj- such as —NHNH—.

Compounds will generally not comprise a hydrazine at both G and X. Typical hydrazines within Formula I, wherein m and n are zero include compounds of the partial structures Ija-Ijb below:

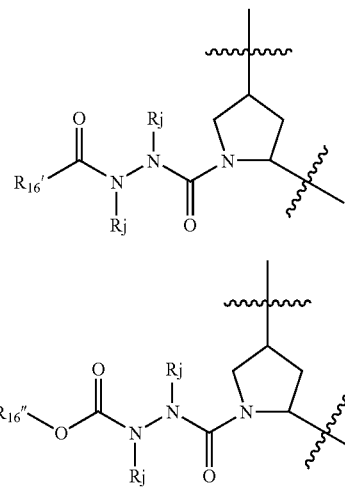

Ija

Ijb $R^{16'}$ in formulae Ija and Ijb can be regarded as an alkyl (or $C_1$-$C_3$-alkylheterocyclyl or $C_1$-$C_3$alkyl carbocyclyl) wherein the first alkyl carbon is substituted with an oxo group to define the keto function and $R^{16'}$ is the remainder of the alkyl, alkylheterocyclyl or alkylcarbocyclyl moiety. Formula Ijb depicts a variant where $R^{15}$ is a methylene group whose carbon is substituted with an oxo substituent and also —ORb, where Rb is as defined above, typically, $C_1$-$C_6$ alkyl, such as t-butyl, $C_0$-$C_3$alkylheterocyclyl such as pyridyl, or $C_0$-$C_3$alkylcarbocyclyl, such as benzyl or phenyl, any of which is optionally substituted as defined above. Compounds of partial structures Ija and Ijb can be linear molecules as shown (both Rj are H), or preferably one of the depicted Rj groups can be macrocyclised via J to an appropriate $R^7$ group.

Alternative hydrazines of Formula I where m is 1 include those of partial structures Ijc and Ijd below:

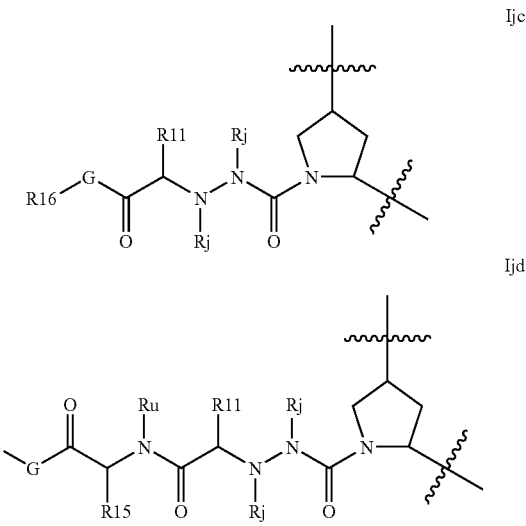

Ijc

Ijd where $R^{16}$, G, $R^{11}$, $R^{15}$, Rj and Ru are as defined for formula I above. Compounds of partial structures Ijc and Ijd can be linear molecules as shown (both Rj are H), or preferably one of the depicted Rj groups, or the $R^{11}$ group can be macrocyclised via J to an appropriate $R^7$ group Although formulae Ija-Ijd are depicted with a proline analogue as P2, it will be apparent that this aspect of the invention is equally adapted to other configurations of q and k.

Alternative hydrazine-like configuration are found when G is amino, and m and n are 0, and $R^{16}$ is an N-linked unsaturated heterocycle as defined below, for example pyridyl or pyrimidyl or a saturated heterocycle as defined below, such as piperazinyl, piperidinyl and especially morpholinyl. Examples of such embodiments include those of the formulae Ije:

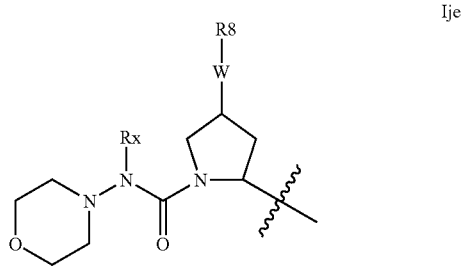

Ije

Compounds of partial structures Ije can be linear molecules as shown or preferably Rx can be macrocyclised via J to an appropriate $R^7$ group. Although these partial structures are depicted with a five membered ring for P2, it will be readily apparent that this configuration extends to other values of q and k. Similarly these configurations will be applicable to other N-linked heterocycles as $R^{16}$.

Returning now to Formulae I in general, favoured $R^{16}$ groups for the compounds of the invention include 2-indanol, indanyl, 2-hydroxy-1-phenyl-ethyl, 2-thiophenemethyl, cyclohexylmethyl, 2,3-methylenedioxybenzyl, cyclohexyl, phenyl, benzyl, 2-pyridylmethyl, cyclobutyl, iso-butyl, n-propyl, methyl, or 4-methoxyphenylethyl.

Currently preferred $R^{16}$ groups include 2-indanol, indan, 2-hydroxy-1-phenyl-ethyl, 2-thiophenemethyl, 2,3-methylenedioxybenzyl, or cyclohexylmethyl.

Unnatural amino acids include L-amino acids wherein the side chain is not one of the 20 naturally occurring amino acids. Examples of non-natural amino acids include L-beta-methylsulfonylmethylalanine, L-cyclohexylalanine, L-tertiary-leucine, L-norleucine, L-norvaline, L-ornithine, L-sarcosine, L-citruline, L-homophenylalanine, L-homoserine, L-beta-(1-napthyl)alanine, L-beta-(2-napthyl)alanine etc. Non natural amino acids also include the D-amino acids corresponding to the 20 natural amino acids and D-amino acids bearing other side chains, such as those listed above.

'$C_1$-$C_6$alkyl' (also abbreviated as $C_1$-$C_6$alk, or used in compound expressions such as $C_1$-$C_6$alkyloxy etc) as applied herein is meant to include straight and branched chain aliphatic carbon chains such as methyl, ethyl, n-propyl, isopropyl, n-butyl, isobutyl, t-butyl, pentyl, isopentyl, hexyl, heptyl and any simple isomers thereof. The alkyl group may have an unsaturated bond. Additionally, any C atom in $C_1$-$C_6$alkyl may optionally be substituted by one, two or where valency permits three halogens and/or substituted or the alkyl chain interrupted by a heteroatom S, O, NH. If the heteroatom is located at a chain terminus then it is appropriately substituted with one or 2 hydrogen atoms. $C_1$-$C_4$alkyl and $C_1$-$C_5$alkyl have the corresponding meaning to $C_1$-$C_6$alkyl adjusted as necessary for the carbon number.

'$C_1$-$C_3$alkyl' as applied herein includes methyl, ethyl, propyl, isopropyl, cyclopropyl, any of which may be optionally substituted or heteroatom interrupted as described in the paragraph above, or in the case of $C_2$ or $C_3$, bear an unsaturated bond such as $CH_2=CH$.

"$C_1$-$C_3$alkylene" as applied herein describes a divalent $C_1$-$C_3$alkyldiyl moiety, including propylene, ethylene and especially methylene. The typically longer alkylene chains for J may comprise 1 to 3 unsaturations and/or interruptions with heteroatoms as defined above.

'Amino' includes $NH_2$, $NHC_1$-$C_6$alkyl or $N(C_1$-$C_6$-alkyl)$_2$, especially $C_1$-$C_3$ alkyl variants 'Amido' includes $C(=O)NH_2$, and alkylamido, such as $C(=O)NHC_1$-$C_6$alkyl, $C(=O)N(C_1$-$C_6$alkyl)$_2$ especially $C(=O)NHC_1$-$C_3$alkyl, $C(=O)N(C_1$-$C_3$alkyl)$_2$ or —NH$(C=O)C_1$-$C_6$alkyl, for example —NHC(=O)CHC(CH$_3$)$_3$, including —NH(C=O)$C_1$-$C_3$alkyl.

'Halo' or halogen as applied herein is meant to include F, Cl, Br, I, particularly chloro and preferably fluoro.

'$C_0$-$C_3$alkylaryl' as applied herein is meant to include an aryl moiety such as a phenyl, naphthyl or phenyl fused to a $C_3$-$C_7$cycloalkyl (for example indanyl), which aryl is directly bonded (i.e. $C_0$) or through an intermediate methyl, ethyl, or propyl group as defined for $C_1$-$C_3$alkylene above. Unless otherwise indicated the aryl and/or its fused cycloalkyl moiety is optionally substituted with 1-3 substituents selected from halo, hydroxy, nitro, cyano, carboxy, $C_1$-$C_6$alkyl, $C_1$-$C_6$alkoxy, $C_1$-$C_6$alkoxy$C_1$-$C_6$alkyl, $C_1$-$C_6$alkanoyl, amino, azido, oxo, mercapto, nitro $C_0$-$C_3$alkylcarbocyclyl, $C_0$-$C_3$alkylheterocyclyl. "Aryl" has the corresponding meaning, i.e. where the $C_0$-$C_3$alkyl linkage is absent.

'$C_0$-$C_3$alkyl$C_3$-$C_7$cycloalkyl' as applied herein is meant to include a $C_3$-$C_7$cycloalkyl group such as cyclopropyl, cyclobutyl, cyclopentyl, cyclohexyl or cycloheptyl, which cycloalkyl is directly bonded (i.e. $C_0$alkyl) or through an intermediate methyl, ethyl, proyl or isopropyl group as defined for $C_1$-$C_3$alkylene above. The cycloalkyl group may contain an unsaturated bond. Unless otherwise indicated the cycloalkyl moiety is optionally substituted with 1-3 substituents selected from halo, hydroxy, nitro, cyano, carboxy, $C_1$-$C_6$alkyl, $C_1$-$C_6$alkoxy, $C_1$-$C_6$alkoxy$C_1$-$C_6$alkyl, $C_1$-$C_6$alkanoyl, amino, azido, oxo, mercapto, nitro $C_0$-$C_3$alkylcarbocyclyl, $C_0$-$C_3$alkylheterocyclyl.

'$C_0$-$C_3$alkylcarbocyclyl' as applied herein is meant to include $C_0$-$C_3$alkylaryl and $C_0$-$C_3$alkyl$C_3$-$C_7$cycloalkyl. Unless otherwise indicated the aryl or cycloalkyl group is optionally substituted with 1-3 substituents selected from halo, hydroxy, nitro, cyano, carboxy, $C_1$-$C_6$alkyl, $C_1$-$C_6$alkoxy, $C_1$-$C_6$alkoxy$C_1$-$C_6$alkyl, $C_1$-$C_6$alkanoyl, amino, azido, oxo, mercapto, nitro, $C_0$-$C_3$alkylcarbocyclyl and/or $C_0$-$C_3$alkylheterocyclyl. "Carbocyclyl" has the corresponding meaning, i.e. where the $C_0$-$C_3$alkyl linkage is absent '$C_0$-$C_3$alkylheterocycylyl' as applied herein is meant to include a monocyclic, saturated or unsaturated, heteroatom-containing ring such as piperidinyl, morpholinyl, piperazinyl, pyrazolyl, imidazolyl, oxazolyl, isoxazolyl, thiazinolyl, isothiazinolyl, thiazolyl, oxadiazolyl, 1,2,3-triazolyl, 1,2,4-triazolyl, tetrazolyl, furanyl, thienyl, pyridyl, pyrimidyl, pyridazinyl, pyrazolyl, or any of such groups fused to a phenyl ring, such as quinolinyl, benzimidazolyl, benzoxazolyl, benzisoxazolyl, benzothiazinolyl, benzisothiazinolyl, benzothiazolyl, benzoxadiazolyl, benzo-1,2,3-triazolyl, benzo-1,2,4-triazolyl, benzotetrazolyl, benzofuranyl, benzothienyl, benzopyridyl, benzopyrimidyl, benzopyridazinyl, benzopyrazolyl etc, which ring is bonded directly i.e. ($C_0$), or through an intermediate methyl, ethyl, propyl, or isopropyl group as defined for $C_1$-$C_3$alkylene above. Any such non-saturated rings having an aromatic character may be referred to as heteroaryl herein. Unless otherwise indicated the hetero ring and/or its fused phenyl moiety is optionally substituted with 1-3 substituents selected from halo, hydroxy, nitro, cyano, carboxy, $C_1$-$C_6$alkyl, $C_1$-$C_6$alkoxy, $C_1$-$C_6$alkoxy$C_1$-$C_6$alkyl, $C_1$-$C_6$alkanoyl, amino, azido, oxo, mercapto, nitro, $C_0$-$C_3$alkylcarbocyclyl, $C_0$-$C_3$alkylheterocyclyl. "Heterocyclyl" and "Heteroaryl" have the corresponding meaning, i.e. where the $C_0$-$C_3$alkyl linkage is absent.

Typically heterocycyl and carbocyclyl moieties within the scope of the above definitions are thus a monocyclic ring with 5 or especially 6 ring atoms, or a bicyclic ring structure comprising a 6 membered ring fused to a 4, 5 or 6 membered ring.

Typical such groups include $C_3$-$C_8$cycloalkyl, phenyl, benzyl, tetrahydronaphthyl, indenyl, indanyl, heterocyclyl such as from azepanyl, azocanyl, pyrrolidinyl, piperidinyl, morpholinyl, thiomorpholinyl, piperazinyl, indolinyl, pyranyl, tetrahydropyranyl, tetrahydrothiopyranyl, thiopyranyl, furanyl, tetrahydrofuranyl, thienyl, pyrrolyl, oxazolyl, isoxazolyl, thiazolyl, imidazolyl, pyridinyl, pyrimidinyl, pyrazinyl, pyridazinyl, tetrazolyl, pyrazolyl, indolyl, benzofuranyl, benzothienyl, benzimidazolyl, benzthiazolyl, benzoxazolyl, benzisoxazolyl, quinolinyl, tetrahydroquinolinyl, isoquinolinyl, tetrahydroisoquinolinyl, quinazolinyl, tetrahydroquinazolinyl and quinoxalinyl, any of which may be optionally substituted as defined herein.

The saturated heterocycle moiety thus includes radicals such as pyrrolinyl, pyrrolidinyl, pyrazolinyl, pyrazolidinyl, piperidinyl, morpholinyl, thiomorpholinyl, pyranyl, thiopyranyl, piperazinyl, indolinyl, azetidinyl, tetrahydropyranyl, tetrahydrothiopyranyl, tetrahydrofuranyl, hexahydropyrimidinyl, hexahydropyridazinyl, 1,4,5,6-tetrahydropyrimidinylamine, dihydro-oxazolyl, 1,2-thiazinanyl-1,1-dioxide, 1,2, 6-thiadiazinanyl-1,1-dioxide, isothiazolidinyl-1,1-dioxide and imidazolidinyl-2,4-dione, whereas the unsaturated heterocycle include radicals with an aromatic character such as furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl. In each case the heterocycle may be condensed with a phenyl ring to form a bicyclic ring system.

Synthesis

Synthesis of the compounds of the present invention can be performed by different chemical strategies in solution or solid phase or a combination of both. The suitably protected individual building blocks can first be prepared and subsequently coupled together i.e. P2+P1→P2–P1. Alternatively, precursors of the building blocks can be coupled together and modified at a later stage of the synthesis of the inhibitor sequence. Further building blocks, precursors of building blocks or prefabricated bigger fragments of the desired structure, can then be coupled to the growing chain, e.g. $R^{16}$-G-P3+E-P2-P1→$R^{16}$-G-P3-P2-P1 or $R^{16}$-G-P4-P3+E-P2-P1→$R^{16}$-G-P4-P3-E-P2-P1.

Coupling between two amino acids, an amino acid and a peptide, or two peptide fragments can be carried out using standard coupling procedures such as the azide method, mixed carbonic-carboxylic acid anhydride (isobutyl chloroformate) method, carbodiimide (dicyclohexylcarbodiimide, diisopropylcarbodiimide, or water-soluble carbodiimide) method, active ester (pnitrophenyl ester, N-hydroxysuccinic imido ester) method, Woodward reagent K-method, carbonyldiimidazole method, phosphorus reagents or oxidation-reduction methods. Some of these methods (especially the carbodiimide method) can be enhanced by adding 1-hydroxybenzotriazole or 4-DMAP. These coupling reactions can be performed in either solution (liquid phase) or solid phase.

More explicitly, the coupling step involves the dehydrative coupling of a free carboxyl of one reactant with the free amino group of the other reactant in the present of a coupling agent to form a linking amide bond. Descriptions of such coupling agents are found in general textbooks on peptide chemistry, for example, M. Bodanszky, "Peptide Chemistry", 2nd rev ed., Springer-Verlag, Berlin, Germany, (1993) hereafter simply referred to as Bodanszky, the contents of which are hereby incorporated by reference. Examples of suitable coupling agents are N,N'-dicyclohexylcarbodiimide, 1-hydroxybenzotriazole in the presence of N,N'-dicyclohexylcarbodiimide or N-ethyl-N'-[(3dimethylamino) propyl]carbodiimide. A practical and useful coupling agent is the commercially available (benzotriazol-1-yloxy)tris-(dimethylamino)phosphonium hexafluorophosphate, either by itself or in the present of 1-hydroxybenzotriazole or 4-DMAP. Another practical and useful coupling agent is commercially available 2-(1H-benzotriazol-1-yl)-N,N, N',N'-tetramethyluronium tetrafluoroborate. Still another practical and useful coupling agent is commercially available 0-(7-azabenzotrizol-1-yl)-N,N,N',N'-tetramethyluronium hexafluorophosphate.

The coupling reaction is conducted in an inert solvent, e.g. dichloromethane, acetonitrile or dimethylformamide. An excess of a tertiary amine, e.g. diisopropylethylamine, N-methylmorpholine, N-methylpyrrolidine or 4-DMAP is added to maintain the reaction mixture at a pH of about 8. The reaction temperature usually ranges between 0° C. and 50° C. and the reaction time usually ranges between 15 min and 24 h.

The functional groups of the constituent amino acids generally must be protected during the coupling reactions to avoid formation of undesired bonds. The protecting groups that can be used are listed in Greene, "Protective Groups in Organic Chemistry", John Wiley & Sons, New York (1981) and "The Peptides: Analysis, Synthesis, Biology", Vol. 3, Academic Press, New York (1981), hereafter referred to simply as Greene, the disclosures of which are hereby incorporated by reference.

The α-carboxyl group of the C-terminal residue is usually protected as an ester that can be cleaved to give the carboxylic acid. Protecting groups that can be used include 1) alkyl esters such as methyl, trimethylsilyl and t.butyl, 2) aralkyl esters such as benzyl and substituted benzyl, or 3) esters that can be cleaved by mild base or mild reductive means such as trichloroethyl and phenacyl esters.

The α-amino group of each amino acid to be coupled is typically protected. Any protecting group known in the art can be used. Examples of such groups include: 1) acyl groups such as formyl, trifluoroacetyl, phthalyl, and p-toluenesulfonyl; 2) aromatic carbamate groups such as benzyloxycarbonyl (Cbz or Z) and substituted benzyloxycarbonyls, and 9-fluorenylmethyloxycarbonyl (Fmoc); 3) aliphatic carbamate groups such as tertbutyloxycarbonyl (Boc), ethoxycarbonyl, diisopropylmethoxycarbonyl, and allyloxycarbonyl; 4) cyclic alkyl carbamate groups such as cyclopentyloxycarbonyl and adamantyloxycarbonyl; 5) alkyl groups such as triphenylmethyl and benzyl; 6) trialkylsilyl such as trimethylsilyl; and 7) thiol containing groups such asphenylthiocarbonyl and dithiasuccinoyl. The preferred α-amino protecting group is either Boc or Fmoc. Many amino acid derivatives suitably protected for peptide synthesis are commercially available.

The α-amino protecting group is cleaved prior to the next coupling step. When the Boc group is used, the methods of choice are trifluoroacetic acid, neat or in dichloromethane, or HCl in dioxane or in ethyl acetate. The resulting ammonium salt is then neutralized either prior to the coupling or in situ with basic solutions such as aqueous buffers, or tertiary amines in dichloromethane or acetonitrile or dimethylformamide. When the Fmoc group is used, the reagents of choice are piperidine or substituted piperidine in dimethylformamide, but any secondary amine can be used. The deprotection is carried out at a temperature between 0° C. and room temperature usually 20-22° C.

Any of the natural or non-natural amino acids having side chain functionalities will typically be protected during the preparation of the peptide using any of the above described groups. Those skilled in the art will appreciate that the selection and use of appropriate protecting groups for these side chain functionalities depend upon the amino acid and presence of other protecting groups in the peptide. In the selection of such protecting groups it is desirable that the group is not removed during the deprotection and coupling of the α-amino group.

For example, when Boc is used as the α-amino protecting group, the following side chain protecting groups are suitable: p-toluenesulfonyl (tosyl) moieties can be used to protect the amino side chain of amino acids such as Lys and Arg; acetamidomethyl, benzyl (Bn), or tert-butylsulfonyl moieties can be used to protect the sulfide containing side chain of cysteine; benzyl (Bn) ethers can be used to protect the hydroxy containing side chains of serine, threonine or hydroxyproline; and benzyl esters can be used to protect the carboxy containing side chains of aspartic acid and glutamic acid.

When Fmoc is chosen for the α-amine protection, usually tert. butyl based protecting groups are acceptable. For instance, Boc can be used for lysine and arginine, tert.butyl ether for serine, threonine and hydroxyproline, and tert-butyl ester for aspartic acid and glutamic acid. Triphenylmethyl (Trityl) moiety can be used to protect the sulfide containing side chain of cysteine.

Once the inhibitor sequence is completed any protecting groups are removed in whatever manner is dictated by the choice of protecting groups. These procedures are well known to those skilled in the art.

In compounds of Formula I, the P2 unit comprises a nitrogen-containing ring residue which is substituted with the W and R8 moieties.

Synthesis of Heterocyclic P2 Building Blocks

The $R^8$ group can be coupled to the P2 scaffold at any convenient stage of the synthesis of compounds according to the present invention. One approach is to first couple the $R^8$ group to the P2 scaffold and subsequently add the other desired building blocks, i.e. P1 and optionally P3 and P4. Another approach is to couple the P1 and, if present P3 and P4 using an unsubstituted P2 scaffold and add the $R^8$ group afterwards.

Compounds wherein W is O and $R^8$ is alkyl, $C_0$-$C_3$alkylcarbocycylyl, $C_0$-$C_3$alkylheterocycylyl can be prepared according to the procedure described by E. M. Smith et al. (J. Med. Chem. (1988), 31, 875-885), as depicted in Scheme 1, which illustrates the technique in a moiety wherein q and k are 1.

Scheme 1

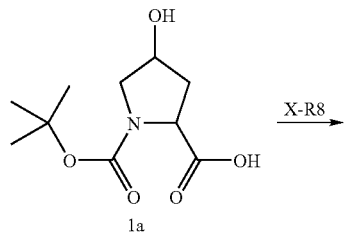

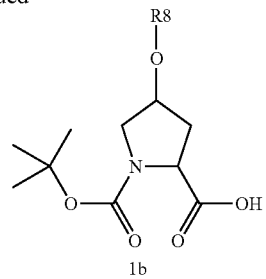

1b

Commercially available Boc-4-(R)-hydroxyproline, or any suitable hydroxy substituted proline analogue, such as an hydroxypiperidoic acid is treated with a base such as sodium hydride or potassium t.butoxide in a solvent like dimethylformamide and the resulting alkoxide is reacted with an alkylating agent, $R^8$—X, wherein X is a suitable leaving group such as a halide, mesylate, triflate or tosylate or the like, providing the desired substituted proline derivative.

Alternatively, when W is O or S and $R^8$ is carbocyclyl such as phenyl or heterocyclylyl such as heteroaryl, the P2 building blocks can also be prepared via a Mitsunobu reaction (Mitsunobu, 1981, Synthesis, January, 1-28; Rano et al., Tetrahedron Lett., 1995, 36, 22, 3779-3792; Krchnak et al., Tetrahedron Lett., 1995, 36, 5, 6193-6196; Richter et al., Tetrahedron Lett., 1994, 35, 27, 4705-4706) as shown in Scheme 2, which illustrates the technique in a moiety wherein q and k are 1.

Scheme 2

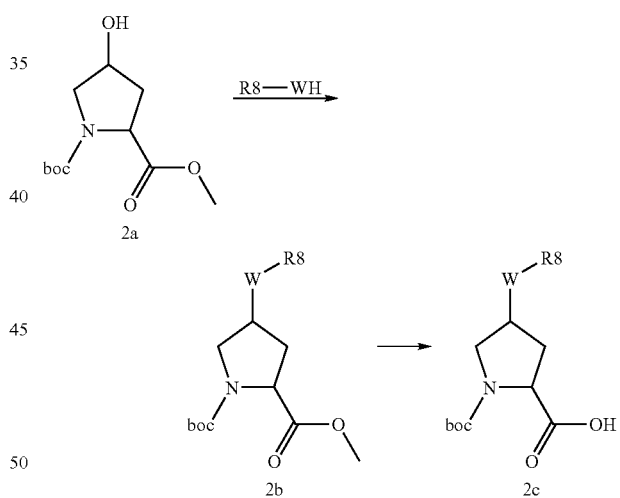

Treatment of the appropriate hydroxy substituted proline analogue, such as a hydroxypiperidoic acid, here shown as commercially available Boc-4-hydroxyproline methyl ester, with the desired alcohol or thiol ($R^8$—WH) in the presence of triphenylphosphine and an activating agent like diethyl azodicarboxylate (DEAD), diisopropyl azodicarboxylate (DIAD) or the like, provides the ester compound (2b). Hydrolysation of the ester to the acid by standard procedures provides the P2 building block (2c).

Alcohol (2a) can alternatively be treated with phosgene thus providing the corresponding chloroformate which upon reaction with an amine, $R^8NH_2$, in the presence of a base like sodium hydrogen carbonate or triethylamine, provides carbamates i.e. W is —OC(=O)NH—, whereas reaction of alcohol (2a) with an acylating agent, R8—CO—X, like an acid anhydride or acid halide for instance the acid chloride, to provide esters, i.e. W is —OC(=O)—.

Various alcohols $R^8$—OH, and alkylating agents $R^8$—X are described in WO 00/09543 and WO00/59929. An example of the synthesis wherein $R^8$ is a substituted quinoline derivative is shown in Scheme 3.

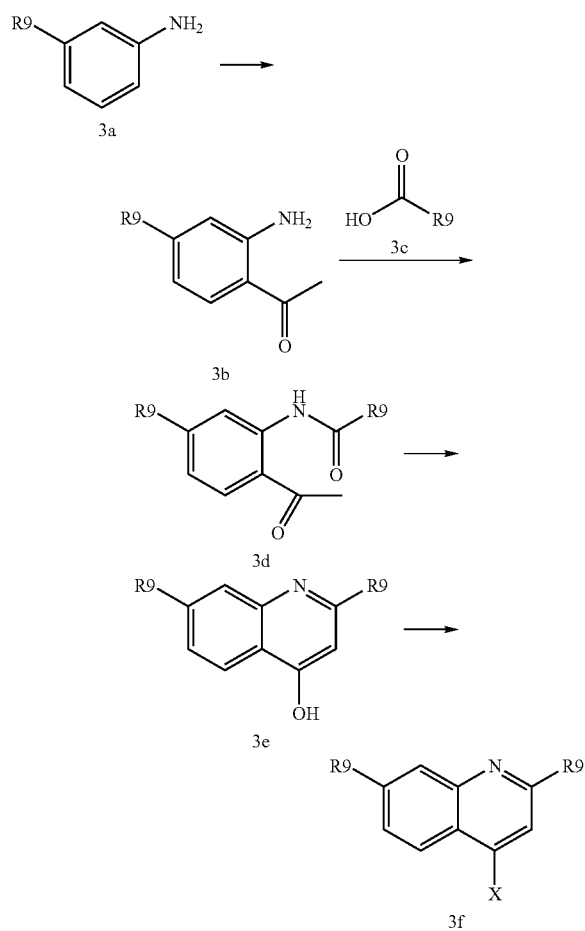

Friedel-Craft acylation of a suitable substituted aniline (3a), available either commercially or in the literature, using an acylating agent like acetyl chloride or the like in the presence of boron trichloride and aluminium trichloride in a solvent like dichloromethane provides (3b). Coupling of (3b) to a heterocyclic carboxylic acid (3c) under basic conditions, such as in pyridine, in the presence of an activating agent for the carboxylate group, for instance $POCl_3$, followed by ring closure and dehydration under basic conditions like potassium tert-butoxide in tert-butanol provides quinoline derivative (3e). Quinoline derivative (3e) can be coupled in a Mitsunobu reaction to an alcohol as described above, or the hydroxy group can be displaced by a suitable leaving group such as a halide like chloride, bromide or iodide, by treatment of quinoline (3e) with an appropriate halogenating agent for example phosphoryl chloride or the like.

A variety of carboxylic acids with the general structure (3c) can be used in Scheme 3. These acids are available either commercially or in the literature. An example of the preparation of 2-(substituted)-amino-carboxy-aminothiazole derivatives, following the procedure by Berdikhina et al. Chem. Heterocycl. Compd. (Engl. Transl.) (1991), 427-433, is shown below.

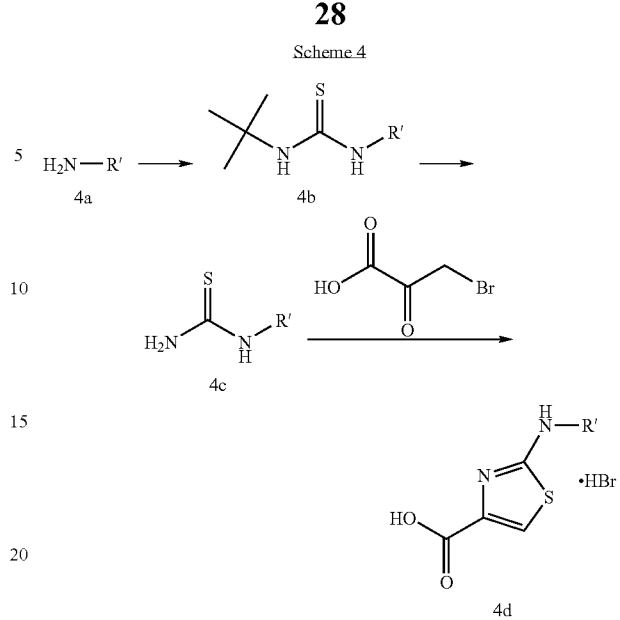

Thiourea (4c) with different alkyl substituents R' can be formed by reaction of the appropriate amine (4a) with tert-butylisothiocyanate in the presence of a base like diisopropylethylamine in a solvent like dichloromethane followed by removal of the tert-butyl group under acidic conditions. Subsequent condensation of thiourea derivative (4c) with 3-bromopyruvic acid provides the acid (4d).

P2 building blocks wherein the $R^8$ substituent is attached via an amine, amide, urea or sulphonamide, can be prepared from aminoproline analogues achieved either from a suitable commercially available aminoproline, etc derivative or by transforming the hydroxy group of the corresponding hydroxy derivative into an azide group for example by transforming the hydroxy group into a suitable leaving group such as a mesylate or halogen like chloride, followed by substitution of the leaving group with azide or by the use of an azide transfer agent like diphenylphosphoryl azide (DPPA). Reduction of the azide by catalytic hydrogenation or any other suitable reduction method provides the amine. The amino derivative can be reacted in a displacement reaction with an alkylating agent of the general formula $R^8$—X wherein $R^8$ and X are as described for scheme 1, to form P2 building blocks for use in the preparation of compounds of general formula I, wherein W is —NH—. Reaction of the aminoproline analogue with an acid of the general formula $R^8$—COOH under standard amide coupling conditions provides compounds wherein the $R^8$ substituent is linked via an amide bond, whereas reaction of the aminoproline analogue with an appropriate derivative of sulphonic acid, $R^8$—$S(O)_2$—X where X is a leaving group for example chloride, in the presence of a base, provides sulphonamides. Compounds wherein the linkage between the cyclic scaffold and the R8 substituent is constituted of a urea group can for example be achieved by treatment of amino proline analogue with phosgene to afford the corresponding chlorocarbamate followed by reaction with the desired amine. Alternatively, the amino proline analogue can be reacted with the carbamoyl chloride or isocyanate of the desired R8 substituent for the formation of the urea linkage. It will be apparent that corresponding reactions will be available for P2 groups with other ring sizes and substitution pattern.

4-Substituted heterocyclyl derivatives such as 4-substituted proline for use as P2 building blocks where W is —$CH_2$— can be prepared as shown in Scheme 5, which illustrates the technique on a moiety where q and k is 1, according to the procedures described by J. Ezquerra et al., Tetrahedron, 1993, 38, 8665-8678 and C. Pedregal et al. Tetrahedron Lett., 1994, 35, 2053-2056.

Scheme 5

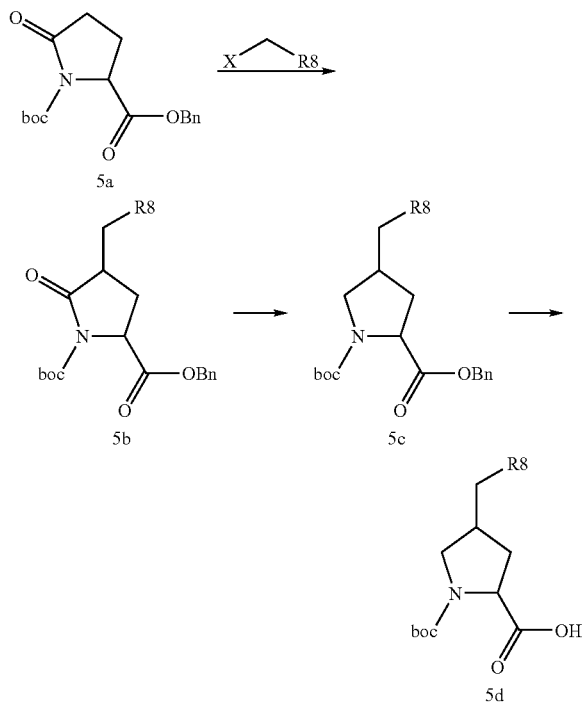

Treatment of suitably acid protected pyrrolidone or piperidinone such as commercially available Boc-pyroglutamic acid (5a) with a strong base such as lithium diisopropylamide in a solvent like tetrahydrofuran followed by addition of an alkylating agent $R^8$—$CH_2$—X where X is a suitable leaving group such as a halide like chloride or bromide, followed by reduction of the amide and deprotection of the ester gives the desired compound (5d).

Compounds of the present invention wherein a heterocyclic $R^8$ group is attached directly to the cyclic P2 scaffold, i.e. W is a bond in general formula I, can be prepared for example by using a replacement reaction wherein a suitable leaving group on the P2 scaffold is replaced by the desired $R^8$ group such as a heterocyclic group.

Alternatively the R8 group can be introduced by way of a Mitsunobu reaction wherein the hydroxy group of the P2 scaffold is reacted with a nitrogen atom in the heterocyclic $R^8$ group.

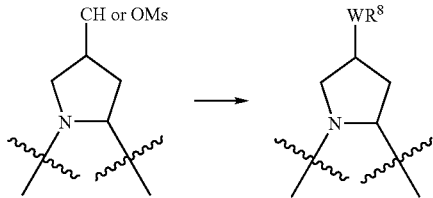

Compounds wherein a tetrazole derivative is attached through a carbon atom of the heterocyclic ring are conveniently prepared by building up the tetrazole moiety directly on the P2 precursor. This can be achieved for instance by transforming the hydroxy group of the P2 precursor into a cyano group followed by reaction with an azide reagent like sodium azide. Triazole derivatives can also be built up directly on the P2 precursor for example by transforming the hydroxy group of the P2 precursor into an azide group followed by a 3+2 cycloaddition reaction of the afforded azide and a suitable alkyne derivative.

Structurally diverse tetrazoles for use in the above described substitution or Mitsunobu reactions can be prepared by reacting commercially available nitrile compounds with sodium azide. Triazole derivatives can be prepared by reaction of an alkyne compound and trimethylsilyl azide. Useful alkyne compounds are available either commercially or they can be prepared for instance according to the Sonogashira reaction i.e. reaction of a primary alkyne, an aryl halide and triethylamine in the presence of $PdCl_2(PPh)_3$ and CuI as described for example in A. Elangovan, Y.-H. Wang, T.-I. Ho, Org. Lett., 2003, 5, 1841-1844. The heterocyclic substituent can also be modified when attached to the P2 building block either before or after coupling of the P2 building block to the other building blocks.

These methods and further alternatives for the preparation of compounds wherein W is a bond and R8 is an optionally substituted heterocycle are extensively described in WO2004/072243.

Compounds with alternative ring size and/or position of the W—$R^8$ substituent of the proline derivatives in scheme 1, 2 and 5 may also be used in the preparation of compounds according to the present invention. For example, alkylation of commercially available 3-hydroxyproline provides compounds of the general formula (I) wherein k is 0 and q is 2. Correspondingly, alkylation of 5-hydroxyproline, prepared for example as described by Hallberg et al., J. Med. Chem. (1999), 4524-4537, provides compounds of the general formula (I) wherein k is 2 and q is 0.

Various methods for the preparation of hydroxylated 2-piperidine carboxylic acids are described in the literature se for instance Celestini et al., Org. Lett., (2002), 1367-1370, Hoarau et al., Tetrahedron: Asymmetry, (1996), 2585-2594, Zhu et al., Tetrahedron Lett., 41, (2000), 7033-7036. For example, the corresponding pyridine carboxylic acids can be reduced to provide hydroxylated 2-piperidine carboxylic acids. Enzymatical methods can also be used for the preparation of hydroxylated proline analogues. For example, a 3-hydroxy substituent can be introduced on commercially available 4, 5, and 6 membered heterocyclic acids by the use of proline 3-hydroxylase as described by Ozaki et al., Tet. Letters, 40, (1999), 5227-5230.

Synthesis and Introduction of P1 Building Blocks.

The amino acids used in the preparation of P1 fragments are available either commercially or in the literature, see for example WO 00/09543 and WO00/59929 from Boehringer-Ingelheim or US2004/0048802 from BMS.

Scheme 6 shows an example of the preparation of a sulphonamide derivative to be used as a P1 fragment, and the subsequent coupling to a Boc protected P2 building block.

Scheme 6

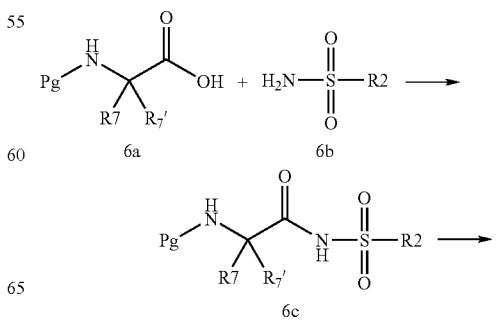

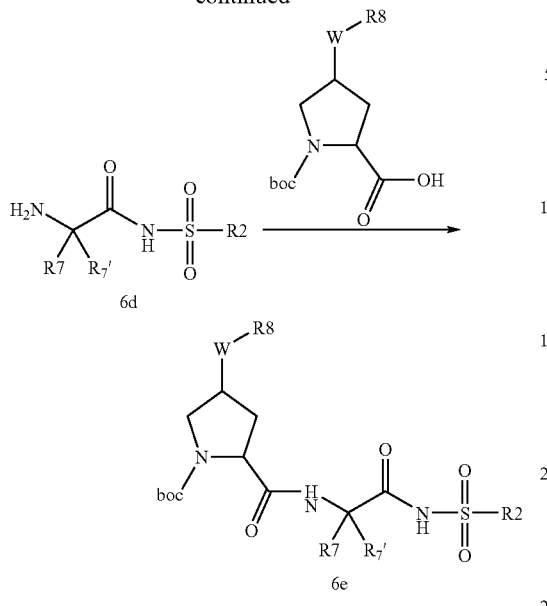

32

M. D. Bailey et al. in J. Med. Chem., 47, (2004), 3788-3799, and an example is shown in scheme 6A.

Scheme 6A

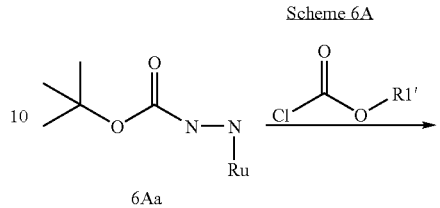

6Aa

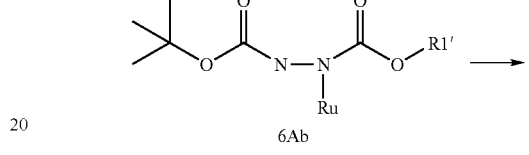

6Ab

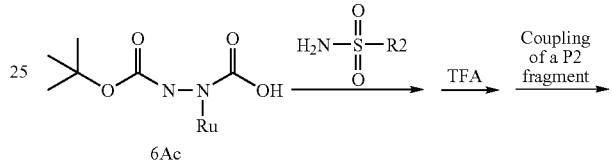

6Ac

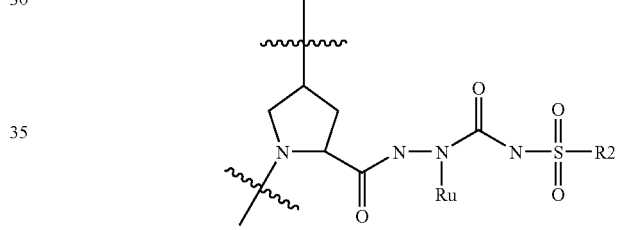

6Ad

R1' is as defined for R1 but is not H

The sulphonamide group can be Introduced on a suitably protected amino acid (6a) by treatment of the amino acid with a coupling agent, for example N,N'-carbonyldiimidazole (CDI) or the like, in a solvent like THF followed by reaction with the desired sulphonamide (6b) in the presence of a strong base such as 1,8-diazabicyclo[5.4.0]undec-7-ene (DBU). Alternatively the amino acid can be treated with the desired sulphonamide (6b) in the presence of a base like diisopropyl ethylamine followed by treatment with a coupling agent like PyBOP® to effect the introduction of the sulphonamide group. Removal of the amino protecting group by standard methods and subsequent coupling to a P2 building block, prepared as described above, using standard methods for amide bond formation, like with a coupling agent as O-(7-azabenzotriazol-1-yl)-N,N,N',N'-tetramethyluronium hexafluorophosphate (HATU) in the presence of a base such as diisopropylamine in a solvent like dimethylformamide, gives Boc protected P2-P1 compound (6e). Alternatively, the sulphonamide group can be introduced at a later stage of the synthesis, for example as the last step. In this case an amino acid with the reversed protection pattern, i.e. having an unprotected amino function and a protected acid function, is coupled to the acid function of the P2 building block using standard peptide coupling conditions for example as described above. Removal of the acid protection group, using the appropriate conditions for the protection group used, followed by coupling of the sulphonamide as described above, yields compound 6e P1 building blocks for the preparation of compounds according to general formula I wherein A is an ester or an amide can be prepared by reacting amino acid (6a) with the appropriate amine or alcohol respectively under standard conditions for amide or ester formation. Compounds according to general formula I wherein A is $CR^4R^{4'}$ can be prepared by coupling of the appropriate P1 building block to the P2 building block as described in Oscarsson et al Bioorg Med Chem 2003 11(13) 2955-2963 and PCT/EP03/10595 filed 23 Sep. 2003, the contents of which are incorporated by reference.

Compounds comprising an azapeptide P1 residue, i.e. Q is NRu in general formula I can be prepared by using a suitable P1 aza-amino acyl moiety in the coupling to the P2 fragment. The preparation of aza-amino acyl moieties is described by Incorporation of the appropriate N-linked side chain, Ru, on commercially available tert-butylhydrazine can be performed for example by a reductive amination reaction with the appropriate aldehyde or ketone as described in scheme 19 below which produces the N-alkylated carbazate (6Aa). Condensation of 6Aa with a desired chloroformate in the presence of a base like triethylamine or diisopropylethylamine in a solvent like THF provides 6Ab. The R1' moiety can then optionally be removed using the appropriate conditions depending on the specific R1', such as catalytic hydrogenation for R1' being benzyl, which gives the corresponding acids. Subsequent reaction of the afforded acid with a desired sulphonamide derivative as described in scheme 6 yields sulphonamide capped building blocks. Alternatively, reaction of carbazate 6Aa with an isocyanate, R3-N=C=O, provides building blocks for the preparation of compounds according to general formula I, wherein M is NRu and A is $CONHR^3$.

The P2 and P3 moieties may be linked together prior to or after the introduction of the P1 building block.

Synthesis of Capped P3 and P3-P4 Building Blocks

The building blocks $R^{16}$-G-P3 and $R^{16}$-G-P4-P3 can be prepared as generally depicted in scheme 7.

33

Scheme 7

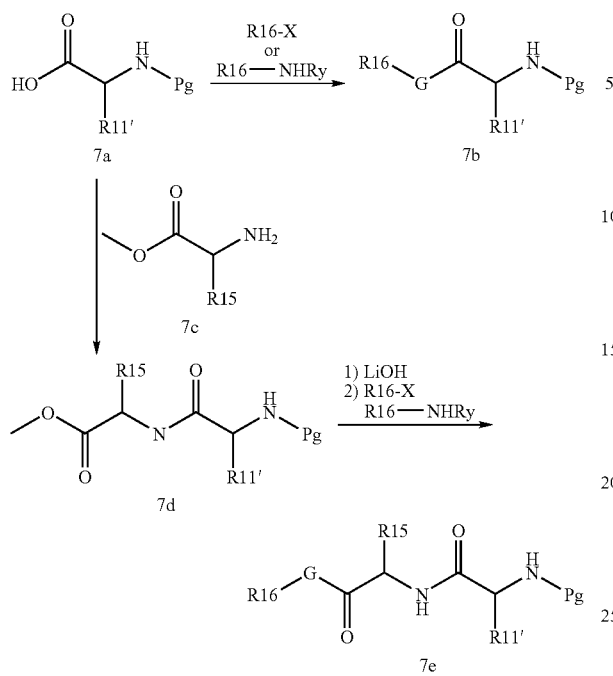

R11' has the same definition as R11 but is not part of a macrocycle

A suitable N-protected amino acid (7a) can be coupled with an amino capping group ($R^{16}$—NHRy) using standard peptide coupling conditions like with coupling agents such as HATU, DCC, HOBt or the like in the presence of a base such as DIEA or DMAP in a solvent like dichloromethane, chloroform or dimethylformamide or a mixture thereof and ester formation conditions like providing amides i.e. G is NHRy (7b). Alternatively, reaction of amino acid (7a) with a compound of general formula $R^{16}$—X where $R^{16}$ is as defined above and X is a leaving group such as a halide, in the presence of a base like cesium carbonate or silver (I) oxide provides esters, i.e. G is O (7b). On the other hand, amino acid (7a) can be coupled to a second, suitably O-protected, amino acid (7d) using standard peptide coupling conditions as described above, providing (7e). Displacement of the ester group with a suitable capping group (7b) provides fragment (7f) useful for the preparation of compounds according to the present invention wherein m and n are 1.

When G is N-Ry, the capped P3 or P2 building block can also be prepared on solid support as exemplified in Scheme 8.

34

Scheme 8

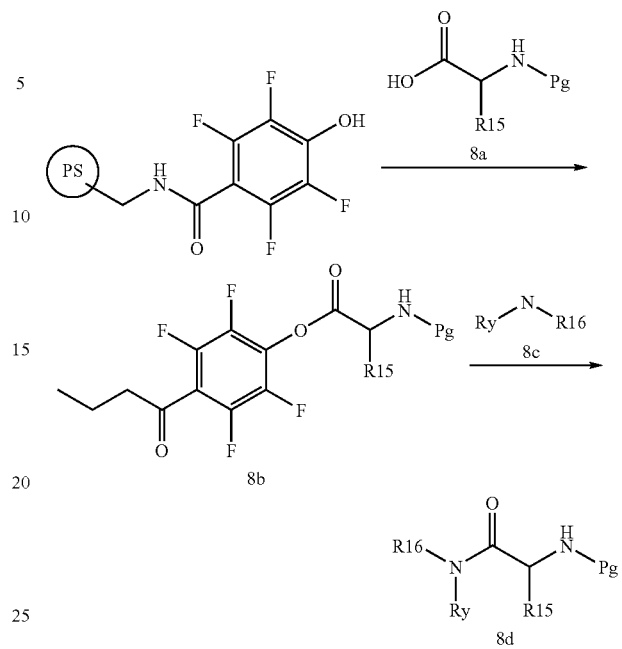

An appropriate N-protected, for example Boc protected, amino acid (8a) can be Immobilized on a solid support, here exemplified by Agronaut resin PS-TFP, by reacting the amino acid with the desired solid support in the presence of coupling reagent like N,N'-diisopropylcarbodiimide and a base like DMAP in a solvent like dichloromethane and dimethylformamide. The immobilized amino acid can then be cleaved from the support with a suitable capping group (8c) thus giving fragments useful for the preparation of compounds according to the present invention wherein m or n is 1. Optionally the amino protecting group can be removed followed by coupling of an appropriate amino acid using standard methods thus providing fragments useful for the preparation of compounds according to the present invention wherein m and n are 1.

Coupling of a Capping Group or a Capped Building Block to the P2-P1 Construct

The $R^{16}$-G, $R^{16}$-G-P3 or $R^{16}$-G-P4-P3 building block linked via a urea functionality to the P2-P1 construct, can be introduced as depicted in scheme 9, which illustrates the technique with a variant in which the P2 scaffold is a 5-membered ring.

Scheme 9

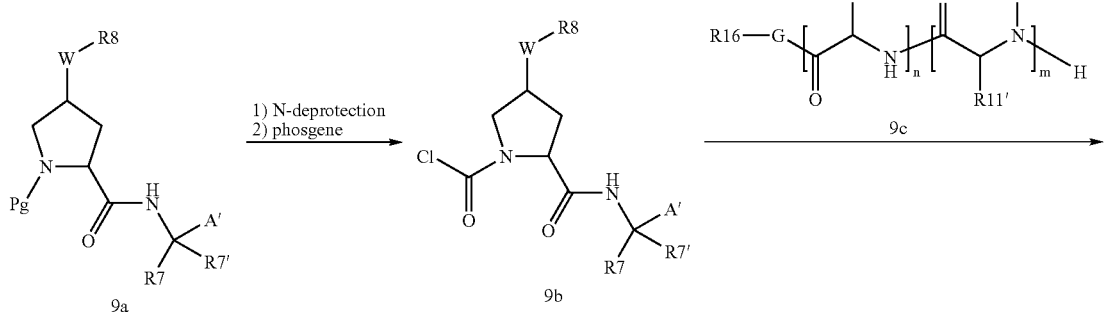

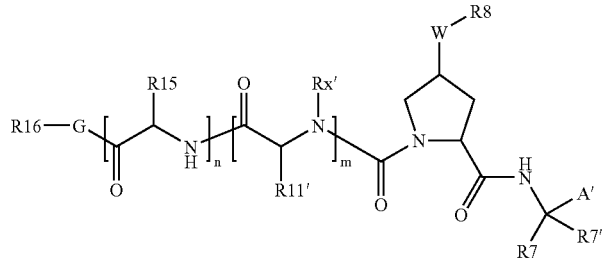

9d

Rx' and R11' have the same definitions as Rx and R11 respectively but are not part of a macrocycle. A' is a protected carboxylic acid, substituted amide or sulphone amide or CR4R4'.

A chlorocarbamate group can be formed onto the ring amine of the P2-P1 construct (9a) by removal of the amine protection group by standard procedures, like acidic treatment with for example TFA in dichloromethane or the like when the Boc group is used, followed by reaction of the free amine with phosgene in toluene in the presence of a base such as sodium hydrogen carbonate or triethylamine in a solvent like tetrahydrofuran. Subsequent reaction of the formed electrophilic center with the amino group of a $R^{16}$—$NH_2$, $R^{16}$—NH—$NH_2$, $R^{16}$-G-P3 or $R^{16}$-G-P4-P3 building block (9c) in a solvent like dichloromethane in the presence of a base like sodium hydrogen carbonate provides (9d). Compounds of general formula (I) wherein E is C=S, S(=O) or S(=O)$_2$ can be prepared according to the above procedure but with the use of reagents like thiocarbonyl diimidazole, thionyl chloride or sulphuryl chloride respectively instead of phosgene.

Compounds containing a hydrazine group linked to the P2 unit, i.e. X is —NRjNRj- in general formula I, or when the P3 and P4 units are absent and G is NRjNRj, can be prepared as depicted below. Scheme 10 shows the introduction of a hydrazine derivative to a 5-membered P2 building block.

Scheme 10

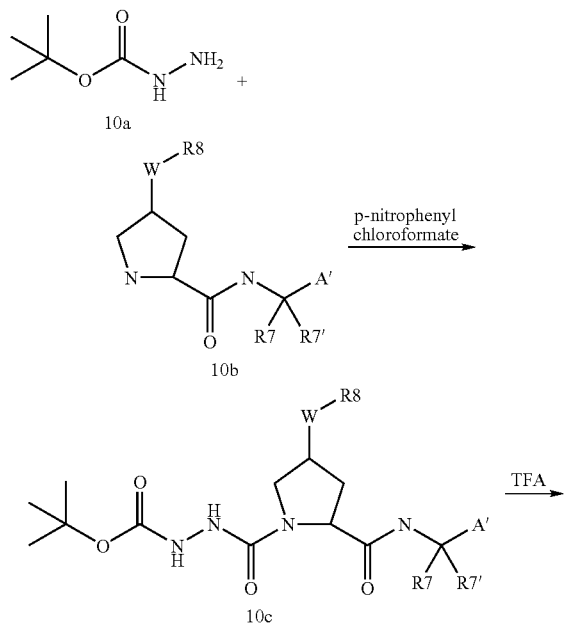

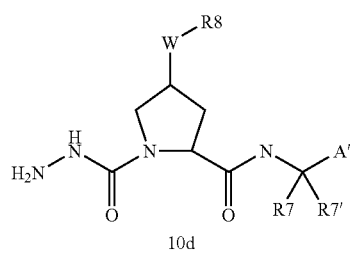

10d

A' is a protected carboxylic acid, substituted amide or sulphone amide or CR4R4'

Reaction of tert-butyl carbazate (10a), optionally alkyl substituted on one or both nitrgogens, with p-nitrophenyl chloroformate in the presence of a base like sodium hydrogen carbonat followed by addition of the P2 building block (10b) provides the urea derivative 10c. The phosgene method described in scheme 9 can alternatively be used to effect the linkage of the fragments 10a and 10b. Optional removal of the boc group by standard procedures like acidic treatment with for example TFA in a suitable solvent such as dichloromethane, provides the hydrazine containing derivative (10d). Alternatively, any appropriate hydrazine derivative, such as morpholin-1-ylamine, piperidin-1-ylamine or the like can be linked to 9Ab instead of the tert-butyl carbazate derivative.

The achieved compound can then be further extended by coupling of a P3 or P4-P3 building block to the primary amine of compound 9Ad for example as shown in scheme 11.

Scheme 11

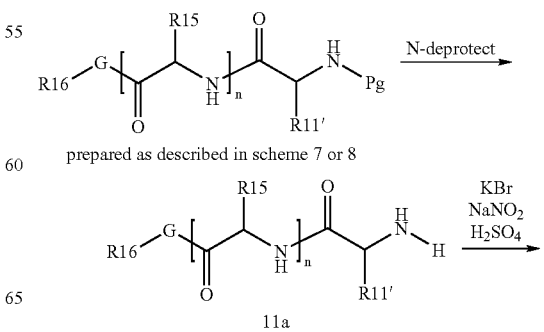

prepared as described in scheme 7 or 8

-continued

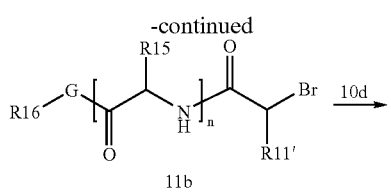
11b

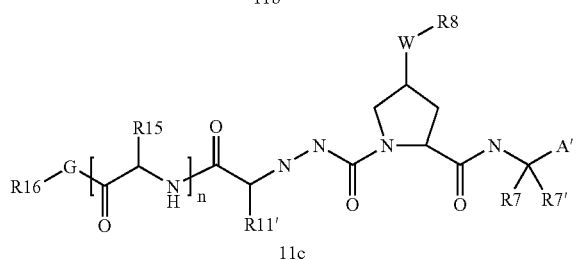
11c

R11' has the same definition as R11 but is not part of a macrocycle.
A' is a protected carboxylic acid, substituted amide or sulphone amide or CR4R4'

Treatment of the α-amino compound (11a) with sodium nitrite, potassium bromide and sulphuric acid (Yang et al. J. Org. Chem. (2001), 66, 7303-7312) provides the corresponding α-bromo compound (11b) which upon reaction with the above described derivative (10d) provides the hydrazine containing derivative (11c).

The linkage between the P2 and P3 building blocks may also be constituted of a carbamate group and a general route to such compounds is depicted in Scheme 12, which illustrates the technique with a variant in which P2 is a proline derivative.

Scheme 12

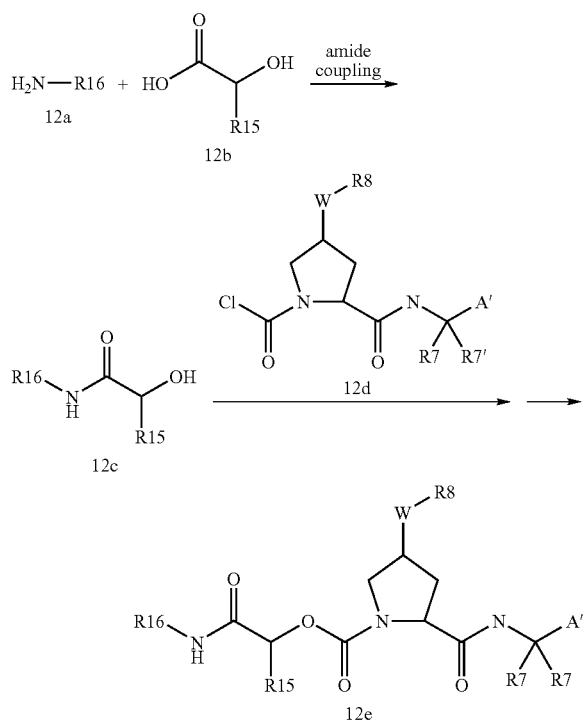

A' is a protected carboxylic acid, substituted amide or sulphone amide or CR4R4'.

The desired, optionally protected, amino capping group (12a) is coupled to a hydroxy acid (10b) using standard pep-tide coupling techniques followed by reaction with the electrophilic P2 building block (12d) described above and optional deprotection provides construct (12e).

Compounds lacking a carboxy group in the P3 unit can be prepared as illustrated in Scheme 13, which illustrates the technique as applied to a compound of Formula I Scheme 13

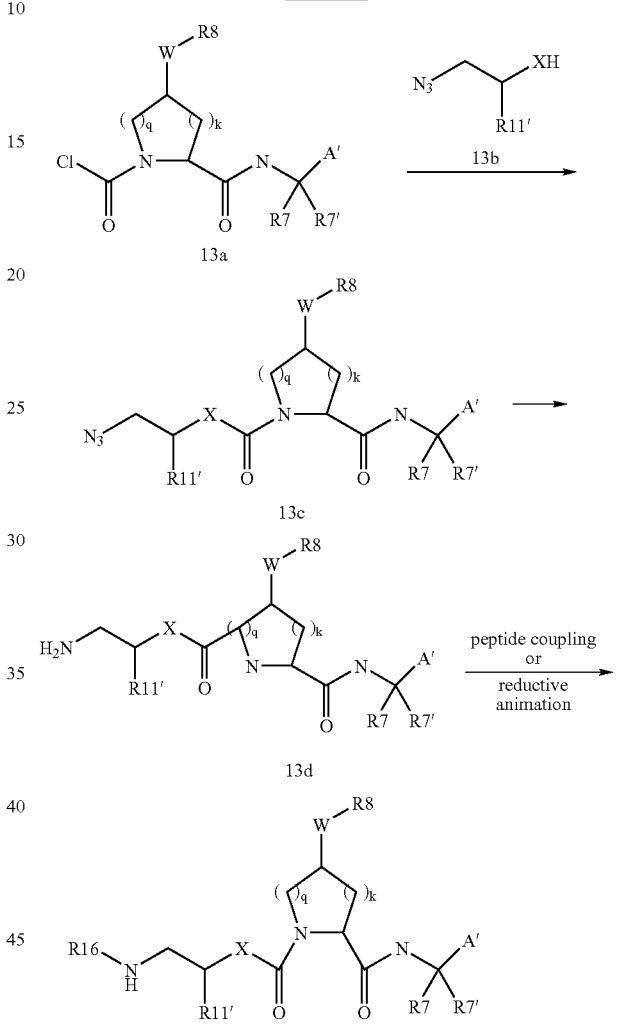

R11' has the same definition as R11 but is not part of a macrocycle.
A' is a protected carboxylic acide, a substituted amide or sulphone amide or CR4R4'.

Chlorocarbamoyl derivative (13a) can be reacted in a displacement reaction with an azide derivative (13b), prepared by methods known from the literature, in the presence of a base like sodium hydrogen carbonate to give (13c). X is as described for general formula (I). Reduction of the azide function for example by polymer bound triphenyl phosphine in a solvent like methanol or any other suitable reduction method provides intermediate (13d) which subsequently can be reacted with an acid under peptide coupling conditions or with an amine in a reductive amination reaction providing amides and secondary amines respectively.

Scheme 14 shows an alternative route towards compounds lacking a carboxy group in the P3 unit.

39

Scheme 14

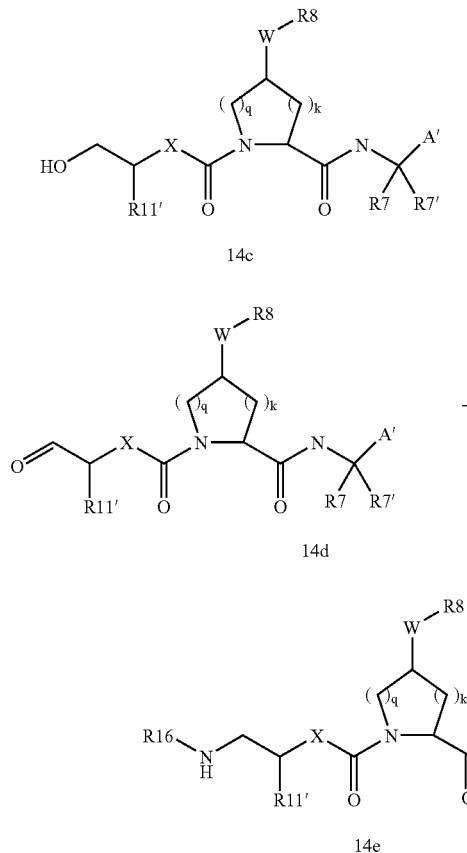

R11' has the same definition as R11 but is not part of a macrocycle.
A' is a protected carboxylic acide, a substituted amide or sulphone amide or CR4R4'.

Instead of using the azide derivative (13b) in scheme 13 the corresponding, optionally protected, hydroxy derivative (14b) can be used in the displacement reaction with the chlorocarbamate (14a) and thus introducing a primary alcohol. The alcohol (14c) can then, after optional deprotection, be oxidized with a suitable oxidizing agent like for example Dess-Martin periodinane to form the corresponding aldehyde. Reaction of the aldehyde with a desired amine in a reductive amination reaction using a reagent like for example polystyrene bound cyanoborohydride in a solvent like THF provides amine derivatives (14e).

40

Alternatively alcohol (14c) can be reacted with a suitable acylating or alkylating agent under the appropriate conditions to provide ester and ether compounds respectively, i.e. G is O in general formula (I).

Subsequent reaction of the formed alcohol with a suitable acylating or alkylating agent using the appropriate conditions provides the ester and ether compounds respectively, i.e. G is O in general formula (I).

Alternatively the linkage between the P2 and P3 building blocks can be via a guanidine group and a general route to such compounds is depicted in Scheme 15.

Scheme 15

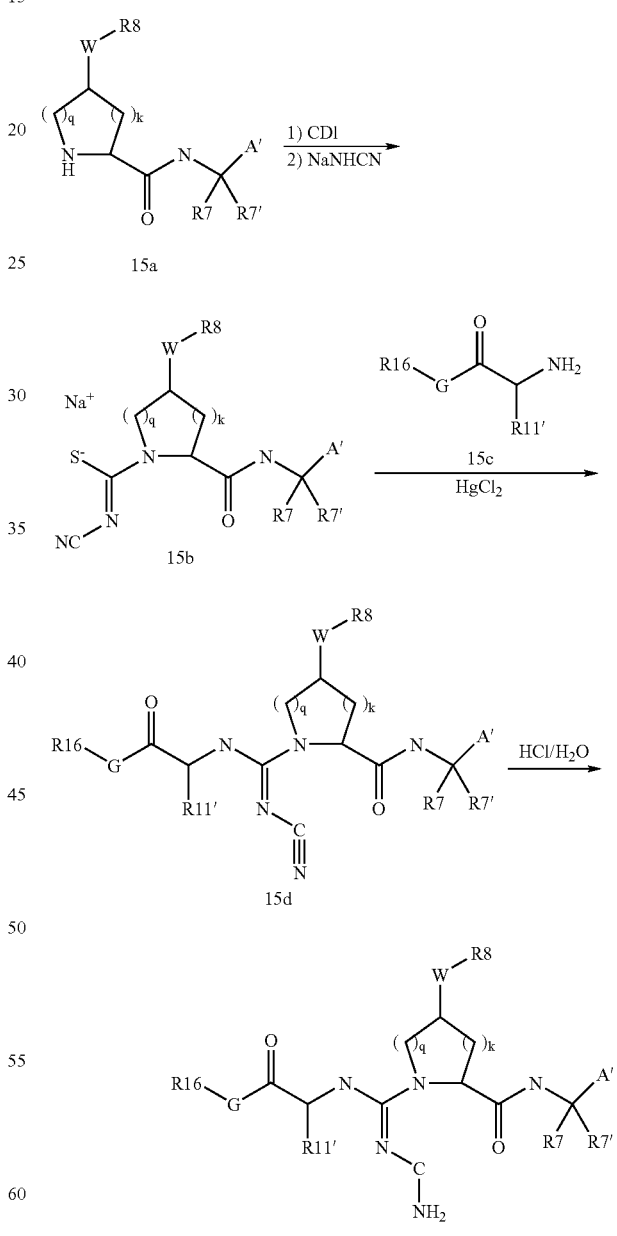

R11' has the same definition as R11 but is not part of a macrocycle.
A' is a protected carboxylic acide, a substituted amide or sulphone amide or CR4R4'.

Treatment of the P2-building block (15a) with thiocarbonyl diimidazole or the like in a solvent like dimethylformamide followed by condensation with sodium cyanamide in a solvent like ethanol affords the thiolate intermediate (15b). Reaction of intermediate (15b) with the desired building block, here shown as a capped P3 building block (12c) provides the cyanoguanidine derivative (15d). Other building blocks, $R^{16}$-G or $R^{16}$-G-P4-P3, can alternatively be coupled to the intermediate (15b). Hydrolysis of the cyano group by treatment of (15d) with diluted hydrochloric acid gives the guanylurea derivative (15e.

When R7, R7' and A' contains functional groups, these are suitably protected by methods recognized by persons skilled in the art, see for example Bodanzky or Greene cited above.

Formation of Macrocyclic Compounds

Compounds according to the present invention wherein an alkylene chain extending from the $R^7/R^{7'}$ cycloalkyl to Rx or $R^{11}$ thus forming a macrocycle, can be prepared as described below. Suitable P1, P2 and P3 building blocks, or precursors thereof, are coupled together using the strategies described above, followed by a ring-closing reaction (macrocyclization). The substituent W—$R^8$ of the P2 building block can be incorporated via a Mitsunobu reaction as described above, before or after formation of the macrocycle or the desired building blocks can be coupled together using the appropriately substituted P2-building block. For macrocyclic structures extending from the $R^7/R^{7'}$ cycloalkyl to $R^{11}$, P3 amino acids containing the appropriate side chain can be prepared as described in WO00/59929.

A typical route to macrocyclic compounds is shown in Scheme 18 which illustrates the technique applied to a compound having a 5-membered P2 scaffold and a spiro-cyclopropyl group in the P1 moiety, where the macrocycle extends from the P3 side chain.

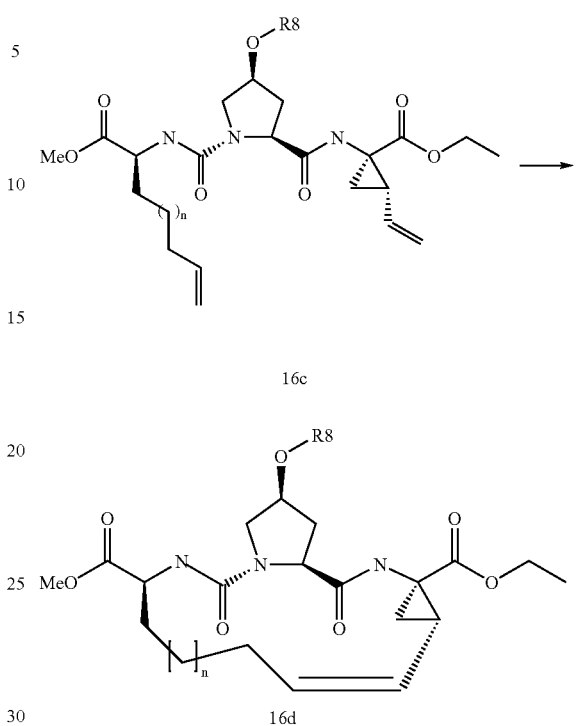

n = 1, 2, 3, 4, 5, 6, 7

Coupling of proline derivative (16a) with the appropriate, acid protected, amino acid (16b) using e.g. the phosgene conditions described above provides (16c). Formation of the macrocycle can then be carried out via an olefin metathesis reaction using a Ru-based catalyst such as the one reported by Miller, S. J., Blackwell, H. E.; Grubbs, R. H. J. Am. Chem. Soc. 118, (1996), 9606-9614, Kingsbury, J. S., Harrity, J. P. A., Bonitatebus, P. J., Hoveyda, A. H., J. Am. Chem. Soc. 121, (1999), 791-799 and Huang et al., J. Am. Chem. Soc. 121, (1999), 2674-2678. It will also be recognized that catalysts containing other transition metals such as Mo can be used for this reaction. Optionally the double bond is reduced and/or the ethyl ester is hydrolysed by standard hydrogenation and/or hydrolysation methods respectively well known in the art. Alternatively the methyl ester can be selectively hydrolysed followed by coupling of a $R^{16}$-G-P4 building block by standard peptide coupling conditions. The macrocyclisation step described in Scheme 16 can also be applied to the corresponding carbocyclic analogues described above. When the linker contains a nitrogen atom the ring closure can be carried out by reductive amination as described in WO00/59929.

Macrocyclic compounds without the cyclopropyl moiety in the P1 part, i.e. the macrocyclic ring extends directly from the peptidic backbone at the carbon adjacent $R^7$, can be prepared using the methods described herein. An example wherein a proline derivative is used as the cyclic P2 scaffold is shown in scheme 17.

Scheme 17

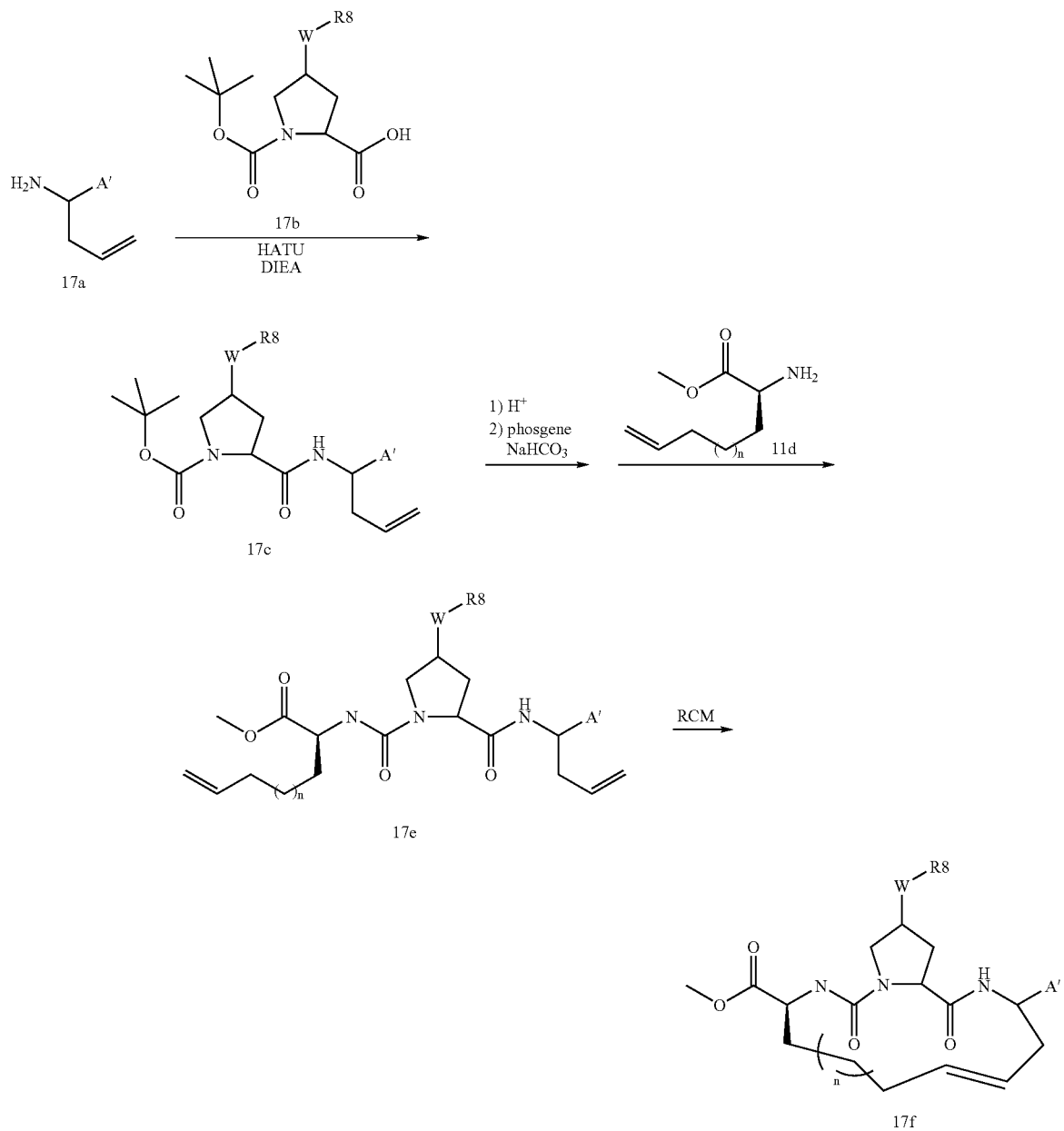

A' is a protected carboxylic acid, substituted amide or sulfon amide.
n is 1, 2, 3, 4 or 5

Coupling of a suitable allylglycine derivative (17a), to the acid function of the P2 building block (17b) using standard peptide coupling conditions yields the amide derivative (17c). Removal of the Boc protection group by acidic treatment followed by formation of a chlorocarbamate by treatment with phosgene in the presence of sodium hydrogencarbonate and subsequent reaction with the olefin substituted amino acid (17d) provides the urea compound (17e). A ring closing metathesis reaction is then effected by using for example Hoveyda-Grubbs catalyst which gives the macrocyclic compound (17f).

Even though scheme 17 shows the synthetic sequence using a P2 building block wherein the R8 substituent is attached to the scaffold, it will be apparent that an unsubstituted P2 scaffold could be used and the $R^8$ group introduced at any suitable stage of the synthesis, using any of the methods described herein.

Building blocks to be used in the preparation of compounds wherein the macrocycle extends from the nitrogen in the linkage between the P2 and P3 fragments i.e. X is NRx in general formula I, or in the preparation of compounds wherein the P3 and P4 fragments are absent, i.e. m and n are 0 and G is NRj in general formula I, can typically be prepared as outlined in scheme 18B.

Scheme 18

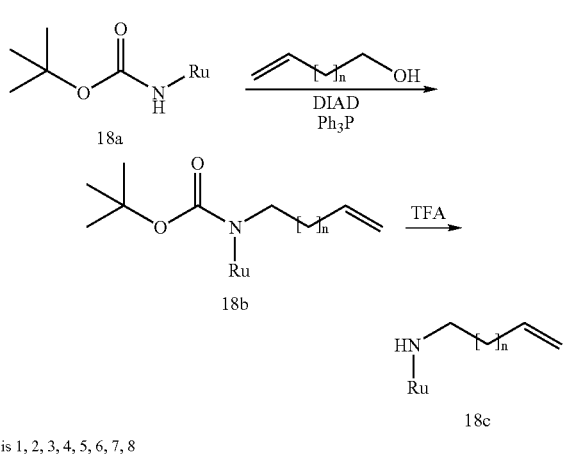

n is 1, 2, 3, 4, 5, 6, 7, 8

Carbamate 18a, which is commercially available or is readily prepared for instance by reaction of the desired alkyl amine with di-tert-butyl dicarbonate, can be reacted with an appropriate ω-unsaturated alcohol under Mitsunobu conditions to provide the alkylated carbamate (18b). Subjection of 18b to acidic conditions like for example treatment with trifluoroacetic acid in a solvent like dichloromethane gives the free amine (18c) which can be linked to a P2 fragment using any of the previously described strategies.

Macrocyclic structures containing a hydrazine group i.e. X is NRjNRj or m and n are 0 and G is NRjNRj, in general formula I, can be prepared by linking a suitably N-alkylated carbazate derivative to the P2 fragment. Alkylated carbazate derivatives can be prepared, for example, as described in Scheme 19.

Scheme 19

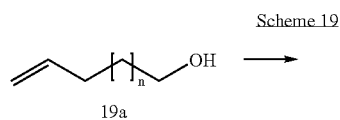

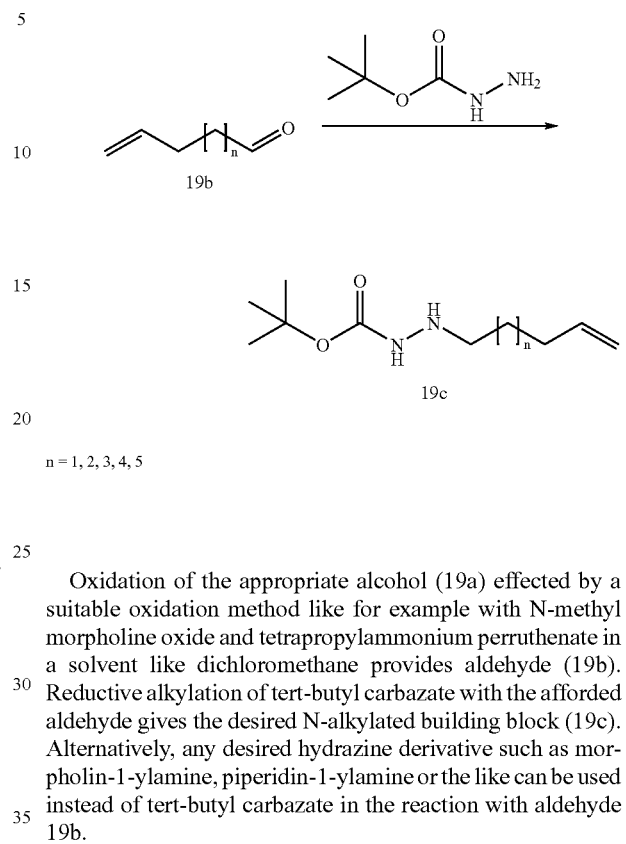

n = 1, 2, 3, 4, 5

Oxidation of the appropriate alcohol (19a) effected by a suitable oxidation method like for example with N-methyl morpholine oxide and tetrapropylammonium perruthenate in a solvent like dichloromethane provides aldehyde (19b). Reductive alkylation of tert-butyl carbazate with the afforded aldehyde gives the desired N-alkylated building block (19c). Alternatively, any desired hydrazine derivative such as morpholin-1-ylamine, piperidin-1-ylamine or the like can be used instead of tert-butyl carbazate in the reaction with aldehyde 19b.

Scheme 20 illustrates synthetic sequences to building blocks suitable for the preparation of compounds wherein the "outer" nitrogen of the hydrazine group is alkylated, either with an ω-unsaturated alkyl chain appropriate for subsequent macrocycle formation or with any other suitable alkyl group.

Scheme 20

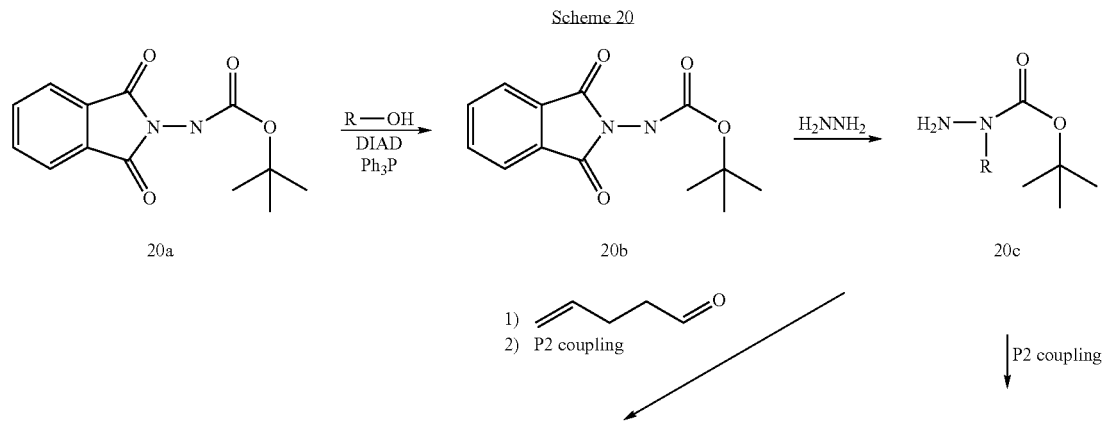

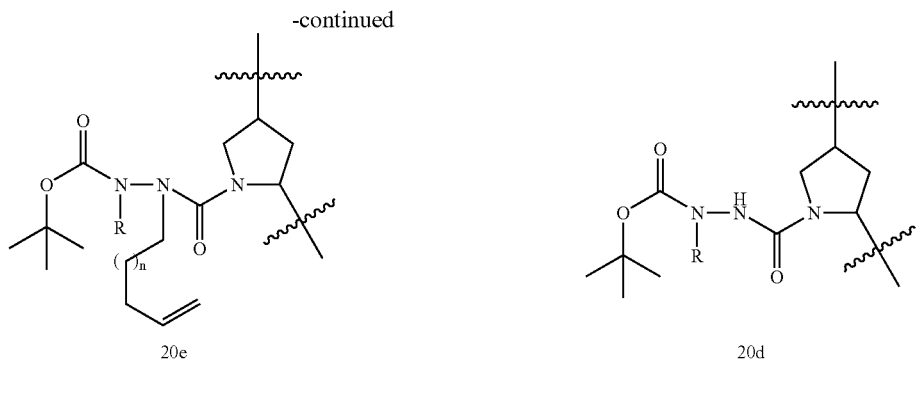

20e

R is $C_1$–$C_6$ alkyl or
ω-unsaturated $C_5$–$C_{11}$ alkyl chain
n is 1, 2, 3, 4, 5, 6, 7

20d

Reaction of a suitably protected hydrazine derivative, for example (1,3-dioxo-1,3-dihydro-isoindol-2-yl)-carbamic acid tert-butyl ester (20a), which can easily be prepared by a person skilled in the art, with a desired alcohol, R—OH, under Mitsunobu conditions provides N-alkylated hydrazine compound (20b). Removal of the phthalimido group effected by treatment with hydrazine or a derivative thereof like hydrazine hydrate or hydrazine acetate provides the carbazate (20c). The afforded primary amine can then either be be coupled to any desired P2 fragment using any of the methods previously described to give the urea derivative (20d) or alternatively it can be further alkylated using for example the reductive amination method described in scheme 19 followed by coupling to a P2 fragment as previously described to give 20e.

Scheme 21 exemplifies the coupling of a hydrazine containing P3 building block to a cyclopentane scaffold followed by macrocyclisation.

Scheme 21

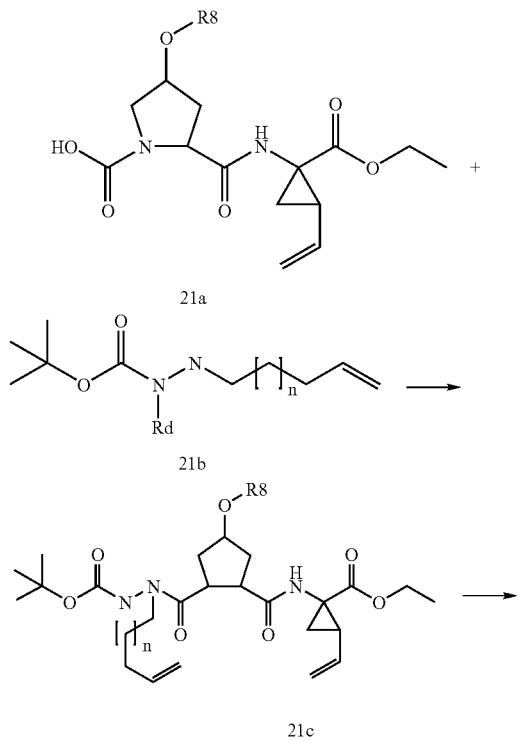

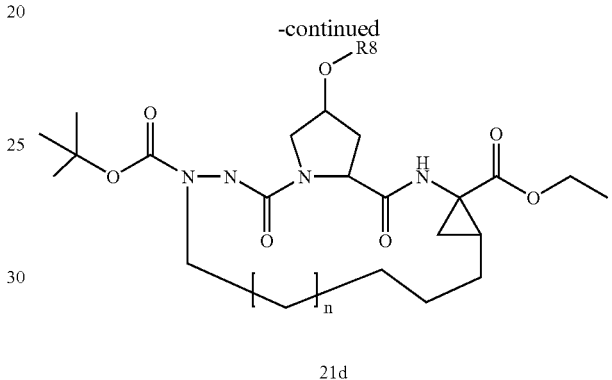

21d n = 1, 2, 3, 4, 5

Coupling of the carbazate derivative (21 b) to the P2-P1 building block (21a) using standard peptide coupling conditions provides intermediate (21c). Ring closure of (21c) by an olefin metathesis reaction as described in scheme 18 gives the macrocyclic compound (21d).

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in Greene, "Protective Groups in Organic Synthesis" (John Wiley & Sons, New York, 1981), which is hereby incorporated by reference. N-protecting groups include acyl groups such as formyl, acetyl, propionyl, pivaloyl, t-butylacetyl, 2-chloroacetyl, 2-bromoacetyl, trifluoracetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl, and the like, carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butoxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl, and the like; alkyl groups such as benzyl, triphenylmethyl, benzyloxymethyl and the like; and silyl groups such as trimethylsilyl and the like. Favoured N-protecting groups include formyl, acetyl, benzoyl, pivaloyl, t-butylacetyl, phenylsulfonyl, benzyl, t-butoxycarbonyl (BOC) and benzyloxycarbonyl (Cbz).

Hydroxy protecting group as used herein refers to a substituent which protects hydroxyl groups against undesirable reactions during synthetic procedures such as those O-protecting groups disclosed in Greene, "Protective Groups In Organic Synthesis," (John Wiley & Sons, New York (1981)). Hydroxy protecting groups comprise substituted methyl ethers, for example, methoxymethyl, benzyloxymethyl, 2-methoxyethoxymethyl, 2-(trimethylsilyl)ethoxymethyl, t-butyl and other lower alkyl ethers, such as isopropyl, ethyl and especially methyl, benzyl and triphenylmethyl; tetrahydropyranyl ethers; substituted ethyl ethers, for example, 2,2,2-trichloroethyl; silyl ethers, for example, trimethylsilyl, t-butyldimethylsilyl and t-butyldiphenylsilyl; and esters prepared by reacting the hydroxyl group with a carboxylic acid, for example, acetate, propionate, benzoate and the like.

In treating conditions caused by flavivirus such as HCV, the compounds of formula I are typically administered in an amount to achieve a plasma level of around 100 to 5000 nM, such as 300 to 2000 nM. This corresponds to a dosage rate, depending on the bioavailability of the formulation, of the order 0.01 to 10 mg/kg/day, preferably 0.1 to 2 mg/kg/day. A typical dosage rate for a normal adult will be around 0.05 to 5 g per day, preferably 0.1 to 2 g such as 500-750 mg, in one to four dosage units per day.

As with all pharmaceuticals, dosage rates will vary with the size and metabolic condition of the patient as well as the severity of the infection and may need to be adjusted for concomitant medications.

As is good prescribing practice with antiviral therapy, the compounds of formula I are typically coadministered with other HCV therapies to avoid the generation of drug escape mutants. Examples of such additional HCV antiviral therapies include ribavirin, interferons, including pegylated interferons. Additionally a number of nucleoside analogues and protease inhibitors are in clinical or preclinical development and will be amenable to co-administration with the compounds of the invention.

Accordingly a further aspect of the invention provides a composition comprising a compound of formula I and at least one further HCV antiviral in a common dosage unit, such as any of the dosage forms described below, but especially an orally administered tablet, or capsule or a liquid suspension or solution for oral or injection use. A further aspect of the invention provides a method for the treatment or prophylaxis of flavivirus infection, such as HCV, comprising the sequential or simultaneous administration of a compound of formula I and at least one further HCV antiviral. A related aspect of the invention provides a patient pack comprising a first pharmaceutical composition, preferably in unit dosage form, of the compound of formula I and a second pharmaceutical composition, typically also in unit dosage form and generally in a separate container within the patient pack, of a second HCV antiviral. A patient pack will conveniently also be provided with instructions printed on the package or a container therein, or on a package insert, for the simultaneous or sequential administration of the respective pharmaceutical compositions.

Many HCV patients are co-infected, or prone to superinfection, with other infectious diseases. Accordingly, a further aspect of the invention provides combination therapies comprising the compound of the invention co-formulated in the same dosage unit or co-packaged with at least one further anti-infective pharmaceutical. The compound of the invention and the at least one further anti-infective are administered simultaneously or sequentially, typically at doses corresponding to the monotherapy dose for the agent concerned. However, certain antifectives can induce a synergistic response, allowing one or both of the active ingredients to be administered at a lower dose that the corresponding monotherapy. For example in drugs prone to rapid metabolism by Cyp3A4, co-dosing with the HIV protease inhibitor ritonavir can allow lower dosage regimes to be administered.

Typical coinfections or superinfections with HCV include hepatitis B virus or HIV. Accordingly the compound of the invention is advantageously co-administered (either in the same dosage unit, co-packaged or separately prescribed dosage unit) with at least one HIV antiviral and/or at least one HBV antiviral.

Representative HIV antivirals include NRTI such as alovudine (FLT), zudovudine (AZT, ZDV), stavudine (d4T, Zerit), zalcitabine (ddC), didanosine (ddI, Videx), abacavir, (ABC, Ziagen), lamivudine (3TC, Epivir), emtricitabine (FTC, Emtriva), racevir (racemic FTC), adefovir (ADV), entacavir (BMS 200475), alovudine (FLT), tenofovir disoproxil fumarate (TNF, Viread), amdoxavir (DAPD), D-d4FC (DPC-817), -dOTC (Shire SPD754), elvucitabine (Achillion ACH-126443), BCH 10681 (Shire) SPD-756, racivir, D-FDOC, GS7340, INK-20 (thioether phospholipid AZT, Kucera), 2'3'-dideoxy-3'-fluoroguanosine (FLG) & its prodrgus such as MIV-210, reverset (RVT, D-D4FC, Pharmasset DPC-817).

Representative NNRTI include delavirdine (Rescriptor), efavirenz (DMP-266, Sustiva), nevirapine (BIRG-587, Viramune), (+)calanolide A and B (Advanced Life Sciences), capravirine (AG1549f S-1153; Pfizer), GW-695634 (GW-8248; GSK), MIV-150 (Medivir), MV026048 (R-1495; MedivirAB/Roche), NV-05 2 2 (Idenix Pharm.), R-278474 (Johnson & Johnson), RS-1588 (Idenix Pharm.), TMC-120/125 (Johnson & Johnson), TMC-125 (R-165335; Johnson & Johnson), UC-781 (Biosyn Inc.) and YM215389 (Yamanoushi).

Representative HIV protease inhibitors include PA-457 (Panacos), KPC-2 (Kucera Pharm.), 5 HGTV-43 (Enzo Biochem), amprenavir (VX-478, Agenerase), atazanavir (Reyataz), indinavir sulfate (MK-639, Crixivan), Lexiva (fosamprenavir calcium, GW-433908 or 908, VX-175), ritonavir (Norvir), lopinavir +ritonavir (ABT-378, Kaletra), tipranavir, nelfinavir mesylate (Viracept), saquinavir (Invirase, Fortovase), AG1776 (JE-2147, KNI-764; Nippon Mining Holdings), AG-1859 (Pfizer), DPC-681/684 (BMS), GS224338; Gilead Sciences), KNI-272 (Nippon Mining Holdings), Nar-DG-35 (Narhex), P(PL)-100 (P-1946; Procyon Biopharma), P-1946 (Procyon Biopharma), R-944 (Hoffmann-LaRoche), RO-0334649 (Hoffmann-LaRoche), TMC-114 (Johnson & Johnson), VX-385 (GW640385; GSK/Vertex), VX-478 (Vertex/GSK).

Other HIV antivirals include entry inhibitors, including fusion inhibitors, inhibitors of the CD4 receptor, inhibitors of the CCR5 co-receptor and inhibitors of the CXCR4 coreceptor, or a pharmaceutically acceptable salt or prodrug thereof. Examples of entry inhibitors are AMD-070 (AMD11070; AnorMed), BlockAide/CR (ADVENTRX Pharm.), BMS 806 (BMS-378806; BMS), Enfurvirtide (T-20, R698, Fuzeon), KRH1636 (Kureha Pharmaceuticals), ONO-4128 (GW-873140, AK-602, E-913; ONO Pharmaceuticals), Pro-140 (Progenics Pharm), PRO542 (Progenics Pharm.), SCH-D (SCH417690; Schering-Plough), T-1249 (R724; Roche/Trimeris), TAK-220 (Takeda Chem. Ind.), TNX-355 (Tanox) and UK-427,857 (Pfizer). Examples of integrase inhibitors are L-870810 (Merck & Co.), c-2507 (Merck & Co.) and S(RSC)-1838 (shionogi/GSK).

Examples of HBV antivirals include adefovir dipivoxil (Hepsera), and especially lamivudine and 2'3'-dideoxy-3'- fluoroguanosine (FLG) & its prodrugs such as MIV-210, the 5'-O-valyl-L-lactyl prodrug of FLG. These latter HBV antivirals are particularly convenient as they are also active against HIV.

While it is possible for the active agent to be administered alone, it is preferable to present it as part of a pharmaceutical formulation. Such a formulation will comprise the above defined active agent together with one or more acceptable carriers or excipients and optionally other therapeutic ingredients. The carrier(s) must be acceptable in the sense of being compatible with the other ingredients of the formulation and not deleterious to the recipient.

The formulations include those suitable for rectal, nasal, topical (including buccal and sublingual), vaginal or parenteral (including subcutaneous, intramuscular, intravenous and intradermal) administration, but preferably the formulation is an orally administered formulation. The formulations may conveniently be presented in unit dosage form, e.g. tablets and sustained release capsules, and may be prepared by any methods well known in the art of pharmacy.

Such methods include the step of bringing into association the above defined active agent with the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of Formula I or its pharmaceutically acceptable salt in conjunction or association with a pharmaceutically acceptable carrier or vehicle. If the manufacture of pharmaceutical formulations involves intimate mixing of pharmaceutical excipients and the active ingredient in salt form, then it is often preferred to use excipients which are non-basic in nature, i.e. either acidic or neutral. Formulations for oral administration in the present invention may be presented as discrete units such as capsules, cachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion and as a bolus etc.

With regard to compositions for oral administration (e.g. tablets and capsules), the term suitable carrier includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, stearic acid, glycerol stearate, silicone fluid, talc waxes, oils and colloidal silica. Flavouring agents such as pepper-mint, oil of wintergreen, cherry flavouring or the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

The compounds of formula I can form salts which form an additional aspect of the invention. Appropriate pharmaceutically acceptable salts of the compounds of formula I include salts of organic acids, especially carboxylic acids, including but not limited to acetate, trifluoroacetate, lactate, gluconate, citrate, tartrate, maleate, malate, pantothenate, isethionate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-napthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids. The invention further extends to salts of the compounds of formula I which may or may not be pharmaceutically acceptable, but which are useful as synthetic intermediates, the salt moiety being displaced or replaced as necessary.

The invention includes prodrugs of the compounds of formula I. Prodrugs of the compounds of formula I are those compounds which following administration to a patient release a compound of the formula I in vivo generally following hydrolysis in the gut, liver or plasma. Typical prodrugs are pharmaceutically acceptable ethers and especially esters (including phosphate esters) of hydroxy functions, pharmaceutically acceptable amides or carbamates of amine functions or pharmaceutically acceptable esters of carboxy functions. Preferred pharmaceutically acceptable esters include alkyl esters, including acetyl, ethanoyl, butyryl, t-butyryl, stearyl and pivaloyl, phosphate esters and sulphonic esters (ie those derived from $RSO_2OH$, where R is lower alkyl or aryl). Pharmaceutically acceptable esters include lower alkyl ethers and the ethers disclosed in WO00/47561, especially methoxyaminoacyl and ethoxyaminoacyl.

The compounds of the invention have various steric centres and the invention extends to racemates and enantiomers at each of these steric centres.

Typically, the stereochemistry of the groups corresponding to the P3 and P4 side chains (ie $R^{15}$ and/or $R^{11}$) will correspond to an L-amino acid configuration, although the invention also extends to D-isomers at one or both of these centres. It is noteworthy that the L configuration is active notwithstanding that the nature of the E moiety means that P3 and P4 are typically translated one atom relative to a conventional polypeptide and the fact that the reversal of a peptide residue, as envisaged for P3 and P4 then pitches the amine acid side chain to the opposite side compared to a conventional peptide substrate.

The stereochemistry of the backbone component of the cyclic P2 group (i.e. spanning the carbonyl of the P1 amide bond and the carbonyl or E extending of P3 will typically correspond to L-proline. The stereochemistry of the P2 ring atom to which W is bonded is typically as shown:

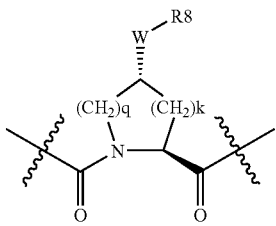

In compounds of the invention wherein $R^7$ and $R^{7'}$ together define a spiroalkyl group, such a spiro-cycloalkyl will typically comprise an $R^{7'a}$ substituent on the spiro-cyclopropyl ring which is orientated syn to A:

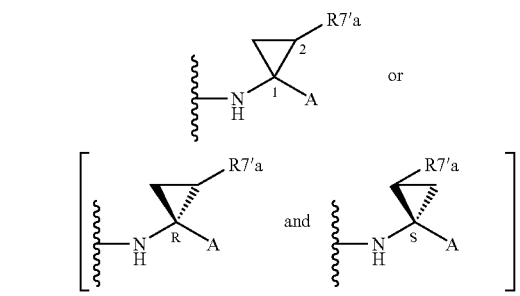

or anti to A:

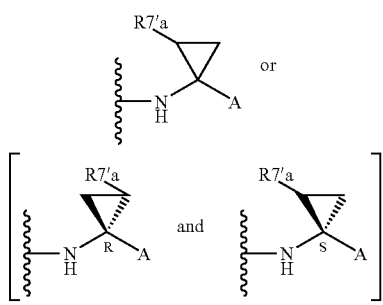

Conveniently, the spiro carbon of such a spiro-cyclopropyl ring has the R configuration:

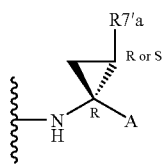

Conveniently an $R^{7'a}$ substituent on a spiro-cyclopropyl ring adjacent to A is in a syn orientation in the following absolute configuration:

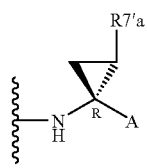

Particularly preferred variants have $R^{7'a}$ include ethyl, hence the asymmetric carbon atoms at position 1 and 2 have the R, R configuration. Alternative preferred $R^{7'a}$ include vinyl, hence the asymmetric carbon atoms at position 1 and 2 have the R, S configuration.

Where the compound of the invention is a macrocycle comprising a J group, J is preferably a diastereomer represented by partial structures (i) or (ii):

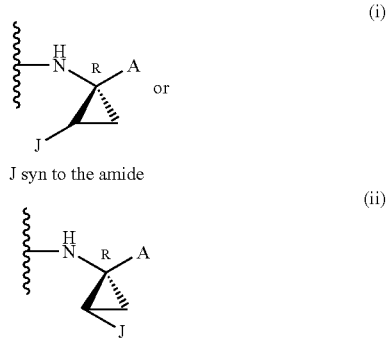

especially where J is syn to A.

DETAILED DESCRIPTION OF THE EMBODIMENTS

Various embodiments of the invention will now be described by way of illustration only with reference to the following non-limiting examples.

Example 1

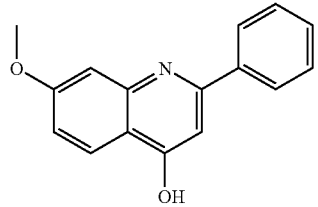

7-Methoxy-2-phenyl-quinolin-4-ol (1)

To a stirred round bottled flask with toluene (100 mL) ethyl benzoyl acetate (18.7 g, 97 mmol) and m-anisidine (12 g, 97 mmol) was added. 4 M HCl in dioxane (0.5 mL) was added and the reaction mixture was refluxed for 6 h (140° C.). The mixture was coevaporated with toluene. To the crude mixture diphenyl ether (50 mL) was added and the mixture was heated to 280° C. for 2 h. When the theoretical amount ethanol (6 mL) was collected in a Dean Stark trap the heating was stopped and the mixture was cooled to rt. The crude mixture was dissolved in $CH_2Cl_2$ (100 mL) and stirred for 30 min. The formed precipitate was filtered off and dried which gave 1 (4.12 g, 16.4 mmol, 17%): pale yellow powder.

$^1$H (300 MHz, DMSO-$D_6$): δ 3.8 (s, 3H), 6.24 (s, 1H), 6.88-6.96 (dd, 1H, J=9.07 Hz, J=2.47 Hz), 7.19 (d, 1H, J=2.19 Hz), 7.56 (t, 3H, J=2.19 Hz), 7.8 (dd, 2H, J=7.14 Hz, J=2.19 Hz), 8.0 (d, 1H, J=9.06 Hz); $^{13}$C (75.5 MHz, DMSO-$D_6$): δ

55.3, 99.6, 106.9, 113.1, 119.1, 126.4, 127.5, 128.8, 130.2, 134.1, 142.2, 149.4, 161.8, 176.4.

Example 2

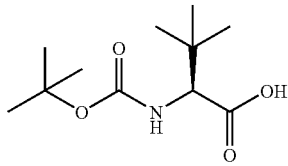

Boc-L-tert-leucine-OH (2)

Triethylamine (890 μL, 6.40 mmol) was added dropwise to a stirred solution of L-tert-leucine (300 mg, 2.29 mmol) and di-tert-butyl dicarbonate (599 mg, 2.74 mmol) in dioxane/water 1:1 (8 mL) and the solution was stirred overnight. The mixture was extracted with petroleum ether (2×) and the aqueous phase was cooled to 0° C. and carefully acidified to pH 3 by slow addition of 4M $NaHSO_4.H_2O$. The acidified water phase was extracted with EtOAc (3×) and the combined organic phases were washed with brine (2×) and was then dried, filtered and concentrated to give the title compound (522 mg, 99%) as a colorless powder. No further purification was needed.

$^1$H-NMR (300 MHz, $CD_3OD$) δ 0.99 (s, 9H), 1.44 (s, 9H), 3.96 (s, 1H); $^{13}$C-NMR (75.5 MHz, $CD_3OD$) δ 27.1, 28.7, 34.9, 68.0, 80.5, 157.8, 174.7.

Example 3

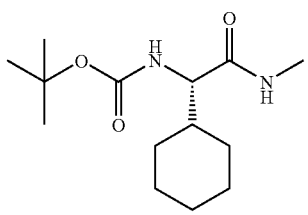

((S)-Cyclohexyl-methylcarbamoyl-methyl)-carbamic acid tert-butyl ester (3)

Boc-Chg-OH (387 mg, 1.50 mmol) was coupled to methylamine hydrochloride (111 mg, 1.65 mmol) using the same HATU coupling conditions as in the synthesis of compound 7. The crude product was extracted with EtOAc, washed with brine and concentrated. Purification by flash column chromatography (EtOAc) provided the title compound (307 mg, 76%) as a colorless solid.

$^1$H-NMR (300 MHz, $CDCl_3$) δ 0.91-1.13 (m, 2H), 1.14-1.31 (m, 3H), 1.44 (s, 9H), 1.61-1.80 (m, 6H), 2.80 (d, J=4.7 Hz, 3H), 3.91 (dd, J=7.1, 9.1 Hz, 1H), 5.23 (b, 1H), 6.52 (bs, 1H); $^{13}$C-NMR (75.5 MHz, $CDCl_3$) δ 25.9, 26.0, 26.1, 28.3, 28.5, 29.6, 40.5, 59.5, 79.7, 155.9, 172.4.

Example 4

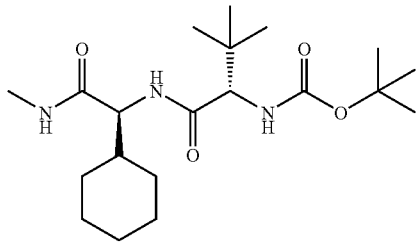

{(S)-1-[((S)-Cyclohexyl-methylcarbamoyl-methyl)-carbamoyl]-2,2-dimethyl-propyl} carbamic acid tert-butyl ester (4)

To a solution of compound 3 (98 mg, 0.362 mmol) in methylene chloride (3 mL) were added triethylsilane (115 mL, 0.742 mmol) and TFA (3 mL). The mixture was stirred for 2 h at room temperature and was then evaporated and coevaporated with toluene.

The deprotected amine was dissolved in DMF (5 mL) and coupled to compound 2 (84 mg, 0.363 mmol) using the same HATU coupling conditions as in the synthesis of 7. The crude product was extracted with EtOAc, washed with brine, dried, filtered and concentrated. Purification by flash column chromatography (toluene/EtOAc 1:1) provided the title compound (128 mg, 92%) as a colorless solid.

$^1$H-NMR (300 MHz, $CDCl_3$) δ 0.99 (s, 9H), 1.02-1.30 (m, 5H), 1.44 (s, 9H), 1.58-1.77 (m, 4H), 1.78-1.89 (m, 2H), 2.79 (d, J=4.7 Hz, 3H), 4.11 (d, J=9.3 Hz, 1H), 4.33 (app. t, J=8.5 Hz, 1H), 5.65 (b, 1H), 7.25 (b, 1H), 7.39 (b, 1H); $^{13}$C-NMR (75.5 MHz, $CDCl_3$) δ 25.9, 25.9, 26.0, 26.2, 26.8, 28.4, 29.0, 29.7, 34.5, 39.7, 58.4, 62.4, 79.4, 156.0, 171.4, 171.8.

Example 5

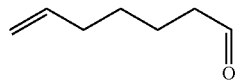

Hept-6-enal (5)

To a solution of hept-6-en-1-ol (1 mL, 7.44 mmol) and N-methylmorpholine N-oxide (1.308 g, 11.17 mmol) in DCM (17 mL) was added ground molecular sieves (3.5 g, 4 Å). The mixture was stirred for 10 min at room temperature under nitrogen atmosphere before tetrapropylammonium perruthenate (TPAP) (131 mg, 0.37 mmol) was added. After stirring for additional 2.5 h the solution was filtered through celite. The solvent was then carefully evaporated and the remaining liquid was purified by flash column chromatography (DCM) to give the volatile aldehyde 5 (620 mg, 74%) as an oil.

Example 6

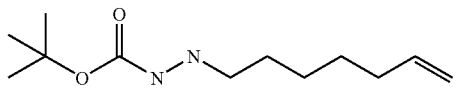

N'-Hept-6-en-(E)-ylidene-hydrazinecarboxylic acid tert-butyl ester (6)

To a solution of 5 (68 mg, 0.610 mmol) and tert-butyl carbazate (81 mg, 0.613 mmol) in MeOH (5 mL) was added ground molecular sieves (115 mg, 3 Å). The mixture was stirred for 3 h after which it was filtered through celite and evaporated. The residue was dissolved in dry THF (3 mL) and AcOH (3 mL). NaBH$_3$CN (95 mg, 1.51 mmol) was added and the solution was stirred over night. The reaction mixture was diluted with saturated NaHCO$_3$ solution (6 mL) and EtOAc (6 mL). The organic phase was washed with brine, saturated NaHCO$_3$, brine, dried over MgSO$_4$ and evaporated. The cyanoborane adduct was hydrolyzed by treatment with MeOH (3 mL) and 2 M NaOH (1.9 mL). The mixture was stirred for 2 h and the MeOH was evaporated. H$_2$O (5 mL) and DCM (5 mL) were added and the water phase was extracted three times with DCM. The combined organic phases were dried and evaporated. Purification by flash column chromatography (toluene/ethyl acetate 9:1 with 1% triethylamine and toluene/ethyl acetate 6:1 with 1% triethylamine) provided the title compound (85 mg, 61%) as an oil.

Example 7

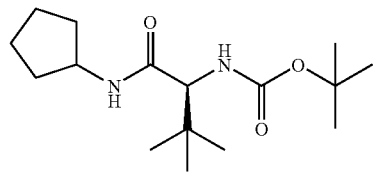

((S)-1-Cyclopentylcarbamoyl-2,2-dimethyl-propyl)-carbamic acid tert-butyl ester (7)

To a cold solution of 2 (133 mg, 0.575 mmol), cyclopentylamine (64 µL, 0.648 mmol) and DIEA (301 µL, 1.73 mmol) in DMF (3 mL) was added the coupling reagent HATU (240 mg, 0.631 mmol). The mixture was stirred for half an hour and for additional two hours at room temperature. The solvent was removed by heating the reaction flask in a water bath under diminished pressure and the residue was dissolved in ethyl acetate, after which the organic phase was washed three times with brine, dried, filtered and evaporated. Purification by flash column chromatography (toluene/ethyl acetate 4:1) provided the title compound (140 mg, 82%) as colorless crystals.

$^1$H-NMR (300 MHz, CDCl$_3$): δ 0.95 (s, 9H), 1.28-1.48 (m, overlapped, 2H), 1.40 (s, 9H), 1.49-1.71 (m, 4H), 1.86-2.01 (m, 2H), 3.76 (b, 1H), 4.09-4.23 (m, 1H), 5.32 (b, 1H), 5.91 (b, 1H); $^{13}$C-NMR (75.5 MHz, CDCl$_3$): δ 23.6, 23.7, 26.5, 28.3, 32.6, 33.1, 34.5, 51.0, 62.2, 79.4, 155.9, 170.3.

Example 8

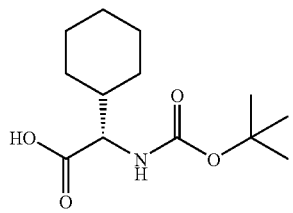

(S)-teit-Butoxycarbonylamino-cyclohexyl-acetic acid methyl ester (8)

To a solution of Boc-Chg-OH (53 mg, 0.206 mmol) in acetone (3 mL) were added methyl iodide (195 µL, 3.1 mmol) and silver (I) oxide (53 mg, 0.229 mmol). The mixture was allowed to stir over night in a reaction flask that was covered with aluminium foil. Thereafter the solution was filtered through celite and evaporated. Purification by flash column chromatography (toluene/ethyl acetate 15:1) provided methyl ester 8 (56 mg, 100%) as a colorless oil.

$^1$H-NMR (300 MHz, CDCl$_3$): δ 1.00-1.34 (m, 5H), 1.44 (s, 9H), 1.54-1.82 (m, 6H), 3.73 (s, 3H), 4.20 (dd, J=2.8, 5.0 Hz, 1H), 5.05 (bs, 1H); $^{13}$C-NMR (75.5 MHz, CDCl$_3$): δ 26.0, 28.2, 28.3, 29.5, 41.1, 52.0, 58.3, 79.7, 155.6, 172.9.

Example 9

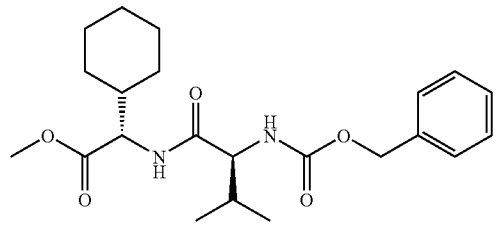

(S)—((S)-2-Benzyloxycarbonylamino-3-methyl-butyrylamino)-cyclohexyl-acetic acid methyl ester (9)

Compound 8 (93 mg, 0.343 mmol) was deprotected and coupled to Z-Val-OH (95 mg, 0.378 mmol) according to the method for the preparation of 39. Flash column chromatography (toluene/ethyl acetate 4:1) gave the title compound (131 mg, 94%) as a colorless solid.

$^1$H-NMR (300 MHz, CDCl$_3$): δ 0.92-1.30 (m, 11H), 1.54-1.88 (m, 6H), 2.02-2.18 (m, 1H), 3.72 (s, 3H), 4.05-4.18 (m, 1H), 4.52 (dd, J=3.0, 5.5 Hz, 1H), 5.12 (s, 2H), 5.49 (bs, 1H), 6.52 (bs, 1H), 7.34 (s, 5H); $^{13}$C-NMR (75.5 MHz, CDCl$_3$): δ 17.8, 19.0, 25.8, 28.2, 29.3, 31.2, 40.5, 51.9, 56.8, 60.0, 66.8, 127.7, 127.9, 128.1, 128.3, 136.2, 156.3, 171.3, 172.2.

Example 10

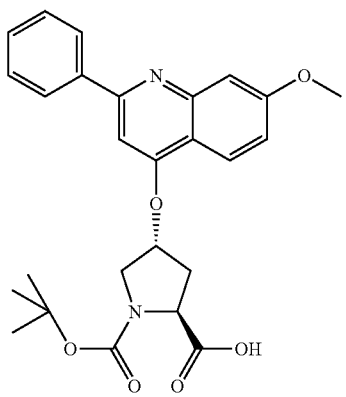

N-Boc4R-(2-phenyl-7-methoxyquinoilne-4-oxo)proline (10)

To a stirred solution of N-Boc-trans-4-hydroxy-L-proline (3.9 g, 16.9 mmol) in DMSO (90 mL) was added potassium tert.butoxide (4.5 g, 40.1 mmol). After 1 hrs 4-chloro-2-phenyl-7-methoxy quinoline (4.5 g, 16.7 mmol) was added and stirred at RT for 12 hrs. The mixture was diluted with water (180 mL), washed with ethyl acetate (1×30 mL) and neutralized with 1N HCl. The solid was filtered, washed with water and dried giving (4.65 g, 10 mmol) of product. >95% purity by HPLC. M+H$^+$464.2.

Example 11

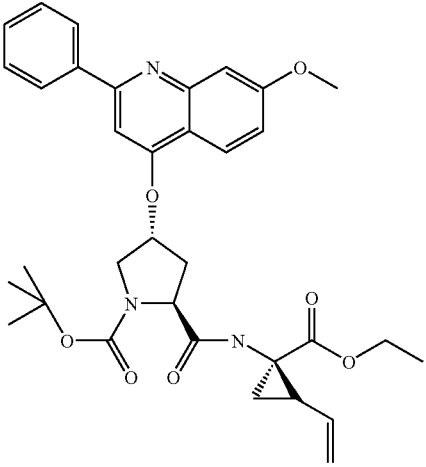

2-(1-Ethoxycarbonyl-2-vinyl-cyclopropylcarbamoyl)-4-(7-methoxy-2-phenyl-quinoline-4-yloxy)-pyrrolidine-1-carboxylic acid tert.butyl ester (11)

To a solution of 1-amino-2-vinyl-cyclopropanecarboxylic acid ethyl ester (41 mg, 0.26 mmol), 10 (11 mg, 0.22 mmol), HATU (204 mg, 0.54 mmol) in DMF (4 mL) was added diisopropylethylamine (187 µL, 1.08 mmol). After stirring at RT for 1 hrs, dichloromethane (4 mL) was added. The solution was washed with aqueous NaHCO$_3$ (sat) and with two portions of water. The organic layer was dried and concentrated. The product was pure enough (>95% by HPLC) to be used in the next step. M+H$^+$602.2.

Example 12

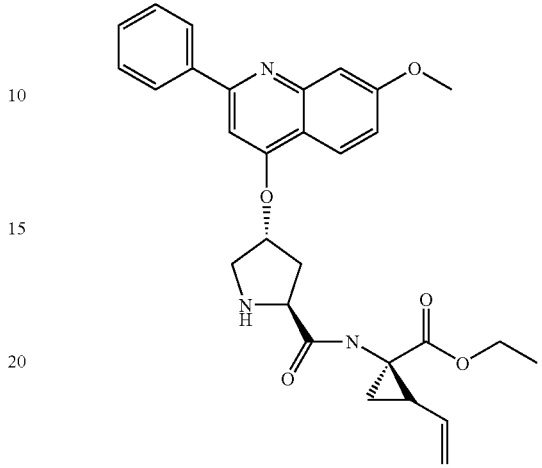

1-{[4-(7-Methoxy-2-phenyl-quinolin-4-yloxy)-pyrrolidine-2-carbonyl]-amino}-2-vinyl-cyclopropanecarboxylic acid ethyl ester (12)

Compound 11 was kept in TFA-DCM 1:2 (3 mL) at RT for 60 min. Toluene (3 mL) was added. The sample was co-evaporated to dryness. Purity by HPLC>95%. M+H$^+$502.4.

Example 13

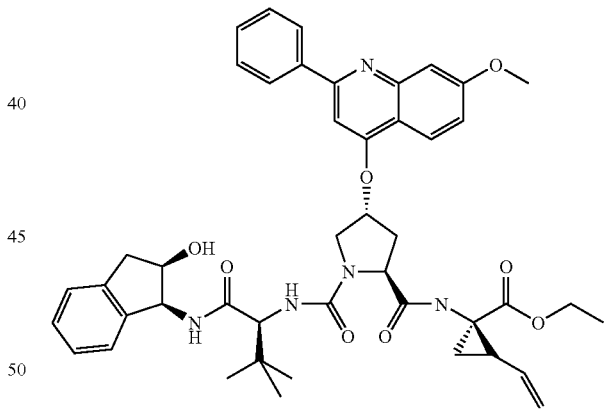

1-{[1-[1-(2-Hydroxy-indan-1-ylcarbamoyl)-2,2-dimethyl-propylcarbamoyl]4-(7-methoxy-2-phenyl-quinolin-4-yloxy)-pyrrolidin e-2-carbonyl]-amino}-2-vinyl-cyclopropanecarboxylic acid ethyl ester (13)

To a solution of compound 12 (0.13 mmol) in THF (2 mL), was added a large excess of NaHCO$_3$ (s) and a solution of phosgene in toluene (1.6 M, 600 µL). After 10 min of agitation the slurry was filtered and concentrated to dryness. The solid was redissolved in dichloromethane and a large excess of NaHCO$_3$ (s) and 2-Amino-N-(2-hydroxy-indan-1-yl)-3,3-dimethyl-butyramide (0.65 mmol) was added. The slurry was agitated for 24-40 hrs at RT. The slurry was filtered, concentrated and subjected to silica column chromatography (gradient elution from 100% DCM to MeOH/DCM 2:98) to give the title compound (89.6 mg, 0.11 mmol). Purity by HPLC>95%. M+H⁺790.3.

Example 14

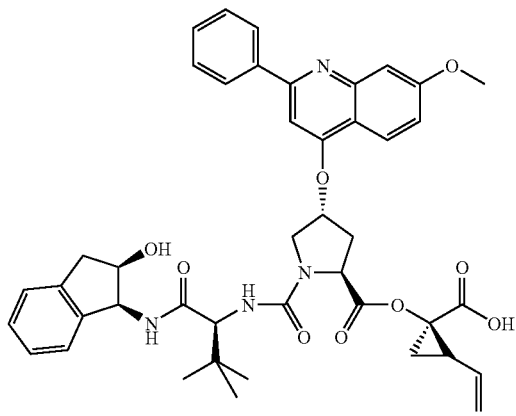

1-[1-[1-(2-Hydroxy-indan-1-ylcarbamoyl)-2,2-dimethyl-propyl]-4-(6-methoxy-3-phenyl-naphthalen-1-yloxy)-pyrrolidin-2-yl]-2-vinyl-cyclopropanecarboxylic acid (14)

To a solution of 13 (76.7 mg, 0.097 mmol) in THF-MeOH 2:3 (2 mL) was added 1M LiOH 5 equiv. The solution was kept at 60° C. for 60 min. After cooling to RT, HOAc 15-30 eq. was added followed by toluene (2 mL) and then concentrated to dryness. The residue was taken up in DCM and washed with water. The organic layer was dried and concentrated to give the title compound (72 mg, 0.094 mmol). Purity >95% by HPLC M+H⁺762.2.

Example 15

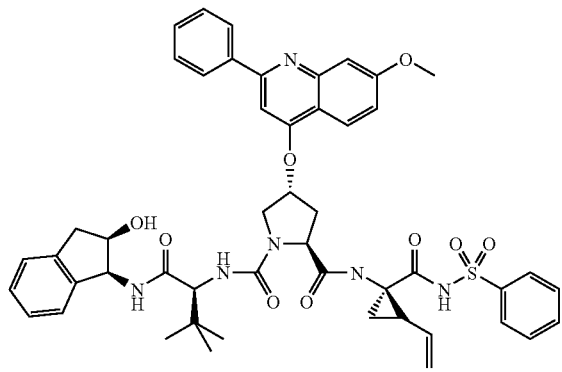

N-(2-Hydroxy-indan-1-yl)-2-[4-(6-methoxy-3-phenyl-naphthalen-1-yloxy)-2-(1-phenylmethanesulfonylaminocarbonyl-2-vinyl-cyclopropyl)-pyrrolidin-1-yl]-3,3-dimethyl-butyramide (15)

To solution of 14 (25 mg, 0.033 mmol) in chloroform (1 mL) was added benzenesulfonamide (10.5 mg, 0.066 mmol) followed by diisopropylethylamine (34 μL, 0.197 mmol). The solution was stirred at RT for 10 min and then at −20° C. for 30 min. PyBOP (76 mg, 0.13 mmol) was then added as a solid. The solution was kept at −20° C. for 48 hours. The solution was then poured into aqueous NaHCO₃ (sat.) and washed with water. The organic layer was dried, concentrated and subjected to purification by HPLC, affording the title compound as a white solid.

Example 16

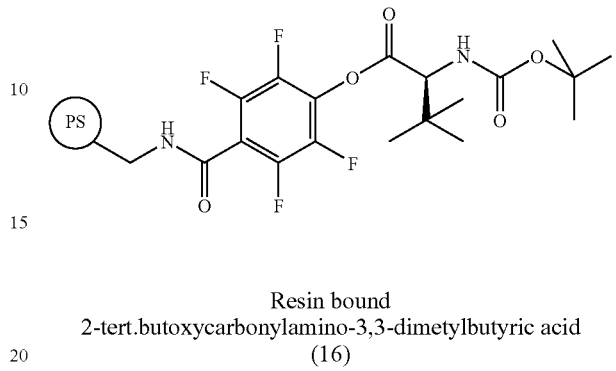

Resin bound 2-tert.butoxycarbonylamino-3,3-dimetylbutyric acid (16)

To Argonaut resin PS-TFP (1.38 mmol/g, 10 g) and 2-tert-butoxycarbonylamino-3,3-dimethyl-butyric acid (4.5 g, 20.7 mmol) was added dichloromethane (40 mL) and DMF (10 mL). To this mixture was added DMAP (1 g, 8.28 mmol) and then DIC (9.5 mL, 60.7 mmol). After 3 hrs of agitation at RT the resin was filtered and washed successively with DMF, THF, DCM, THF, DCM and ether and then dried in a vacuum.

Example 17

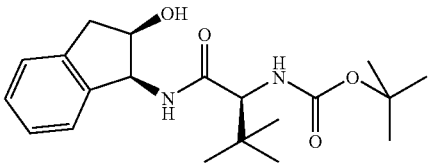

[1-(2-Hydroxy-indan-1-ylcarbamoyl)-2,2-dimethyl-propyl]-carbamic acid tert.butyl ester (17)

To a portion of 16 (200 mg) in DCM aminoindanol (0.14 mmol) was added. The mixture was agitated for 2 hrs. The liquid was filtered of and the resin washed with 2×DCM. The combined liquids were combined and concentrated to dryness to afford the title compound (20.5 mg, 0.055 mmol) Purity >95% by HPLC. M+H⁺363.15.

¹³C NMR $\delta_c$ (100 MHz; CDCl₃; Me₄Si) 27.0, 28.5, 34.2, 39.8, 50.8, 57.9, 68.2, 73.7, 124.8, 125.6, 127.4, 128.5, 140.4, 171.6. ¹H NMR $\delta_H$ (400 MHz; CDCl₃; Me₄Si) 1.07 (9H, s, CCH₃), 1.44 (9H, s, OCCH₃), 2.93 (1H, dd, $J_{gem}$16.4 Hz, $J_{3,2}$ 2.3 Hz, CH₂), 3.15 (1H, dd, $J_{gem}$ 16.4 Hz, $J_{3,2}$ 5.2 Hz, CH₂),

Example 18

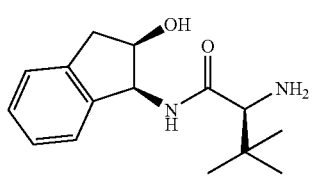

2-Amino-N-(2-hydroxy-indan-1-yl)-3,3-dimethyl butyramide (18)

Compound 17 was kept in DCM-TFA 2:1 (2 mL) for 60 min at RT. The solution was cb-evaporated with toluene to dryness.

Example 19

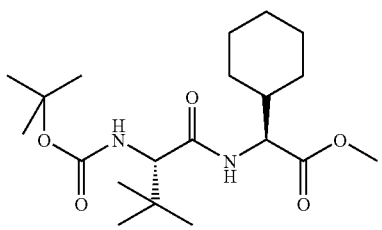

(2-tert-Butoxycarbonylamino-3,3-dimethyl-butyrylamino)-cyclohexyl-acetic acid methyl ester (19)

To a solution of 2-tert.butoxycarbonylamino-3,3-dimethyl butyric acid (500 mg, 2.16 mmol), Amino-cyclohexyl-acetic acid methyl ester (444 mg, 2.59 mmol) and HATU (2 g, 5.40 mmol) in DMF (20 mL) was added diisopropylethylamine (1.88 mL, 10.8 mmol). The solution was stirred for 1 hrs at r.t. and diluted with dichloromethane (40 mL). This solution was washed with aqueous. NaHCO$_3$ (sat.) and water (x2), dried and concentrated. The product was >95% pure. M+H$^+$385.4.

Example 20

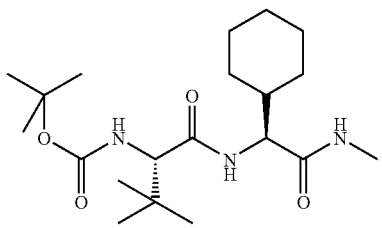

{1-[(Cyclohexyl-methylcarbamoyl-methyl)-carbamoyl]-2,2-dimethyl-propyl}-carbamic acid tert-butyl ester (20)

To compound 19 in EtOH-THF 1:2 was added a large excess of methylamine (30% in water) and left at rt. for 2 weeks. The solution was concentrated to dryness and the residue subjected to a short silica gel column eluted with 2% MeOH in dichloromethane to give a pure (>95%) product M+H$^+$384.5.

Example 21

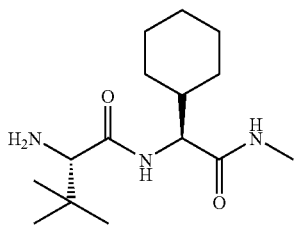

2-Amino-N-(cyclohexyl-methylcarbamoyl-methyl)-3,3-dimethyl-butyramide (71)

Compound 20 was kept in dichloromethane-trifluoroacetic acid 2:1 for 1 h at rt and concentrated to dryness. The residue was dried in a vacuum for 16 hrs. Reversed phase C18 HPLC showed >95% purity M+H$^+$283.1.

Example 22

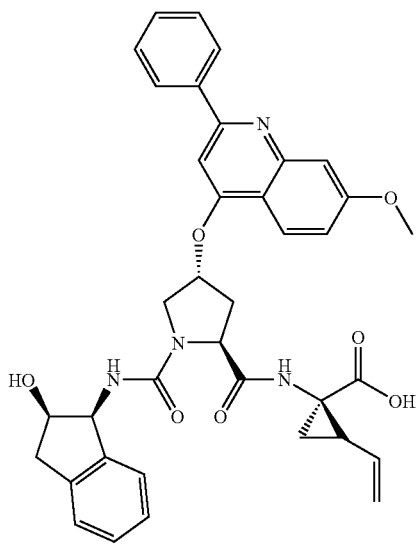

(1R,2S)-1-{[(2S,4R)-1-((1S,2R)-2-Hydroxy-indan-1-ylcarbamoyl)-4-(7-methoxy-2-phenyl-quinolin-4-yloxy)-pyrrolidine-2-carbonyl]-amino}-2-vinyl-cyclopropanecarboxylic acid (22).

Compound 12 was treated as described for the preparation of 13 but with the use of (1S,2R)-cis-1-amino-2-indanol instead of 2-amino-N-(2-hydroxyindan-1-yl)-3,3-dimethyl butyramide followed by ester hydrolysis as described for the preparation of compound 14 which gave the title compound. Purity by HPLC>95%. M+H$^+$649.1.

Example 23

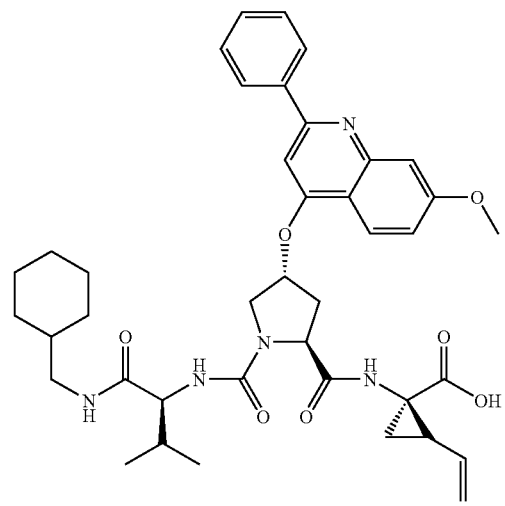

(1R,2S)-1-{[(2S,4R)-1-[(1S)-1-(Cyclohexylmethyl-carbamoyl)-2-methyl-propylcarbamoyl]-4-(7-methoxy-2-phenyl-quinolin-4-yloxy)-pyrrolidine-2-carbonyl-amino}-2-vinyl-cyclopropanecarboxylic acid (23).

N-(tert-butoxycarbonyl)-L-valine was attached to the resin as described for the preparation of compound 16 followed by reaction with cyclohexylamine as described for the preparation of 17 and removal of the Boc group as described for 18. The afforded compound was then reacted with the chlorocarbamate achieved from 12 as described for the preparation of 13 which gave the title compound. Purity by HPLC >95%. M+H+712.3.

Example 24

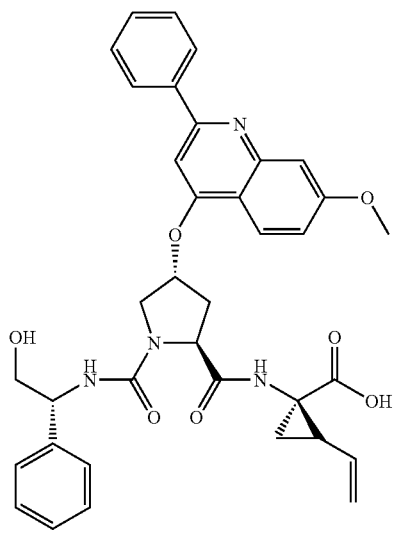

(1R,2S)-1-{[(2S,4R)-1-((1R)-2-Hydroxy-1-phenyl-ethylcarbamoyl)-4-(7-methoxy-2-phenyl-quinolin-4-yloxy)-pyrrolidine-2-carbonyl]-amino}-2-vinyl-cyclopropanecarboxylic acid (24)

Compound 12 was treated as described for the preparation of 13 but with the use of (R)-2-phenylglycinol instead of 2-amino-N-(2-hydroxyindan-1-yl)-3,3-dimethyl butyramide instead of 2-amino-N-(2-hydroxy-indan-1-yl)-3,3-dimethyl-butyramide followed by ester hydrolysis as described for the preparation of compound 14 which gave the title compound. Purity by HPLC>95%. M+H+637.1.

Example 25

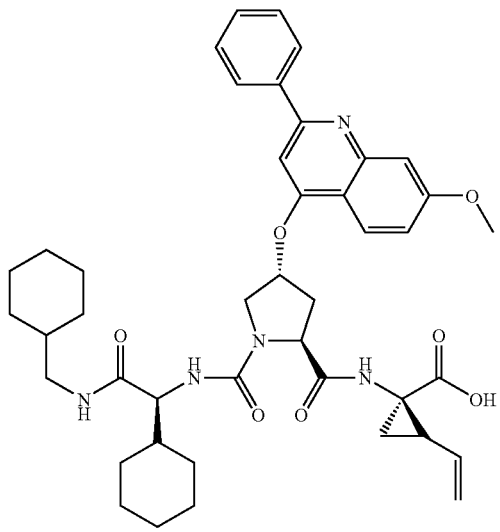

(1R,2S)-1-{[(2S,4R)-1-{[(1S)-Cyclohexyl-(cyclohexylmethyl-carbamoyl)-methyl]-carbamoyl}4-(7-methoxy-2-phenyl-quinolin-4-yloxy)-pyrrolidine-2-carbonyl]-amino}-2-vinyl-cyclopropanecarboxylic acid (25)

N-(tert-butoxycarbonyl)-L-cyclohexylglycine was attached to the resin as described for the preparation of compound 16 followed by reaction with cyclohexanemethylamine as described for the preparation of 17 and removal of the Boc group as described for 18. The afforded compound was then reacted with the chlorocarbamate achieved from 12 as described for the preparation of 13 which gave the title compound. Purity by HPLC>95%. M+H+752.4.

Example 26

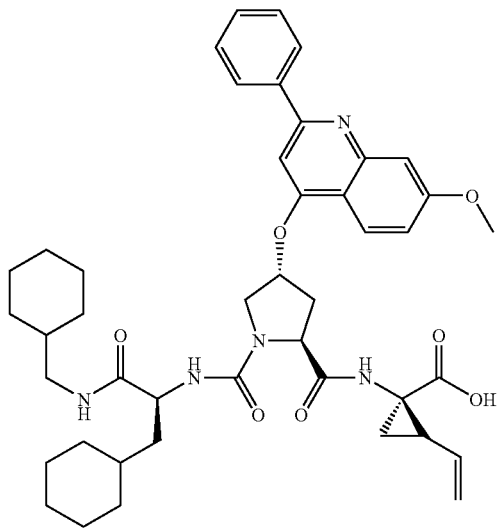

67

(1R,2S)-1-{[(2S,4R)-1-[(1S)-2-Cyclohexyl-1-(cyclohexylmethyl-carbamoyl)-ethylcarbamoyl]4-(7-methoxy-2-phenyl-quinolin-4-yloxy)-pyrrolidine-2-carbonyl]-amino}-2-vinyl-cyclopropanecarboxylic acid (26)

N-(tert-butoxycarbonyl)-L-cyclohexylalanine was attached to the resin as described for the preparation of compound 16 followed by reaction with cyclohexanemethylamine as described for the preparation of 17 and removal of the Boc group as described for 18. The afforded compound was then reacted with the chlorocarbamate achieved from 12 as described for the preparation of 13 which gave the title compound. Purity by HPLC>95%. M+H$^+$766.4.

Example 27

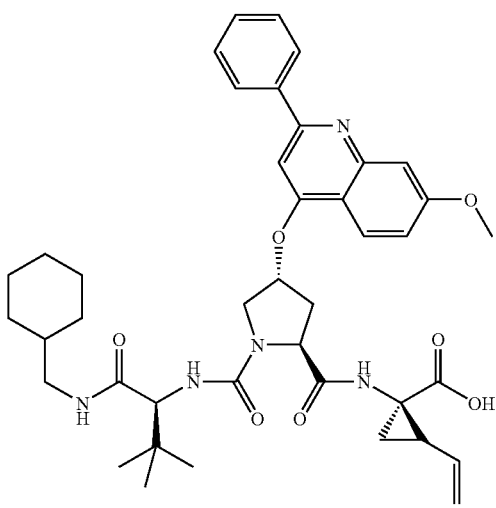

(1R,2S)-1-{[(2S,4R)-1-[(1S)-1-(Cyclohexylmethyl-carbamoyl)-2,2-dimethyl-propylcarbamoyl]-4-(7-methoxy-2-phenyl-quinolin-4-yloxy)-pyrrolidine-2-carbonyl]-amino}-2-vinyl-cyclopropanecarboxylic acid (27)

N-(tert-butoxycarbonyl)-L-tert-butylglycine was attached to the resin as described for the preparation of compound 16 followed by reaction with cyclohexanemethylamine as described for the preparation of 17 and removal of the Boc group as described for 18. The afforded compound was then reacted with the chlorocarbamate achieved from 12 as described for the preparation of 13 which gave the title compound. Purity by HPLC>95%. M+H$^+$726.3.

68

Example 28

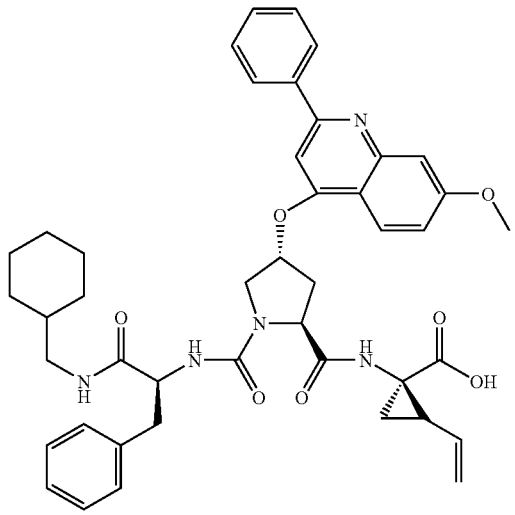

(1R,2S)-1 {[(2S,4R)-1-[(1S)-1-(Cyclohexylmethyl-carbamoyl)-2-phenyl-ethylcarbamoyl]4-(7-methoxy-2-phenyl-quinolin-4-yloxy)-pyrrolidine-2-carbonyl]-amino}-2-vinyl-cyclopropanecarboxylic acid (28)

N-(tert-butoxycarbonyl)-L-phenylalanine was attached to the resin as described for the preparation of compound 16 followed by reaction with cyclohexanemethylamine as described for the preparation of 17 and removal of the Boc group as described for 18. The afforded compound was then reacted with the chlorocarbamate achieved from 12 as described for the preparation of 13 which gave the title compound. Purity by HPLC>95%. M+H$^+$760.4.

Example 29

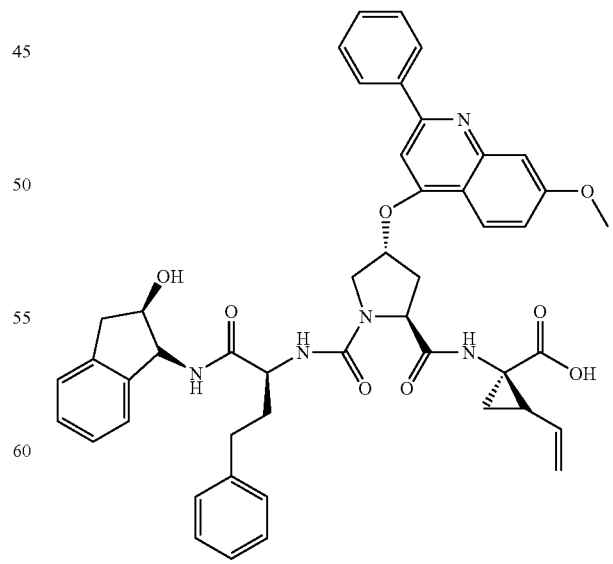

(1R,2S)-1-{[(2S,4R)-1-[(1S)-1-((1S,2R)-2-Hydroxy-indan-1-ylcarbamoyl)-3-phenyl-propylcarbamoyl]-4-(7-methoxy-2-phenyl-quinolin-4-yloxy)-pyrrolidine-2-carbonyl]-amino}-2-vinyl-cyclopropanecarboxylic acid (29)

N-(tert.butoxycarbonyl)-L-phenethylglycine was attached to the resin as described for the preparation of compound 16 followed by reaction with (1S,2R)-cis-1-amino-2-indanol as described for the preparation of 17 and removal of the Boc group as described for 18. The afforded compound was then reacted with the chlorocarbamate achieved from 12 as described for the preparation of 13 which gave the title compound. Purity by HPLC>95%. M+H⁺810.4.

Example 30

(1R,2S)-1-{[(2S,4R)-1-((1S)-1-Benzylcarbamoyl-2-methyl-propylcarbamoyl)-4-(7-methoxy-2-phenyl-quinolin-4-yloxy)-pyrrolidine-2-carbonyl]-amino}-2-vinyl-cyclopropanecarboxylic acid (30)

N-(tert-butoxycarbonyl)-L-valine was attached to the resin as described for the preparation of compound 16 followed by reaction with benzylamine as described for the preparation of 17 and removal of the Boc group as described for 18. The afforded compound was then reacted with the chlorocarbamate achieved from 12 as described for the preparation of 13 which gave the title compound. Purity by HPLC>95%. M+H⁺ 706.2.

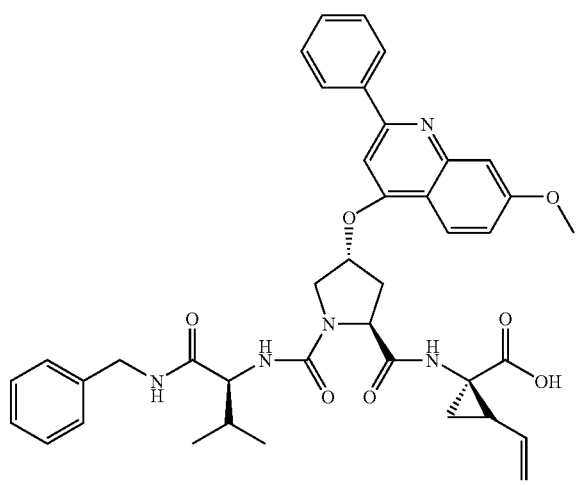

Example 31

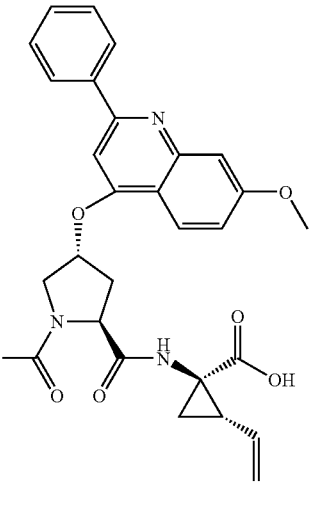

(1R,2S)-1-{[(2S,4R)-1-[(1S)-1-((1R)-2-Hydroxy-1-phenyl-ethylcarbamoyl)-2,2-dimethyl-propylcarbamoyl]-4-(7-methoxy-2-phenylquinolin-4-yloxy)-pyrrolidine-2-carbonyl]-amino}-2-vinyl-cyclopropanecarboxylic acid (31)

N-(tert-butoxycarbonyl)-L-tert-butylglycine was attached to the resin as described for the preparation of compound 16 followed by reaction with (R)-2-phenylglycinol as described for the preparation of 17 and removal of the Boc group as described for 18.

The afforded compound was then reacted with the chlorocarbamate achieved from 12 as described for the preparation of 13 which gave the title compound. Purity by HPLC >95%. M+H⁺750.3.

Example 32

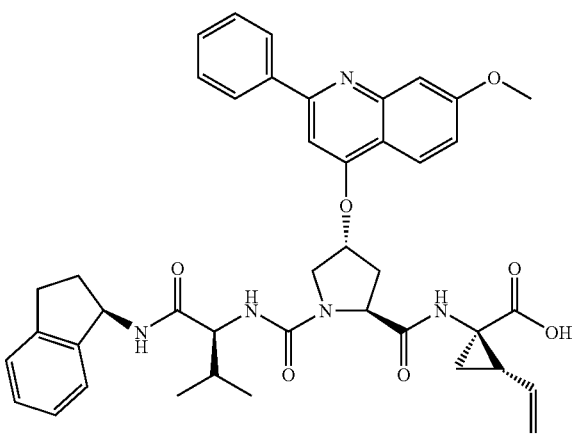

(1R,2S)-1-{[(2S,4R)-1-[(1S)-1-((1R)-Indan-1-ylcar-
bamoyl)-2-methyl-propylcarbamoyl]-4-(7-methoxy-
2-phenyl-quinolin-4-yloxy)-pyrrolidine-2-carbonyl]-
amino}-2-vinyl-cyclopropanecarboxylic acid (32)

(2S)-tert-butoxycarbonylamino-3-methylbutyric acid was attached to the resin as described for the preparation of compound 16 followed by reaction with (1R)-1-aminoindane as described for the preparation of 17 and removal of the Boc group as described for 18. The afforded compound was then reacted with the chlorocarbamate achieved from 12 as described for the preparation of 13 which, after purification by HPLC, gave the title compound (12.5 mg, 28% yield), Purity by HPLC>90%. M+H$^+$732.2.

Example 33

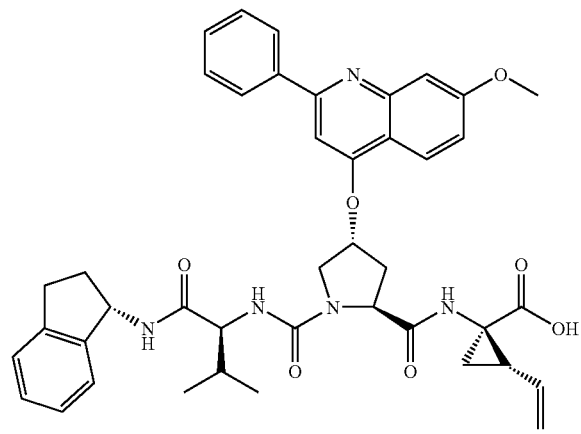

(1R,2S)-1-{[(2S,4R)-1-[(1S)-1-((1S)-Indan-1-ylcar-
bamoyl)-2-methyl-propylcarbamoyl]-4-(7-methoxy-
2-phenyl-quinolin-4-yloxy)-pyrrolidine-2-carbonyl]-
amino}-2-vinyl-cyclopropanecarboxylic acid (33)

(2S)-tert-butoxycarbonylamino-3-methylbutyric acid was attached to the resin as described for the preparation of compound 16 followed by reaction with (1S)-1-aminoindane as described for the preparation of 17 and removal of the Boc group as described for 18. The afforded compound was then reacted with the chlorocarbamate achieved from 12 as described for the preparation of 13 which, after purification by HPLC, gave the title compound (22 mg, 49% yield), Purity by HPLC>90% M+H$^+$732.2.

Example 34

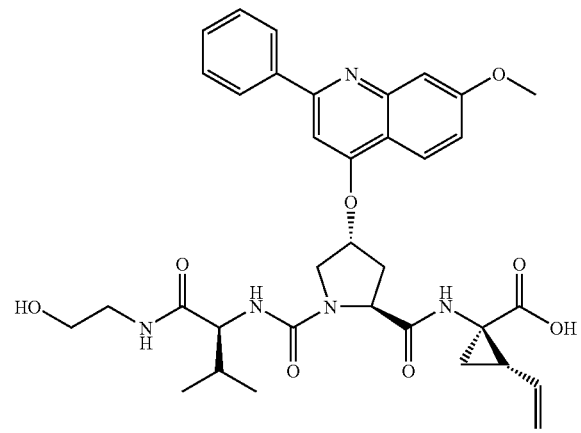

(1R,2S)-1-{[(2S,4R)-1-[(1S)-1-(2-hydroxyethylcar-
bamoyl)-2-methyl-propylcarbamoyl]-4-(7-methoxy-
2-phenyl-quinolin-4-yloxy)-pyrrolidine-2-carbonyl]-
amino}-2-vinyl-cyclopropanecarboxylic acid (34)

(2S)-tert-butoxycarbonylamino-3-methylbutyric acid was attached to the resin as described for the preparation of compound 16 followed by reaction with 2-aminoethanol as described for the preparation of 17 and removal of the Boc group as described for 18. The afforded compound was then reacted with the chlorocarbamate achieved from 12 as described for the preparation of 13 which, after purification by HPLC, gave the title compound (3 mg, 8% yield), Purity by HPLC>90% M+H$^+$660.2.

Example 35

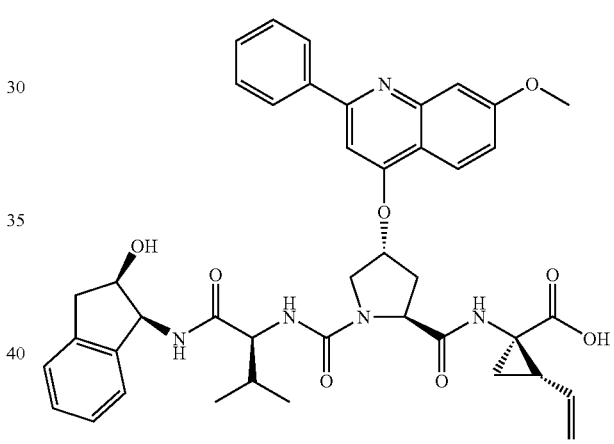

(1R,2S)-1-{[(2S,4R)-1-[(1S)-1-((1S,2R)-2-Hydroxy-
indan-1-ylcarbamoyl)-2-methyl-propylcarbamoyl]-4-
(7-methoxy-2-phenyl-quinolin-4-yloxy)-pyrrolidine-
2-carbonyl]-amino}-2-vinyl-cyclopropanecarboxylic
acid (35)

(2S)-tert-butoxycarbonylamino-3-methylbutyric acid was attached to the resin as described for the preparation of compound 16 followed by reaction with (1S,2R)-1-amino-2-indanol as described for the preparation of 17 and removal of the Boc group as described for 18. The afforded compound was then reacted with the chlorocarbamate achieved from 12 as described for the preparation of 13 which, after purification by HPLC, gave the title compound (10 mg, 22% yield), Purity by HPLC >90% M+H$^+$748.2.

Example 36

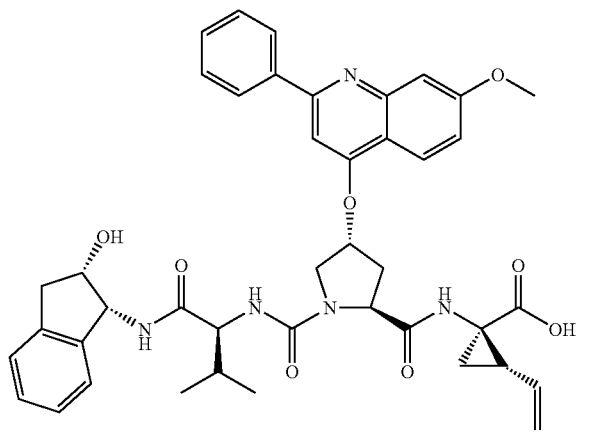

(1R,2S)-1-{[(2S,4R)-1-[(1S)-1-((1R,2S)-2-Hydroxy-indan-1-ylcarbamoyl)-2-methyl-propylcarbamoyl]-4-(7-methoxy-2-phenyl-quinolin-4-yloxy)-pyrrolidine-2-carbonyl]-amino}-2-vinyl-cyclopropanecarboxylic acid (36)

(2S)-tert-butoxycarbonylamino-3-methylbutyric acid was attached to the resin as described for the preparation of compound 16 followed by reaction with (1R,2S)-1-amino-2-indanol as described for the preparation of 17 and removal of the Boc group as described for 18. The afforded compound was then reacted with the chlorocarbamate achieved from 12 as described for the preparation of 13 which, after purification by HPLC, gave the title compound (11 mg, 24% yield), Purity by HPLC >75% M+H$^+$748.

Example 37

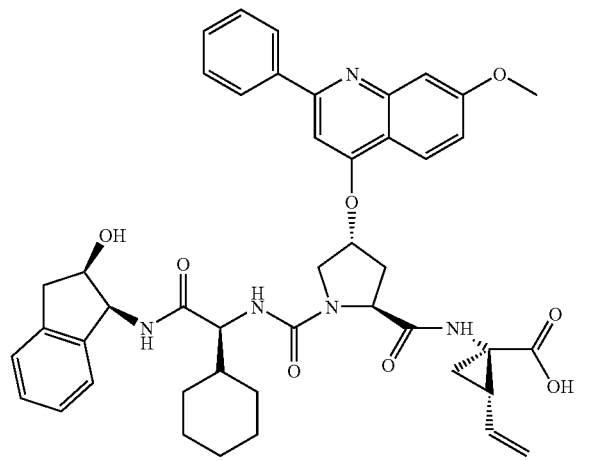

(1R,2S)-1-{[(2S,4R)-{[Cyclohexyl-(S)-((1S,2R)-2-hydroxy-indan-1-ylcarbamoyl)-methyl]-carbamoyl}-4-(7-methoxy-2-phenyl-quinolin-4-yloxy)-pyrrolidine-2-carbonyl]-amino}-2-vinyl-cyclopropanecarboxylic acid (37)

(2S)-tert.butoxycarbonylamino-cyclohexylacetic acid was attached to the resin as described for the preparation of compound 16 followed by reaction with (1S,2R)-1-amino-2-indanol as described for the preparation of 17 and removal of the Boc group as described for 18. The afforded compound was then reacted with the chlorocarbamate achieved from 12 as described for the preparation of 13 which, after purification by HPLC, gave the title compound (7.5 mg, 16% yield), Purity by HPLC >95% M+H$^+$788.3.

Example 38

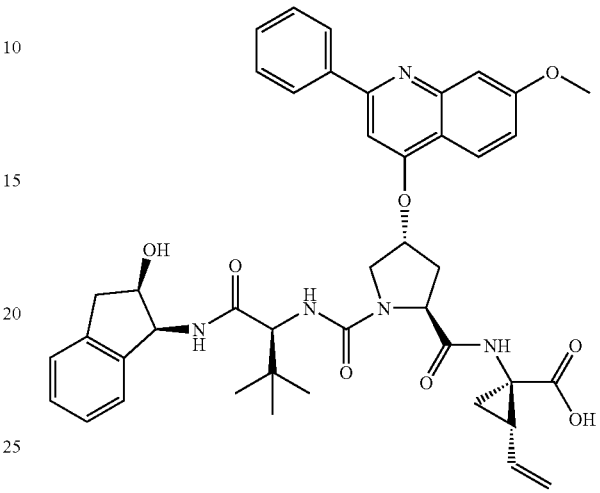

(1R,2S)-1-{[(2S,4R)-1-[(1S)-1-((1S,2R)-2-Hydroxy-indan-1-ylcarbamoyl)-2,2-dimethyl-propylcarbamoyl-4-(7-methoxy-2-phenyl-quinolin-4-yloxy)-pyrrolidine-2-carbonyl]-amino}-2-vinyl-cyclopropanecarboxylic acid (38)

(2S)-tert-butoxycarbonylamino-3,3-dimethylbutyric acid was attached to the resin as described for the preparation of compound 16 followed by reaction with (1S,2R)-1-amino-2-indanol as described for the preparation of 17 and removal of the Boc group as described for 18. The afforded compound was then reacted with the chlorocarbamate achieved from 12 as described for the preparation of 13 which, after purification by HPLC, gave the title compound (12 mg, 26% yield), Purity by HPLC >95% M+H$^+$762.3.

Example 39

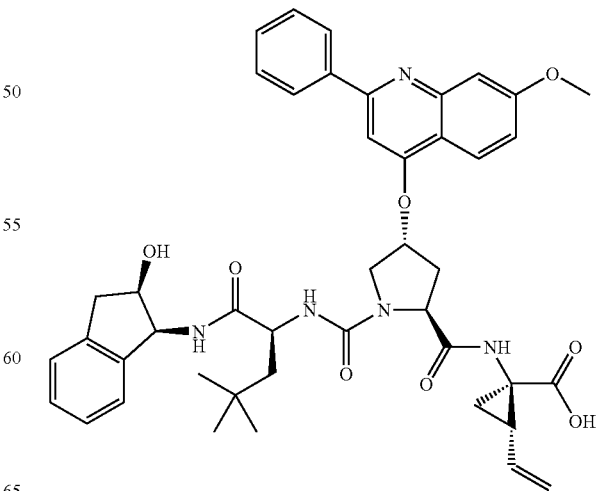

(1R,2S)-{[(2S,4R)-1-[(1S)-1-((1S,2R)-2-Hydroxy-indan-1-ylcarbamoyl)-3,3-dimethyl-butylcarbamoyl]-4-(7-methoxy-2-phenyl-quinolin-4-yloxy)-pyrrolidine-2-carbonyl]-amino}-2-vinyl-cyclopropanecarboxylic acid (39)

(2S)-tert-butoxycarbonylamino-4,4-dimethylpentanoic acid was attached to the resin as described for the preparation of compound 16 followed by reaction with (1S,2R)-1-amino-2-indanol as described for the preparation of 17 and removal of the Boc group as described for 18. The afforded compound was then reacted with the chlorocarbamate achieved from 12 as described for the preparation of 13 which, after purification by HPLC, gave the title compound (14.2 mg, 30% yield), Purity by HPLC >95% M+H⁺776.3.

Example 40

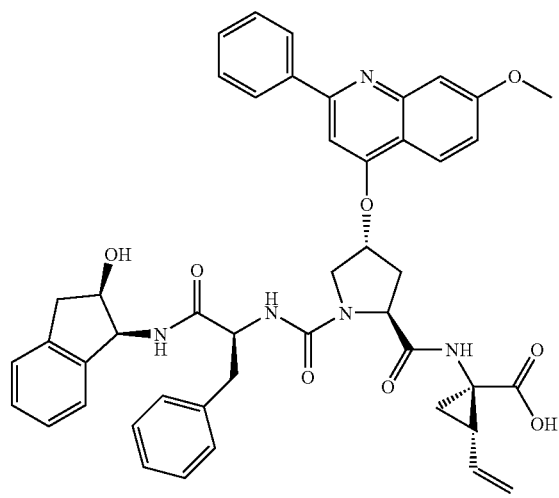

(1R,2S)-1-{[(2S,4R)-1-[(1S)-1-((1S,2R)-2-Hydroxy-indan-1-ylcarbamoyl)-2-phenyl-ethylcarbamoyl]-4-(7-methoxy-2-phenyl-quinolin-4-yloxy)-pyrrolidine-2-carbonyl]-amino}-2-vinyl-cyclopropanecarboxylic acid (40)

(2S)-tert-butoxycarbonylamino-3-phenylpropanoic acid was attached to the resin as described for the preparation of compound 16 followed by reaction with (1S,2R)-1-amino-2-indanol as described for the preparation of 17 and removal of the Boc group as described for 18. The afforded compound was then reacted with the chlorocarbamate achieved from 12 as described for the preparation of 13 which, after purification by HPLC, gave the title compound (2.4 mg, 5% yield), Purity by HPLC >95% M+H⁺796.2.

Example 41

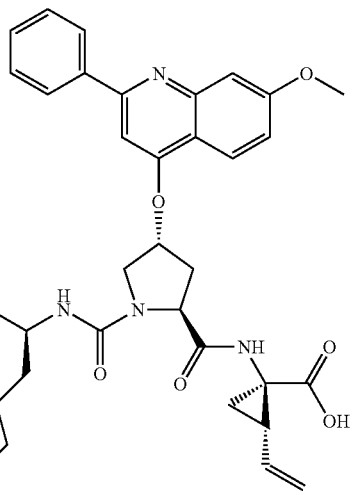

(1R,2S)-1-{[(2S,4R)-1-[(1S)-2-Cyclohexyl-1-((1S,2R)-2-hydroxy-indan-1-ylcarbamoyl)-ethylcarbamoyl]-4-(7-methoxy-2-phenyl-quinolin-4-yloxy)-pyrrolidine-2-carbonyl]-amino}-2-vinyl-cyclopropanecarboxylic acid (41)

(2S)-tert-Butoxycarbonylamino-3-cyclohexylpropanoic acid was attached to the resin as described for the preparation of compound 16 followed by reaction with (1S,2R)-1-amino-2-indanol as described for the preparation of 17 and removal of the Boc group as described for 18. The afforded compound was then reacted with the chlorocarbamate achieved from 12 as described for the preparation of 13 which, after purification by HPLC, gave the title compound (12.3 mg, 25% yield), Purity by HPLC >95% M+H⁺802.3.

Example 42

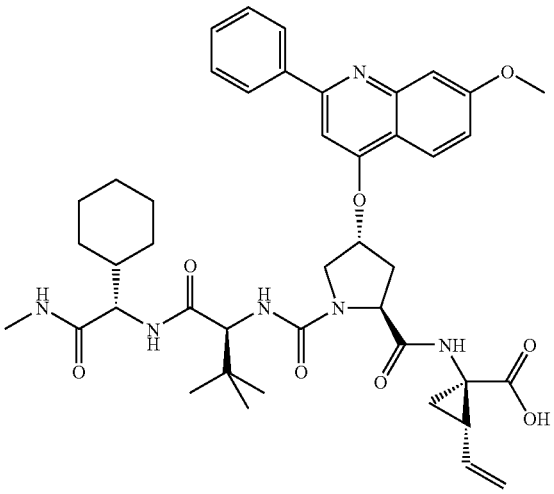

(1R,2S)-1-{[(2S,4R)-1-{(1S)-1-[(S)-(Cyclohexyl-methylcarbamoyl-methyl)-carbamoyl]-2,2-dimethyl-propylcarbamoyl)-4-(7-methoxy-2-phenyl-quinolin-4-yloxy)-pyrrolidine-2-carbonyl]-amino}-2-vinyl-cyclopropanecarboxylic acid (42)

Compound 12 was treated as described for the preparation of 13 but with the use of 21 instead of 2-amino-N-(2-hydroxy-indan-1-yl)-3,3-dimethyl-butyramide followed by ester hydrolysis as described for the preparation of compound 14 which, after purification by HPLC, gave the title compound (8.6 mg, 18% yield). Purity by HPLC >95%. M+H⁺783.3.

Example 43

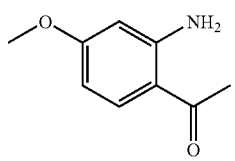

1-(2-Amino-4-methoxyphenyl)ethanone (43)

m-Anisidine (10.0 g, 82 mmol) was dissolved in CH₂Cl₂ (50 mL), and the solution was cooled to −50° C. BCl₃ (1 M in CH₂Cl₂, 82 mL, 82 mmol) was added slowly during 20 min, after which the mixture was stirred at −50° C. for 30 min, followed by sequential addition of AcCl (6.0 mL, 84 mmol) and AlCl₃ (11 g, 82 mmol). The mixture was stirred at −50° C. for 1 h and was then allowed to assume rt. After stirring at rt overnight, the solution was heated at 40° C. for 4 h, after which the mixture was poured over ice. The aqueous mixture was made alkaline with 10% NaOH (w/v) and extracted with EtOAc (4×200 mL). The combined organic phases were washed with brine, dried (MgSO₄), and evaporated to give a black solid, which was purified by flash column chromatography (ether/CH₂Cl₂ 20:80). The resulting solid was recrystallized from ether/hexane to give compound 93 as shiny tan leaflets (5.6 g, 42%).

Example 44

N-(tert-Butyl)-N'-isopropylthiourea (44)

To a solution of tert-butylisothiocyanate (5.0 mL, 39 mmol) in CH₂Cl₂ (200 mL) were added isopropylamine (4.0 mL, 47 mmol) and diisopropylethylamine (DIEA) (6.8 mL, 39 mmol), and the mixture was stirred at rt for 2 h. The reaction mixture was diluted with EtOAc, washed with 10% citric acid (2×), saturated NaHCO₃ (2×), H₂O (2×), and brine (1×). The organic layer was dried (MgSO₄) and evaporated to yield compound 94 (3.3 g, 52%) as a white solid which was used without further purification.

Example 45

N-Isopropylthiourea (45)

Compound 44 (3.3 g, 20 mmol) was dissolved in conc. HCl (45 mL) and the solution was refluxed for 40 min. The mixture was allowed to cool to rt and then cooled in an ice bath and basified to pH 9.5 with solid and saturated NaHCO₃, after which the product was extracted into EtOAc (3×). The combined organic phases were washed with H₂O (2×) and brine (1×), dried (MgSO₄), and evaporated to yield crude compound 95 (2.1 g, 90%) which was used without further purification.

Example 46

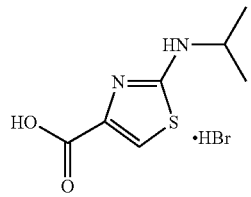

2-(Isopropylamino)-1,3-thiazole-4-carboxylic acid hydrobromide (46)

A suspension of compound 45 (2.1 g, 18 mmol) and 3-bromopyruvic acid (3.0 g, 18 mmol) in dioxane (180 mL) was heated to 80° C. Upon reaching 80° C. the mixture became clear, and soon thereafter the product started to precipitate as a white solid. After 2 h of heating, the reaction mixture was cooled to rt and the precipitate was filtered off and collected. This yielded pure compound 46 (4.4 g, 94%).

Example 47

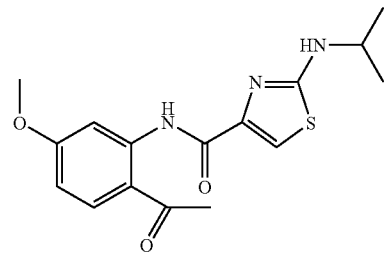

N-(2-Acetyl-5-methoxyphenyl)-2-(isopropylamino)-1,3-thiazole-4-carboxamide (47)

A mixture of compound 46 (4.4 g, 16.5 mmol) and the aniline derivative 93 (2.75 g, 16.5 mmol) in pyridine (140 mL) was cooled to −30° C. (upon cooling, the clear solution became partially a suspension). POCl₃ (3.3 mL, 35 mmol) was added slowly over a 5 min period. The mixture was stirred at −30° C. for 1 h, and was then allowed to assume rt. After stirring at rt for 1.5 h the reaction mixture was poured over ice, and the pH was adjusted to about 9-10 using solid and saturated NaHCO₃. The crude product was extracted into CH₂Cl₂ (3×) and the combined organic phases were dried (MgSO₄) and evaporated. The crude dark-beige solid was purified by flash column chromatography (hexane/EtOAc 55:45) to give compound 47 (5.6 g, 76%) as a pale yellow solid.

Example 48

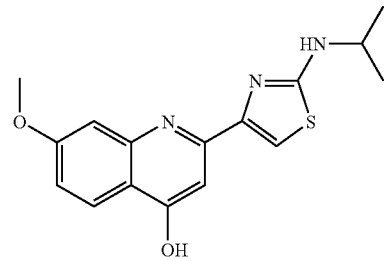

2-[2-(Isopropylamino)-1,3-thiazol-4-yl]-7-methoxyquinolin-4-ol (48)

A solution of t.BuOK (2.42 g, 21 mmol) in anhydrous t.BuOH (40 mL) was heated to reflux. Compound 47 (1.8 g, 5.4 mmol) was added portion-wise over a 5 min period, and the dark red solution formed was stirred at reflux for an additional 20 min. The mixture was cooled to rt, and HCl (4 M in dioxane, 8.0 mL, 32 mmol) was added, after which the reaction mixture was concentrated under vacuum. In order to assure that all of the HCl and dioxane were removed, the crude product was re-dissolved in $CH_2Cl_2$ twice and thoroughly evaporated to obtain the slightly impure HCl salt of compound 98 (1.62 g) as a brown solid. The product was dissolved in $CH_2Cl_2$ and washed with saturated $NaHCO_3$, after which the aqueous phase was extracted several times with $CH_2Cl_2$. The combined organic phases were dried ($MgSO_4$) and evaporated to give the title compound (1.38 g, 81%) as a light brown solid (>95% pure according to HPLC tests). $^1$H-NMR (MeOH-$d_4$, 400 MHz): δ 1.30 (d, J=6.0 Hz, 6H), 3.93 (s, 3H), 3.95-4.07 (m, 1H), 6.73 (s, 1H), 6.99 (dd, J=2.4, 9.2 Hz, 1H), 7.26 (d, J=2.4 Hz, 1H), 7.37 (s, 1H), 8.10 (d, J=9.2 Hz, 1H).

Example 49

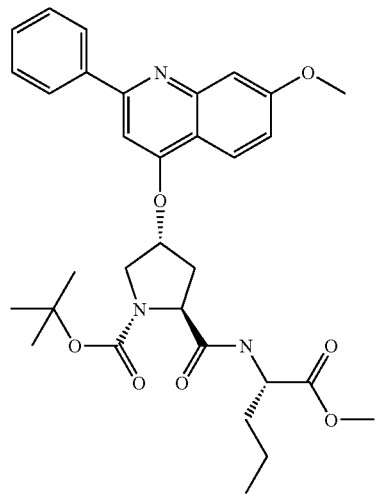

(1S)-1-{[(2S,4R)-2-(1-Methoxycarbonyl-butylcarbamoyl)-4-(7-methoxy-2-phenyl-quinolin-4-yloxy)]-pyrrolidine}-carboxylic acid tert-butyl ester (49)

Reaction of 10 with Nva-OMe hydrochloride according to the method described in example 11 provided the title compound. Purity >95% by HPLC, M+H$^+$578.24.

Example 50

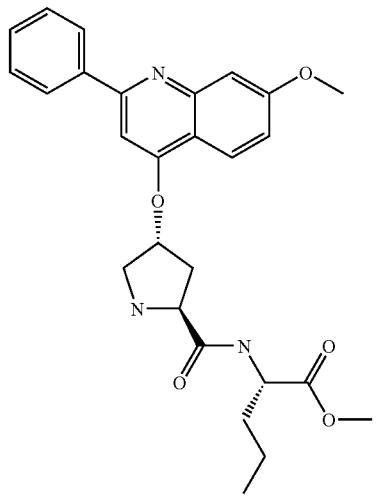

(1S)-1-{[(2S,4R)-2-[4-(7-Methoxy-2-phenyl-quinolin-4-yloxy)-pyrrolidine-2-carbonyl]-amino]pentanoic acid methyl ester (50)

Compound 49 was kept in TFA-DCM 1:2 (3 mL) at RT for 60 min. Toluene (3 mL) was added. The sample was co-evaporated to dryness. Purity by HPLC>95%. M+H$^+$478.21.

Example 51

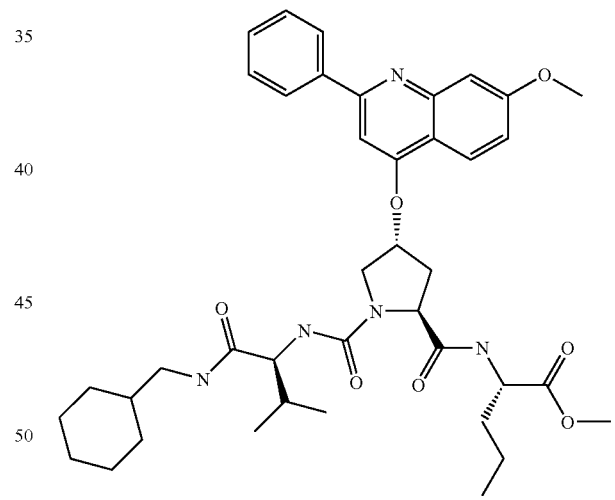

(1S)-2-[(2S,4R)-1-[(1S)-1-(Cyclohexylmethyl-carbamoyl)-2-methyl-propylcarbamoyl]-4-(7-methoxy-2-phenyl-quinolin-4-yloxy)-pyrrolidine-2-carbonyl]-amino]-pentanoic acid methyl ester (51)

To a solution of 50 (0.1 mmol) in THF (4 mL), cooled to 0° C., was added a large excess of NaHCO$_3$ (s) and a solution of phosgene in toluene (0.2 mmol, 21 μL). After 10 min of agitation the slurry was filtered and concentrated to dryness. The solid was redissolved in dichloromethane and a large excess of NaHCO$_3$ (s) and 2-amino-N-cyclohexylmethyl-3-methyl-butyramide, described in example 23, (0.15 mmol) was added. The slurry was agitated 30 hrs at RT. The slurry was filtered, concentrated and subjected to silica column chromatography (gradient elution from 100% DCM to MeOH/DCM 2:98) to give the title compound (30 mg, 0.042 mmol). Purity by HPLC>95%. M+H⁺716.40.

Example 52

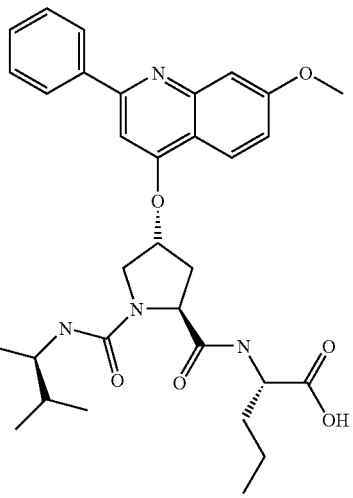

(1S)-2-[(2S,4R)-1-[[(1S)-1-(Cyclohexylmethyl-carbamoyl)-2-methyl-propylcarbamoyl]-4-(7-methoxy-2-phenyl-quinolin-4-yloxy)-pyrrolidine-2-carbonyl]-amino}-pentanoic acid (52)

To a solution of 51 (26 mg, 0.036 mmol) in THF-MeOH 2:3 (2 mL) was added 1M LiOH 1.5 equiv. The solution was kept at 60° C. for 60 min. After cooling to RT, HOAc was added followed by toluene (2 mL) and then concentrated to dryness to give the title compound (25 mg, 0.035 mmol). Purity >95% by HPLC M+H⁺702.34.

Example 53

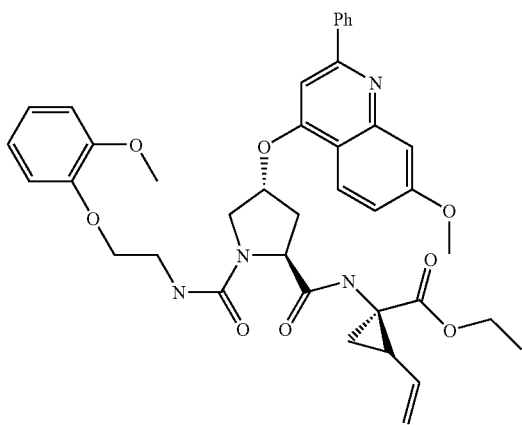

(1R,2S)-1-{[(2S,4R)-1-[2-(2-Methoxy-phenoxy)-ethylcarbamoyl]-4-(7-methoxy-2-phenyl-quinolin-4-yloxy)-pyrrolidine-2-carbonyl]-amino}-2-vinyl-cyclopropanecarboxylic acid ethyl ester (53)

To a solution of 12 (0.06 mmol) in THF (2 mL), was added a large excess of NaHCO₃ (s) and a solution of phosgene in toluene (0.078 mmol). After 10 min of agitation the slurry was filtered and concentrated to dryness. The solid was redissolved in dichloromethane and a large excess of NaHCO₃ (s) and 2-(2-methoxy-phenoxy)-ethylamine (15 mg, 0.09 mmol) was added. The slurry was agitated for 30 hrs at RT. The slurry was filtered, concentrated to dryness, redissolved in MeOH and subjected HPLC purification to give the title compound (10.6 mg, 0.015 mmol). Purity by HPLC >95%. M+H⁺695.17.

Example 54

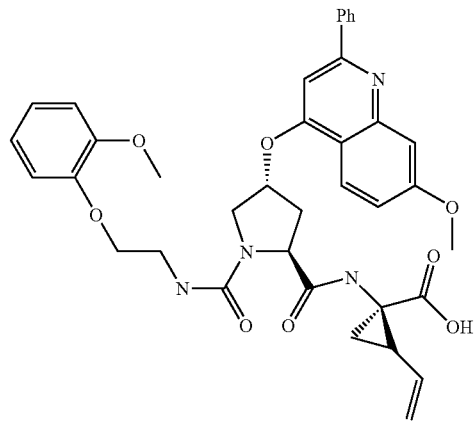

(1R,2S)-1-[(2S,4R)-1-[2-(2-Methoxy-phenoxy)-ethylcarbamoyl]-4-(7-methoxy-2-phenyl-quinolin-4-yloxy)-pyrrolidine-2-carbonyl]-amino}-2-vinyl-cyclopropanecarboxylic acid (54)

To a solution of 53 (10.6 mg, 0.0153 mmol) in THF-MeOH 2:3 (2 mL) was added 1M LiOH 10 equiv. The solution was kept at 50° C. for 60 min. After cooling to RT, HOAc 25 equiv. was added followed by toluene (2 mL) and then concentrated to dryness. The residue was taken up in ethyl acetate, filtered and concentrated to dryness to give the title compound (9.4 mg, 0.014 mmol). Purity >95% by HPLC M+H⁺667.14.

Example 55

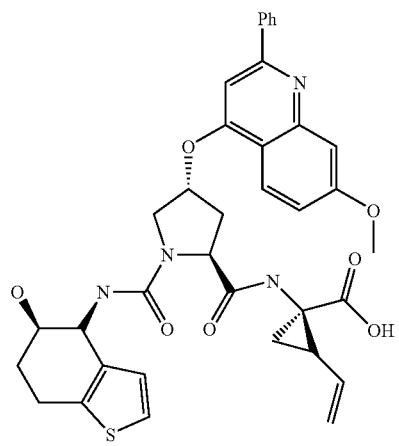

(1R,2S)-1-{[(2S,4R)-1-((1S,2R)-5-Hydroxy-4,5,6,7-tetrahydro-benzo[b]thiophen-4-yl-carbamoyl))-4-(7-methoxy-2-phenyl-quinolin-4-yloxy)-pyrrolidine-2-carbonyl]-amino}-2-vinyl-cyclopropanecarboxylic acid (55)

The procedure described in example 53 was followed but with the use of 2-amino-4,5,6,7-tetrahydro-benzo[b]

thiophen-5-ol instead of 2-(2-methoxy-phenoxy)-ethylamine, followed by hydrolysis of the ethyl ester as described in example 54 which gave the title compound (7.5 mg, 0.011 mmol). Purity >95% by HPLC M+H⁺669.

Example 56

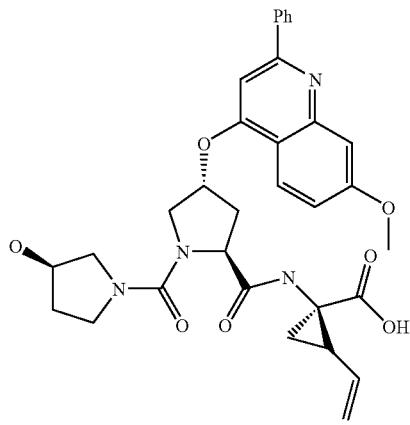

(1R,2S)-1-{[(2S,4R)-1-[(3R)-3-Hydroxy-pyrrolidine-1-carbonyl)]-4-(7-methoxy-2-phenyl-quinolin-4yloxy)-pyrrolidine-2-carbonyl]-amino}-2-vinyl-cyclopropanecarboxylic acid (56)

The procedure described in example 53 was followed but with the use of (R)-3-pyrrolidinol instead of 2-(2-methoxyphenoxy)-ethylamine, followed by hydrolysis of the ethyl ester as described in example 54 which gave the title compound (4 mg, 0.007 mmol). Purity >95% by HPLC M+H⁺ 587.1.

Example 57

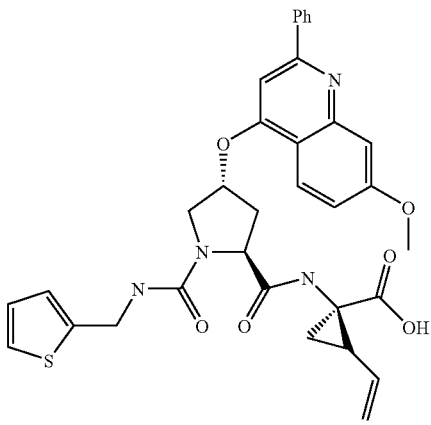

(1R,2S)-1-{[(2S,4R)-4-(7-Methoxy-2-phenyl-quinolin-4-yloxy)-1-[(thiophen-2-yl-methyl)-carbamoyl]-pyrrolidine-2-carbonyl-amino)-2-vinyl-cyclopropanecarboxylic acid (57)

The procedure described in example 53 was followed but with the use of thiophene-2-methylamine instead of 2-(2-methoxy-phenoxy)-ethylamine, followed by hydrolysis of the ethyl ester as described in example 54 which gave the title compound (8 mg, 0.013 mmol). Purity >95% by HPLC M+H⁺613.08.

Example 58

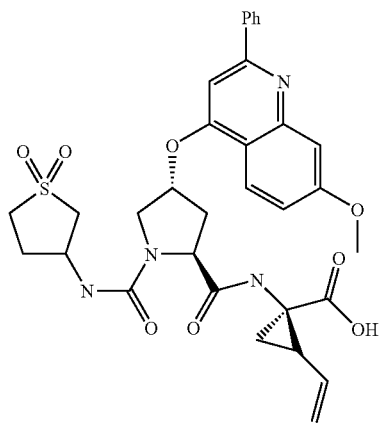

(1R,2S)-1-{[(2S,4R)-1[(1,1-Dioxo-tetrahydro-1-$\lambda^6$-thiophen-3-yl-carbamoyl)-4-(7-methoxy-2-phenyl-quinolin-4-yloxy)-pyrrolidine-2-carbonyl]-amino}-2-vinyl-cyclopropanecarboxylic acid (58)

The procedure described in example 53 was followed but with the use of 3-aminotetrahydro-1H-1$\lambda^6$-thiophene-1,1-dione instead of 2-(2-methoxy-phenoxy)-ethylamine, followed by hydrolysis of the ethyl ester as described in example 54 which gave the title compound (13 mg, 0.02 mmol). Purity >95% by HPLC M+H⁺635.05.

Example 59

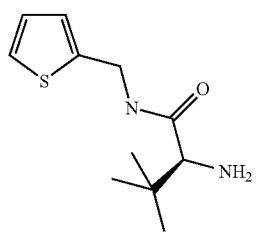

2-Amino-3,3-dimethyl-N-thiophen-2-yl-methyl-butyramide (59)

The title compound was prepared as described in example 17 but with the use of thiophene-2-methylamine instead of aminoindanole followed by removal of the Boc group as described in example 18.

Example 60

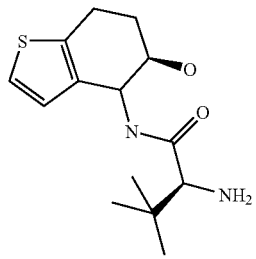

2-Amino-N-(6-hydroxy-4,5,6,7-tetrahydro-benzo[b]thiophen-5-yl)-3,3-dimethyl-butyramide (60)

The title compound was prepared as described in example 17 but with the use of 2-amino-4,5,6,7-tetrahydro-benzo[b]thiophen-5-ol instead of aminoindanole followed by removal of the Boc group as described in example 18.

Example 61

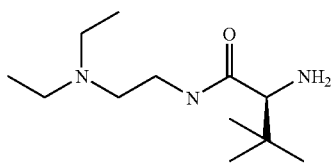

2-Amino-N-(2-diethylamino-ethyl)-3,3-dimethyl-butyramide (61)

The title compound was prepared as described in example 17 but with the use of N,N-diethylethylenediamine instead of aminoindanole followed by removal of the Boc group as described in example 18.

Example 62

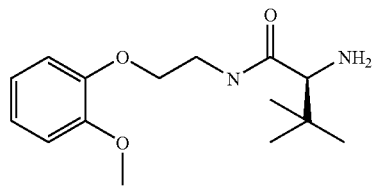

2-Amino-N-[2-(2-methoxy-phenoxy)-ethyl]-3,3-dimethyl-butyramide (62)

The title compound was prepared as described in example 17 but with the use of 2-methoxyphenoxyethylamine instead of aminoindanole followed by removal of the Boc group as described in example 18.

Example 63

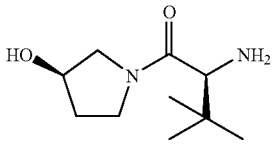

2-Amino-1-(3-hydroxy-pyrrolidin-1-yl)-3,3-dimethyl-butan-1-one (63)

The title compound was prepared as described in example 17 but with the use of (R)-3-pyrrolidinone instead of aminoindanole followed by removal of the Boc group as described in example 18.

Example 64

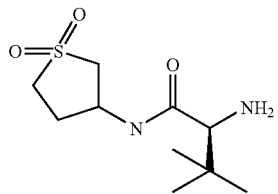

2-Amino-N-(1,1-dioxo-tetrahydro-1-$\lambda^6$-thiophen-3-yl)-3,3-dimethyl-butyramide (64)

The title compound was prepared as described in example 17 but with the use of 2-methoxyphenoxyethylamine instead of aminoindanole followed by removal of the Boc group as described in example 18.

Example 65

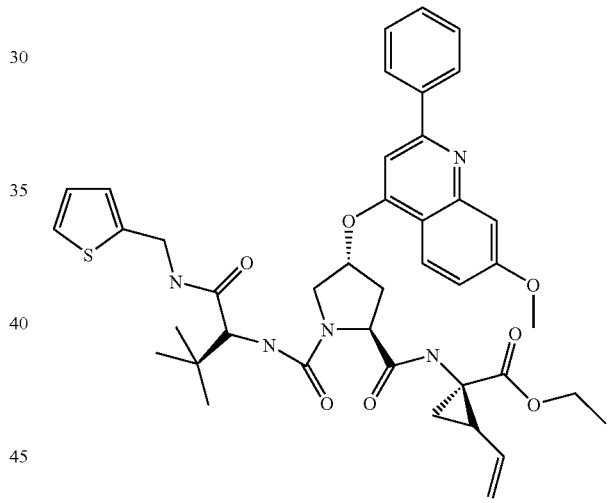

(1R,2S)-1-{[(2S,4R)-1-[(1S)-1-(2,2-Dimethyl-1-[(thiophen-2-yl-methyl)-carbamoyl]-propylcarbamoyl}-4-(7-meth oxy-2-phenyl-quinolin-4-yloxy)-pyrrolidine-2-carbonyl]-amino-2-vinyl-cyclopropanecarboxylic acid ethyl ester (65)

To a solution of 12 (0.06 mmol) in THF (2 mL), was added a large excess of NaHCO$_3$ (s) and a solution of phosgene in toluene (0.078 mmol). After 10 min of agitation the slurry was filtered and concentrated to dryness. The solid was redissolved in dichloromethane and a large excess of NaHCO$_3$ (s) and 59 (0.09 mmol) was added.

The slurry was agitated for 30 hrs at RT. The slurry was filtered, concentrated to dryness, re-dissolved in MeOH and subjected HPLC purification to give the title compound (15.5 mg, 0.02 mmol). Purity by HPLC>95%. M+H$^+$754.2.

Example 66

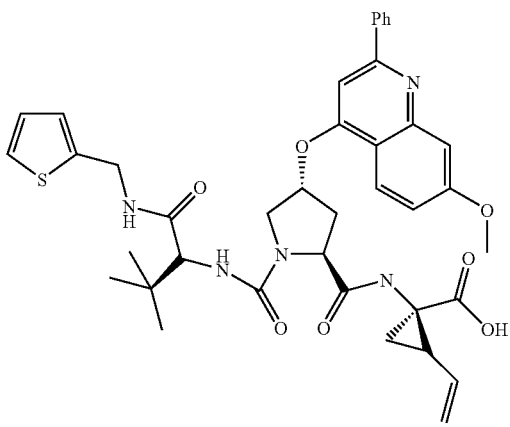

(1R,2S)-1-{[(2S,4R)-1-[(1S)-1-(2,2-Dimethyl-1-[(thiophen-2-ylmethyl)-carbamoyl)-propylcarbamoyl}-4-(7-methoxy-2-phenyl-quinolin-4-yloxy)-pyrrolidine-2-carbonyl]-amino]-2-vinyl-cyclopropanecarboxylic acid (66)

To a solution of 65 (14 mg, 0.017 mmol) in THF-MeOH 2:3 (2 mL) was added 1M LiOH 10 equiv. The solution was kept at 50° C. for 60 min. After cooling to RT, HOAc 20 equiv. was added followed by toluene (2 mL) and then concentrated to dryness. The residue was taken up in ethyl acetate, filtered and concentrated to dryness to give the title compound (13 mg, 0.017 mmol). Purity >95% by HPLC M+H$^+$748.13.

Example 67

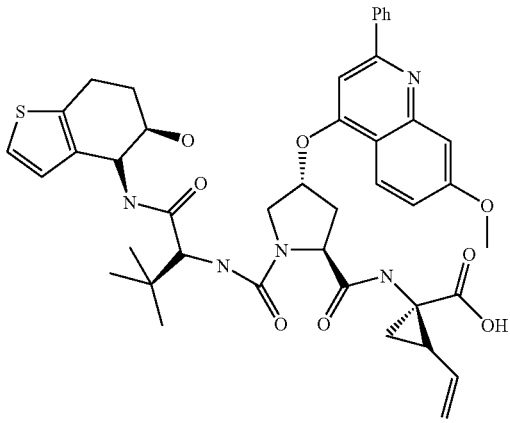

(1R,2S)-1-{((2S,4R)-(1S)-1-[(1S,2R)-1-[1-(5-Hydroxy-4,5,6,7-tetrahydro-benzo[b]thiophen-4-ylcarbamoyl)-2,2-dimethyl-propylcarbamoyl]4-(7-methoxy-2-phenyl-quinolin-4-yloxy)-pyrrolidine-2-carbonyl]-amino)-2-vinyl-cyclopropanecarboxylic acid (67)

The procedure described in example 65 was followed but with the use of 60 instead of 59, followed by hydrolysis of the ethyl ester as described in example 66 which gave the title compound (4 mg, 0.005 mmol). Purity >95% by HPLC M+H$^+$782.16.

Example 68

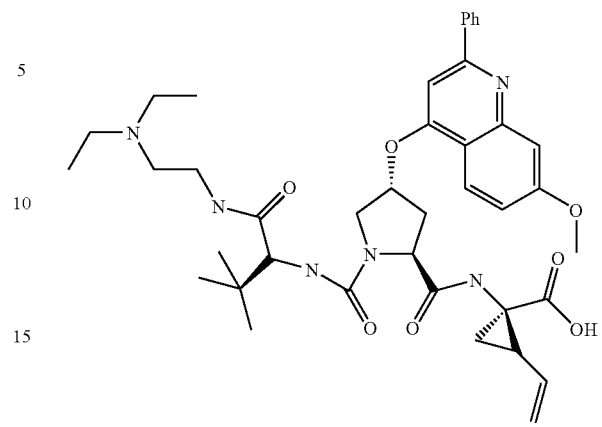

(1R,2S)-1-{[(2S,4R)-1-[(1S)-1-(2-Diethylamino-ethylcarbamoyl)-2,2-dimethyl-propylcarbamoyl]-4-(7-methoxy-2-phenyl-quinolin-4-yloxy)-pyrrolidine-2-carbonyl]-amino}-2-vinyl-cyclopropanecarboxylic acid (68)

The procedure described in example 65 was followed but with the use of 61 instead of 59, followed by hydrolysis of the ethyl ester as described in example 66 which gave the title compound (6 mg, 0.008 mmol). Purity >95% by HPLC M+H$^+$729.24.

Example 69

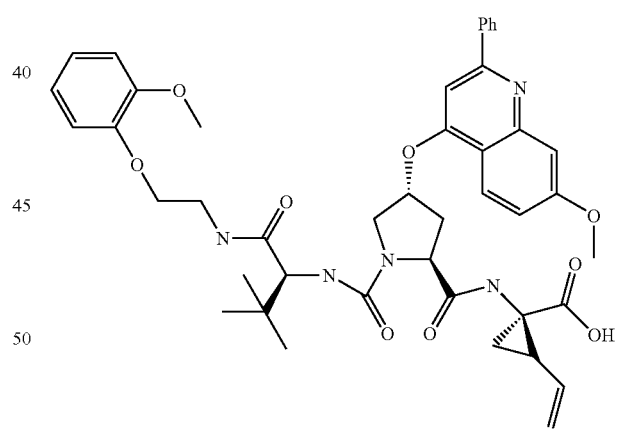

(1R,2S)-1-{[(2S,4R)-1-[(1S)-1-[2-(2-Methoxy-phenoxy)-ethylcarbamoyl]-2,2-dimethyl-propylcarbamoyl}-4-(7-methoxy-2-phenyl-quinolin-4-yloxy)-pyrrolidine-2-carbonyl]-amino}-2-vinyl-cyclopropanecarboxylic acid (69)

The procedure described in example 65 was followed but with the use of 62 instead of 59, followed by hydrolysis of the ethyl ester as described in example 66 which gave the title compound (3 mg, 0.004 mmol). Purity >95% by HPLC M+H$^+$780.19.

Example 70

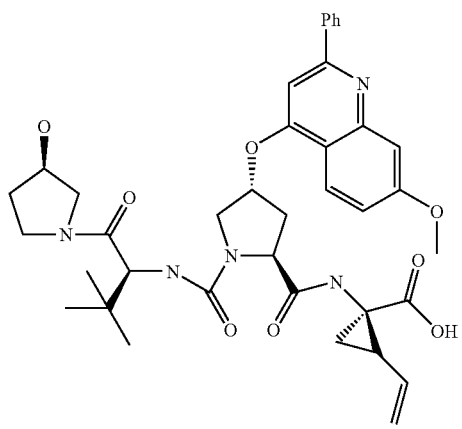

(1R,2S)-1-{[(2S,4R)-(1S)-1-[(3R)-1-(3-Hydroxy-pyrrolidine-1-carbonyl)-2,2-dimethyl-propylcarbamoyl]-4-(7-methoxy-2-phenyl-quinolin-4-yloxy)-pyrrolidine-2-carbonyl]-amino}-2-vinyl-cyclopropanecarboxylic acid (70)

The procedure described in example 65 was followed but with the use of 63 instead of 59, followed by hydrolysis of the ethyl ester as described in example 66 which gave the title compound (12.4 mg, 0.02 mmol). Purity >95% by HPLC M+H$^+$700.16.

Example 71

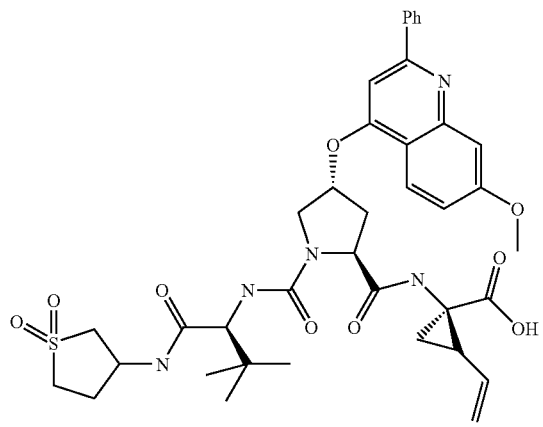

(1R,2S)-1-{[(2S,4R)-1-[(1S)-1-(1,1-Dioxo-tetrahydro-1-λ$^6$-thiophen-3-yl-carbamoyl)-2,2-dimethyl-propylcarbamoyl]-4-(7-methoxy-2-phenyl-quinolin-4-yloxy)-pyrrolidine-2-carbonyl]-amino)-2-vinyl-cyclopropanecarboxylic acid (71)

The procedure described in example 65 was followed but with the use of 64 instead of 59, followed by hydrolysis of the ethyl ester as described in example 66 which gave the title compound (13 mg, 0.014 mmol). Purity >95% by HPLC M+H$^+$748.13.

Example 72

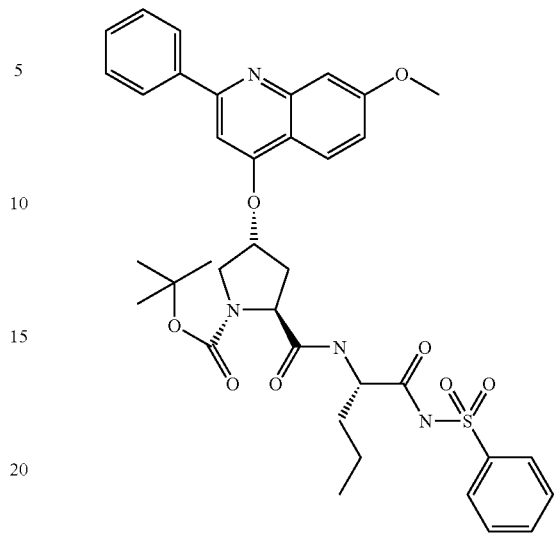

(4R)-1-(tert-butoxycarbonyl)-4-[(7-methoxy-2-phenylquinolin-4-yl)oxy]-L-prolyl-N$^1$-(phenylsulfonyl)-L-norvalinamide (72)

To a solution of 10 (60 mg, 0.13 mmol) in DMF, HATU (124 mg, 0.325 mmol), diisopropylethylamine (114 µL, 0.65 mmol) was added and agitated for 30 min at RT. A solution of 75 (0.157 mmol) in DMF was added. The slurry was agitated for 16 hrs at RT followed by concentration to dryness. The residue was taken up in DCM and washed with NaHCO$_3$ (sat.), and water. The organic layer was dried, concentrated and subjected to silica column chromatography (gradient elution from 100% DCM to 2% MeOH/DCM) to give the title compound (61 mg, 0.087 mmol). Purity >90% by HPLC. M+H$^+$703.23.

Example 73

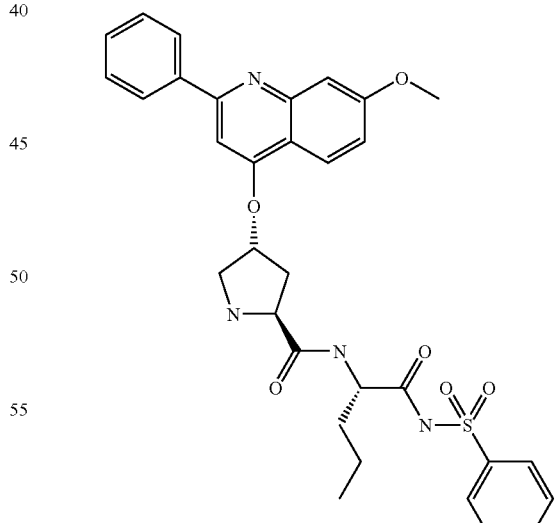

(4R)-4-[(7-methoxy-2-phenylquinolin-4-yl)oxy]-L-prolyl-N$^1$-(phenylsulfonyl)-L-norvalinamide (73)

Compound 72 was kept in DCM-TFA 2:1 (2 mL) for 2.5 hr at RT. The solution was co-evaporated with toluene to dryness. Yield 100%. M+H 603.12

Example 74

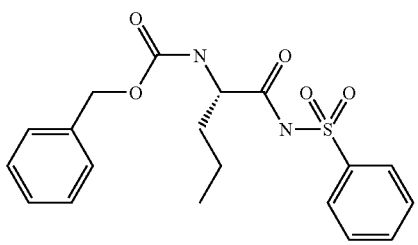

Carbamic acid,
[(1S)-1-[[(phenylsulfonyl)amino]carbonyl]butyl]-,
phenylmethyl ester (74)

To a stirred solution of Z-Nva-OH (150 mg, 0.59 mmol) in THF (6 mL), CDI (400 mg, 2.4 mmol) was added. The slurry was agitated for 30 min at RT followed by the addition of DBU (200 μL, 1.3 mmol) and a solution of benzenesulfonamide (250 mg, 1.59 mmol) in THF (2 mL). The mixture was stirred at 60° C. for 48 hrs followed by concentration to dryness. The residue was dissolved in MeOH and subjected to HPLC purification to give the title compound (118.5 mg, 0.304 mmol). Purity >95% by HPLC. M−H$^+$389.0, +Na 412.96.

Example 75

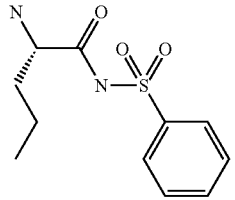

(2S)-2-Amino-N-(phenylsulphonyl)pentanamide (75)

Compound 74 was dissolved in MeOH (5 mL) followed by the addition of Pd/C and subjected to hydrogenation for 2 hrs. The slurry was filtered through celite, washed with MeOH and concentrated to dryness to give the title compound. Yield 100%. M+H$^+$257.3.

Example 76

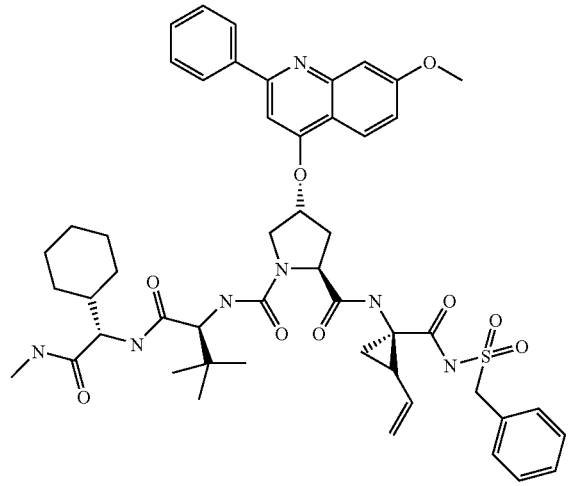

4-(7-Methoxy-2-phenyl-quinolin-4-yloxy)-pyrrolidine-1,2-dicarboxylic acid 1-({1-[(cyclohexyl-methylcarbamoyl-methyl)-carbamoyl]-2,2-dimethyl-propyl}-amide)-2-[(1-phenylmethanesulfonylaminocarbonyl-2-vinyl-cyclopropyl)-amide] (76)

To solution of 42 (8.7 mg, 0.011 mmol) in chloroform (1 ml) was added α-toluenesulfonamide (7 mg, 0.04 mmol) followed by diisopropylethylamine (21 μL, 0.12 mmol). The solution was stirred at RT for 10 min and then at −20° C. for 30 min. PyBOP (46.5 mg, 0.08 mmol) was then added as a solid. The solution was kept at −20° C. for 48 hours. The solution was then poured into aqueous NaHCO$_3$ (sat.) and washed with water. The organic layer was dried, concentrated and subjected to purification by HPLC, affording the title compound as a white solid (2.8 mg, 0.0049 mmol), Purity by HPLC>95%, M+H$^+$936.26.

Example 77

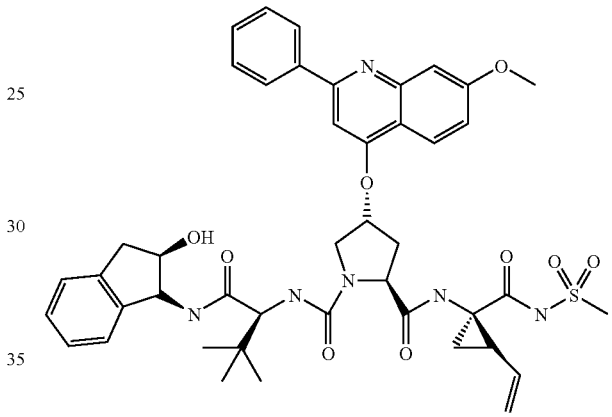

N-(2-Hydroxy-indan-1-yl)-2-[4-(6-methoxy-3-phenyl-naphthalen-1-yloxy)-2-(1-methanesulfonylaminocarbonyl-2-vinyl-cyclopropyl)-pyrrolidin-1-yl]-3,3-dimethyl-butyramide (77)

The title compound was prepared as described in example 76, using 14 as carboxylic acid starting material and methanesulfonamide instead of α-toluenesulfonamide.
Yield 13%, Purity by HPLC>95%, M+H$^+$839.16.

Example 78

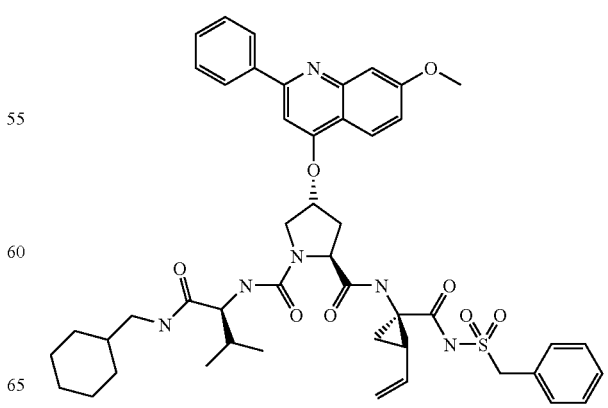

4-(7-Methoxy-2-phenyl-quinolin-4-yloxy)-pyrroli-
dine-1,2-dicarboxylic acid 1-{[1-(cyclohexylmethyl-
carbamoyl)-2-methyl-propyl]-amide} 2-[(1-phenyl-
methanesulfonylaminocarbonyl-2-vinyl-
cyclopropyl)-amide] (78)

The title compound was prepared as described in example 76, using 23 as carboxylic acid starting material. Yield 2%. Purity >95% by HPLC. M+H⁺865.28.

Example 79

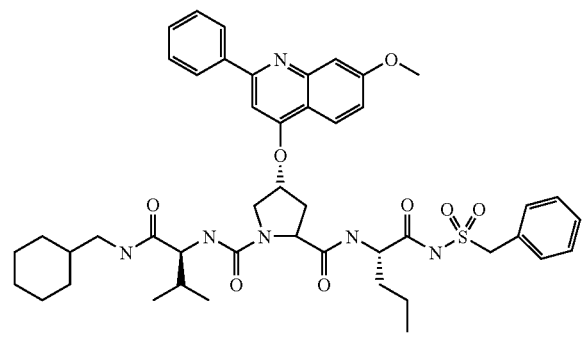

4-(7-Methoxy-2-phenyl-quinolin-4-yloxy)-pyrroli-
dine-1,2-dicarboxylic acid 1-{[1-(cyclohexylmethyl-
carbamoyl)-2-methyl-propyl]-amide} 2-[(1-phenyl-
methanesulfonylaminocarbonyl-butyl)-amide] (79)

The title compound was prepared as described in example 76, using 52 as carboxylic acid starting material. Yield 8%. Purity >95% by HPLC. M+H⁺855.28.

Example 80

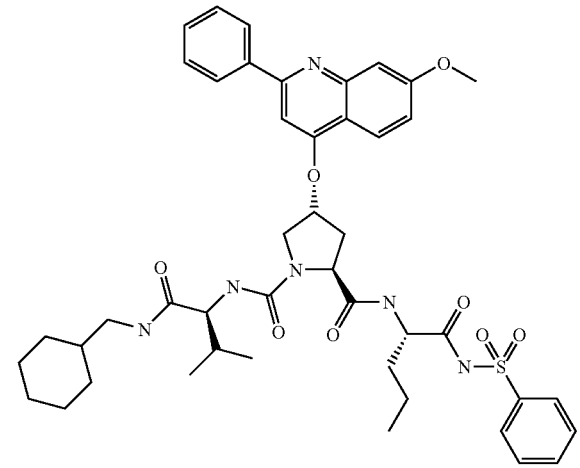

4-(7-Methoxy-2-phenyl-quinolin-4-yloxy)-pyrroli-
dine-1,2-dicarboxylic acid 2-[(1-benzenesulfony-
laminocarbonyl-butyl)-amide] 1-{[1-(cyclohexylm-
ethyl-carbamoyl)-2-methyl-propyl]-amide} (80)

The title compound was prepared as described in example 76, using 52 as carboxylic acid starting material and benzensulfonamide instead of α-toluenesulfonamide.
Yield 21.5%. Purity >95% by HPLC. M+H⁺841.28.

Example 81

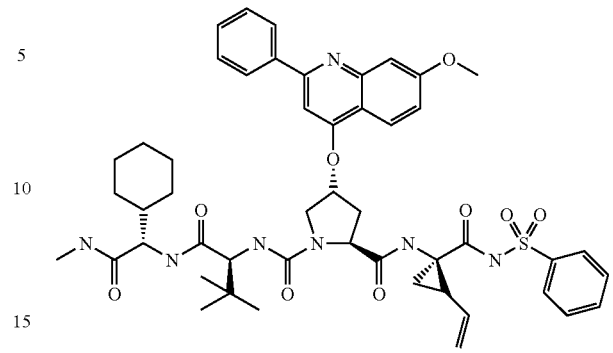

4-(7-Methoxy-2-phenyl-quinolin-4-yloxy)-pyrroli-
dine-1,2-dicarboxylic acid 2-[(1-benzenesulfony-
laminocarbonyl-2-vinyl-cyclopropyl)-amide] 1-({1-
[(cyclohexyl-methylcarbamoyl-methyl)-carbamoyl]-
2,2-dimethyl-propyl}-amide) (81)

The title compound was prepared as described in example 76, using benzenesulfonamide instead of α-toluenesulfonamide. Yield 26%. Purity by HPLC>95%, M+H⁺922.23.

Example 82

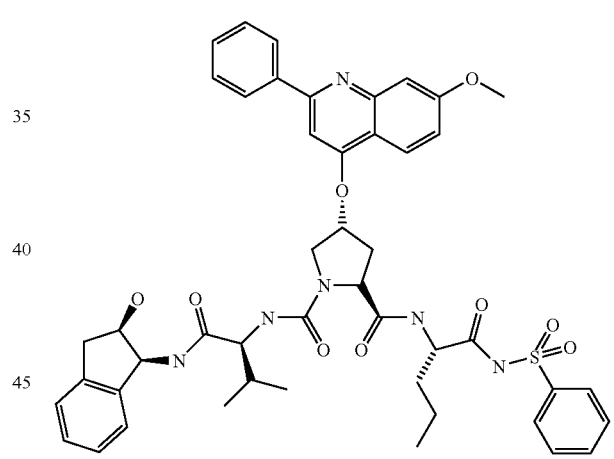

4-(7-Methoxy-2-phenyl-quinolin-4-yloxy)-pyrroli-
dine-1,2-dicarboxylic acid 2-[(1-benzenesulfony-
laminocarbonyl-butyl)-amide] 1-{[1-(2-hydroxy-
indan-1-ylcarbamoyl)-2-methyl-propyl]-amide} (82)

To a solution of 73 (24.1 mg, 0.04 mmol) in DCM (2 ml), was added a large excess of NaHCO₃ (s) and a solution of phosgene in toluene (50 μL, 0.096 mmol). After 10 min of agitation the slurry was filtered and concentrated to dryness. The solid was redissolved in DCM and a large excess of NaHCO₃ (s) and 2-amino-N-(2-hydroxy-indan-1-yl)-3-methyl-butyramide, described in example 35, (0.1 mmol) was added. The slurry was agitated for 40 hrs at RT. The slurry was filtered, concentrated and subjected to HPLC purification, to give the title compound (1.6 mg, 0.0018 mmol). Purity >95% by HPLC. M+H⁺877.21.

Example 83

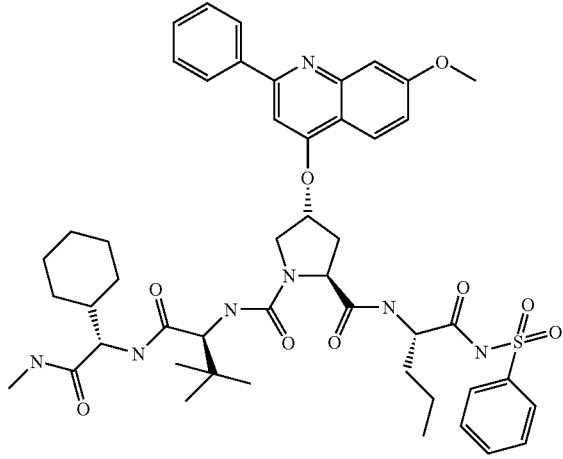

4-(7-Methoxy-2-phenyl-quinolin-4-yloxy)-pyrrolidine-1,2-dicarboxylic acid 2-[(1-benzenesulfonylaminocarbonyl-butyl)-amide] 1-({1-[(cyclohexylmethylcarbamoyl-methyl)-carbamoyl]-2,2-dimethyl-propyl}-amide) (83)

The title compound was prepared as described in example 82 but using 21 instead of 2-amino-N-(2-hydroxy-indan-1-yl)-3-methyl-butyramide. Yield 2%. Purity >95% by HPLC. M+H$^+$912.25.

Example 84

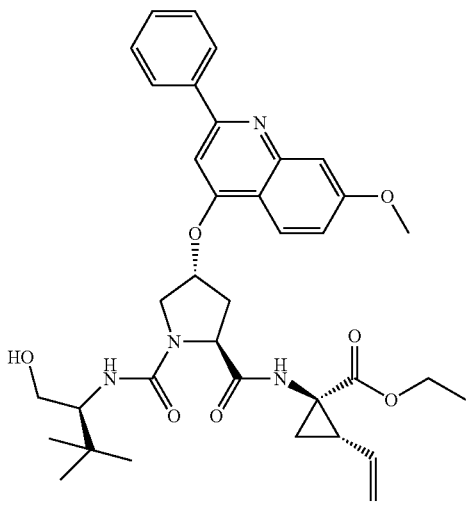

(1R,2S)-1-{[(4R,2S)1-(1-(1S)-Hydroxymethyl-2,2-dimethyl-propylcarbamoyl)-4-(7-methoxy-2-phenyl-quinolin-4-yloxy)-pyrrolidine-2-carbonyl]-amino}-2-vinyl-cyclopropanecarboxylic acid ethyl ester (84)

Treatment of compound 12 as described for the preparation 13 but with the use of (S)-tert-leucinol instead of 2-amino-N-(2-hydroxy-indan-1-yl)3,3-dimethyl-butyramide provided the title product. M+H$^+$645.2.

Example 85

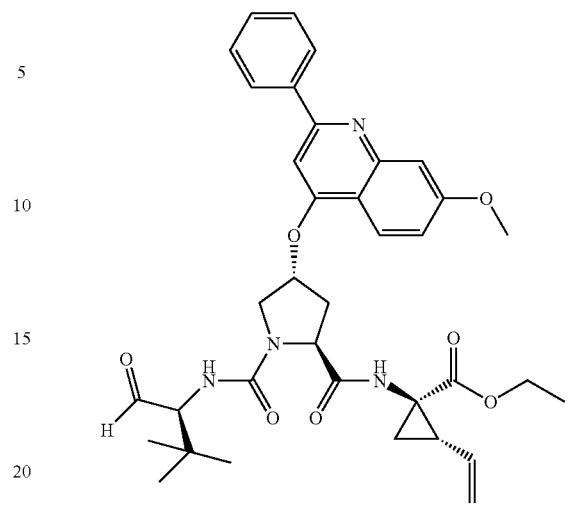

(1R,2S)-1 {[(4R,2S)1-(1-(1S)-Formyl-2,2-dimethyl-propylcarbamoyl)-4-(7-methoxy-2-phenyl-quinolin-4-yloxy)-pyrrolidine-2-carbonyl]-amino}-2-vinyl-cyclopropanecarboxylic acid ethyl ester (85)

To a stirred solution of compound 84 (64 mg) in dichloromethane Dess-Martin periodinane (80 mg) was added at ambient temperature. After 4 hrs the slurry was filtered through basic alumina and concentrated to dryness. M+H$^+$ 643.2.

Example 86

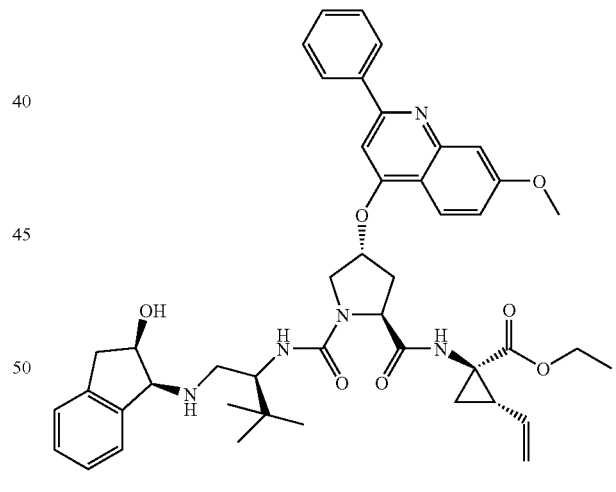

(1R,2S)-1-{[(4R,2S)1-{1-[((1S,2R)-2-Hydroxy-indan-1-ylamino)-methyl]-2,2-dimethyl-propylcarbamoyl}-4-(7-methoxy-2-phenyl-quinolin-4-yloxy)-pyrrolidine-2-carbonyl]-amino-2-vinyl-cyclopropanecarboxylic acid ethyl ester (86)

To a solution of compound 85 in THF (2 ml) and HOAc (0.5 mL) polystyrene bound cyanoborohydride (2.36 mmol/g, 100 mg) and (1S,2R)-1-aminoindan-2-ol (18 mg) was added and agitated for 4 hrs. The mixture was filtered, concentrated and purified on a prep. HPLC. Purity by HPLC>90%. M+H$^+$776.5

Example 87

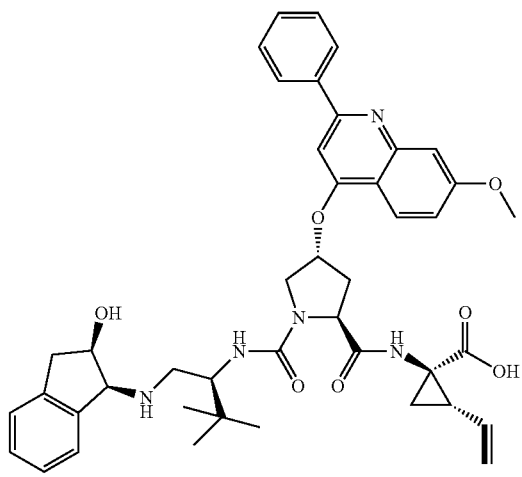

(1R,2S)-1-{[(4R,2S)1-{1-[((1S,2R)-2-Hydroxy-indan-1-yl amino)-methyl]-2,2-dimethyl-propylcarbamoyl}-4-(7-methoxy-2-phenyl-quinolin-4-yloxy)-pyrrolidine-2-carbonyl]-amino}-2-vinyl-cyclopropanecarboxylic acid (87)

To a solution of compound 86 in THF (2 mL) and MeOH (1 mL) 1N LiOH (0.2 mL) was added and the solution was kept at 60° C. for 1.5 hrs. The slurry was neutralized with 1N HCl to pH 7, concentrated and purified on a prep. HPLC giving pure product by HPLC>95%. M+H⁺748.4.

Example 88

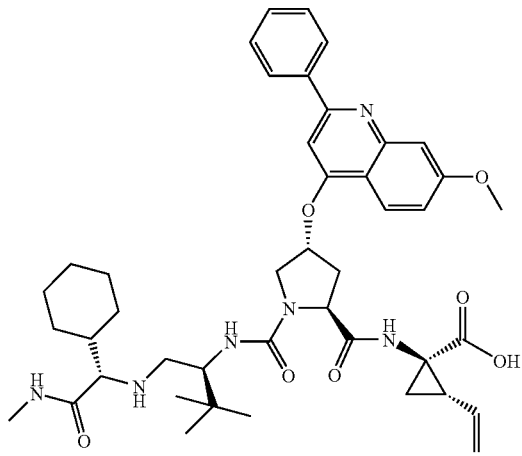

(1R,2S)-1-{[(4R,2S)1-(1-{[(1S)-(Cyclohexyl-methylcarbamoyl-methyl)-amino]-methyl}-2,2-dimethyl-propylcarbamoyl)-4-(7-methoxy-2-phenyl-quinolin-4-yloxy)-pyrrolidine-2-carbonyl]-amino)-2-vinyl-cyclopropanecarboxylic acid (B8)

Treatment of compound 85 as described for the preparation of 86 but with the use of 2-amino-2-cyclohexyl-N-methyl-acetamide (17 mg) instead of (1S,2R)-1-aminoindan-2-ol followed by hydrolysis of the ethyl ester as described in example 87 provided the title product. Purity by HPLC>95%. M+H⁺ 769.5

Example 89

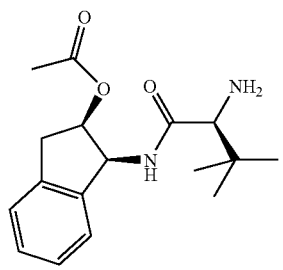

Acetic acid (1S,2R)-1-((2S)-2-amino-3,3-dimethyl-butyrylamino)-indan-2-yl ester (89)

A solution of compound 17 (4 g) was kept in pyridine-acetic anhydride 2:1 for 30 min. DCM was added and the solution was washed with citric acid (aq) and NaHCO₃ (aq). The organic layer was concentrated to dryness which gave the acetylated product >90% pure by HPLC. The afforded compound was then kept in a solution of 30% TFA in DCM for 1.5 hrs and then concentrated to dryness. Co-evaporation twice from toluene gave the title product >90% pure by HPLC.

Example 90

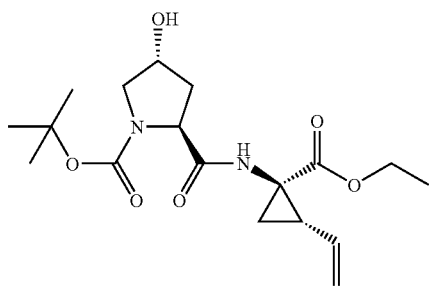

(2S,4R)-2-((1S,2R)1-Ethoxycarbonyl-2-vinyl-cyclopropylcarbamoyl)-4-hydroxy-pyrrolidine-1-carboxylic acid tert.butyl ester (90)

A solution of HATU (6 g), diisopropylethylamine (6.8 mL), (1R,2S)-1-amino-2-vinyl-cyclopropanecarboxylic acid ethyl ester (1.5 g) and BOC-L-hydroxyproline (1.6 g) in dichloromethane was stirred for 1 hrs. The mixture was extracted with DCM-NaHCO₃ (aq) dried and concentrated. HPLC purity ca 90% M+H⁺369.1.

Example 91

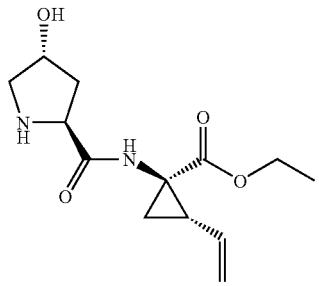

(1S,2R)-1-[(2S,4R)-(4-Hydroxy-pyrrolidine-2-carbonyl)-amino]-2-vinyl-cyclopropanecarboxylic acid ethyl ester (91)

Compound 90 was kept in 30% trifluoroacetic acid in dichloromethane and 1% MeOH for 2 hrs before it was concentrated to dryness. The residue was re-dissolved In dichloromethane and during stirring 1N NaOH was added to pH 10-11. The organic layer was separated and concentrated which gave 1.6 g of the title product. HPLC purity ca. 90% M+H⁺269.1.

Example 92

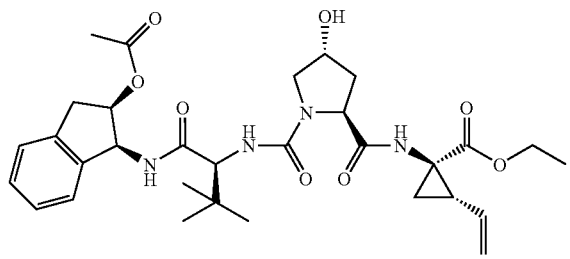

(1R,2S)-1-({(2S,4R)-1-[(1S)-1-((1S,2R)-2-Acetoxy-indan-1-ylcarbamoyl)-2,2-dimethyl-propylcarbamoyl]-4-hydroxy-pyrrolidine-2-carbonyl}-amino)-2-vinyl-cyclopropanecarboxylic acid ethyl ester (92)

To a stirred solution of compound 89 (1.81 g) in acetonitrile at 0° C. solid NaHCO₃ (800 mg) and p-nitrophenychlorocarbonate (1.2 g) was added. The slurry was taken up to ambient temperature and stirred for another 30 min. To this slurry a solution of compound 91 (1.6 g) in acetonitrile (5 mL) diisopropylethylamine (1 mL) was added. After 10 min the resulting mixture was concentrated, re-dissolved in ethyl acetate and washed with K₂CO₃ (aq) and then with 0.5 N HCl. Dried and concentrated which gave a >80% pure product by HPLC M+H⁺599.6

Example 93

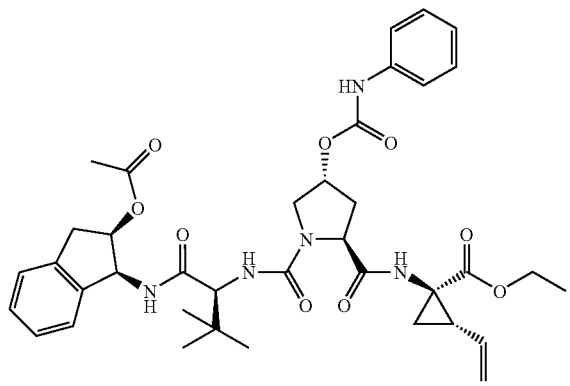

(1R,2S)-1-({(2S,4R)-1-[(1)-1-((1S,2R)-2-Acetoxy-indan-1-ylcarbamoyl)-2,2-dimethyl-propylcarbamoyl]-4-phenylcarbamoyloxy-pyrrolidine-2-carbonyl}-amino)-2-vinyl-cyclopropanecarboxylic acid ethyl ester (93)

To a stirred solution of compound 92 (20 mg) in DCM and solid K₂CO₃ (200 mg) 20% phosgene in toluene (1 mL) was added. After 6 hrs the slurry was filtered and concentrated to dryness. To this residue a mixture of aniline (30 mg) DCM (3 mL) and solid NaHCO₃ (50 mg) was added and agitated for 10 hrs. The mixture was filtered, concentrated and purified on a prep. HPLC which gave the title product, >95% pure M+H⁺ 718.6.

Example 94

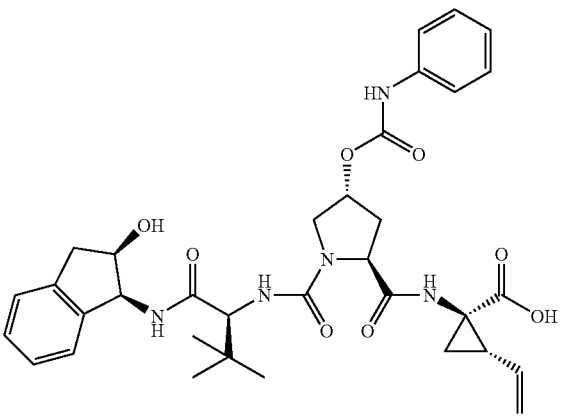

(1R,2S)-1-({(2S,4R)-1-[1-((1S,2R)-2-Hydroxy-indan-1-ylcarbamoyl)-2,2-dimethyl-propylcarbamoyl] 4phenylcarbamoyloxy-pyrrolidine-2-carbonyl}-amino)-2-vinyl-cyclopropanecarboxylic acid (94)

To a solution of compound 93 in THF-MeOH 2:1 (3 mL) was added 1N LiOH (0.2 mL). The solution was heated to 60° C. for 2 hrs. After cooling to ambient temperature acetic acid (0.5 mL) was added and the solution was concentrated to dryness. The remaining residue was purified on a prep. HPLC which gave the title product >95% pure M+H+648.5.

Example 95

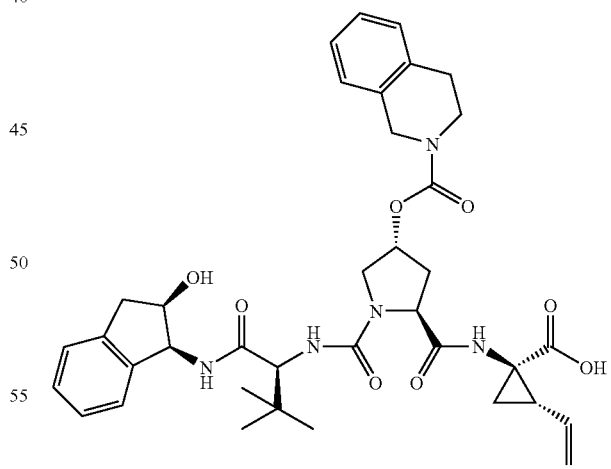

(5S,3R)-3,4-Dihydro-1H-isoquinoline-2-carboxylic acid 5-((1R,2S)-1-carboxy-2-vinyl-cyclopropylcarbamoyl)-1-[1-((1S,2R)-2-hydroxy-indan-1-ylcarbamoyl)-2,2-dimethyl-propylcarbamoyl]-pyrrolidin-3-yl ester (95)

Treatment of compound 92 as described for the preparation of 93 but with the use of 1,2,3,4-tetrahydro-isoquinoline instead of aniline followed by hydrolysis of the ethyl ester as described in example 94 gave the title compound. Purity >90%. M+H⁺688.6.

Example 96

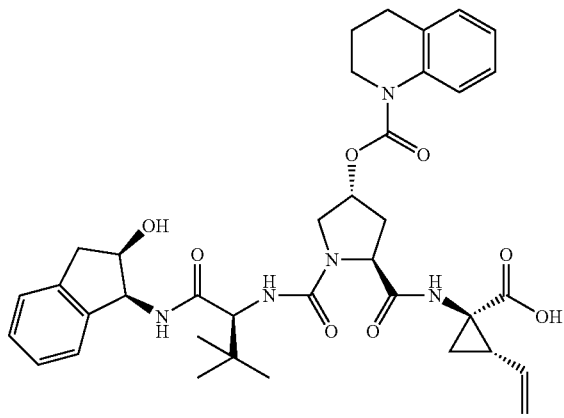

(5S,3R)-3,4-Dihydro-2H-quinoline-1-carboxylic acid 5-((1R,2S)-1-carboxy-2-vinyl-cyclopropylcarbamoyl)-1-[1-((1S,2R)-2-hydroxy-indan-1-ylcarbamoyl)-2,2-dimethyl-propylcarbamoyl]-pyrrolidin-3-yl ester (96)

Treatment of compound 92 as described for the preparation of 93 but with the use of 1,2,3,4-tetrahydro-quinoline instead of aniline followed by hydrolysis of the ethyl ester as described in example 94 gave the title compound. Purity >90%. M+H⁺688.6.

Example 97

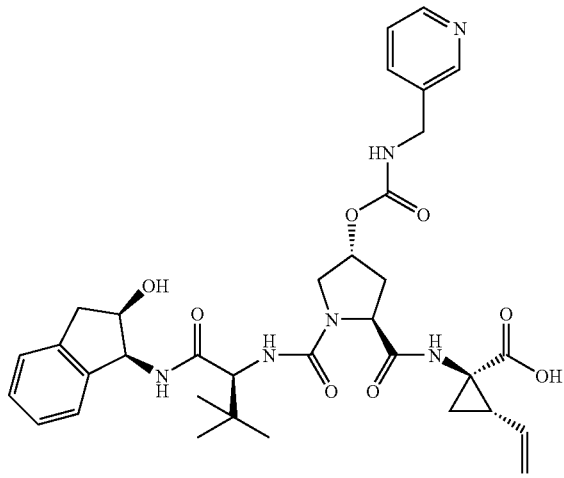

(1R,2S)-1-{[(2S,4R)-1-[(1 S)-1-((1 S,2R)-2-Hydroxy-indan-1-ylcarbamoyl)-2,2-dimethyl-propylcarbamoyl]-4-(pyridin-3-ylmethylcarbamoyloxy)-pyrrolidine-2-carbonyl]-amino}-2-vinyl-cyclopropanecarboxylic acid (97)

Treatment of compound 92 as described for the preparation of 93 but with the use of 2-pyridine-3-yl-ethylamine instead of aniline followed by hydrolysis of the ethyl ester as described in example 94 gave the title compound. Purity >90%. M+H⁺663.5.

Example 98

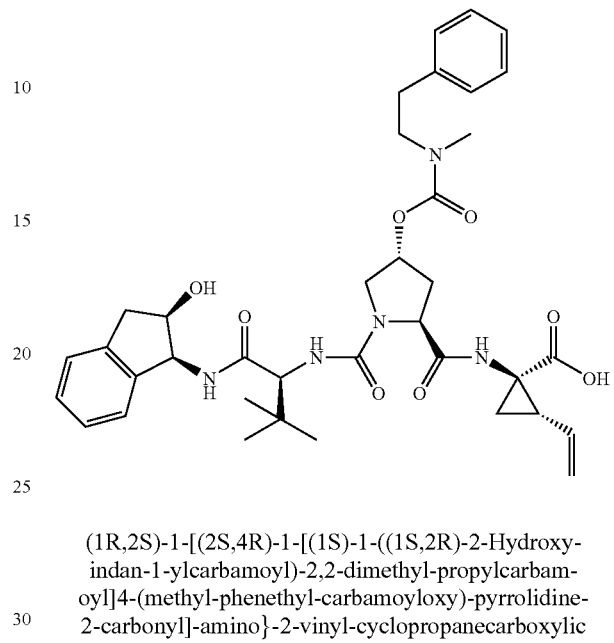

(1R,2S)-1-[(2S,4R)-1-[(1S)-1-((1S,2R)-2-Hydroxy-indan-1-ylcarbamoyl)-2,2-dimethyl-propylcarbamoyl]4-(methyl-phenethyl-carbamoyloxy)-pyrrolidine-2-carbonyl]-amino}-2-vinyl-cyclopropanecarboxylic acid (98)

Treatment of compound 92 as described for the preparation of 93 but with the use of N-methylphenethylamine instead of aniline followed by hydrolysis of the ethyl ester as described in example 94 gave the title compound. Purity >90%. M+H⁺ 690.6.

Example 99

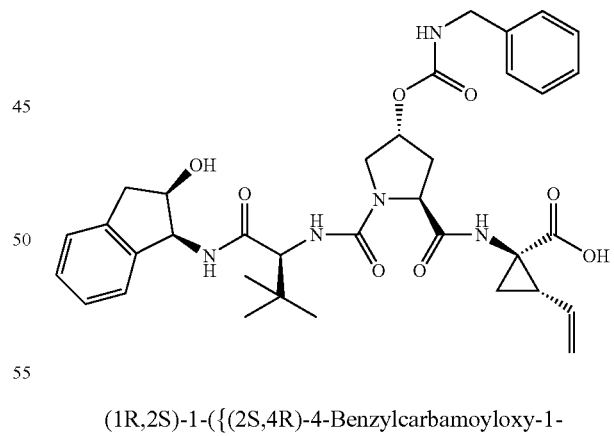

(1R,2S)-1-({(2S,4R)-4-Benzylcarbamoyloxy-1-[(1S)-1-((1S,2R)-2-hydroxy-indan-1-ylcarbamoyl)-2, 2-dimethyl-propylcarbamoyl]-pyrrolidine-2-carbonyl}amino)-2-vinyl-cyclopropanecarboxylic acid (99)

Treatment of compound 92 as described for the preparation of 93 but with the use of benzylamine instead of aniline followed by hydrolysis of the ethyl aster as described in example 94 gave the title compound. Purity >90%. M+H⁺ 662.4.

Example 100

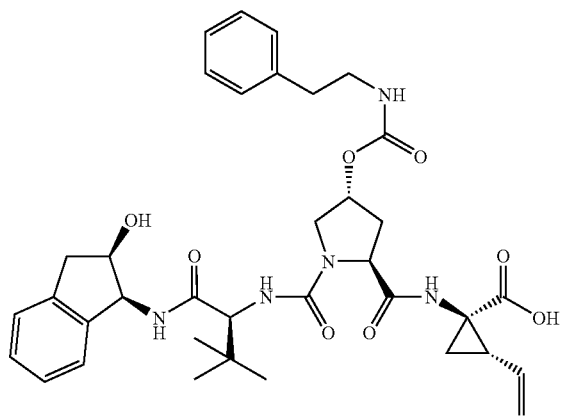

(1R,2S)-1-({(2S,4R)-1-[(1S)-1-((1S,2R)-2-Hydroxy-indan-1-ylcarbamoyl)-2,2-dimethyl-propylcarbamoyl]-4-phenethylcarbamoyloxy-pyrrolidine-2-carbonyl}-amino)-2-vinyl-cyclopropanecarboxylic acid (100)

Treatment of compound 92 as described for the preparation of 93 but with the use of phenethylamine instead of aniline followed by hydrolysis of the ethyl aster as described in example 94 gave the title compound. Purity >90%. M+H$^+$ 676.5.

Example 101

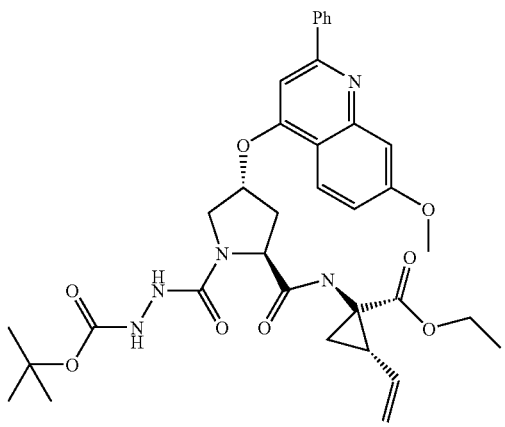

(1R,2S)-1-({(4R)-1-[2-(tert-butoxycarbonyl)hydrazino]carbonyl}-4-[(7-methoxy-2-phenylquinolin-4-yl)oxy]-L-prolyl}q}amino)-2-vinylcyclopropanecarboxylic acid ethyl ester (101)

To a solution of tert-butyl carbazate (0.3 mmol) and p-nitro phenyl chloroformate (0.3 mmol) in acetonitrile (6 ml) was added sodium hydrogen carbonate (0.48 mmol) as solid. The solution was stirred at RT for 5 hrs and then cooled down to 0° C. Compound 62 (0.3 mmol) dissolved in acetonitrile (10 mL) was mixed together with diisopropylethylamine (0.75 mmol) at 0° C., and then added to the previous solution. The mixture was stirred at RT overnight and then concentrated to dryness. The residue was dissolved in DCM and then washed with citric acid pH 4, followed by NaHCO$_3$ (aq) and water, dried over anhydrous sodium sulphate, filtrated and concentrated to dryness. The crude was dissolved in DCM and purified by column chromatography eluted with 0.1 to 0.2% MeOH/DCM to yield the title compound (101 mg). Purity >95% by HPLC, M+H$^+$660.1.

Example 102

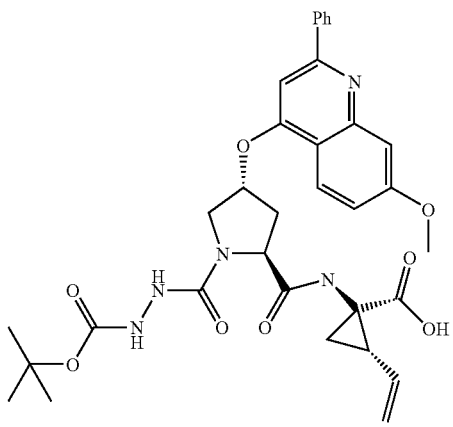

(1R,2S)-1-({(4R)-1-{[2-(tert-butoxycarbonyl)hydrazino]carbonyl}-4-[(7-methoxy-2-phenylquinolin-4-yl)oxy]-L-prolyl}amino)-2-vinylcyclopropanecarboxylic acid (159)

Method A: To a solution of compound 101 (0.0115 mmol) in THF-MeOH 2:3 (2 ml) was added 1M LiOH (10 equiv) The solution was kept at 50° C. for 60 min. After cooling to RT, HOAc (20 equiv) was added followed by toluene (2 ml) and then concentrated to dryness. The residue was taken up in MeOH and then purified by Prep LCMS which gave the title compound (0.7 mg). Purity >95% by HPLC M+H$^+$732.2.

Method B: To a solution of tert-butyl carbazate (0.07 mmol) and p-nitrophenyl chloroformate (0.07 mmol) in acetonitrile (3 ml) was added sodium hydrogen carbonate (0.112 mmol) as a solid. The solution was stirred at RT for 2.5 hrs and then cooled to 0° C. Compound 103 (described below) (0.07 mmol) dissolved in acetonitrile (10 ml) was mixed together with diisopropylethylamine (0.175 mmol) at 0° C., and then added to the previous solution. The mixture was stirred at RT overnight and then concentrated to dryness. The crude material was dissolved In MeOH and purified by Prep LCMS which gave the title compound (4.8 mg). Purity >95% by HPLC M+H$^+$632.2

Example 103

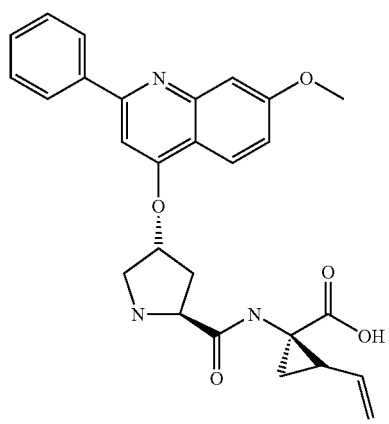

(1R,2S)-1-{[(2S,4R)-4-(7-Methoxy-2-phenyl-quinolin-4-yloxy)-pyrrolidine-2-carbonyl]-amino-2-vinyl-cyclopropanecarboxylic acid (103)

To a solution of compound 12 (0.067 mmol) in THF-MeOH 2:3 (2 ml) was added 1M LiOH 10 equiv. The solution was kept at 50° C. for 2.5 hrs. After cooling to RT, HOAc 20 equiv. was added followed by toluene (2 ml) and then concentrated to dryness. The residue was taken up in DCM and filtered form the salts which gave the title compound (0.07 mmol). Purity >95% by HPLC M+H$^+$474.

Example 104

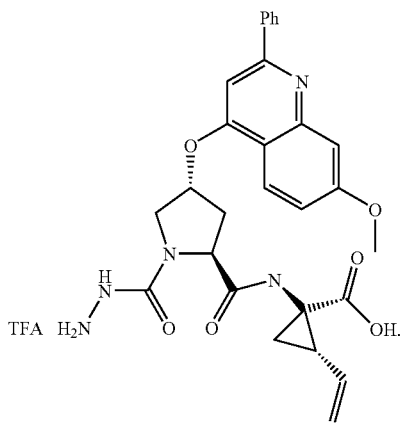

(1R,2S)-1-({(4R)-1-(hydrazinocarbonyl)-4-[(7-methoxy-2-phenylquinolin-4-yl)oxy]-L-prolyl}amino)-2-vinylcyclopropanecarboxylic acid (104)

Compound (102) was kept in TFA-DCM 1:2 (3 ml) at RT for 60 min. Toluene (1 ml) was added. The sample was co-evaporated to dryness which gave the title compound (10.5 mg) as the trifluoracetic acid salt. Purity by HPLC>95%. M+H$^+$532.

Example 105

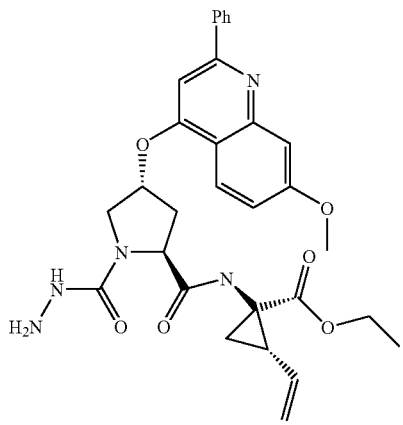

(1R,2S)-1-({(4R)-1-(hydrazinocarbonyl)-4-[(7-methoxy-2-phenylquinolin-4-yl)oxy]-L-prolyl}amino)-2-vinylcyclopropanecarboxylic acid ethyl ester (105)

Compound 101 (50 mg) was kept in TFA-DCM 1:2 (3 ml) at RT for 60 min. Toluene (1 ml) was added. The sample was co-evaporated to dryness and then taken up in DCM and washed with K$_2$CO$_3$, dried over anhydrous sodium sulphate and concentrated to dryness which gave the title compound (41.8 mg). Purity by HPLC>95%. M+H$^+$560.

Example 106

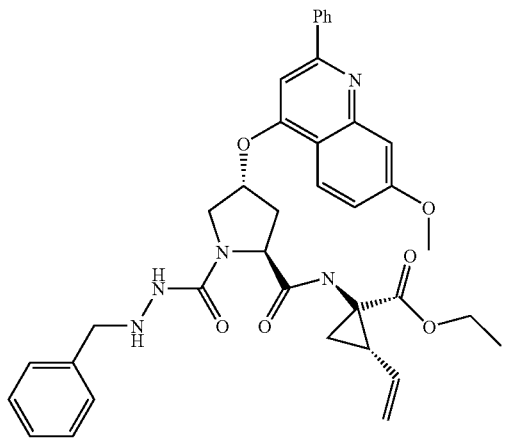

(1R,2S)-1-({(4R)-1-[(2-Benzylhydrazino)carbonyl]4-[(7-methoxy-2-phenylquinolin-4-yl)oxy]-L-prolyl}amino)-2-vinylcyclopropanecarboxylic acid ethyl ester (106)

To a solution of compound 105 (0.037 mmol) in MeOH: THF (4:1) was added benzaldehyde (0.0448 mmol). The solution was stirred at RT for 18 hrs. Borane-pyridine complex (0.37 mmol) was added followed by HCl (37%, 400 µl). The solution was stirred for 1.5 hrs and then filtrated and concentrated to dryness. The crude material was dissolved in MeOH and purified by Prep LCMS which gave the title compound (0.01 mmol). Purity by HPLC>95%. M+H$^+$650.

Example 107

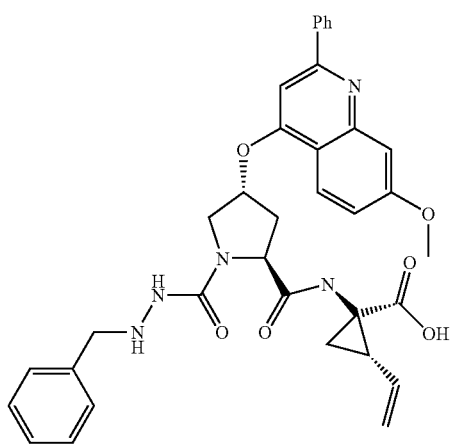

(1R,2S)-1-({(4R)-1-[(2-benzylhydrazino)carbonyl]-4-[(7-methoxy-2-phenylquinolin-4-yl)oxy]-L-prolyl}amino)-2-vinylcyclopropanecarboxylic acid (164107

To a solution compound 106 (0.0101 mmol) in THF-MeOH 2:3 (3 ml) was added 1M LiOH 10 equiv. The solution was kept at 50° C. for 18 hrs. After cooling to RT the sample was neutralized with HCl and concentrated to dryness. The crude material was dissolved in DCM (2 ml) and a solution of TFA: TES 1:1 (1 ml) was added. The mixture was stirred for 3 hrs at RT and then concentrated to dryness. The crude material was dissolved in MeOH and purified by Prep LCMS which gave the title compound (0.6 mg). Purity by HPLC>95%. M+H⁺622.

Example 108

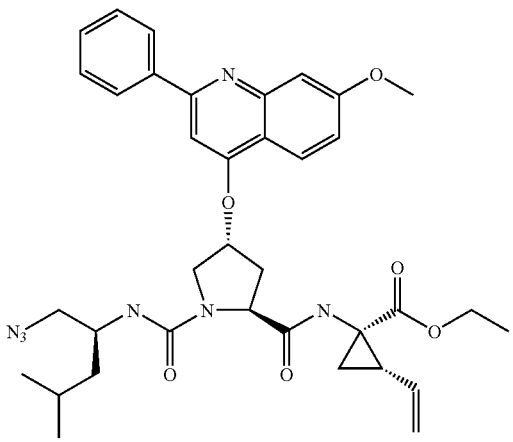

(1R,2S)-1-{[(2S,4R)-1-((1S)-1-Azidomethyl-3-methyl-butylcarbamoyl)-4-(7-methoxy-2-phenyl-quinolin-4-yloxy)-pyrrolidine-2-carbonyl]-amino}-2-vinyl-cyclopropanecarboxylic acid ethyl ester (108)

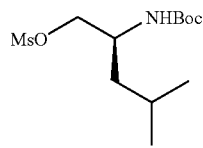

i) (2S)-Methanesulphonic acid 2-tert.butoxycarbonylamino-4-methyl-pentyl ester To a solution of ((1S)-1-hydroxymethyl-3-methyl-butyl)-carbamic acid tert-butyl ester (25 g, 115 mmol) in dichloromethane (500 ml) cooled by an ice-water bath was successively added diisopropylethylamine (35.7 g, 276 mmol) and methanesulphonyl chloride (15.81 g, 138 mmol). The resulting solution was stirred over night during which time the mixture was allowed to gradually warm up to ambient temperature. The mixture was washed successively with water, 10% citric acid (aq), water and saturated NaHCO₃ (aq), then dried with Na₂SO₄ and concentrated to a brown solid (32.6 g, 96%) which was used in the next reaction without further purification.

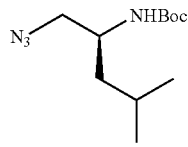

ii) ((1S)-1-Azidomethyl-3-methyl-butyl)-carbamic acid tert.butyl ester

The mesylate from step i (32.6 g, 110 mmol) was treated with sodium azide (21.45 g, 330 mmol) in DMF at 80° C. for 24 hrs. The solvent was evaporated, the residue was taken up in DCM, filtered and washed with saturated NaHCO₃ (aq). The solution was dried with Na₂SO₄ and concentrated to a brown oil which was purified by flash chromatography using a gradient of ethyl acetate and hexane to afford the title compound as a white solid (19.55 g, 73%).

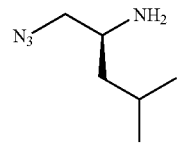

iii) (1S)-1-Azidomethyl-3-methyl-butylamine ((1S)-1-Azidomethyl-3-methyl-butyl)-carbamic acid tert-butyl ester (9.64 g, 39.78 mmol) was treated with TFA (30 ml) in DCM (150 ml) for 3 hrs, the mixture was evaporated under reduced pressure and the residue was dissolved in ethyl acetate and washed with aqueous 1 M K₂CO₃, dried with Na₂SO₄ and concentrated to a yellow liquid (4.55 g, 80%).

Compound 12 was treated with phosgene as described in example 13 which gave the corresponding chlorocarbamate compound. The afforded chlorocarbamate (568 mg, 1.13 mmol) was dissolved in a solution of DCM-THF (1:1, 10 ml) and (1S)-1-azidomethyl-3-methyl-butylamine (401 mg, 2.82 mmol) and a large excess of NaHCO₃ (s) was added. The resulting mixture was stirred for 18 hrs, filtered and washed with dilute citric acid (aq, pH 5). The organic layer was dried with Na₂SO₄ and evaporated to afford the desired product as a light yellow oil (837 mg, 99%) sufficiently pure to be used in the next step.

M+H⁺670.1.

Example 109

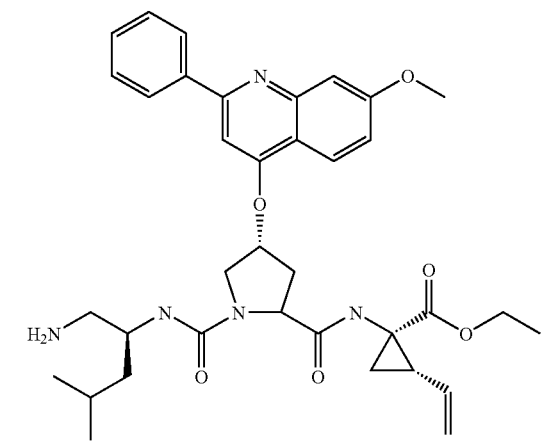

(1R,2S)-1-{[(2S,4R)-1-((1S)-1-Aminomethyl-3-methyl-butylcarbamoyl)-4-(7-methoxy-2-phenyl-quinolin-4-yloxy)-pyrrolidine-2-carbonyl]-amino}-2-vinyl-cyclopropanecarboxylic acid ethyl ester (109)

A solution of 108 (717 mg, 1.07 mmol) in THF (25 ml) was shaken together with PS-triphenylphosphine resin (diphenylphosphino polystyrene) (3.24 g, 1.65 mmol PPh3/g) and methanol (2.5 ml) for 78 hrs. The mixture was filtered and the polymer was washed repeatedly with DCM and methanol. The combined filtrates were evaporated to yield the title compound as a light beige solid foam (685 mg, 99%) with more than 95% purity as determined by reversed phase HPLC. M+H⁺644.1.

General Procedure 1A for the Preparation of Compounds 110-116

To a solution of the acyl chloride (0.075 mmol) in DCM (0.5 ml) was added NaHCO$_3$ (s) (60 mg, 07 mmol) and a solution of the amine 109 (25 mg, 0.037 mmol) in THF (1 ml). The resulting mixture was stirred at room temperature overnight, filtered and then shaken in the presence of PS-trisamine resin (tris-(2-aminoethyl)aminomethyl polystyrene) (3.91 mmol g, 50 mg, 0.2 mmol) for 5 hrs. The mixture was filtered and evaporated. The resulting solid residue was dissolved in MeOH-THF (2:1, 1.5 ml) and treated with 1 M LiOH (aq) (170 µl) at 50° C. between 2 and 16 hrs. The reaction was monitored by HPLC-MS. The mixture was acidified with acetic acid and evaporated to dryness. The residue was dissolved in methanol and purified by reversed phase HPLC.

General Procedure 1B for the Preparation of Compounds 110-116

To the acid (0.039 mmol) was successively added a solution of HATU (14.7 mg, 0.039 mmol) in DMF (0.5 ml), a solution of the amine 109 (20 mg, 0.031 mmol) in DMF (0.5 ml) and diisopropylethylamine (30 µl, 0.155 mmol). The resulting mixture was stirred for 16 hrs then the solvent was evaporated and the residue was dissolved in DCM and washed with water and aqueous saturated NaHCO$_3$. The solvent was evaporated and the residue was dissolved in methanol-THF (2:1, 1.5 ml). To this was added 1 M LiOH (aq) (155 µl) and the mixture was stirred at 60° C. for 3-5 hrs. Glacial acetic acid (50 µl) was added and the mixture was concentrated, dissolved in methanol and purified by reversed phase HPLC.

Example 110

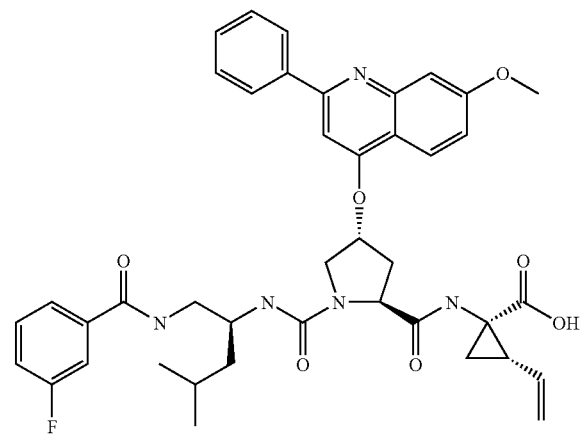

(1R,2S)-1-{[(2S,4R)-1-{(1S)-1-[(3-Fluoro-benzoylamino)-methyl]-3-methylbutylcarbamoyl}-4-(7-methoxy-2-phenyl-quinolin-4-yloxy)-pyrrolidine-2-carbonyl]-amino}-2-vinyl-cyclopropanecarboxylic acid (110)

General procedure 1A was followed using 3-fluorobenzoyl chloride (12 mg) as acyl chloride which gave the title compound as a solid (13.6 mg, 50%). M+H$^+$738.1.

Example 111

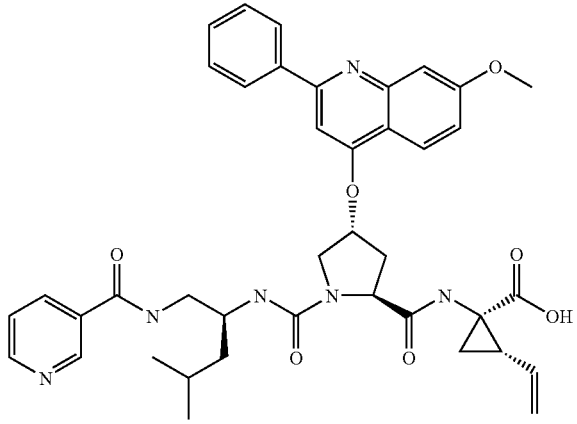

(1R,2S)-1-{[(2S,4R)-4-(7-Methoxy-2-phenyl-quinolin-4-yloxy)-1-((1S)-3-methyl-1-{[(pyridine-3-carbonyl)-amino]-methyl}-butylcarbamoyl)-pyrrolidine-2-carbonyl]-amino}-2-vinyl-cyclopropanecarboxylic acid (111)

General procedure 1A was followed using nicotinoyl chloride (10.5 mg) as acyl chloride which gave the title compound as a solid (10 mg, 37%). M+H$^+$721.1.

Example 112

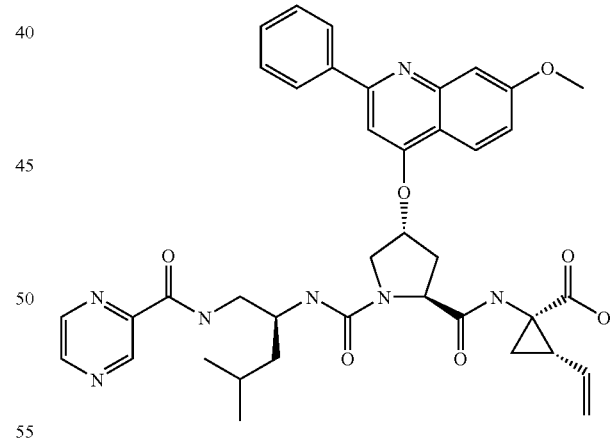

(1R,2S)-1-{[(2S,4R)-4-(7-Methoxy-2-phenyl-quinolin-4-yloxy)-1-((1S)-3-methyl-1-{[(pyrazine-2-carbonyl)-amino]-methyl}-butylcarbamoyl)-pyrrolidine-2-carbonyl]-amino-2-vinyl-cyclopropanecarboxylic acid (112)

General procedure 1B was followed using pyrazine-2-carboxylic acid (5 mg) as acid which gave the title compound as a solid (5.7 mg, 25%). M+H$^+$722.1.

Example 113

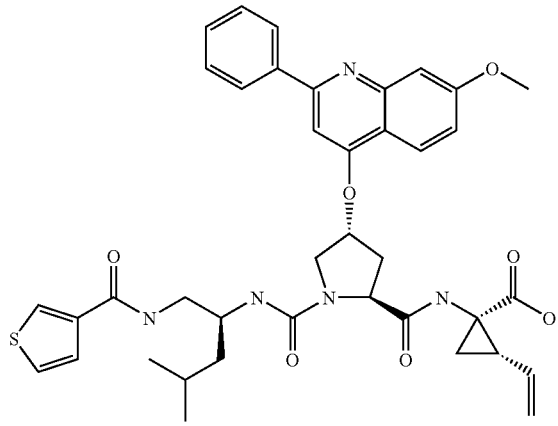

(1R,2S)-{[(2S,4R)-4-(7-Methoxy-2-phenyl-quinolin-4-yloxy)-1-((1S)-3-methyl-1-{[(thiophene-3-carbonyl)-amino]-methyl}-butylcarbamoyl)-pyrrolidine-2-carbonyl]-amino)-2-vinyl-cyclopropanecarboxylic acid (113)

General procedure 1A was followed using thiophene-3-carbonyl chloride (11 mg) which gave the title compound as a solid (4.3 mg, 16%). M+H$^+$726.1.

Example 114

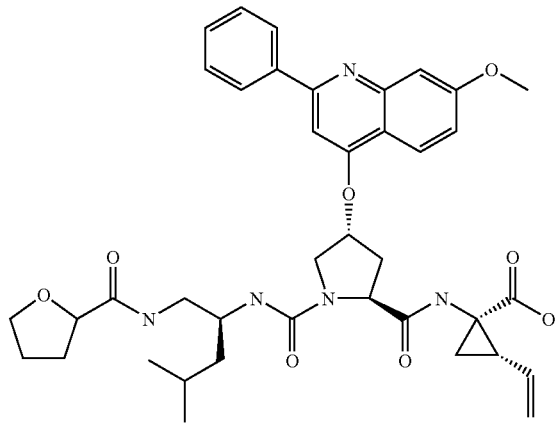

(1R,2S)-1-{[(2S,4R)-4-(7-Methoxy-2-phenyl-quinolin-4-yloxy)-1-((1S)-3-methyl-1-{[(tetrahydro-furan-2-carbonyl)-amino]-methyl}butylcarbamoyl)-pyrrolidine-2-carbonyl]-amino}-2-vinyl-cyclopropanecarboxylic acid (114)

General procedure 1B was followed using tetrahydro-furane-2-carboxylic acid (4.5 mg) as acid which gave the title compound as a solid (7.9 mg, 36%). M+H$^+$714.1.

Example 115

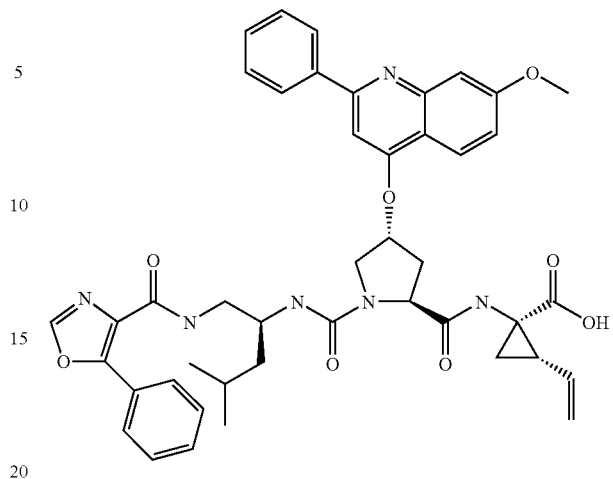

(1R,2S)-1-{[(2S,4R)-4-(7-Methoxy-2-phenyl-quinolin-4-yloxy)-1-((1S)-3-methyl-1-{[(5-phenyl-oxazole-4-carbonyl)-amino]-methyl}-butylcarbamoyl)-pyrrolidine-2-carbonyl]-amino}-2-vinyl-cyclopropanecarboxylic acid (115)

General procedure 1B was followed using 5-phenyl-oxazole-4-carboxylic acid (7.5 mg) as acid which gave the title compound as a solid (7.5 mg, 31%). M+H$^+$787.1.

Example 116

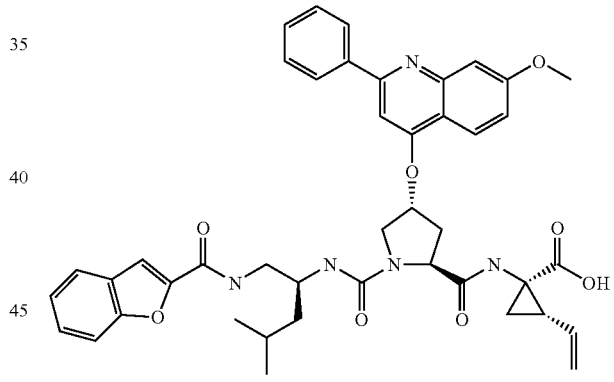

(1R,2S)-1-{[(2S,4R)-1-((1S)-1-{[(Benzofuran-2-carbonyl)-amino]-methyl}-3-methyl-butylcarbamoyl)-4-(7-methoxy-2-phenyl-quinolin-4-yloxy)-pyrrolidine-2-carbonyl]-amino-2-vinyl-cyclopropanecarboxylic acid (116)

General procedure 1B was followed using benzofuran-2-carboxylic acid (6.5 mg) as acid which gave the title compound as a solid (5.4 mg, 23%). M+H$^+$760.1.

General Procedure 2 for the Preparation of Compounds 117-119

To a solution of the sulphonyl chloride (0.075 mmol) in DCM (0.5 ml) was added NaHCO$_3$ (s) (60 mg) and a solution of the amine 109 (25 mg, 0.037 mmol) in THF (1 ml). The resulting mixture was stirred at room temperature for 18 hrs, filtered and then shaken with PS-trisamine (tris-(2-aminoethyl)aminomethyl polystyrene, 3.91 mmol/g, ~50 mg) for 5 hrs.

The mixture was filtered and the polymer was washed successively with DCM, THF and methanol. The solid residue resulting from evaporation of the combined filtrates was dissolved in MeOH-THF (2:1, 1.5 ml) and treated with 1 M LiOH (aq) (170 µl) at 50° C. for reaction times varying from 18 hrs to one week depending on the actual structure. The reaction was monitored by HPLC-MS. The mixture was acidified with acetic acid and evaporated to dryness. The residue was dissolved in methanol and purified by reversed phase HPLC.

Example 117

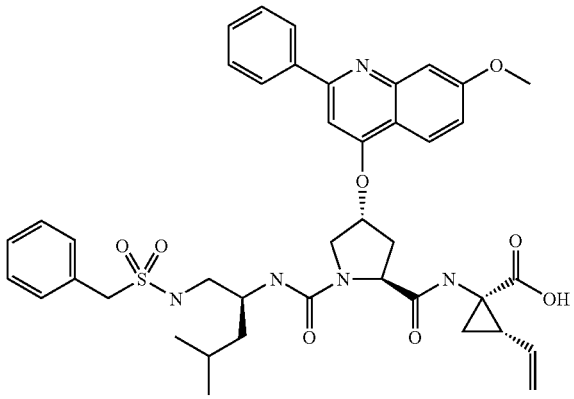

(1R,2S)-1-({(2S,4R)-4-(7-Methoxy-2-phenyl-quinolin-4-yloxy)-1-[(1S)-3-methyl-1-(phenylmethane-sulphonylamino-methyl)-butylcarbamoyl]-pyrrolidine-2-carbonyl}amino)-2-vinyl-cyclopropanecarboxylic acid (117)

General procedure 2 was followed using α-toluenesulphonyl chloride (14 mg) as sulphonyl chloride which gave the title compound as a white solid (4.9 mg, 17%). M+H⁺770.1.

Example 118

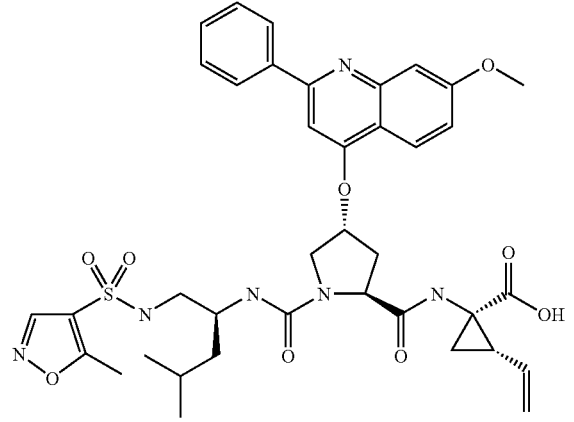

(1R,2S)-1-[((2S,4R)-4-(7-Methoxy-2-phenyl-quinolin-4-yloxy)-1-{(1S)-3-methyl-1-[(5-methyl-isoxazole-4-sulphonylamino)-methyl]-butylcarbamoyl}-pyrrolidine-2-carbonyl)-amino]-2-vinyl-cyclopropanecarboxylic acid (118)

General procedure 2 was followed using 5-methyl-isoxazole-4-sulphonyl chloride (14 mg) as sulphonyl chloride which gave the title compound as a white solid (1.6 mg, 6%). M+H⁺761.0.

Example 119

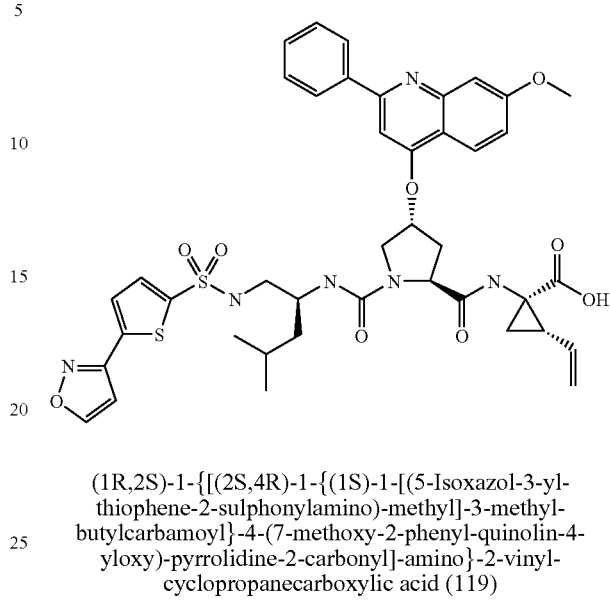

(1R,2S)-1-{[(2S,4R)-1-{(1S)-1-[(5-Isoxazol-3-yl-thiophene-2-sulphonylamino)-methyl]-3-methyl-butylcarbamoyl}-4-(7-methoxy-2-phenyl-quinolin-4-yloxy)-pyrrolidine-2-carbonyl]-amino}-2-vinyl-cyclopropanecarboxylic acid (119)

General procedure 2 was followed using 5-isoxazol-3-yl-thiophene-2-sulphonyl chloride (19 mg) as sulphonyl chloride which gave the title compound as a white solid (3.0 mg, 10%). M+H⁺828.98.

Example 120

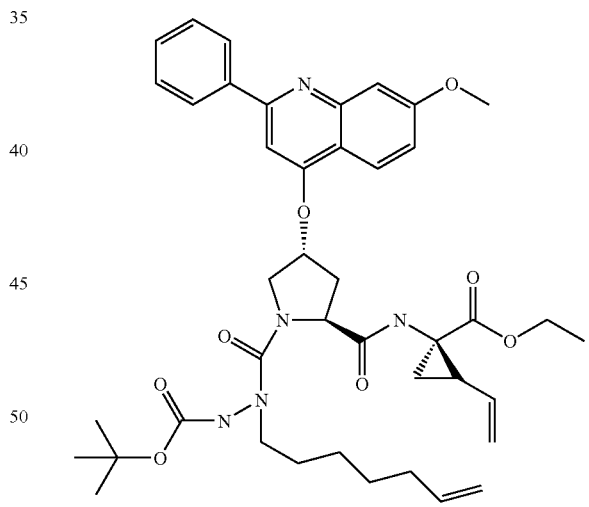

1-{[1-(N'-tert. Butoxycarbonyl-N-hept-6-enyl-hydrazinocarbonyl)-4-(7-methoxy-2-phenyl-quinolin-4-yloxy)-pyrrolidine-2-carbonyl]-amino}-2-vinyl-cyclopropanecarboxylic acid ethyl ester (120)

Compound 12 (200 mg, 0.4 mmol) was dissolved in tetrahydrofuran (10 ml). A tea-spoon of sodium hydrogencarbonate was added, followed by phosgene (1.8 µl, 1.9 M in toluene). The reaction mixture was stirred for 30 min and filtrated. The solvent was evaporated and the crude chloride was re-dissolved in dichloromethane (10 ml). Sodium hydrogencarbonate (1 tea-spoon) and N'-hept-6-enyl-hydrazinecarboxylic acid tert.butyl ester (182 mg, 0.8 mmol). The reaction mixture was stirred at room temp. for 40 h. and then filtrated and purified by silica chromatography (1% methanol in ether →2% methanol in ether) to give pure title product (240 mg, 79%).

Example 121

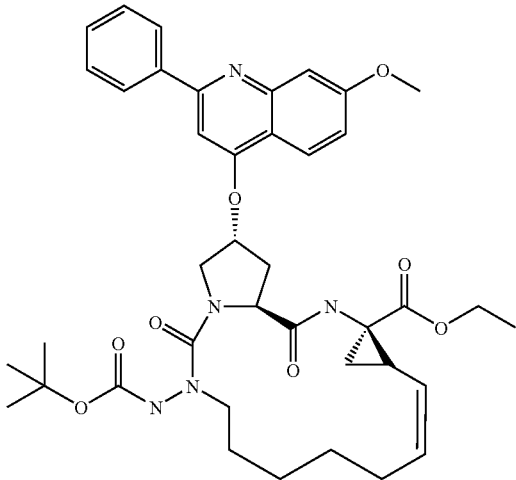

14-tert.Butoxycarbonylamino-18-(7-methoxy-2-phenyl-quinolin-4-yloxy)-2,15-dioxo-3,14,16-triaza-tricyclo[14.3.0.0*4,6*]nonadec-7-ene-4-carboxylic acid ethyl ester (121)

Compound 120 (200 mg, 0.26 mmol) was dissolved in degassed dichloromethane (30 ml). Hoveyda-Grubbs catalyst II generation (16 mg, 0.026 mmol) was then added and the mixture was refluxed under argon atmosphere overnight. The solvent was then evaporated and the crude product was purified by silica chromatography (1% methanol in ether) which gave 39 mg (20%) of the title product. MS (M+H$^+$) 728.2

Example 122

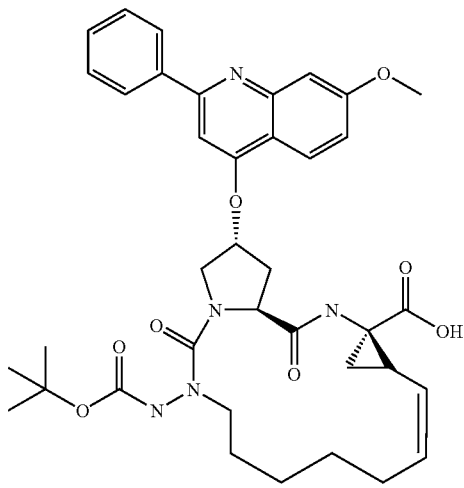

14-tert. Butoxycarbonylamino-18-(7-methoxy-2-phenyl-quinolin-4-yloxy)-2,15-dioxo-3,14,16-triaza-tricyclo[14.3.0.0*4,6*]nonadec-7-ene-4-carboxylic acid (122)

Compound 121 (39 mg, 0.054 mmol) was dissolved in tetrahydrofuran (3.5 ml), water (1.75 ml) and methanol (1.75 ml). Lithium hydroxide (430 μl, 1 M in water) was then added and the reaction was stirred at room temperature for 24 h. The volume was reduced to half and water (10 ml) was added. Acidification (pH=5) followed by extraction with chloroform gave 34 mg (90%) of the pure acid 179. MS (M+H$^+$) 700.2

Example 123

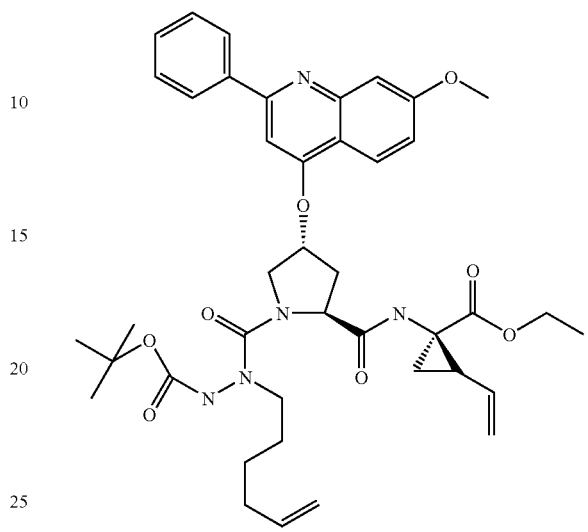

1-{[1-(N'-tert.Butoxycarbonyl-N-hex-5-enyl-hydrazinocarbonyl)-4-(7-methoxy-2-phenyl-quinolin-4-yloxy)-pyrrolidine-2-carbonyl]-amino}-2-vinyl-cyclopropanecarboxylic acid ethyl ester (123)

The title compound was prepared from compound 12 (800 mg, 1.6 mmol) and N'-hex-5-enyl-hydrazinecarboxylic acid tert.butyl ester (620 mg, 2.9 mmol) according to the procedure described in Example 120 which gave 1 g (85%). MS (M+H$^+$) 742.37

Example 124

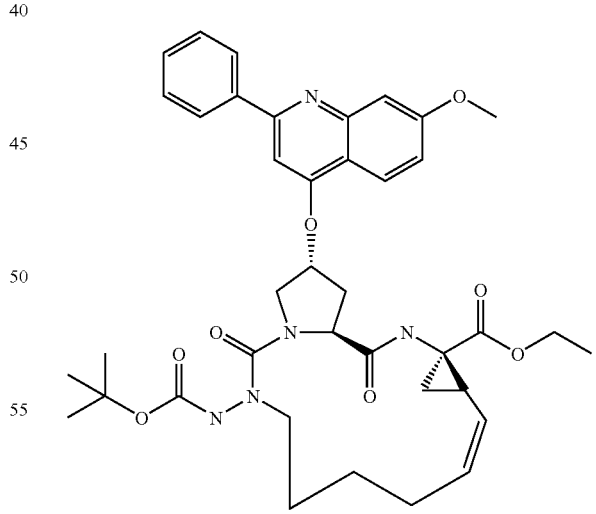

13-tert.Butoxycarbonylamino-17-(7-methoxy-2-phenyl-quinolin-4-yloxy)-2,14-dioxo-3,13,15-triaza-tricyclo[13.3.0.0*4,6*]octadec-7-ene-4-carboxylic acid ethyl ester (124)

Treatment of compound 123 (400 mg, 0.54 mmol) according to the procedure described in example 121 gave a crude product. Purification by silica gel chromatography (1% methanol in ether) gave the title product (67 mg, 17%). MS (M+H⁺) 714.29

Example 125

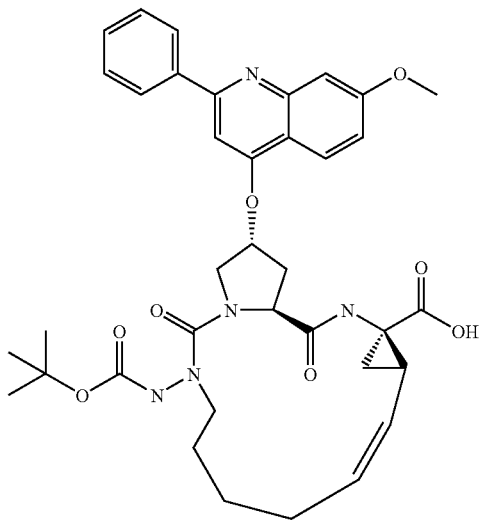

13-tert. Butoxycarbonylamino-17-(7-methoxy-2-phenyl-quinolin-4-yloxy)-2,14-dioxo-3,13,15-triaza-tricyclo[13.3.0.0*4,6*]octadec-7-ene-4-carboxylic acid (125)

The title compound was prepared from compound 124 (67 mg, 0.09 mmol) by the same procedure as described for 122 which gave 46 mg (71%) of the pure acid. Chloroform was replaced by 1, 2-dichloroethane in the extraction step for the preparation of this compound. MS (M+H⁺) 686.33

Example 126

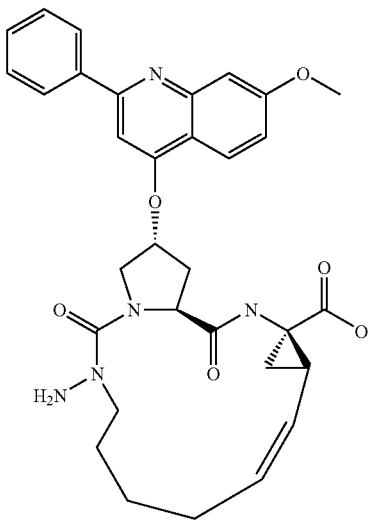

13-tert.Amino-17-(7-methoxy-2-phenyl-quinolin-4-yloxy)-2,14-dioxo-3,13,15-triaza-tricyclo [13.3.0.0*4,6*]octadec-7-ene-4-carboxylic acid (126)

Compound 125 (10 mg) was dissolved in dichloromethane (4 ml)

Trifluoromethanesulphonic acid (4 ml) was added and the mixture was left at 50° C. for 6 hours. The solvent was removed and the residue was washed with acetonitrile which gave 3 mg of the pure title product (35%). MS (M+H⁺) 586.25

Example 127

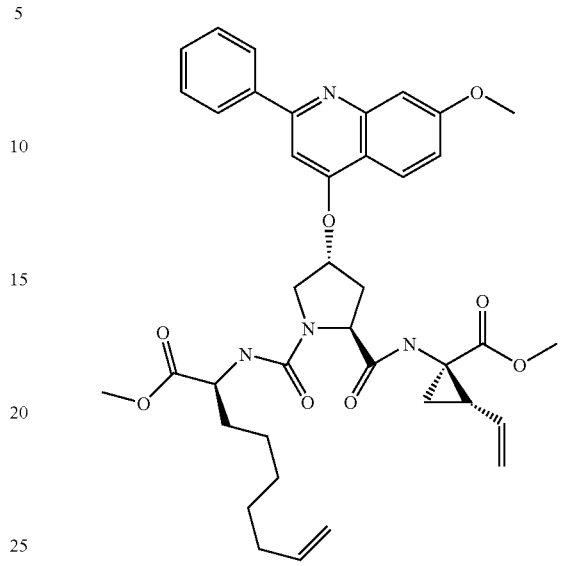

1-{[1-(1-Methoxycarbonyl-oct-7-enylcarbamoyl)-4-(7-methoxy-2-phenyl-quinolin-4-yloxy)-pyrrolidine-2-carbonyl]-amino}-2-vinyl-cyclopropanecarboxylic acid ethyl ester (127)

The title compound was prepared from compound 12 (380 mg, 0.758 mmol) and 2-aminononan-8-enyl-carboxylic acid methyl ester (250 mg, 1.89 mmol) using the conditions described in Example 120 which gave the pure product (405 mg, 75%).

Example 128

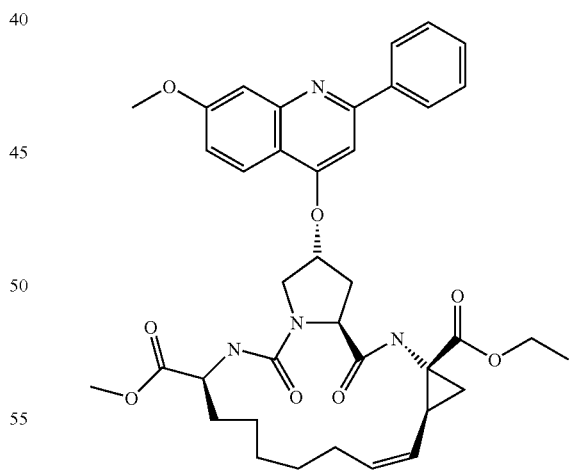

19-(7-Methoxy-2-phenyl-quinolin-4-yloxy)-2,16-dioxo-3,15,17-triaza-tricyclo[15.3.0.0*4,6*]icos-7-ene-4,14-dicarboxylic acid 4-ethyl ester 14 methyl ester (128)

Compound 127 (170 mg, 0.2385 mmol) was dissolved in dichloromethane (40 ml) and degassed by bubbling nitrogen for 20 min. Hoveyda-Grubbs catalyst II generation (10 mg, 0.016 mmol, 6.7 mol %) was then added and the mixture was refluxed under nitrogen atmosphere overnight. The solvent was then evaporated, catalyst and salts were removed by flash chromatography (5% methanol in chloroform) and the crude product (120 mg, 73% yield, 85-90% purity) was used in next step MS (M+H⁺) 685

Example 129

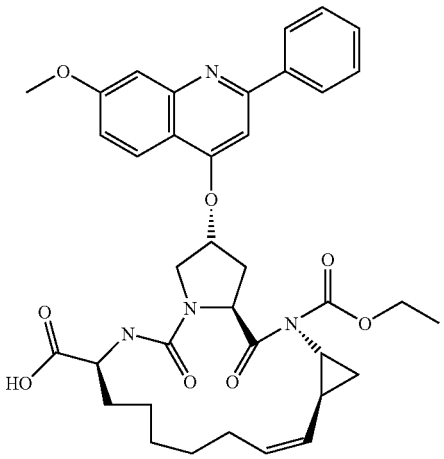

19-(7-Methoxy-2-phenyl-quinolin-4-yloxy)-2,16-dioxo-3,15,17-triaza-tricyclo[15.3.0.0*4,6*]icos-7-ene-3,14-dicarboxylic acid 3-ethyl ester (129)

Compound 128 (120 mg, 0.175 mmol) was dissolved in dioxane (9 ml) and water (6 ml). Lithium hydroxide (12 mg, 0.526 mmol) was added and the reaction was stirred at room temperature for 3.5 h. The mixture was acidified with acetic acid to pH=5, and co-evaporated with toluene. The crude product was used in the next step. MS (M+H⁺) 671

Example 130

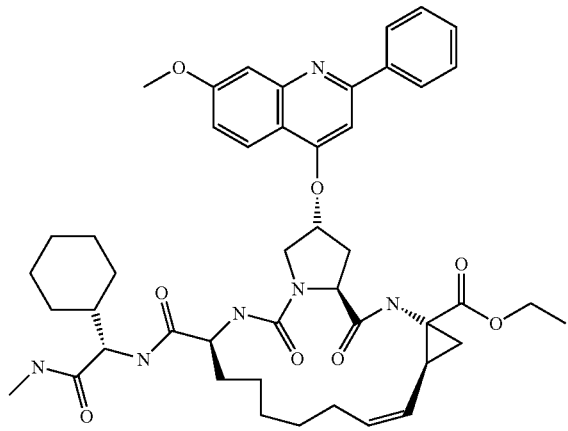

14-[(Cyclohexyl-methylcarbamoyl-methyl)-19-(7-methoxy-2-phenyl-quinolin-4-yloxy)-2,16-dioxo-3,15,17-triaza-tricyclo[15.3.0.0*4,6*]icos-7-ene-4-carboxylic acid 3-ethyl ester (130)

Compound 129 (crude, 100 mg), indanolamine (33 mg, 0.209 mmol) and Hunig's base (DIEA) (0.2 ml) were dissolved in DMF (14 ml). After stirring at 0° C. for 10 min HATU was added. The reaction was monitored by LC-MS. After 5 h conversion was 100%. DMF and DIEA were removed in vacuo. The residue was partitioned between ethyl acetate and water. The organic layer was washed with brine, dried and concentrated in vacuo. The crude yield was 120 mg, the purification by prep. HPLC gave 21 mg (25%) of title product. MS (M+H⁺) 802

Example 131

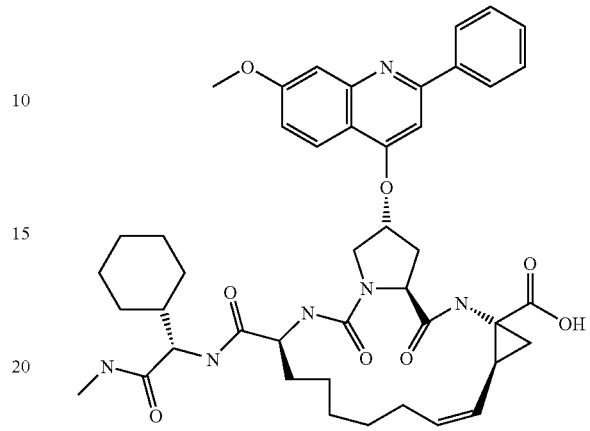

14-[(Cyclohexyl-methylcarbamoyl-methyl)-19-(7-methoxy-2-phenyl-quinolin-4-yloxy)-2,16-dioxo-3,15,17-triaza-tricyclo[15.3.0.0*4,6*]icos-7-ene-4-carboxylic acid (131)

To a solution of the ester 130 (19 mg, 0.024 mmol) in the mixture of THF (0.2 ml) and methanol (0.3 ml) was added solution of LiOH (6 mg, 0.237 mmol) in 0.15 ml of water. The resulting mixture was stirred at 60° C. for 3.5 h. After cooling to room temperature, acetic acid was added (30 eq). The mixture was co-evaporated with toluene. The residue was distributed between chloroform and water phases, the water one was extracted with chloroform and ethyl acetate, organic phases were combined, dried over sodium sulphate, evaporated to give 15 mg of pure product.
MS (M+H⁺) 774

Example 132

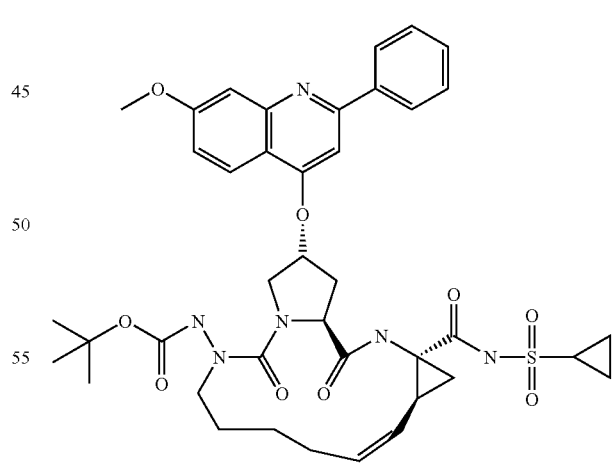

[14-Cyclopropanesulfonylaminocarbonyl-17-(7-methoxy-2-phenyl-quinolin-4-yloxy)-2,14-dioxo-3,13,15-triaza-tricyclo[13.3.0.0*4,6*]octadec-7-en-13-yl]-carbamic acid ter.butyl ester (132)

To the acid 125 (19 mg, 0.028 mmol) in 0.5 ml of DMF was added 5.5 mg (0.044 mmol) of DMAP and 10.7 mg (0.056 mmol) of EDC. After 6.5 h of stirring 20 mg of cyclopropyl-sulphone amide and 0.04 ml of DBU were added. The mixture was stirred overnight, acidified with 5% citric acid (in water) and extracted with ethyl acetate. Dried, evaporated, purified by 5% to 10% methanol in chloroform (or prep LC-MS) which gave 8 mg of the title compound (37%) MS (M+H$^+$) 783

Example 133

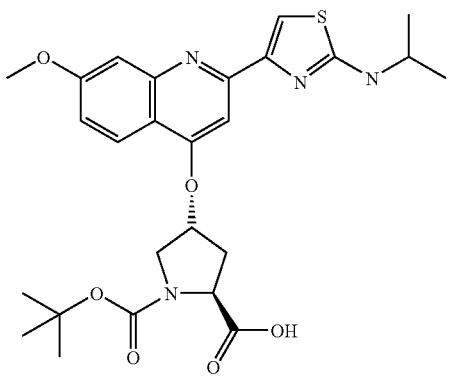

4-[2-(2-isopropylamino-thiazol-4-yl)-7-methoxy-quinolin-4-yloxy]-pyrrolidine-1,2-dicarboxylic acid 1-tert.butyl ester (133)

To a stirred solution of N-Boc-trans-4-hydroxy-L-proline (221 mg, 0.96 mmol) in DMSO was added potassium tert.butoxide (320 mg, 2,9 mmol). After 1h 2-[2-isopropylamino)-1,3-thiazol-4-yl]-7-methoxyquinolin-4-ol (319 mg, 0,96 mmol) was added and the mixture was stirred at 70° C. for 72 hours. The mixture was diluted with water and extracted with ethyl acetate. The product was used without further purification. Yield 429 mg, 85%.

Example 134

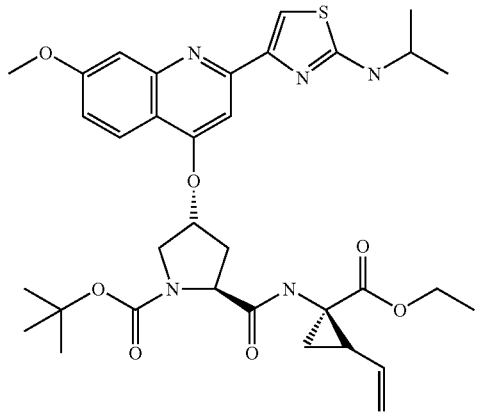

2-(1-Ethoxycarbonyl-2-vinyl-cyclopropylcarbamoyl)-4-[2-(2-isopropylamino-thiazol-4-yl)-7-methoxy-quinolin-4-yloxy]-pyrrolidine-1-carboxylic acid tert.butyl ester (134)

Compound 133 (300 mg, 0.56 mmol) was reacted with 1-amino-2-vinyl-cyclopropanecarboxylic acid ethyl ester (130 mg, 0.84 mmol) as described in Example 11 which gave the title compound (302 mg, 80%).

Example 135

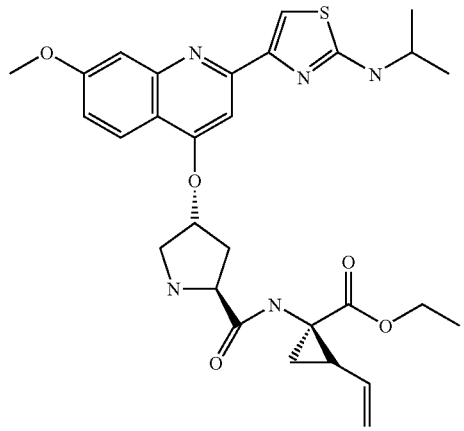

1-({4-[2-(2-Isopropylamino-thiazol-4-yl)-7-methoxy-quinolin-4-yloxy]-pyrrolidine-2-carbonyl}amino)-2-vinyl-cyclopropanecarboxylic acid ethyl ester (135)

Compound 134 (302 mg, 0.45 mmol) was treated as described in Example 12 which gave the title compound (195 mg, 76%).

Example 136

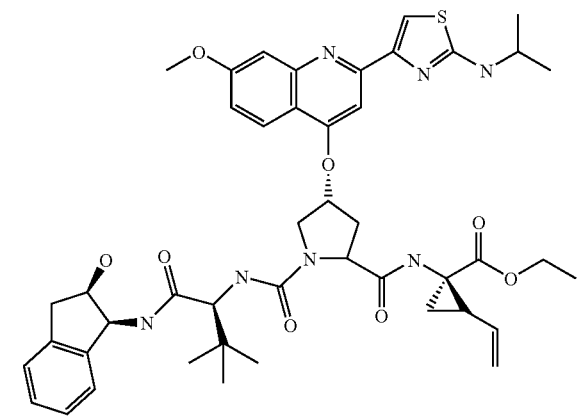

1-({1-[1-(2-Hydroxy-indan-1-ylcarbamoyl)-2,2-dimethyl-propylcarbamoyl]-4-[2-(2-isopropylamino-thiazol-4-yl)-7-methoxy-quinolin-4-yloxy]-pyrrolidine-2-carbonyl}-amino-2-vinyl-cyclopropanecarboxylic acid ethyl ester (136)

Compound 135 (80 mg, 0.14 mmol) was treated as described in Example 13 which gave the title product (87 mg, 72%).

Example 137

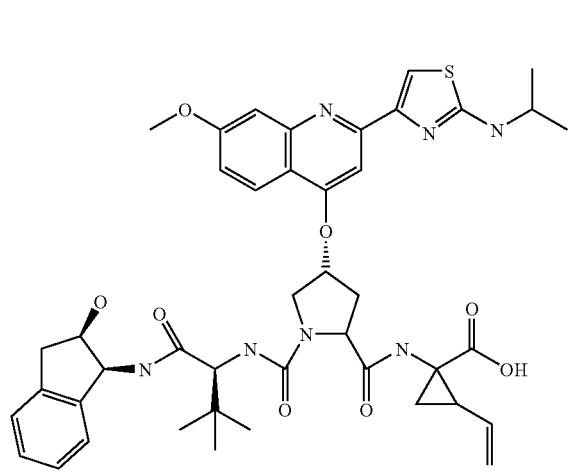

1-({1-[1-(2-Hydroxy-indan-1-ylcarbamoyl)-2,2-dimethyl-propylcarbamoyl]-4-[2-(2-isopropylaminothiazol-4-yl)-7-methoxy-quinolin-4-yloxy]-pyrrolidine-2-carbonyl}-amino-2-vinyl-cycloprpoanecarboxylic acid (137)

The ethyl ester of compound 136 (80 mg, 0.09 mmol) was hydrolyzed following the procedure described in Example 14 which gave the title product Yield after preparative LC-MS (7.5 mg, 10%).

Example 138

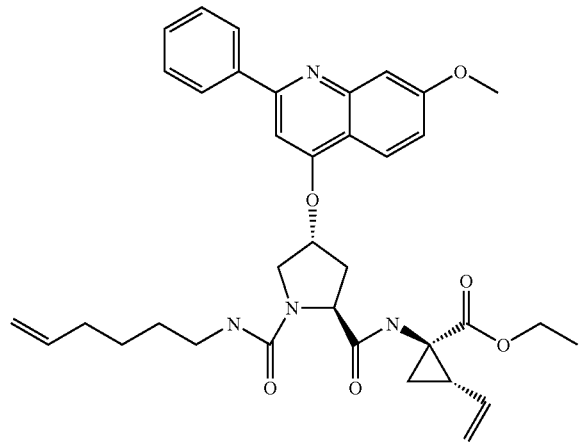

1-{[1-Ethylcarbamoyl-4-(7-methoxy-2-phenyl-quinolin-4-yloxy)-pyrrolidine-2-carbonyl]amino}-2-vinyl-cyclopropanecarboxylic acid ethyl ester (138)

Reaction of compound 12 (330 mg, 0.66 mmol), phosgene (1.6 ml, 1.9 M in toluene, 3 mmol) and hex-5-enylamine hydrochloride (500 mg, 3.68 mmol) following the procedure described in Example 120 gave the pure title product (328 mg, 80%), MS (M+H$^+$) 627.

Example 139

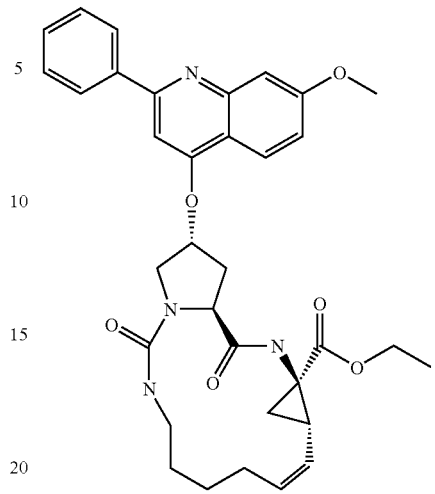

17-(7-Methoxy-2-phenyl-quinolin-4-yloxy)-2,14-dioxo-3,13,15triaza-tricyclo[13.3.0.0*4,6*]octadec-7-ene-4-carboxylic acid ethyl ester (139)

Compound 138 (200 mg, mol) was dissolved in degassed dry dichloromethane (200 ml), bubbled with nitrogen. Then Hoveyda-Grubbs (second generation) catalyst (5 mg, 2 mol %) was added and the reaction mixture was refluxed for 20 h under nitrogen. The resulting mixture was cooled down to room temperature and concentrated by rotary evaporation. The resulting oil was purified by column chromatography on YMC silica (ethyl acetate-toluene 1:1 to 9:1) to give 55 mg of the title compound as a beige solid. Yield 29%. MS (M+H$^+$) 599.

Example 140

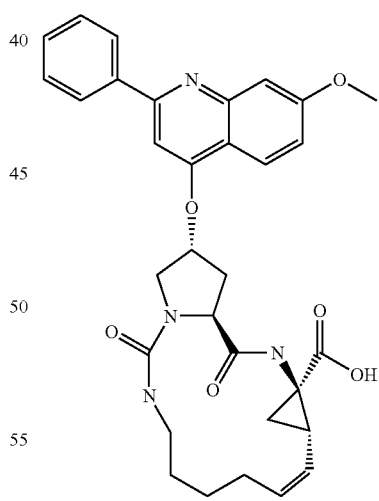

17-(7-Methoxy-2-phenyl-quinolin-4-yloxy)-2,14-dioxo-3,13,15-triaza-tricyclo[13.3.0.0*4,6*]octadec-7-ene-4-carboxylic acid (140)

Compound 139 (55 mg, mol) was dissolved in 2 ml of methanol and mixed with 3 eq. of aqueous NaOH and heated for 2 h at 60° C. in a closed vial. The reaction mixture was then extracted into ethyl acetate. The water solution was collected and acidified with 1N HCl solution to pH 2. The resulting solution was concentrated by rotary evaporation, dissolved in methanol and purified by preparative HPLC (acetonitrile-water) to give 34 mg of the title product. Yield 65%. MS (M+H⁺) 571.

Example 141

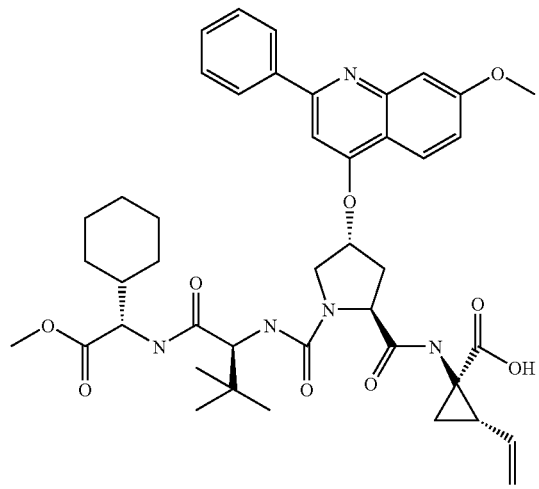

1-{[1-{(Cyclohexyl-methoxycarbonyl-methyl)-carbamoyl]-2,2-dimethyl-propylcarbamoyl}-4-(7-methoxy-2-phenyl-quinolin-4-yloxy)-pyrrolidine-2-carbonyl]-amino}-2-vinyl-cyclopropanecarboxylic acid (141)

Compound 103 was dissolved In dichloromethane (3 ml) and solid sodium bicarbonate (100 mg) and phosgene 20% in toluene (0.1 ml) was added. After 30 min at room temperature the mixture was concentrated to dryness. (S)-(2S2-Amino-3,3-dimethyl-butyrylamino)-cyclohexyl-acetic acid methyl ester (12 mg in dichloromethane 2 ml) was added. After 3 days of agitation at room temperature, the reaction mixture was filtered, concentrated to dryness and purified on preparative HPLC-MS which gave the title product (4.4 mg). M+H⁺ 784.7.

Example 142

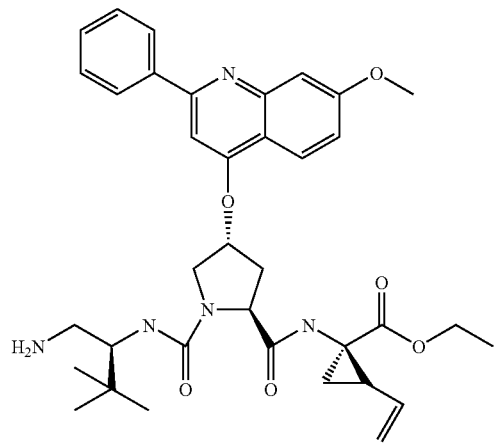

1-{[1-(1-Aminomethyl-2,2-dimethyl-propylcarbamoyl-4-(7-methoxy-2-phenyl-quinolin-4-yloxy)-pyrrolidine-2-carbonyl]-amino}-2-vinyl-cyclopropanecarboxylic acid ethyl ester (142)

The title compound was prepared from compound 12 (1.22 g, 2.43 mmol) by following the procedure described for the preparation for compound 108 but using methanesulphonic acid 2-tert.butoxycarbonylamino-3,3-dimethyl-butyl ester instead of methanesulphonic acid 2-tert.butoxycarbonyl-lamino-4-methyl-pentyl ester, in Example 165 step i). Reduction of the azide as described in Example 109 gave the title compound (1.49 g, 95%). Purity according to HPLC>95%, M+H⁺644.2.

Example 143

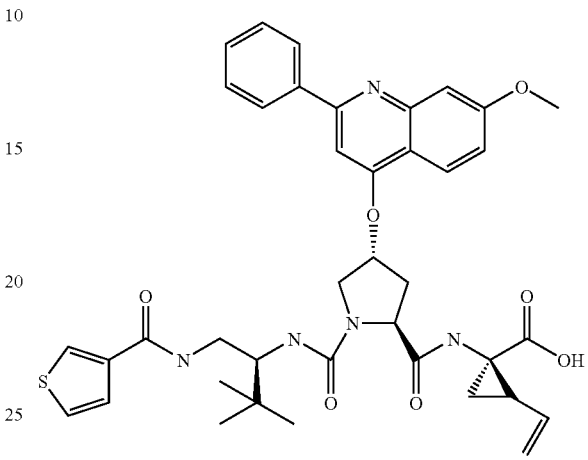

1-{[1-(2,2-Dimethyl-1-{[thiophene-3-carbonyl)-amino]-methyl}-propylcarbamoyl)-4-(7-methoxy-2-phenyl-quinolin-4-yloxy)-pyrrolidine-2-carbonyl]-amino}-2-vinyl-cyclopropanecarboxylic acid (143)

Compound 142 (100 mg, 0,155 mmol) was reacted according to the general procedure 1A for the preparation of compounds 110-116, using thiophene-3-carbonyl chloride (28.5 mg, 0.194 mmol) as acyl chloride which gave the title compound as a white solid (45 mg, 40%). Purity according to HPLC>95%, M+H⁺726.

Example 144

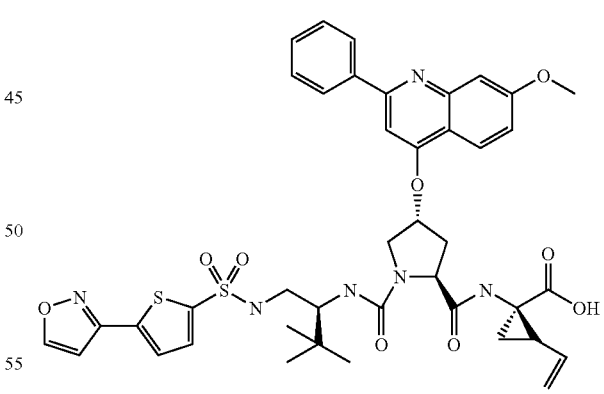

1-{[1-{1-[(5-Isoxazol-3-yl-thiophene-2-sulphony-lamino)-methyl]-2,2-dimethyl-propylcarbamoyl}-4-(7-methoxy-2-phenyl-quinolin-4-yloxy)-pyrrolidine-2-carbonyl]-amino}-2-vinyl-cyclopropanecarboxylic acid (144)

Compound 142 (25 mg, 0.039 mmol) was reacted according to the general procedure 1A for the preparation of compounds 110-116, using 5-isoxazole-3-yl-thiophene-2-sulphonyl chloride (14.5 mg, 0.058 mmol) as acyl chloride which gave the title compound as a white solid (1.8 mg, 6%). Purity according to HPLC was >94%, M+H⁺829.

Example 145

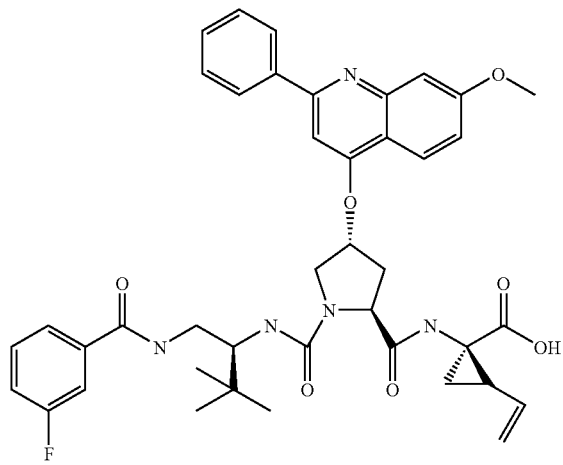

1-{[1-(3-Fluoro-benzoylamino)-methyl]-propylcarbamoyl}-4-(7-methoxy-2-phenyl-quinolin-4-yloxy)-pyrrolidine-2-carbonyl]-amino}-2-vinyl-cyclopropanecarboxylic acid (145)

Compound 142 (25 mg, 0.039 mmol) was reacted according to the general procedure 1A for the preparation of compounds 110-116, using 3-fluorobenzoyl chloride (12.3 mg, 0.078 mmol) as acyl chloride which gave the title compound as a white solid (4.1 mg, 14%). Purity according to HPLC was >94%, M+H⁺738.

Example 146

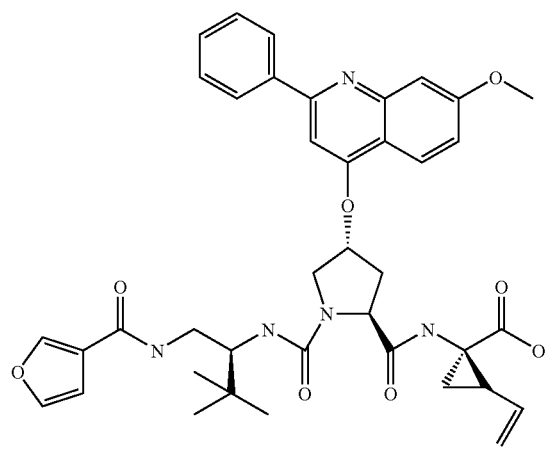

1-{[1-(1 {[(-Furan-3bcarbonyl)-amino]-methyl]-2,2-dimethyl-propylcarbamoyl}-4-(7-methoxy-2-phenyl-quinolin-4-yloxy)-pyrrolidine-2-carbonyl]-amino}-2-vinyl-cyclopropanecarboxylic acid (146)

Compound 142 (25 mg, 0.039 mmol) was reacted according to the general procedure 1B for the preparation of compounds 110-116, using 3-furanoic acid (5.5 mg, 0.049 mmol) as acyl chloride which gave the title compound as a white solid (4.1 mg, 14%). Purity according to HPLC was >99%, M+H⁺710.

Example 147

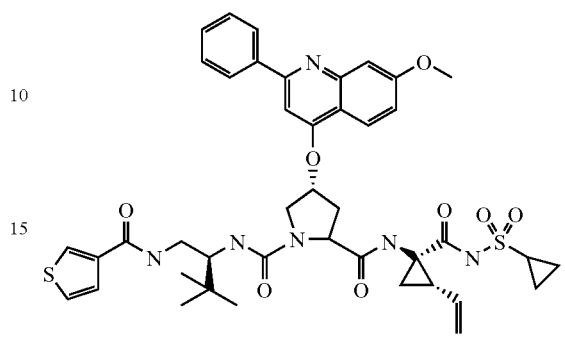

4-(7-Methoxy-2-phenyl-quinolin-4-yloxy)-pyrrolidine-1,2-dicarboxylic acid 2-[(1-cyclopropanesulphonylaminocarbonyl-2-vinyl-cyclopropyl)-amide] 1-[(2,2-dimethyl-1-{[(thiophene-3-carbonyl)amino]-methyl}-propyl)-amide] (147)

To solution of compound 143 (42.2 mg, 0.058 mmol) in chloroform (3 ml) was added cyclopropylsulphonamide (14 mg, 0.116 mmol) followed by diisopropylethylamine (60.5 µl, 0.17 mmol). The solution was stirred at RT for 10 min and then at −20° C. for 30 min. PyBOP (121 mg, 0.116 mmol) was then added as a solid. The solution was kept at −20° C. for 10 days. The solution was then poured into aqueous NaHCO₃ (sat.) and washed with water. The organic layer was dried, concentrated and subjected to purification by HPLC, affording the title compound as a white solid (2.3 mg, 0.0028 mmol), Purity by HPLC>95%, M+H⁺830.

Example 148

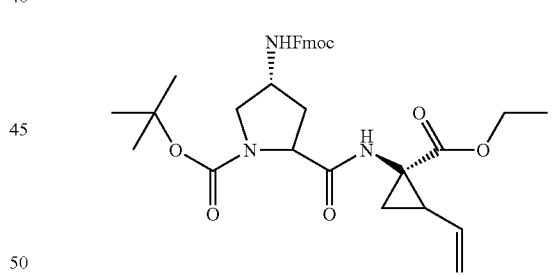

Fmoc-4-amino-2-(1-ethoxycarbonyl-2-vinyl-cyclopropylcarbamoyl)-pyrrolidine-1-carbocyclic acid tert.butyl ester (148)

(2S,4R) Fmoc-4-amino-1-Boc-pyrrolidine-2-carboxylic acid (5.3 g, 11.8 mmol) was dissolved in DCM (100 ml), HATU (4.94 g, 12.99 mmol), DIEA (4.63 ml, 26.57 mmol) and vinylcyclopropylglycine ethyl ester (2.26 g, 11.81 mmol) were added successively. The mixture was stirred for 16 h at room temperature, and was then diluted with DCM (50 ml), washed with citric acid (10% aq), water, NaHCO₃ (sat.aq) and water. The organic phase was dried over Na₂SO₄ and concentrated to afford a beige solid foam (8.11 g) which was subjected to silica gel column chromatography to afford the title compound (7.14 g, 12.11 mmol).

Example 149

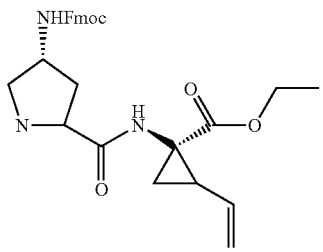

1-[(Fmoc-4-amino-pyrrolidine-2-carbonyl)-amino]-2-vinyl-cyclopropanecarboxylic acid ethyl ester (149)

Compound 148 (3.65 g, 6.04 mmol) was treated with a solution of TFA/DCM (10 ml TFA, 50 ml DCM) for 2.5 h and then concentrated to afford the titled compound (2.99 g, 6.12 mmol).

Example 150

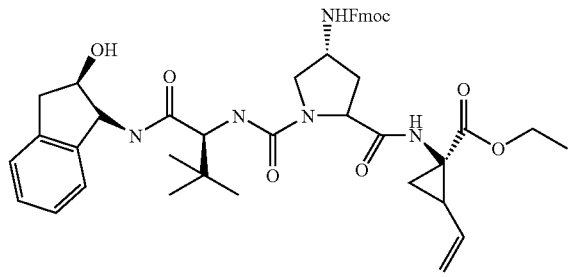

1-({Fmoc-4-amino-1-[1-(2-hydroxy-indan-1-ylcarbamoyl-2,2-dimethyl-propylcarbamoyl]-pyrrolidine-2-carbonyl amino)-2-vinyl-cyclopropanecarboxylic acid ethyl ester (150)

The aminoproline derivative 149 (2.96 g, 6.04 mmol) was stirred together with phosgene (1.93 M in toluene, 4 ml, 7.55 mmol) for 10 min. The solvents and excess of phosgene were evaporated. The residue was dissolved in DCM (30 ml) and t-Bug-aminoindanol (1.9 g, 7.24 mmol) was added as a solution in DCM (30 ml), followed by NaHCO$_3$ (2 g). The mixture was stirred for 48 h, then diluted with DCM, washed with water, 10% citric acid and NaHCO$_3$ (sat, aq), dried over Na$_2$SO$_4$, and evaporated to dryness. The residue was subjected to column chromatography purification, EtOAc-hexane 0-30% to afford the title compound (1 g, 1.3 mmol).

Example 151

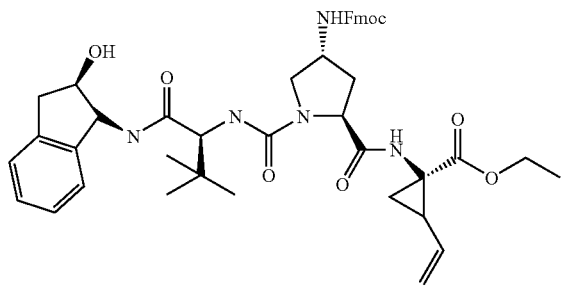

1-({4-Amino-1-[1-(2-hydroxy-indan-1-ylcarbamoyl)-2,2-dimethyl-propylcarbamoyl]-pyrrolidine-2-carbonyl}-amino)-2-vinyl-cyclopropanecarboxylic acid ethyl ester (151)

Compound 150 (595 mg, 0.765 mmol) was dissolved in DMF (20 ml) and treated with Si-piperazine (0.08 mmol/g, 4.78 g, 3.82 mmol) for 48 h. The silica was filtered and washed once with DMF and then with several portions of DCM. The solvents were evaporated and the residue subjected to column chromatography to afford the title compound (170 mg, 0.3 mmol).

Example 152

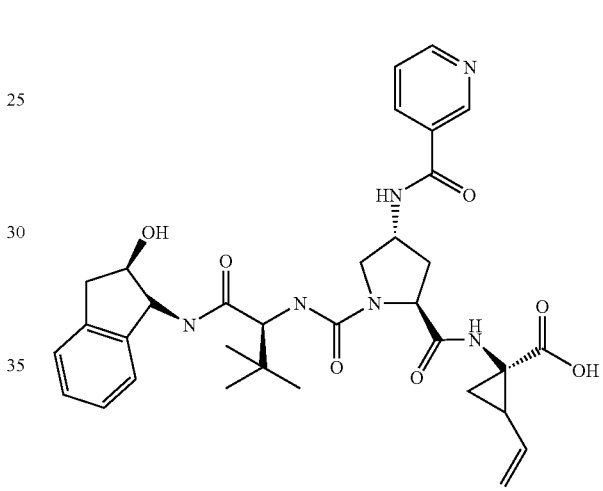

1-({1-[1-(2-Hydroxy-indan-1-ylcarbamoyl)-2,2-dimethyl-propylcarbamoyl]-4-[(pyridine-3-carbonyl)-amino]-pyrrolidine-2-carbonyl}amino)-2-vinyl-cyclopropanecarboxylic acid (152)

To a stirred solution of compound 151 (35 mg, 0.064 mmol) in DCM (1 ml), was added DIEA (0.12 mmol, 19 μl) and nicotinoyl chloride hydrochloride (0.12 mmol, 17 mg). The solution was stirred at RT for 18 h, PS-trisamine was added then stirred at RT for 4 h. After filtration, the solution was washed with citric acid (10% aq) and NaHCO$_3$ (sat, aq), the organic phase was dried over Na$_2$SO$_4$ and concentrated. The residue was dissolved in THF:MeOH (2:1, 1.5 ml). LiOH (1N aq, 3.2 mmol, 320 μl) was added. The solution was stirred at 60° C. for 24 h. Acetic acid was added and then concentrated. The residue was dissolved in MeOH and subjected to purification by HPLC, affording the title compound (19.5 mg, 0.03 mmol). Purity by HPLC>98%, M+H$^+$ 633.1.

Example 153

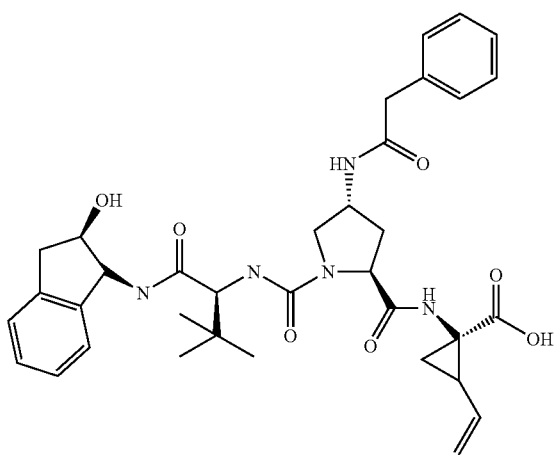

1-({1-[1-(2-Hydroxy-indan-1-ylcarbamoyl)-2,2-dimethyl-propylcarbamoyl]-4-phenylacetamino-pyrrolidine-2-carbonyl}-amino)-2-vinyl-cyclopropanecarboxylic acid (153)

The procedure described in Example 152 but using phenyl acetyl chloride instead of nicotinoyl chloride hydrochloride, was followed which gave the title compound (12.7 mg, 0.019 mmol). Purity by HPLC>90%, M+H$^+$646.1.

Example 154

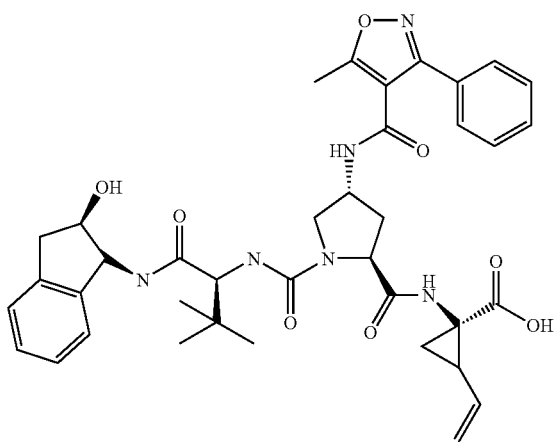

1-({1-[1-(2-Hydroxy-indan-1-ylcarbamoyl)-2,2-dimethyl-propylcarbamoyl]4-[(5-methyl-3-phenyl-isoxazole-4-carbonyl)-amino]-pyrrolidine-2-carbonyl}amino)-2-vinyl-cyclopropanecarboxylic acid (154)

The procedure described in Example 152 but using 5-methyl-3-phenyl-isoxazole-4-carbonyl chloride instead of nicotinoyl chloride hydrochloride, was followed which gave the title compound (3.6 mg, 00055 mmol). Purity by HPLC>98%, M+H$^+$713.1.

Example 155

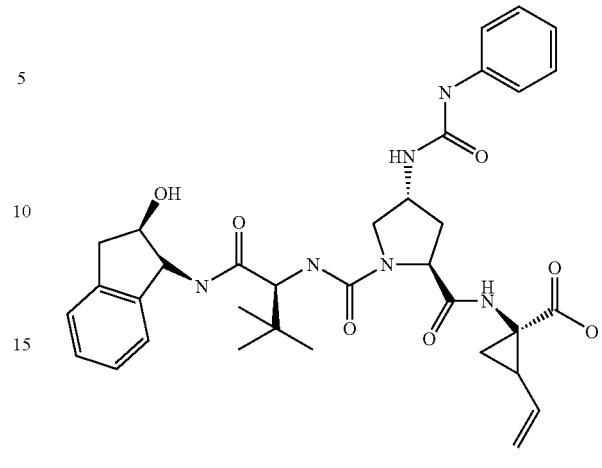

1-{[1-[1-(2-Hydroxy-indan-1-ylcarbamoyl)-2,2-dimethyl-propylcarbamoyl]-4-(3-phenyl-ureido)-pyrrolidine-2-carbonyl]-amino}-2-vinyl-cyclopropanecarboxylic acid (155)

To a stirred solution of compound 151 (30 mg, 0.054 mmol) in acetonitrile:dichloromethane (2:1, 3 ml), triethylamine (0.0648 mmol, 9 µl) and phenylisocyanate (0.0648 mmol, 7 µl) was added The solution was stirred at room temperature for 3 h, methanol was added (1 ml) and then it was concentrated. The residue was dissolved in methanol and subjected to purification by HPLC, affording the ester compound as a white solid (32.7 mg, 0.047 mmol), Purity by HPLC>95%, M+H$^+$675.31. LiOH 1N aq. (0.47 mmol, 475 µl) was added to the ester dissolved in THF:MeOH (2:1). The reaction was stirred at 50° C. for 15 min and then at 8° C. for 12 h followed by addition of acetic acid (0.98 mmol, 53 µl) before concentration. The residue was dissolved in MeOH and subjected to purification by HPLC, affording the title compound as a white solid (3.8 mg, 0.006 mmol), Purity by HPLC>98%, M+H$^+$675.31.

Example 156

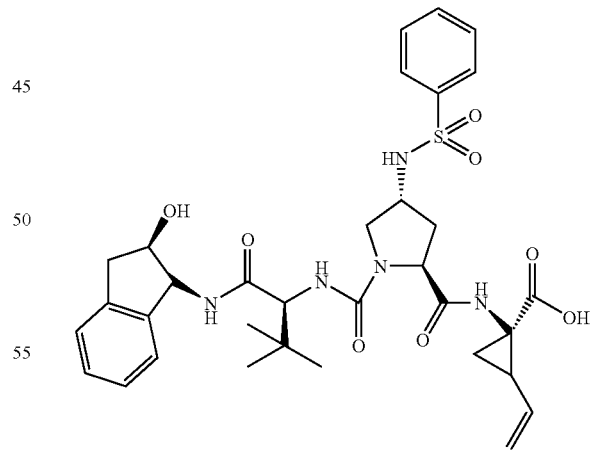

1-({4-Benzenesulphonylamino-1-[1-(2-hydroxy-indan-1-ylcarbamoyl)-2,2-dimethyl-propylcarbamoyl]-pyrrolidine-2-carbonyl}-amino)-2-vinyl-cyclopropanecarboxylic acid (156)

To a stirred solution of compound 151 (30 mg, 0.054 mmol) in DCM (2 ml), DIEA (0.0648 mmol, 11.5 µl) and phenylsulfonylchloride (0.0648 mmol, 11.5 µl) were successively added. The solution was stirred at RT for 3 h, and then it was concentrated. The residue was dissolved in MeOH and subjected to purification by HPLC, affording the ester compound as a white solid (17.9 mg, 0.0257 mmol), Purity by HPLC>95%, M+H$^+$696.24. LiOH 1N aq, (0.25 mmol, 257 µl) was added to the ester dissolved in THF:MeOH (2:1). The reaction was stirred at 50° C. for 1.5 h prior to the addition of acetic acid (0.98 mmol, 53 µl). The solution was concentrated. The residue was dissolved in DCM and washed with water; the aqueous phase was acidified to pH 5 and then extracted with dichloromethane and ethyl acetate. The combined organic phases were dried over Na$_2$SO$_4$ and concentrated, affording the title compound as a white solid (7.1 mg, 0.01 mmol), Purity by HPLC>98%, M+H$^+$668.19.

Example 157

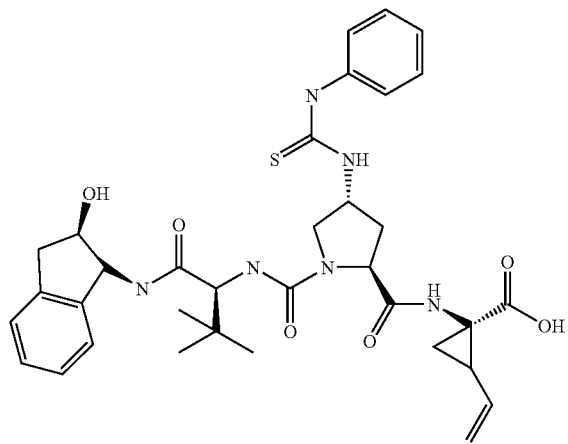

1-{[1-[1-(2-Hydroxy-indan-1-ylcarbamoyl)-2,2-dimethyl-propylcarbamoyl]-4-(3-phenyl-thioureido)-pyrrolidine-2-carbonyl}-amino)-2-vinyl-cyclopropanecarboxylic acid (157)

To a stirred solution of compound 151 (30 mg, 0.054 mmol) in acetonitril (3 ml), TEA (0.0648 mmol, 9 µl) and phenylthioisocyanate (0.0648 mmol, 7.8 µl) were successively added. The solution was stirred at RT for 16 h, and then it was concentrated. The residue was dissolved in MeOH and subjected to purification by HPLC, affording the ester compound as a white solid (22.7 mg, 0.0328 mmol), Purity by HPLC>95%, M+H$^+$691.2. LiOH 1N aq, (0.33 mmol, 328 µl) was added to the ester dissolved in THF:MeOH (2:1). The reaction was stirred at 50° C. for 2.5 h prior to the addition of acetic acid (0.98 mmol, 53 µl). The solution was concentration. The residue was dissolved in dichloromethane and washed with water, the aqueous phase was extracted with EtOAc. The combined organic phases were dried over Na$_2$SO$_4$ and concentrated, affording the title compound as a white solid (7.2 mg, 0.01 mmol), Purity by HPLC>98%, M+H$^+$663.26.

Assays

The compounds of the invention are conveniently assayed for activity against the NS3 protease of flavivirus such as HCV using conventional in vitro (enzyme) assays or cell culture assays.

A useful assay is the Bartenshlager replicon assay disclosed in EP 1043399. An alternative replicon assay is described in WO 03064416.

A convenient enzyme assay involving the inhibition of full-length hepatitis C NS3 is essentially as described in Poliakov, 2002 Prot Expression & Purification 25 363 371.

Briefly, the hydrolysis of a depsipeptide substrate, Ac-DED(Edans)EEAbuψ[COO]ASK(Dabcyl)-NH$_2$ (AnaSpec, San José, USA), is measured spectrofluorometrically in the presence of a peptide cofactor, KKGSWIVGRIV-LSGK, as described by Landro, 1997 Biochem 36 9340-9348. The enzyme (1 nM) is incubated in a buffer such as 50 mM HEPES, pH 7.5, 10 mM DTT, 40% glycerol, 0.1% n-octyl-β-D-glucoside, with 25 µM cofactor and inhibitor at say 30° C. for 10 min, whereupon the reaction is initiated by addition of substrate, typically 0.5 µM substrate. Inhibitors are typically dissolved in DMSO, sonicated for 30 s and vortexed. The solutions are generally stored at −20° C. between measurements.

An alternative enzyme assay is described in WO 0399316 and employs an HCV NS3/4A protease complex FRET peptide assay. The purpose of this in vitro assay is to measure the inhibition of HCV NS3 protease complexes, derived from the BMS, H77C or J416S strains, as described below, by compounds of the present invention. This assay provides an indication of how effective compounds of the present invention would be in Inhibiting HCV proteolytic activity.

Serum is taken from an HCV-infected patient. An engineered full-length cDNA template of the HCV genome (BMS strain) was constructed from DNA fragments obtained by reverse transcription-PCR (RT-PCR) of serum RNA and using primers selected on the basis of homology between other genotype Ia strains. From the determination of the entire genome sequence, a genotype I a was assigned to the HCV isolate according to the classification of Simmonds et al. (See P Simmonds, K A Rose, S Graham, S W Chan, F McOmish, B C Dow, E A Follett, P L Yap and H Marsden, J. Clin. Microbiol., 31(6), 1493-1503 (1993)). The amino acid sequence of the nonstructural region, NS2-5B, was shown to be >97% identical to HCV genotype Ia (H77C) and 87% identical to genotype Ib (J4L6S). The infectious clones, H77C (I a genotype) and J4L6S (I b genotype) can be obtained from R. Purcell (NIH) and the sequences are published in Genbank (AAB67036, see Yanagi, M., Purcell, R. H., Emerson, S. U. and Bukh. Proc. Natl. Acad. Sci. U.S.A. 94 (16) 8738-8743 (1997); AF054247, see Yanagi, M., St Claire, M., Shapiro, M., Emerson, S. U., Purcell, R. H. and Bukhj, Virology 244 (1), 161 (1998)).

The BMS, H77C and J4L6S strains are conventional for production of recombinant NS3/4A protease complexes. DNA encoding the recombinant HCV NS3/4A protease complex (amino acids 1027 to 1711) for these strains were manipulated as described by P. Gallinari et al. (see Gallinari P, Paolini C, Brennan D, Nardi C, Steinkuhler C, De Francesco R. Biochemistry. 38(17):562032, (1999)). Briefly, a three-lysine solubilizing tail was added at the 3'-end of the 3 0 NS4A coding region. The cysteine in the P1 position of the NS4A-NS4B cleavage site (amino acid 1711) was changed to a glycine to avoid the proteolytic cleavage of the lysine tag. Furthermore, a cysteine to serine mutation can be introduced by PCR at amino acid position 1454 to prevent the autolytic cleavage in the NS3 helicase domain. The variant DNA fragment can be cloned in the pET21b bacterial expression vector (Novagen) and the NS3/4A complex can be expressed in Escherichia coli strain BL21 (DE3) (Invitrogen) following the protocol described by P. Gallinari et al. (see Gallinari P, Brennan D, Nardi C, Brunetti M, Tomei L, Steinkuhler C, De Francesco R., J. Virol. 72(8):6758-69 (1998)) with modifications. Briefly, NS3/4A expression can be induced with 0.5 mM Isopropyl beta-D thiogalactopyranoside (IPTG) for 22 hr at 20° C. A typical fermentation (10 l) yields approximately 80 g of wet cell paste. The cells are resuspended in lysis buffer (10 mL/g) consisting of 25 mM N-(2Hydroxyethyl)piperazine-N'-(2-Ethane Sulfonic acid) (HEPES), pH7.5, 20% glycerol, 500 mM Sodium Chloride (NaCl), 0.5% Triton-X100, 1 ug/mL lysozyme, 5 mM Magnesium Chloride (MgCl2), 1 ug/mL DnaseI, 5 mM beta-Mercaptoethanol (BME), Protease inhibitor-Ethylenediamine Tetraacetic acid (EDTA) free (Roche), homogenized and incubated for 20 mins at VC. The homogenate is sonicated and clarified by ultra-centrifugation at 235000 g for 1 hr at 4° C.

Imidazole is added to the supernatant to a final concentration of 15 mM and the pH adjusted to 8. The crude protein extract is loaded on a Nickel Nitrilotriacetic acid (Ni-NTA) column pre-equilibrated with buffer B (25n-tM 2 0 HEPES, pH8 20% glycerol, 500 mM NaCl, 0.5% Triton-X100, 15 mM imidazole, 5 mM BME). The sample is loaded at a flow rate of 1 mL/min. The column is washed with 15 column volumes of buffer C (same as buffer B except with 0.2% Triton-X100). The protein is eluted with 5 column volumes of buffer D (same as buffer C except with 200 mM imidazole).

NS3/4A protease complex-containing fractions are pooled and loaded on a desalting column Superdex-S200 pre-equilibrated with buffer D (25 MM HEPES, pH7.5, 20% glycerol, 3OO mM NaCl, 0.2% Triton-XIOO, IO mM BME). Sample is loaded at a flow rate of 1 mL/min. NS3/4A protease complex3 0 containing fractions are pooled and concentrated to approximately 0.5 mg/mL. The purity of the NS3/4A protease complexes, derived from the BMS, H77C and J4L6S strains, are typically judged to be greater than 90% by SDS-PAGE and mass spectrometry analyses.

The enzyme is generally stored at −80° C., thawed on ice and diluted prior to use in assay buffer. The substrate used for the NS3/4A protease assay, is conveniently RET S 1 (Resonance Energy Transfer Depsipeptide Substrate; AnaSpec, Inc. cat # 22991)(FRET peptide), described by Taliani et al. in Anal. Biochem. 240(2):6067 (1996). The sequence of this peptide is loosely based on the NS4A/NS4B natural cleavage site except there is an ester linkage rather than an amide bond at the cleavage site. The peptide substrate is incubated with one of the three recombinant NS3/4A complexes, in the absence or presence of a compound of the present invention, and the formation of fluorescent reaction product was followed in real time using a Cytofluor Series 4000. Useful reagents are as follow: HEPES and Glycerol (Ultrapure) can be obtained from GIBCO-BRL. Dimethyl Sulfoxide (DMSO) is obtained from Sigma. Beta-Mercaptoethanol is obtained from Bio Rad.

Assay buffer: 50m.M HEPES, pH7.5; 0.15M NaCl; 0.1% Triton; 15% Glycerol; 10 mM BME. Substrate: 2 uM final concentration (from a 2 mM stock 2 0 solution in DMSO stored at −20° C.). HCV NS3/4A type Ia (Ib), 2-3 nM final concentration (from a 5 uM stock solution in 25 mM HEPES, pH7.5, 20% glycerol, 300m.M NaCl, 0.2% Triton-X100, 10 mM BME). For compounds with potencies approaching the assay limit, the assay can be made more sensitive by adding 50 ug/mL BSA to the assay buffer and/or reducing the end protease concentration to 300 pM.

The assay is conveniently performed in a 96-well polystyrene black plate from Falcon. Each well contains 25ul NS3/4A protease complex in assay buffer, 50ul of a compound of the present invention in 10% DMSO/assay buffer and 25ul substrate in assay buffer. A control (no compound) is also prepared on the same assay plate. The enzyme complex is mixed with compound or control solution, typically for 1 min before initiating the enzymatic reaction by the addition of substrate. The assay plate is generally read immediately using a spectrophotometer such as a Cytofluor Series 4000 (Perspective Biosysterns). The instrument is conveniently set to read an emission of 340 nm and excitation of 490 nm at 25° C. Reactions are generally followed for approximately 15 minutes.

The percent inhibition can be calculated with the following equation.

$$100.-[(dF_{inh}/dF_{con})XI00]$$

where dF is the change in fluorescence over the linear range of the curve. A nonlinear curve fit is applied to the inhibition-concentration data, and the 50% effective concentration ($IC_{50}$) is calculated by the use software such as Excel XI-fit software using the equation:

$$y=A+((B-A)/(1+((C/x)^D))).$$

Enzyme assays conveniently utilize a fluorescence resonance energy transfer (FRET) principle to generate a spectroscopic response to an HCV NS3 serine protease catalyzed NS4A/4B cleavage event. The activity is typically measured in a continuous fluorometric assay using an excitation wavelength of 355 nm and emission wavelength of 500 nm. The initial velocity may be determined from 10 minutes continuous reading of Increased fluorescence intensities as a result of the NS3 protease catalyzed cleavage event.

An alternative enzyme assay can be carried out as follows:

Materials

Recombinant HCV NS3 full length enzyme can be prepared as shown in Poliakov et al Protein Expression & purification 25 (2002) 363-371.

The NS4A cofactor conveniently has an amino acid sequence of KKGSVVIVGRIVLSGK (commercially available), generally prepared as a 10 mM stock solution in DMSO.

The FRET-substrate (Ac-Asp-Glu-Asp(EDANS)-Glu-Glu-Abu-ψ-[COO)Ala-Ser-Lys(DABCYL)-NH2, MW1548.60 can be purchased from AnaSpec RET S1, California. USA) and is typically prepared as a 1.61 mM stock solution in DMSO. Aliquots (50 μl/tube) should be wrapped with aluminum foil to protect from direct light and stored in −20° C.

Reference compound-1, N-1725 with a sequence of AcAsp-D-Gla-Leu-Ile-Cha-Cys, MW 830.95 may be purchased from BACHEM, Switzerland and is generally prepare as a 2 mM stock solution in DMSO and stored in aliquots in −20° C. 1M HEPES buffer may be purchased from Invitrogen Corporation, storage at 20° C. Glycerol may be purchased from Sigma, 99% purity.

CHAPS, 3-[(3-Cholamidopropyl)dimethylammonio]-1-propanesulfonate: may be purchased from Research Organics, Cleveland, Ohio 44125, USA. MW614.90 DTT, DL-Dithiothreitol (Cleland Reagent: DL-DTT) 99% purity, MW.154.2 Storage: +4° C.

DMSO may be purchased from SDS, 13124 Peypin, France. 99.5% purity.

TRIS, ultra pure (TRIS-(hydroxymethylaminomethane), may be purchased from ICN Biomedicals Inc.

N-dodecyl-β-D-maltoside, minimum 98%, may be purchased from Sigma, storage −20° C.

Equipment

Microtiter plates (white cliniplate, ThermoLab Systems cat no. 9502890) Eppendorf pipettes.

Biohit pipette, multi dosing.

Ascent fluorimeter, filterpair ex 355 nm, em500 nm.

Method

Experimental procedure:

10 mM stock solutions of the compounds are made in DMSO. The stock solutions are stored in room temperature while testing and placed in −20° C. at long-time storage.

Assay buffer A:
    50 mM HEPES buffer, pH=7.5, 40% Glycerol, 0.1% CHAPS Storage: room temperature
    10 mM DTT (stored in aliquots at −20° C. and added fresh at each experiment)

Assay buffer B:
  25 mM TRIS pH7.5, 0.15 M NaCl, 10% glycerol, 0.05% n-dodecyl-β-D-maltoside
  5 mM DTT (stored in aliquots at −20° C. and added fresh at each experiment)

Experiment sequence:

Preparation of Reaction Buffer (for One Plate, 100 Reactions) (Buffer A)
  1. Prepare 9500 μl assay buffer (HEPES, pH=7.5, 40% glycerol and 0.1% CHAPS in de ionized water. Add DTT giving a final concentration of 10 mM (freshly prepared for every run).
  2. Thaw rapidly the NS3 protease
  3. Add 13.6 μl NS3 protease and 13.6 μl NS4A peptide and mix properly. Leave the mixture for 15 minutes in room temperature.
  4. Place the enzyme stock solution back into liquid nitrogen or −80° C. as soon as possible.

Preparation of Reaction Buffer (for One Plate, 100 Reactions) (Buffer B)
  5. Prepare 9500 μl assay buffer (TRIS, pH=7.5, 0.15 M NaCl, 0.5 mM EDTA, 10% glycerol and 0.05% n-dodecyl β-D-maltoside in de ionized water. Add DTT giving a final concentration of 5 mM (freshly prepared for every run).
  6. Thaw the NS3 protease rapidly.
  7. Add 27.2 μl NS3 protease and 13.6 μl NS4A peptide and mix properly. Leave the mixture for 15 minutes in room temperature.
  8. Place the enzyme stock solution back into liquid nitrogen or −80° C. as soon as possible.

Preparation of Inhibitor/Reference Compound

Make a dilution series of the inhibitors in DMSO to 100× the final concentrations 10, 1, 0.1, 0.01 and 0.001 μM. The final DMSO concentration in 100 μl total reaction volume is 1%.

Make a dilution series of the reference compound, N-1725 in DMSO to 100× the final concentrations 120, 60, 30, 15, 7.5 and 3.75 nM.

Eight enzyme control wells are needed for every run.

Blank wells contain 95 μL buffer (without NS3 PR), 1 μL DMSO and 5 μL substrate.

Preparation of FRET Substrate

Dilute the substrate stock solution (1.61 mM) with assay buffer to 40 μM working solution. Avoid exposure to light.

Assay Sequence

Use 96-well cliniplate, the total assay volume per well is 100 μl.
  1. Add 95 μL of assay buffer to each well
  2. Add 1 μl inhibitor/reference compound
  3. Pre incubate for 30 minutes at room temperature
  4. Start the reaction by adding 5 μL 40 μM substrate solution (final concentration 2 μM)
  5. Read continuously for 20 minutes at ex=355 nm and em=500 nm, monitoring the increased fluorescence per minute.
  6. Plot the progression curve (within linear range, 8-10 time points) and determine the slope as an initial velocity with respect to each individual inhibitor concentration.
  7. Calculate % inhibition with respect to enzyme control.

Treatment of Results

The result is expressed as % inhibition at a certain concentration (screen) or as a Ki value in nM or μM.
  Calculation of % inhibition.

The initial velocity is determined from 10 minutes continuous reading of increased fluorescence intensities as a result of the NS3 protease catalyzed cleavage event.

The change in slope for the inhibitor compared to the enzyme control gives the % inhibition at a certain concentration.

Calculation of Ki.

All inhibitors are treated as if they follow the rules of competitive inhibition.

The $IC_{50}$ value is calculated from the inhibition values of a series of inhibitor concentrations. The calculated value is used in the following equation:

$$K_i = IC_{50}/(1+S/Km)$$

Plotting of the graph is done by help of two calculation programs: Grafit and Graphpad Various compounds of the invention exemplified above displayed $IC_{50}$s in the range 1 nM to 6.9 micromolar and $ED_{50}$s in the sub-micromolar to micromolar range.

Drug Escape Resistance Pattern and Rate

Replicon cultures in microtitre plates can be used to determine resistance development rates and to select out drug escape mutants. The compounds being tested are added at concentrations around their $ED_{50}$ using, say, 8 duplicates per concentration. After the appropriate replicon incubation period the protease activity in the supernatant or lysed cells is measured.

The following procedure is followed at subsequent passages of the cultures. Virus produced at the concentration of test compound showing >50% of the protease activity of untreated infected cells (SIC, Starting Inhibitory Concentration) are passaged to fresh replicon cultures. An aliquot, say, 15 μl supernatent from each of the eight duplicates are transferred to replicon cells without the test compound (control) and to cells with test compound at the same concentration, and additionally two respectively fivefold higher concentrations. (See the table below below)

When the viral component of replicon propagation (for example as measured by HCV protease activity) is permitted at the highest non-toxic concentration (5-40 μM), 2-4 parallel wells are collected and expanded to give material for sequence analysis and cross-wise resistance.

Key:

Viral Growth Permitted
  Virus production inhibited

| | | | | 125 × SIC |
|---|---|---|---|---|
| | | | 125 × SIC | 25 × SIC → |
| | | | 25 × SIC | 5 × SIC |
| | | 25 × SIC | 5 × SIC → | No compound |
| | 25 × SIC | 5 × SIC → | No compound | |
| | 5 × SIC | SIC | | |
| SIC | SIC → | No compound | | |
| → | No compound | | | |
| Pass 1 | Pass 2 | Pass 3 | Pass 4 | Pass 5 |

Alternative methods for assessing activity on drug escape mutants include the preparation of mutant enzyme bearing the distinctive mutation for use in standard Ki determinations as shown above. For example WO 04/039970 describes constructions allowing access to HCV proteases bearing the 155, 156 and/or 168 drug escape mutants arising from the selective pressure of BILN-2061 and VX-950. Susch constructs can then be engineered into replicon vectors in place of the wild type protease, thereby allowing ready assessment in a cellular assay, of whether a given compound is active against a give drug escape mutant.

P450 Metabolism

The metabolism of compounds of the invention through the main isoforms of the human cytochrome system P450 are conveniently determined in baculovirus infected insect cells transfected with human cytochrome P450 cDNA (supersomes) Gentest Corp. Woburn USA.

The test compounds at concentrations 0.5, 5 and 50 μM are incubated in duplicate in the presence of supersomes overexpressing various cytochrome P450 isoforms, including CYP1A2+P450 reductase, CYP2A6+P450 reductase, CYP2C9-Arg 144+P450 reductase, CYP2C19+P450 reductase, CYP2D6-Val 374+P450 reductase and CYP3A4+P 450 reductase. Incubates contain a fixed concentration of cytochrome P450 (eg 50 pmoles) and are conducted over 1 hour. The involvement of a given isoform in the metabolism of the test compound is determined by UV HPLC chromatographically measuring the disappearance of parent compound.

The invention claimed is:

1. A compound of formula I':

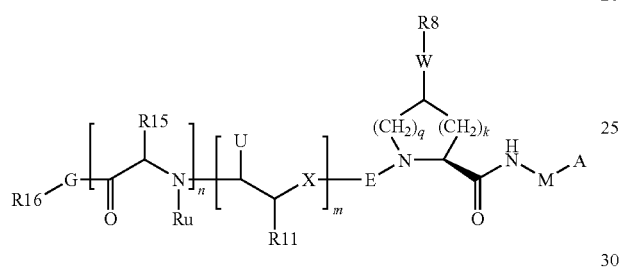

wherein

A is $C(=O)OR^1$, or $C(=O)NHSO_2R^2$, wherein;
$R^1$ is hydrogen, $C_1$-$C_6$alkyl, $C_0$-$C_3$alkylcarbocyclyl, $C_0$-$C_3$alkylheterocyclyl;
$R^2$ is $C_1$-$C_6$alkyl, $C_0$-$C_3$alkylcarbocyclyl, $C_0$-$C_3$alkylheterocyclyl;
wherein
$R^2$ is optionally substituted with 1 to 3 substituents independently selected from the group consisting of halo, oxo, nitrile, azido, nitro, $C_1$-$C_6$alkyl, $C_0$-$C_3$alkylcarbocyclyl, $C_0$-$C_3$alkylheterocyclyl, $NH_2CO$—, Y—NRaRb, Y—O—$R_b$, Y—$C(=O)$Rb, Y—$(C=O)NRaRb$, Y—NRaC$(=O)$Rb, Y—NHSO$_p$Rb, Y—S$(=O)_p$Rb, Y—S$(=O)_p$NRaRb, Y—$C(=O)$ORb, Y—NRaC$(=O)$ORb;
Y is independently a bond or $C_1$-$C_3$alkyl;
Ra is independently H or $C_1$-$C_3$alkyl;
Rb is independently H, $C_1$-$C_6$alkyl, $C_0$-$C_3$alkylcarbocyclyl or $C_0$-$C_3$alkylheterocyclyl;
p is independently 1 or 2;
M is $CR^7R^{7'}$;
$R^7$ taken together with $R^{7'}$ forms a $C_3$-$C_6$cycloalkyl ring substituted with J;
q is 1 and k is 1;
W is —$CH_2$—, —O—, —OC$(=O)$NH, —OC$(=O)$, —S—, —NH—, —NRa, —NHSO$_2$—, —NHC$(=O)$NH— or —NHC$(=O)$—, —NHC$(=S)$NH— or a bond;
$R^8$ is a ring system containing 1 or 2 saturated, partially saturated or unsaturated rings each of which has 4-7 ring atoms and each of which has 0 to 4 hetero atoms independently selected from S, O and N, the ring system being optionally spaced from W by a $C_1$-$C_3$ alkylene group; any of which $R^8$ groups can be optionally mono-, di-, or tri-substituted with $R^9$, wherein
$R^9$ is independently selected from the group consisting of halo, oxo, nitrile, azido, nitro, $C_1$-$C_6$alkyl, $C_0$-$C_3$alkylcarbocyclyl, $C_0$-$C_3$alkylheterocyclyl, $NH_2C(=O)$—, Y—NRaRb, Y—O—Rb, Y—$C(=O)$Rb, Y—$(C=O)NRaRb$, Y—NRaC$(=O)$Rb, Y—NHSO$_p$Rb, Y—S$(=O)_p$Rb, Y—S$(=O)_p$NRaRb, Y—$C(=O)$ORb, Y—NRaC$(=O)$ORb;
wherein said carbocyclyl or heterocyclyl is optionally substituted with $R^{10}$; wherein
$R^{10}$ is $C_1$-$C_6$alkyl, $C_3$-$C_7$cycloalkyl, $C_1$-$C_6$alkoxy, amino, amido, sulfonyl, ($C_1$-$C_3$ alkyl)sulfonyl, $NO_2$, OH, SH, halo, haloalkyl, carboxyl;
E is —$C(=O)$—, —$C(=S)$—, —$S(=O)_2$—, —$S(=O)$—, —$C(=N$—Rf$)$—;
Rf is H, —CN, —$C(=O)NRaRb$; —$C(=O)C_1$-$C_3$alkyl;
J is a single 3 to 10-membered saturated or partially unsaturated alkylene chain that extends from the $R^7/R^{7'}$ cycloalkyl to G and forms a macrocycle, which chain is optionally interrupted by one to three heteroatoms independently selected from: —O—, —S— or —$NR^{12}$—, and wherein 0 to 3 carbon atoms in the chain are optionally substituted with $R^{14}$; wherein;
$R^{12}$ is H, $C_1$-$C_6$alkyl, $C_3$-$C_6$cycloalkyl, or $C(=O)R^{13}$;
$R^{13}$ is $C_1$-$C_6$alkyl, $C_0$-$C_3$alkylcarbocyclyl, $C_0$-$C_3$alkylheterocyclyl;
$R^{14}$ is independently selected from the group consisting of H, $C_1$-$C_6$alkyl, $C_1$-$C_6$haloalkyl, $C_1$-$C_6$alkoxy, hydroxy, halo, amino, oxo, thio and $C_1$-$C_6$thioalkyl;
m is 0 ; n is 0;
G is —NRy-;
Ry is J;
$R^{16}$ is H; or $C_1$-$C_6$alkyl, $C_0$-$C_3$alkylcarbocyclyl, $C_0$-$C_3$alkylheterocyclyl, any of which can be substituted with halo, oxo, nitrile, azido, nitro, $C_1$-$C_6$alkyl, $C_0$-$C_3$alkylcarbocyclyl, $C_0$-$C_3$alkylheterocyclyl, $NH_2CO$—, Y—NRaRb, Y—O—Rb, Y—$C(=O)$Rb, Y—$(C=O)NRaRb$, Y—NRaC$(=O)$Rb, Y—NH SO$_p$Rb, Y—S$(=O)_p$Rb, Y—S$(=O)_p$NRaRb, Y—$C(=O)$ORb, Y—NRac$(=O)$ORb;

or a pharmaceutically acceptable salt thereof.

2. A compound according to claim 1, with the partial structure Ia', Ib' or Iaa':

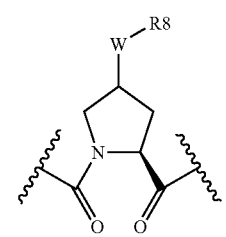

Ia'

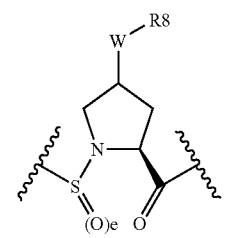

Ib'

-continued

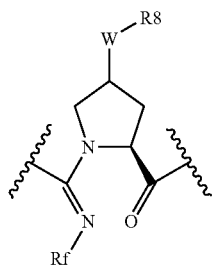

Iaa' where e is 1 or 2.

3. A compound according to claim 1, wherein E is —C(═O)—.

4. A compound according to claim 1, wherein $R^{16}$ is H, $C_1$-$C_3$ alkyl or $C_3$-$C_6$ cycloalkyl.

5. A compound according to claim 1, wherein W is —OC(═O)—, —NRa—, NHS(O)$_2$—; —NHC(═O)— or —OC(═O)NH—.

6. A compound according to claim 1, wherein W is —S—, a bond or —O—.

7. A compound according to claim 5 or 6 wherein $R^8$ is optionally substituted $C_0$-$C_3$alkylcarbocyclyl or optionally substituted $C_0$—$C_3$-alkylheterocyclyl.

8. A compound according to claim 7, wherein the $C_0$-$C_3$ alkyl moiety is methylene or a bond.

9. A compound of formula I':

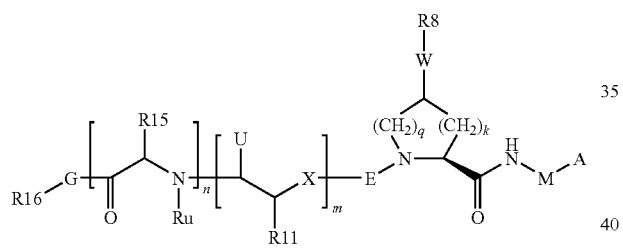

wherein

A is C(═O)OR$^1$, or C(═O)NHSO$_2$R$^2$, wherein;
R$^1$ is hydrogen, $C_1$-$C_6$alkylcarbocyclyl, $C_0$-$C_3$alkylheterocyclyl;
R$^2$ is $C_1$-$C_6$alkyl, $C_0$alkylcarbocyclyl, $C_0$-$C_3$alkylheterocyclyl; wherein
R$^2$ is optionally substituted with 1 to 3 substituents independently selected from the group consisting of halo, oxo, nitrile, azido, nitro, $C_1$-$C_6$alkyl, $C_0$-$C_3$alkylcarbocyclyl, $C_0$-$C_3$alkylheterocyclyl, NH$_2$CO—, Y—NRaRb, Y—O—R$_b$, Y—C(═O)Rb, Y—(C═O)NRaRb, Y—NRaC(═O)Rb, Y—NHSO$_p$Rb, Y—S(═O)$_p$Rb, Y—S(═O)$_p$N-RaRb, Y—C(═O)ORb, Y—NRaC(═O)ORb;
Y is independently a bond or $C_1$-$C_3$alkyl;
Ra is independently H or $C_1$-$C_3$alkyk;
Rb is independently H, $C_1$-$C_6$alkyl, $C_0$-$C_3$alkylcarbocyclyl or $C_0$-$C_3$alkylheterocyclyl;
p is independenly 1 or 2;
M is CR$^7$R$^{7'}$;
R$^7$ taken together with R$^{7'}$ forms a $C_3$-$C_6$cycloalkyl ring substituted with J;
q is 1 and k is 1;
W is —O—, —OC(═O)NH, —OC(═O), —S—, —NRa, —NHSO$_2$—, —NHC(═O)—, or a bond;

R$^8$ is $C_0$-$C_3$alkylaryl, or $C_0$-$C_3$alkylheteroaryl, either of which is optionally mono, di, or tri substituted with R$^9$, wherein;
R$^9$ is $C_1$-$C_6$ alkyl, $C_1$-$C_6$alkoxy, NO$_2$, OH, halo, trifluoromethyl, amino, amido optionally mono- or di-substituted with $C_1$-$C_6$alkyl, $C_0$-$C_3$alkylaryl, $C_0$-$C_3$alkylheteroaryl, carboxyl, aryl or heteroaryl being optionally substituted with R$^{10}$; wherein
R$^{10}$ is $C_1$-$C_6$alkyl, $C_3$-$C_7$cycloalkyl, $C_1$-$C_6$alkoxy, amino optionally mono- or di-substituted with $C_1$-$C_6$alkyl, amido, sulfonyl$C_1$-$C_6$alkyl, NO$_2$, OH, halo, trifluoromethyl, carboxyl, or heteroaryl;
E is —C(═O)—, —C(═S)—, —S(═O)$_2$, —S(═O)—, C(═N—Rf)—;
Rf is H, —H, —CN, —C(═O)NRaRb; —C(═O)$C_1$-$C_3$alkyl;
J is a single 3 to 10-membered saturated or partially unsaturated alkylene chain that extends from the R$^7$/R$^{7'}$ cycloalkyl to G and forms a macrocycle, which chain is optionally interrupted by one to thee heteroatoms independently selected from: —O—, —S— or —NR$^{12}$—, and wherein 0 to 3 carbon atoms in the chain are optionally substituted with R$^{14}$; wherein;
R$^{12}$ is H, $C_1$-$C_6$alkyl, $C_3$-$C_6$cycloalkyl, or C(═O)R$^{13}$;
R$^{13}$ is $C_1$-$C_6$, $C_0$-$C_3$alkylcarbocyclyl, $C_0$-$C_3$alkylheterocyclyl;
R$^{14}$ is independently selected from the group consisting of H, $C_1$-$C_6$alkyl, $C_1$-$C_6$haloalkyl, $C_1$-$C_6$alkoxy, hydroxyl, halo, amino, oxo, thio and $C_1$-$C_6$thioalkyl;
m is 0; n is 0;
G is —NRy-;
Ry is J;
R$^{16}$ is H; or $C_1$-$C_6$alkyl, $C_0$-$C_3$alkylcarbocyclyl, $C_0$-$C_3$alkylheterocyclyl, any of which can be substituted with halo, oxo, nitrile, azido, nitro, $C_1$-$C_6$, $C_0$-$C_3$alkylcarbocyclyl, $C_0$-$C_3$alkylheterocyclyl, NH$_2$CO—, Y—NRaRb, Y—O—Rb, Y—C(═))Rb, Y—(C═O)NRaRb, Y—NRaC(═O)Rb, Y—NH SO$_p$Rb, Y—S(═O)$_p$Rb, Y—S(═O)$_p$NRaRb, Y—C(═O)Orb, Y—NRac(═O)Orb;

or a pharmaceutically acceptable salt thereof.

10. A compound according to claim 9 wherein R$^9$ is $C_1$-$C_6$ alkyl, $C_1$-$C_6$alkoxy, amino, di-($C_1$-$C_3$ alkyl)amino, $C_1$-$C_3$alkylamide, aryl or heteroaryl, the aryl or heteroaryl being optionally substituted with R$^{10}$; wherein
R$^{10}$ is $C_1$-$C_6$alkyl, $C_3$-$C_7$cycloalkyl, $C_1$-$C_6$alkoxy, amino, mono- or di-$C_1$-$C_3$ alkylamino, amido, halo, trifluoromethyl, or heteroaryl.

11. A compound according to claim 10, wherein, R$^{10}$ is $C_1$-$C_6$alkyl, $C_1$-$C_6$alkoxy, amino optionally mono- or di substituted with $C_1$-$C_3$ alkyl, amido, $C_1$-$C_3$-alkylamide, halo, or heteroaryl.

12. A compound according to claim 11 wherein R$^{10}$ is methyl, ethyl, isopropyl, tert-butyl, methoxy, chloro, amino optionally mono- or di substituted with $C_1$-$C_3$ alkyl, amido, or $C_1$-$C_3$alkyl thiazolyl.

13. A compound according to claim 8, wherein R$^8$ is 1-naphthylmethyl, 2-naphthylmethyl, benzyl, 1-naphthyl, 2-naphthyl, or quinolinyl any of which is unsubstituted, mono, or disubstituted with R$^9$.

14. A compound according to claim 13 wherein R$^8$ is 1-naphthylmethyl, or quinolinyl any of which is unsubstituted, mono, or disubstituted with R$^9$.

15. A compound according to claim 14 wherein $R^8$ is

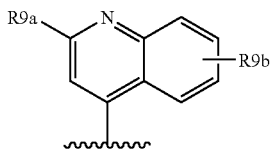

wherein $R^{9a}$ is $C_1$-$C_6$ alkyl; $C_1$-$C_6$alkoxy; thio$C_1$-$C_3$alkyl; amino optionally substituted with $C_1$-$C_6$alkyl; $C_0$-$C_3$alkylaryl; or $C_0$-$C_3$alkylheteroaryl, $C_0$-$C_3$alkylheterocyclyl, said aryl, heteroaryl or heterocycle being optionally substituted with $R^{10}$ wherein
$R^{10}$ is $C_1$-$C_6$alkyl, $C_0$-$C_3$alkyl$C_3$-$C_7$cycloalkyl, $C_1$-$C_6$alkoxy, amino optionally mono- or di-substituted with C1-C6alkyl, amido, C1-C3 amide; and
$R^{9b}$ is $C_1$-$C_6$ alkyl, $C_1$-$C_6$-alkoxy, amino, di($C_1$-$C_3$alkyl) amino, ($C_1$-$C_3$alkyl) amide, $NO_2$, OH, halo, trifluoromethyl, carboxyl.

16. A compound according to claim 15, wherein $R^{9a}$ is aryl or heteroaryl, either of which is optionally substituted with $R^{10}$.

17. A compound according to claim 16, wherein $R^{9a}$ is selected from the group consisted of:

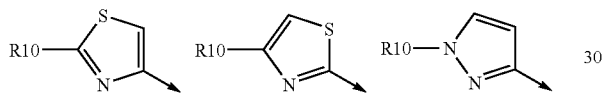

wherein $R^{10}$ is H, $C_1$-$C_6$alkyl, or $C_0$-$C_3$alkylcycloalkyl, amino optionally mono- or di-substituted with $C_1$-$C_6$alkyl, amido, ($C_1$-$C_3$alkyl)amide.

18. A compound according to claim 16, wherein $R^{9a}$ is phenyl, optionally substituted with $C_1$-$C_6$alkyl; $C_1$-$C_6$alkoxy; or halo.

19. A compound according to claim 15, wherein $R^8$ is:

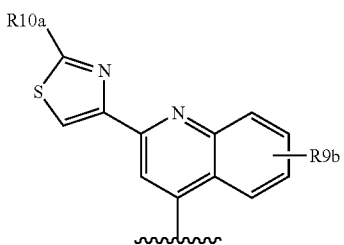

wherein $R^{10a}$ is H, $C_1$-$C_6$alkyl, or $C_0$-$C_3$alkylcarbocyclyl, amino optionally mono- or di-substituted with $C_1$-$C_6$alkyl, amido, heteroaryl or heterocyclyl; and $R^{9b}$ is $C_1$-$C_6$ alkyl, $C_1$-$C_6$-alkoxy, amino, di($C_1$-$C_3$ alkyl)amino, amido, $NO_2$, OH, halo, trifluoromethyl, or carboxyl.

20. A compound according to claim 15, wherein $R^{9b}$ is $C_1$-$C_6$-alkoxy.

21. A compound according to claim 1, wherein A is C(=O)NHSO$_2$R$^2$.

22. A compound according to claim 21, wherein $R^2$ is optionally substituted $C_1$-$C_6$ alkyl.

23. A compound according to claim 21, wherein $R^2$ is optionally substituted $C_3$-$C_7$cycloalkyl.

24. A compound according to claim 21, wherein $R^2$ is optionally substituted $C_0$-$C_6$alkylaryl.

25. A compound according to claim 1, wherein A is C(=O)OR$^1$.

26. A compound according to claim 25, wherein $R^1$ is H or $C_1$-$C_6$ alkyl.

27. A compound according to claim 1, wherein $R^7$ and $R^{7'}$ together define a spiro-cyclopropyl.

28. A compound according to claim 1, wherein J is a 3 to 8-membered saturated or unsaturated alkylene chain optionally containing one to two heteroatoms independently selected from: —O—, —S— or —NR$^{12}$—, wherein R$^{12}$ is H, $C_1$-$C_6$alkyl, or —C(=O)$C_1$-$C_6$alkyl.

29. A compound according to claim 28, wherein J is a 4 to 7-membered saturated or unsaturated, all carbon alkylene chain.

30. A compound according to claim 28, wherein J is saturated or mono-unsaturated.

31. A compound according to claim 28, wherein J is dimensioned to provide a macrocycle of 14 or 15 ring atoms.

32. A pharmaceutical composition comprising a compound as defined in claim 1, and a pharmaceutically acceptable carrier therefor.

33. A pharmaceutical composition according to claim 32, further comprising an additional HCV antiviral, selected from nucleoside analogue polymerase inhibitors, protease inhibitors, ribavirin and interferon.

34. A compound according to claim 1 with formula Ihe':

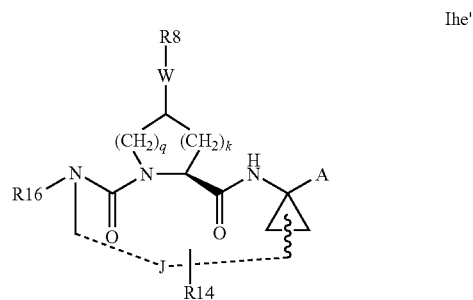

or pharmaceutically acceptable salt thereof
wherein
$R^{16}$ is H, or $C_1$-$C_6$alkyl;
J is a single 3 to 10-membered saturated or partially unsaturated alkylene chain;
q is 1 and k is 1;
A is C(=O)OR$^1$, or C(=O)NHSO$_2$R$^2$, wherein
$R^1$ is hydrogen or $C_1$-$C_6$alkyl;
$R^2$ is $C_1$-$C_6$alkyl, $C_0$-$C_3$alkylcarbocyclyl, $C_0$-$C_3$alkylheterocyclyl;
W is —O— or —OC(=O)NH—;
$R^8$ is $C_0$-$C_3$alkylaryl or $C_0$-$C_3$alkylheteroaryl, either of which is optionally mono, di, or tri substituted with R$^9$, wherein;
$R^9$ is $C_1$-$C_6$alkyl, $C_1$-$C_6$alkoxy, NO$_2$, OH, halo, trifluoromethyl, amino or amido optionally mono- or di-substituted with $C_1$-$C_6$alkyl, $C_0$-$C_3$alkylaryl, $C_0$-$C_3$alkylheteroaryl, carboxyl, said aryl or heteroaryl being optionally substituted with R$^{10}$;wherein
$R^{10}$ is $C_1$-$C_6$alkyl, $C_3$-$C_7$cycloalkyl, $C_1$-$C_6$alkoxy, amino optionally mono- or di-substituted with $C_1$-$C_6$alkyl, $C_1$-$C_3$alkyl amide, sulfonyl$C_1$-$C_3$alkyl, NO$_2$, OH, halo, trifluoromethyl, carboxyl or heteroaryl.

35. A compound according to claim 34, wherein J is a single 5-8 membered saturated or partially unsaturated alkylene chain.

36. A compound according to claims 34, wherein J is monounsaturated.

37. A compound according to claim 36, wherein J has one double bond spaced one carbon atom from the cyclopropyl group depicted in the formula Ihe'.

38. A compound according to claim 34, wherein $R^8$ is the group

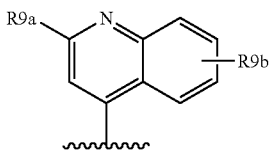

wherein $R^{9a}$ is $C_0$-$C_3$alkylaryl, $C_0$-$C_3$alkylheteroaryl, or $C_0$-$C_3$alkylheterocyclyl; said aryl, heteroaryl or heterocyclyl being optionally substituted with $R^{10}$ wherein $R^{10}$ is $C_1$-$C_6$alkyl, amino, amino mono- or disubstituted with $C_1$-$C_6$alkyl or NHC(=O)$C_1$-$C_6$alkyl; and $R^{9b}$ is $C_1$-$C_6$alkoxy; or $R^8$ is $C_0$-$C_3$alkylaryl wherein the aryl group is optionally substituted with 1-2 substituents selected from $C_0$-$C_3$alkylheterocyclyl and trifluo$C_1$-$C_6$alkyl; and wherein the $C_0$-$C_3$alkylheterocyclyl is optionally substituted with $R^{10}$.

39. A compound according to claim 38, wherein $R^{9a}$ is phenyl,

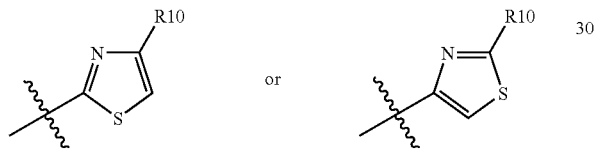

wherein $R^{10}$ is H, $C_1$-$C_6$alkyl, amino, amino mono or disubstituted with $C_1$-$C_3$alkyl.

40. A compound according to claim 34, wherein A is C(=O)NHS(=O)$_2$R$^2$.

41. A compound according to claim 40, wherein $R^2$ is optionally substituted cycloalkyl.

42. The compound according to claim 41 wherein $R^2$ is optionally substituted cyclopropyl.

43. A compound according to claim 4, wherein $R^{16}$ is methyl.

44. A compound according to claim 9, wherein W is —O—.

45. A compound selected from the group consisting of:
- 19-(7-Methoxy-2-phenyl-quinolin-4-yloxy)-2, 16-dioxo-3,15,17-triaza-tricyclo[15.3.0.0*4,6*]icos-7-ene-4,14-dicarboxylic acid 4-ethyl ester 14-methyl ester;
- 19-(7-Methoxy-2-phenyl-quinolin-4-yloxy)-2,16-dioxo-3,15,17-triaza-tricyclo[15.3.0.0*4,6*]icos-7-ene-3,14-dicarboxylic acid 3-ethyl ester;
- 14-[(Cyclohexyl-methylcarbamoyl-methyl)-19-(7-methoxy-2-phenyl-quinolin-4-yloxy)-2,16-dioxo-3, 15,17-triaza-tricyclo[15.3.0.0*4,6*]icos-7-ene-4-carboxylic acid 3-ethyl ester;
- 14-[(Cyclohexyl-methylcarbamoyl-methyl)-19-(7-methoxy-2-phenyl-quinolin-4-yloxy)-2,16-dioxo-3,15,17-triaza-tricyclo[15.3.0.0*4,6*]icos-7-ene-4-carboxylic acid;
- [14-Cyclopropanesulfonylaminocarbonyl-17(7-methoxy-2-phenyl-quinolin-4-yloxy)-2,14-dioxo-3,13,15-triaza-tricyclo[13.3.0.0*4,6*]octadec-7-en-13-yl]-carbamic acid ter.butyl ester;
- 17-(7-Methoxy-2-phenyl-quinolin-4-yloxy)-2,14-dioxo-3,13,15-triaza-tricyclo[13.3.0.0.*4,6*]octadec-7-ene-4-carboxylic acid ethyl ester;
- 17-(7-Methoxy-2-phenyl-quinolin-4-yloxy)-2,14-dioxo-3,13,15-triaza-tricyclo[13.30.0.*4,6*]octadec-7-ene-4-carboxylic acid; or a pharmaceutically acceptable salt thereof.

46. A pharmaceutical composition comprising a compound as defined in claim 45, and a pharmaceutically acceptable carrier therefor.

47. A pharmaceutical composition comprising a compound as defined in claim 10, and a pharmaceutically acceptable carrier therefor.

* * * * *